US006852518B1

(12) United States Patent
Rosen et al.

(10) Patent No.: US 6,852,518 B1
(45) Date of Patent: Feb. 8, 2005

(54) GLYCOSYL SULFOTRANSFERASES GST-4α, GST-4β, AND GST-6

(75) Inventors: Steven D. Rosen, San Francisco, CA (US); Jin Kyu Lee, Alameda, CA (US); Stefan Hemmerich, Berkeley, CA (US)

(73) Assignees: The Regents of the University of California, Oakland, CA (US); Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/593,828

(22) Filed: Jun. 13, 2000

Related U.S. Application Data

(60) Provisional application No. 60/144,694, filed on Jul. 20, 1999.

(51) Int. Cl.[7] .......................... C12N 9/10; C12N 15/00; C12N 5/00; C12N 1/20; C07H 21/04

(52) U.S. Cl. .................... 435/193; 435/320.1; 435/325; 435/252.3; 435/6; 536/23.2

(58) Field of Search ............................. 435/193, 252.3, 435/320.1, 6, 325, 200; 536/23.2, 23.1

(56) References Cited

U.S. PATENT DOCUMENTS

| | | | | | |
|---|---|---|---|---|---|
| 5,695,752 | A | | 12/1997 | Rosen et al. | 424/94.61 |
| 5,776,772 | A | | 7/1998 | Paulson et al. | 435/320.1 |
| 5,910,581 | A | * | 6/1999 | Habuchi et al. | 536/23.2 |
| 6,054,304 | A | | 4/2000 | Taniguchi et al. | 435/193 |
| 6,265,192 | B1 | * | 7/2001 | Bistrup et al. | 435/193 |
| 2002/0061562 | A1 | | 5/2002 | Fukuda | |

FOREIGN PATENT DOCUMENTS

| | | |
|---|---|---|
| EP | 821 066 | 7/1997 |
| WO | WO 9919339 | 4/1999 |
| WO | WO 01/79468 | 10/2001 |

OTHER PUBLICATIONS

Lee et al., BBRC, 263(2), 543–549, 1999.*
GenBank AI 824100, Jul. 12, 1999.
Incyte Lifeseq clone No. 3373406.
Incyte Lifeseq clone No. 3372492.
Incyte Lifeseq clone No. 3126392.
Incyte Lifeseq clone No. 3219891.
Incyte Lifeseq clone No. 1846903.
Incyte Lifeseq clone No. 6869651.
Incyte Lifeseq clone No. 0182182.
Fukuta, et al. "Molecular Cloning and Characterization of Human Keratan Sulfate Gal–6–Sulfotransferase," *J. Biol. Chem.* (Dec. 19, 1997) 272:32321–32328.
Habuchi, et al. "Enzymatic Sulfation of Galactse Residue of Keratan Sulfate by Chondroitin 6–Sulfate by Chondroitin 6–Sulfate by Chondroitin 6–Sulfotransferase," *Glycobiology* (Jan. 1996) 6:51–57.
Fukuta, et al. Molecular Cloning and Expression of Chick Chondrocyte Chondroitin 6–Sulfotransferase,: *J. Biol. Chem.* (1995) 270:185775–18580.
Habuchi, et al. "Purification of Chondroitin 6–Sulfotransferase Secreted from Cultured Chick Embryo Chondrocytes," *J. Biol. Chem.* (1993) 268:21968–21974.
Akama, et al. "Macular corneal dystrophy type I and type II are caused by distinct mutations in a new sulphotransferase gene", *Nature Genet*, (2000) vol. 26(2): 237–241.
Uchimura, et al. "Molecular cloning and characterization of an N–acetyglucosamine–6–0–sulfotransferase", *J. Bio. Chem.*, (1998) vol. 273(35): 22577–22583.
Uchimura, et al. "Mus musculus mRNA for N–acetyglucosamine–6–0–sulfotransferase complete cds", Database Accession No. AB011451, Aug. 1998.
Uchimura, et al. "*Homo sapiens* GN6ST mRNA for N–acetyglucosamine–6–0–sulfotransferase (GlcNc6ST), complete cds", Database Accession No. AB014679, 11/98.
Lee et al., "Mus musculus intestine N–acetylgluco samine 6–0 sulfotransferase (I–GlcNAc–6–ST) gene, complete cds." Sep. 23, 1999 Database accession No. AF17681.
Lee et al., "Mus musculus intestine N–acetylglucosamine 6–0 sulfotransferase (I–GlcNAc–6–ST) gene, complete cds." Sep. 23, 1999 Database accession No. AF176839.
Lee et al., "*Homo sapiens* intestine N–acetylglucosamine–6–0–sulfotransferase, complete cds" Sep. 23, 1999 Database accession No. AF176838.
Doe Joint Genome Inst.: "*Homo sapiens* chromosome 16 clone RP11–455E15, Working Draft Sequence, 17 unordered pieces" Aug. 4, 1999, Database accession No. AC009105.
NCI GCAP: "wj46c01.xl NCI_CGAP_lu19 *Homo sapiens* cDNA clone IMAGE: 2405856" Jul. 13, 1999, Database accession No. AI824100.
Birren et al., "*Home sapiens* chromosome 18, clone RP11–29013, complete sequence" Feb. 7, 2000, Database accession No. AC022662.
Hillier et al. "zu27h10.rl Soares ovary tumor NbHOT *Homo sapiens* cDNA clone IMAGE: 739267" May 19, 1997, Database Accession No. AA421254.
Zhao et al. "–11–25217.TV RPCI–11 *Homo sapiens* genomic clone" Apr. 27, 1999 Database Accession No. AQ481324.
Zhao et al. "CITBI–E1–2563I17.TF CITIBI–EI Homo sapiens genomic clone" Mar. 25, 1999 Database accession No. AQ424845.

(List continued on next page.)

*Primary Examiner*—Maryam Monshipouri
(74) *Attorney, Agent, or Firm*—Paula A. Borden; Bret E. Field; Bozicevic, Field & Francis, LLP

(57) ABSTRACT

Novel glycosylsulfotransferases (GST-4α, GST-4β, and GST-6) and polypeptides related thereto, as well as nucleic acid compositions encoding the same, are provided. The subject polypeptides and nucleic acid compositions find use in a variety of applications, including various diagnostic and therapeutic agent screening applications. Also provided are methods of inhibiting selectin mediated binding events and methods of treating disease conditions associated therewith, particularly by administering an inhibitor of at least one of GST-4α, GST-4β, and GST-6.

27 Claims, 9 Drawing Sheets

OTHER PUBLICATIONS

Nakao et al., Homo sapiens squamous cell carcinoma antigen recognized by T cell (SART–2) mRNA, complete cds.: Oct. 6, 1999 Database accession No. AF098066.

Human Genome SCI Inc. Human secreted protein encoded by gene 5 clone HSABG21 Aug. 17, 1999 Database accession No. AAX79015.

Human Genome SCI Inc.: "Human secreted protein encoded by gene 4 clone HSABG21" Aug. 17, 1999 Database accession No. AAY14415.

Arakawa et al., "Mus musculus adult male diencephalons cDNA, RiKEN full–length enriched library, clone: 9330132E09, 3' end partial sequence" Jun. 14, 2000 Database accession No. BB077136.

Marra et al., ui33cll.yl Soares mouse urogenital ridge NMURMus musculus cDNA clone IMAGE: 1853108 5', mRNA sequence Mar. 24, 1999 Database accession No. AI528511.

Marra et al., ui43b06.xl Sugano mouse embryo mewa Mus musculus cDNA clone IMAGE: 1885139 3', mRNA sequence Oct. 8, 1998 Database accession No. AI173964.

GenBank accession No. AA 261202, Mar. 18, 1997.

GenBank accession No. AI 282873, Nov. 23, 1998.

GenBank accession No. AC 009105, Apr. 25, 2001.

GenBank accession No. AC 009163, Aug. 29, 2003.

GenBank accession No. AC 011934, Mar. 12, 2000.

GenBank accession No. AF 176838, Sep. 22, 1999.

GenBank accession No. AC 026419, May 12, 2002.

GenBank accession No. AI 528511, Mar. 17, 1999.

GenBank accession No. AC 010547, Sep. 29, 2001.

GenBank accession No. AC 025287, Jan. 26, 2002.

Lee et al., "Mus musculus intestine N–acetylgluco samine 6–0 sulfotransferase (I–GlcNAc–6–ST) gene, complete cds." Sep. 23, 1999 Database accession No. AF176841, BBRC, 4263(2) 543–549 (1999).

Lee et al., "Mus musculus intestine N–acetylglucosamine 6–0 sulfotransferase (I–GlcNAc–6–ST) gene, complete cds." Sep. 23, 1999 Database accession No. AF176840.

* cited by examiner

FIG. 1

>human Glycosyl Sulfotransferase 4 (huGST-4α) complete cDNA (ORF in capitals)
ggctcgaggtccactgtgctgaatgtaagtctccttatcagaaagctcccagtgaggaactggtcttctggagactctgtgtggcat
agagtgattcaaccaccttaagaagacctctggctttcctggaacacagatgtcgagacatctcccatggatttgtgatcagcgttg
cagctctcccagcagccctggacggtggcccccagccgcccgcATGTGGCTGCCACGGTTCTCCAGCA
AGACAGTGACAGTGCTCCTCCTGGCACAGACCACCTGCCTCCTGCTCTTCATC
ATCTCCCGGCCAGGGCCCTCATCCCCAGCCGGCGGCGAGGATCGTGTGCACGT
GCTGGTGCTGTCCTCGTGGCGCTCGGGCTCATCCTTCTTGGGCCAGCTCTTCAG
CCAGCACCCCGACGTCTTCTACCTGATGGAGCCCGCGTGGCATGTGTGGACCA
CCCTGTCGCAGGGCAGCGCGGCAACGCTGCACATGGCCGTGCGCGACCTGAT
GCGCTCTATCTTTTTGTGCGACATGGACGTGTTTGATGCCTACATGCCACAGA
GCCGAAACCTGTCCGCCTTTTTCAACTGGGCAACGAGCCGCGCGCTGTGCTCG
CCGCCCGCCTGCAGCGCCTTTCCCCGAGGCACCATCAGCAAGCAGGACGTAT
GCAAGACACTGTGCACGCGGCAGCCATTCAGCCTGGCCCGGGAGGCCTGCCG
CTCCTACAGCCACGTGGTGCTCAAGGAGGTGCGCTTCTTCAACCTGCAGGTGC
TCTACCCGCTGCTCAGCGACCCCGCGCTCAACCTGCGCATCGTGCACCTGGTG
CGCGACCCGCGGGCCGTGCTGCGCTCCCGGGAGGCGGCGGGCCCGATACTGG
CACGCGACAACGGCATCGTGCTGGGCACCAACGGCAAGTGGGTGGAGGCCGA
CCCTCACCTGCGCCTGATTCGCGAGGTGTGCCGCAGCCACGTGCGCATCGCCG
AGGCCGCCACACTCAAGCCGCCACCCTTCCTGCGCGGCCGCTACCGCCTGGTG
CGCTTCGAGGACCTGGCGCGGGAGCCGCTGGCAGAGATCCGCGCACTCTACG
CCTTCACCGGCCTGACCCTCACGCCACAGCTCGAGGCCTGGATCCACAACATC
ACCCACGGGTCGGGGATCGGCAAGCCAATCGAGGCCTTCCATACTTCGTCTAG
GAATGCGCGCAACGTCTCCCAGGCCTGGCGCCACGCGTTGCCCTTCACTAAGA
TCCTGCGCGTGCAGGAGGTGTGCGCCGGCGCGCTGCAGCTGCTGGGCTACCG
GCCTGTGTACTCTGCGGACCAGCAGCGTGACCTCACCCTGGATCTGGTGCTGC
CACGAGGCCCAGACCACTTCAGCTGGGCATCGCCTGACTGAgaactctgggccttagagc
aagccccgaactgtggtcgccaggcccaggaagcgactgcatggtggaaaaggagctggggcgcatggggaacaggtccct
actatcaaccgggagtttggggtcctcccctgaagtaagcaaggactgcacgtttctttctctcctgattctcggttttcctttgagtctt
ctggagctgccttctcatcaggtgcactcttcatggaaaagcaactcttgcccctacctcttctgggcgcagggagtaagttactgc
taaattaaattaaatgtgtgccaggccgggtgcggtggctcatgcctgtaatcccagcattttgagaggctgaggcgggtggatca
cctgaggtcaggattcaaaaccagcctggccaacatagtgaaacccccctctctactaaaaatgcaaaaattagtccggcgtggtg
gcacactcctgtaatcccagctacttaggaggctgaggtgggaaaatcacttggactccaaaggtggaggttgcagtaagctgaa
atcatgccactgcaccctagcttgggtggcaaagcaaaactctatcaaaaaaataattaataaatttgttcaaaagtcctgccgaaa
aaaaaaaaaaaaaaaaaaaaaaaaaaaaaaa (SEQ ID NOS. 03 & 04)

>human Glycosyl Sulfotransferase 4 (huGST-4α) translation of ORF from complete cDNA
MWLPRFSSKTVTVLLLAQTTCLLLFIISRPGPSSPAGGEDRVHVLVLSSWRSGSSFLGQLFSQHPDVF
YLMEPAWHVWTTLSQGSAATLHMAVRDLMRSIFLCDMDVFDAYMPQSRNLSAFFNWATSRALC
SPPACSAFPRGTISKQDVCKTLCTRQPFSLAREACRSYSHVVLKEVRFFNLQVLYPLLSDPALNLRIV
HLVRDPRAVLRSREAAGPILARDNGIVLGTNGKWVEADPHLRLIREVCRSHVRIAEAATLKPPPFLR
GRYRLVRFEDLAREPLAEIRALYAFTGLTLTPQLEAWIHNITHGSGIGKPIEAFHTSSRNARNVSQA
WRHALPFTKILRVQEVCAGALQLLGYRPVYSADQQRDLTLDLVLPRGPDHFSWASPD
(SEQ ID NO: 08)

FIG. 2

>mouse Glycosyl Sulfotransferase 4 (huGST-4) complete cDNA (ORF in capitals)
ctcgagcactgttggcctactggaccaccgactgagcggctctttgtgtgcgccctgggtgcgcagcgcagaagcgcagcgggcagcgcaggccctagc
cagaggtATGCGGCTACCCCGTTTCTCCAGCACTGTCATGCTTTCGCTCCTGATGGTACAGACTGGC
ATCCTGGTCTTCCTGGTCTCCCGGCAAGTGCCATCGTCCCCAGCAGGCCTTGGGGAGCGTGTGC
ACGTGCTGGTACTGTCCTCGTGGCGCTCGGGCTCGTCCTTCGTGGGCCAGCTCTTCAGCCAACA
CCCCGATGTCTTCTACCTGATGGAGCCGGCTTGGCACGTCTGGGATACGTTGTCGCAGGGCAGT
GCCCCCGCACTCCACATGGCCGTGCGTGACCTGATCCGCTCAGTGTTCCTATGCGACATGGACG
TATTTGATGCCTACCTGCCCTGGCGCCGCAACATCTCGGATCTCTTCCAGTGGGCGGTGAGCCG
CGCATTGTGCTCACCTCCGGTCTGCGAAGCCTTCGCTCGTGGCAACATCAGCAGCGAGGAGGT
GTGTAAGCCTCTGTGCGCAACGCGGCCCTTCGGCCTGGCTCAGGAAGCCTGCAGCTCCTATAG
TCACGTCGTGCTCAAGGAGGTGCGCTTCTTTAACCTACAGGTGCTCTACCCGCTGCTCAGCGAC
CCTGCGCTCAACCTGCGCATCGTGCACCTAGTGCGCGACCCGCGGGCCGTGCTGCGCTCCCGA
GAGCAGACAGCCAAGGCGCTGGCACGGGACAATGGCATCGTCCTGGGTACCAACGGCACGTG
GGTGGAGGCGGACCCCCGGCTGCGCGTGGTCAACGAGGTATGCCGCAGCCATGTGCGCATCGC
AGAGGCAGCCTTGCACAAGCCGCCGCCCTTCTTGCAAGATCGCTACCGCCTGGTGCGCTACGA
GGATCTGGCCCGGGACCCACTCACCGTAATCCGTGAACTCTATGCCTTCACCGGCCTGGGTCTC
ACGCCGCAGCTCCAGACTTGGATCCACAATATCACGCATGGTTCAGGGCCAGGCGCGCGCCGT
GAAGCCTTCAAGACCACATCCAGGGATGCGCTCAGTGTATCCCAGGCCTGGCGCCACACGCTG
CCCTTTGCCAAGATTCGCCGGGTCCAGGAACTGTGCGGGGGTGCACTGCAGCTGCTGGGTTAC
CGGTCTGTGCATTCGGAGCTTGAGCAAAGGGACCTCTCTCTGGACCTCCTGCTGCCAAGAGGC
ATGGACAGTTTCAAGTGGGCATCGTCCACGGAGAAGCAACCGGAATCTTAGaatttagtggagagaccca
gctataacattagggtctattggagtatgataaagaaggggcttggagaacccaaaagcaagtagctgggagtgtgagtgatcttgtcctgtactaggaaagg
atggagtccaaatcccacatctctttctgtccagattgtagttttcggttgggtcttttagggtttggattcccaccaagtactatcgaatggaaagcaaaagctgt
gcccacttccttcagagaggcagccagcctcctactaaagcacttcctttctcgttgactctctcccctctttgatcataccatgcaatcgcagagaatggggtcc
caggcctgctctggagtgcgggaaaggcgcggctgtgggctggctcctaaaatctgtgcacctgcctctcgttggctcacccagacctctgctcactgccac
gccctagtatctcagtccatcatagacttggacagttatgggcctggtcaaggaggaaaatgagacgatgcttccctctgtgattctctgcctgaccttctagaa
gggaatccaggcacacacacaaccatacctgaggaggatggcttttaatgaatctttgatttgtcctaaaatgaaagatcctaatttatggaaataaacataaat
atgctgcgtgatcccaaaaaaaaaaaaaaaaaaaaaaaaaaaaa (SEQ ID NOS: 01 & 02)

>mouse Glycosyl Sulfotransferase 4 (huGST-4) translation of ORF from complete cDNA
MRLPRFSSTVMLSLLMVQTGILVFLVSRQVPSSPAGLGERVHVLVLSSWRSGSSFVGQLFSQHPDV
FYLMEPAWHVWDTLSQGSAPALHMAVRDLIRSVFLCDMDVFDAYLPWRRNISDLFQWAVSRALC
SPPVCEAFARGNISSEEVCKPLCATRPFGLAQEACSSYSHVVLKEVRFFNLQVLYPLLSDPALNLRIV
HLVRDPRAVLRSREQTAKALARDNGIVLGTNGTWVEADPRLRVVNEVCRSHVRIAEAALHKPPPF
LQDRYRLVRYEDLARDPLTVIRELYAFTGLGLTPQLQTWIHNITHGSGPGARREAFKTTSRDALSVS
QAWRHTLPFAKIRRVQELCGGALQLLGYRSVHSELEQRDLSLDLLLPRGMDSFKWASSTEKQPES
(SEQ ID NO: 07)

FIG. 3

>human GST-6 cDNA encoding GST-6 polypeptide fragment cttggcggaggaggttggTGAtgcagctggggaaataatcactgcctctcaacatggggaaatggtatttgtgagtggggaagccgtgtctgcttattcttc
agcaatgagactgaaaagtgtatatcgggctttgcttctttaaattcccaaactctgctagttgttgatcatattgagaggcaagaagattccccaataaattctgtc
agtgccttctttcataatttggatattgattttaaatatatcccatataagtttATGAATAGGTATAATGGTGCCATGATGGATGTGT
GGGATGCACATTACAAAATGTTTTGGTTTGATCATCATGGCAATAGTCCCATGGCCAGTATACA
GGAAGCAGAGCAAGCTGCTGAATTTAAAAAACGATGGACTCAATTTGTTAATGTTACTTTTCA
GATGGAATCCACAATCACAAGAATTGCATATGTCTTTTATGGGCCATATATCAATGTCTCCAGC
TGCAGATTTATTGATAGTTCCAATCCTGGACTTCAGATTTCTCTCAATGTCAATAATACTGAAC
ATGTTGTTTCTATTGTAACTGATTACCATAACCTGAAGACAAGATTCAATTATCTGGGATTCGG
TGGCTTTGCCAGTGTGGCTGATCAAGGCCAAATAACCCGATTTGGTTTGGGCACTCAAGCAAT
AGTAAAGCCTGTAAGACATGATAGGATTATTTTCCCCTTTGGATTTAAATTTAATATAGCAGTT
GGATTAATTTTGTGCATTAGCTTGGTGATTTTAACTTTCCAATGGCGTTTTTACCTTTCTTTTAG
AAAACTAATGCGATGGATATTAATACTTGTTATTGCCTTGTGGTTTATTGAGCTTTTGGATGTG
TGGAGCACTTGTAGTCAGCCCATTTGTGCAAAATGGACAAGGACAGAGGCTGAGGGAAGCAA
GAAGTCTTTGTCTTCTGAAGGGCACCACATGGATCTTCCTGATGTTGTCATTACCTCACTTCCTG
GTTCAGGAGCTGAAATTCTCAAACAACTTTTTTTCAACAGTAGTGATTTTCTCTACATCAGGGT
TCCTACAGCCTACATTGATATTCCTGAAACTGAGTTGGAAATCGACTCATTTGTAGATGCTTGT
GAATGGAAGGTGTCAGATATCCGCAGTGGGCATTTTCGTTTACTCCGAGGCTGGTTGCAGTCTT
TAGTCCAGGACACAAAATTACATTTGCAAAACATCCATCTGCATGAACCCAATAGGGGTAAAC
TGGCCCAATATTTTGCAATGAATAAGGACAAAAAAAGAAAATTTAAAAGGAGAGAGTCTTTGC
CAGAACAAAGAAGTCAAATGAAAGGCGCCTTTGATAGAGATGCTGAATATATTAGGGCTTTGA
GGAGACACCTGGTTTACTATCCAAGTGCACGTCCTGTGCTCAGTTTAAGCAGTGGAAGCTGGA
CGTTAAAGCTTCATTTTTTTCAGGAAGTTTTAGGAGCTTCGATGAGGGCATTGTACATAGTAAG
AGACCCTCGGGCATGGATTTATTCAATGTTGTACAATAGTAAACCAAGTCTTTATTCTTTGAAG
AATGTACCAGAGCATTTAGCAAAATTGTTTAAAATAGAGGGAGGTAAAGGCAAATGTAACTTA
AATTCGGGTTATGCTTTCGAGTATGAACCATTGAGGAAAGAATTATCAAAATCCAAATCAAAT
GCAGTGTCCCTCTTGTCTCACTTGTGGCTAGCAAATACAGCAGCAGCCTTGAGAATAAATACA
GATTTGCTGCCTACTAGCTACCAGCTGGTCAAGTTTGAAGATATTGTGCATTTTCCTCAGAAAA
CTACTGAAAGGATTTTTGCCTTTCTTGGAATTCCTTTGTCTCCTGCTAGTTTAAACCAAATATTG
TTTGCCACCTCTACAAACCTTTTTTACCTTCCCTATGAAGGGGAAATATCACCAACTAATACTA
ATGTTTGGAAACAGAACTTGCCTAGAGATGAAATTAAACTAATTGAAAACATCTGCTGGACTC
TGATGGATCGCCTAGGATATCCAAAGTTTATGGACTAAatgctgcaggtcagcagaaatttgcactaataatacttacca
acccactttgtggatatgaatcagaagagtttgtttattctttagtgtgtgtgtgtgtgtgtgcacgcgtgtatgtgttcagtgttgtttgcacagagagattgttttaa
aaaatggcaccatatttggcctagcaggatttatttttatgtcatcacctcccttgcctttgtttctgaaaattttgtctgctaaaaagtttctgctacagagtggtagat
gaagttatatcatggggtcaggggagatgggaaaattttaagtttttgtctaactccccttcatctgtaactgtgctaatctatctagagacctcaaacactgctaa
aggccttgcaattgctgctttacccacgcatctcttgctttcaagaaggactacaaaagttccttatccttttgaaaaggtcttctgacacacttatcttgcacaaag
aaaaagaaattt (SEQ ID NOS: 05 & 06)

>human GST-6 polypeptide fragment (translation of ORF)

MNRYNGAMMDVWDAHYKMFWFDHHGNSPMASIQEAEQAAEFKKRWTQFVNV
TFQMESTITRIAYVFYGPYINVSSCRFIDSSNPGLQISLNVNNTEHVVSIVTDYHNL
KTRFNYLGFGGFASVADQGQITRFGLGTQAIVKPVRHDRIIFPFGFKFNIAVGLILC
ISLVILTFQWRFYLSFRKLMRWILILVIALWFIELLDVWSTCSQPICAKWTRTEAEG
SKKSLSSEGHHMDLPDVVITSLPGSGAEILKQLFFNSSDFLYIRVPTAYIDIPETELEI
DSFVDACEWKVSDIRSGHFRLLRGWLQSLVQDTKLHLQNIHLHEPNRGKLAQYF
AMNKDKKRKFKRRESLPEQRSQMKGAFDRDAEYIRALRRHLVYYPSARPVLSLS
SGSWTLKLHFFQEVLGASMRALYIVRDPRAWIYSMLYNSKPSLYSLKNVPEHLA
KLFKIEGGKGKCNLNSGYAFEYEPLRKELSKSKSNAVSLLSHLWLANTAAALRIN
TDLLPTSYQLVKFEDIVHFPQKTTERIFAFLGIPLSPASLNQILFATSTNLFYLPYEG
EISPTNTNVWKQNLPRDEIKLIENICWTLMDRLGYPKFMD (SEQ ID NO:09)

FIG. 4A

(human GST4β complete cDNA, ORF highlighted in capitals)

```
ggcacgaggacgacgtttgggagcctttgctgagtccagggagagaggcgtcccccaccgtgccgctgcagctcggg
cagagccgccaagctttggggtgctgaggaacctctaatcatctcccatggatttgtgatcagcgttgcagctctcc
cagcagccctggacagtggcccccagcagtcagcATGTGGCTGCCGCGCGTCTCCAGCACAGCAGTGACCGCGCTCC
TCCTGGCGCAGACCTTCCTCCTCCTCTTTCTGGTTTCCCGGCCAGGGCCCTCGTCCCCAGCAGGCGGCGAGGCGCGC
GTGCATGTGCTGGTGCTGTCCTCGTGGCGCTCGGGCTCGTCCTTCGTGGGCCAACTCTTCAACCAGCACCCCGACGT
CTTCTACCTAATGGAGCCCGCGTGGCACGTGTGGACCACCCTGTCGCAGGGCAGCGCCGCAACGCTGCACATGGCTG
TGCGCGACCTGGTGCGCTCCGTCTTCCTGTGCGACATGGACGTGTTTGATGCCTATCTGCCTTGGCGCCGCAACCTG
TCCGACCTCTTCCAGTGGGCCGTGAGCCGTGCACTGTGCTCGCCACCCGCCTGCAGTGCCTTTCCCCGAGGCGCCAT
CAGCAGCGAGGCCGTGTGCAAGCCACTGTGCGCGCGGCAGTCCTTCACCCTGGCCCGGGAGGCCTGCCGCTCCTACA
GCCACGTGGTGCTCAAGGAGGTGCGCTTCTTCAACCTGCAGGTGCTCTACCCGCTGCTCAGCGACCCCGCGCTCAAC
CTACGCATCGTGCACCTGGTGCGCGACCCGCGGGCCGTGCTGCGCTCCCGGGAGCAGACAGCCAAGGCTCTGGCGCG
TGACAACGGCATCGTGCTGGGCACCAACGGCACGTGGGTGGAGGCCGACCCCGGCCTGCGCGTGGTGCGCGAGGTGT
GCCGTAGCCACGTACGCATCGCCGAGGCCGCCACACTCAAGCCGCCACCCTTTCTGCGCGGCCGCTACCGCCTGGTG
CGCTTCGAGGACCTGGCGCGGGAGCCGCTGGCAGAAATCCGTGCGCTCTACGCCTTCACTGGGCTCAGTCTCACGCC
ACAGCTCGAGGCCTGGATCCATAACATCACCCACGGATCTGGACCTGGTGCGCGCCGCGAAGCCTTCAAGACTTCGT
CCAGGAATGCGCTCAACGTCTCCCAGGCCTGGCGCCATGCGCTGCCCTTTGCCAAGATCCGCCGCGTGCAGGAACTG
TGCGCTGGTGCGCTGCAGCTGCTGGGCTACCGGCCTGTGTACTCTGAGGACGAGCAGCGCAACCTCGCCCTTGATCT
GGTGCTGCCACGAGGCCTGAACGGCTTCACTTGGGCATCATCCACCGCCTCGCACCCCCGAAATTAGtggaggccac
agttgtagcaggcgctaggcccgggaggagagtgcatggtgcagaggggggctggggcgcacggagaagcaggtccct
atattgaccaaggagtttgtggtacgacccctccccctccccaagtaggcaaggactgcacgtttctttctctcttg
attcttggttttcctttgagtcctctggagctgccttctcatcaggtgcactcttcatggaaagcaactcttgcccc
tgcctcctctgggcacagggtgtgcgttcagatgacttggctcctactcaagggctttcttccccctggagaagaga
```

FIG. 4B

(human GST4β, translation of ORF)

```
MWLPRVSSTAVTALLLAQTFLLLFLVSRPGPSSPAGGEARVHVLVLSSWRSGSSFVGQLFNQHPDVFYLMEPAWHVWT
TLSQGSAATLHMAVRDLVRSVFLCDMDVFDAYLPWRRNLSDLFQWAVSRALCSPPACSAFPRGAISSEAVCKPLCARQ
SFTLAREACRSYSHVVLKEVRFFNLQVLYPLLSDPALNLRIVHLVRDPRAVLRSREQTAKALARDNGIVLGTNGTWVE
ADPGLRVVREVCRSHVRIAEAATLKPPPFLRGRYRLVRFEDLAREPLAEIRALYAFTGLSLTPQLEAWIHNITHGSGP
GARREAFKTSSRNALNVSQAWRHALPFAKIRRVQELCAGALQLLGYRPVYSEDEQRNLALDLVLPRGLNGFTWASSTA
SHPRN
```

FIG. 5A (human GST6 complete cDNA, ORF highlighted in capitals)

ATGCCTAAGGGAGGAGCTCCCCCATGGATCATGGCGTTAATGTTTACAGGACATTTACTATTCTTAGCATTATTGATG
TTTGCTTTCTCTACTTTTGAGGAATCTGTGAGCAATTATTCCGAATGGGCAGTTTTCACAGATGATATAGATCAGTTT
AAAACACAGAAAGTGCAAGATTTCAGACCCAACCAAAAGCTGAAGAAAAGTATGCTTCATCCAAGTTTATATTTTGAT
GCTGGAGAAATCCAAGCAATGAGACAAAAGTCTCGTGCAAGCCATTTGCATCTTTTAGAGCTATCAGAAGTGCAGTG
ACAGTTATGCTGTCCAACCCAACATACTACCTACCTCCACCAAAGCATGCTGATTTTGCTGCCAAGTGGAATGAAATT
TATGGTAACAATCTGCCTCCTTTAGCATTGTACTGTTTGTTATGCCCAGAAGACAAAGTTGCCTTTGAATTTGTCTTG
GAATATATGGACAGGATGGTTGGCTACAAAGACTGGCTAGTAGAGAATGCACCAGGAGATGAGGTTCCAATTGGCCAT
TCCTTAACAGGTTTTGCCACTGCCTTTGACTTTTTATATAACTTATTAGATAATCATCGAAGACAAAAATACCTGGAA
AAAATATGGGTTATTACTGAGGAAATGTACGAGTATTCCAAGGTCCGCTCATGGGGCAAACAGCTTCTCCATAACCAC
CAAGCCACTAATATGATAGCATTACTCACAGGGGCCTTGGTGACTGGAGTAGATAAAGGATCTAAAGCAAATATATGG
AAACAGGCTGTAGTGGATGTCATGGAAAAGACAATGTTTCTATTGAATCATATTGTTGATGGTTCTTTGGATGAAGGT
GTGGCCTATGGAAGCTACACAGCTAAATCCGTCACACAGTATGTTTTTCTGGCCCAGCGCCATTTTAATATCAACAAC
TTGGATAATAACTGGTTAAAGATGCACTTTTGGTTCTATTATGCCACCCTTTTACCTGGCTTCCAAAGAACTGTGGGT
ATAGCAGATTCCAATTATAATTGGTTTTATGGTCCAGAAAGCCAGCTAGTTTTCTTGGATAAGTTCATCTTAAAGAAT
GGAGCTGGAAATTGGTTAGCTCAGCAAATTAGAAAGCACCGACCTAAAGATGGACCGATGGTTCCTTCAACTGCCCAA
AGGTGGAGTACTCTTCACACTGAATACATCTGGTATGATCCCCAGCTCACACCACAGCCACCTGCTGATTATGGTACT
GCAAAAATACACACATTCCCTAACTGGGGTGTGGTTACTTATGGGGCTGGGTTGCCAAACACACAGACCAACACCTTT
GTGTCTTTTAAATCTGGGAAGCTGGGGGACGAGCTGTGTATCACATAGTTCATTTTCAGCCATATTCCTGGATTGAT
GGGTGGAGAAGTTTTAACCCAGGACATGAGCATCCAGATCAGAACTCATTTACTTTTGCCCCCAATGGACAAGTATTT
GTTTCTGAAGCTCTCTATGGACCCAAGTTGAGCCACCTTAACAATGTATTGGTGTTTGCTCCATCACCCTCAAGCCAG
TGTAATAAGCCCTGGGAAGGTCAACTGGGAGAATGTGCGCAGTGGCTTAAGTGGACTGGCGAGGAGGTTGGTGATGCA
GCTGGGGAAATAATCACTGCCTCTCAACATGGGGAAATGGTATTTGTGAGTGGGGAAGCCGTGTCTGCTTATTCTTCA
GCAATGAGACTGAAAAGTGTATATCGTGCTTTGCTTCTCTTAAATTCCCAAACTCTGCTAGTTGTTGATCATATTGAG
AGGCAAGAAGATTCCCCAATAAATTCTGTCAGTGCCTTCTTTCATAATTTGGATATTGATTTTAAATATATCCCATAT
AAGTTTATGAATAGGTATAATGGTGCCATGATGGATGTGTGGGATGCACATTACAAAATGTTTTGGTTTGATCATCAT
GGCAATAGTCCCATGGCCAGTATACAGGAAGCAGAGCAAGCTGCTGAATTTAAAAAACGATGGACTCAATTTGTTAAT
GTTACTTTTCAGATGGAATCCACAATCACAAGAATTGCATATGTCTTTTATGGGCCATATATCAATGTCTCCAGCTGC
AGATTTATTGATAGTTCCAATCCTGGACTTCAGATTTCTCTCAATGTCAATAATACTGAACATGTTGTTTCTATTGTA
ACTGATTACCATAACCTGAAGACAAGATTCAATTATCTGGGATTCGGTGGCTTTGCCAGTGTGGCTGATCAAGGCCAA
ATAACCCGATTTGGTTTGGGCACTCAAGCAATAGTAAAGCCTGTAAGACATGATAGGATTATTTTCCCCTTTGGATTT
AAATTTAATATAGCAGTTGGATTAATTTTGTGCATTAGCTTGGTGATTTTAACTTTCCAATGGCGTTTTTACCTTTCT
TTTAGAAAACTAATGCGATGGATATTAATACTTGTTATTGCCTTGTGGTTTATTGAGCTTTTGGATGTGTGGAGCACT
TGTAGTCAGCCCATTTGTGCAAAATGGACAAGGACAGAGGCTGAGGGAAGCAAGAAGTCTTTGTCTTCTGAAGGGCAC
CACATGGATCTTCCTGATGTTGTCATTACCTCACTTCCTGGTTCAGGAGCTGAAATTCTCAAACAACTTTTTTTCAAC
AGTAGTGATTTTCTCTACATCAGGGTTCCTACAGCCTACATTGATATTCCTGAAACTGAGTTGGAAATCGACTCATTT
GTAGATGCTTGTGAATGGAAGGTGTCAGATATCCGCAGTGGGCATTTTCGTTTACTCCGAGGCTGGTTGCAGTCTTTA
GTCCAGGACACAAAATTACATTTGCAAAACATCCATCTGCATGAACCCAATAGGGGTAAACTGGCCCAATATTTTGCA
ATGAATAAGGACAAAAAAAGAAAATTTAAAAGGAGAGAGTCTTTGCCAGAACAAAGAAGTCAAATGAAAGGCGCCTTT
GATAGAGATGCTGAATATATTAGGGCTTTGAGGAGACACCTGGTTTACTATCCAAGTCCACGTCCTGTGCTCAGTTTA
AGCAGTGGAAGCTGGACGTTAAAGCTTCATTTTTTTCAGGAAGTTTTAGGAGCTTCGATGAGGGCATTGTACATAGTA
AGAGACCCTCGGGCATGGATTTATTCAATGTTGTACAATAGTAAACCAAGTCTTTATTCTTTGAAGAATGTACCAGAG
CATTTAGCAAAATTGTTTAAAATAGAGGGAGGTAAAGCCAAATGTAACTTAAATTCGGGTTATGCTTTCGAGTATGAA
CCATTGAGGAAAGAATTATCAAAATCCAAATCAAATGCAGTGTCCCTCTTGTCTCACTTGTGGCTAGCAAATACAGCA
GCAGCCTTGAGAATAAATACAGATTTGCTGCCTACTAGCTACCAGCTGGTCAAGTTTGAAGATATTGTGCATTTTCCT
CAGAAAACTACTGAAAGGATTTTTGCCTTTCTTGGAATTCCTTTGTCTCCTGCTAGTTTAAACCAAATATTGTTTGCC
ACCTCTACAAACCTTTTTTACCTTCCCTATGAAGGGGAAATATCACCAACTAATACTAATGTTTGGAAACAGAACTTG
CCTAGAGATGAAATTAAACTAATTGAAAACATCTGCTGGACTCTGATGGATCGCCTAGGATATCCAAAGTTTATGGAC
TAAatgctgcaggtcagcagaaatttgcactaataatacttaccaacccaaaaaaaaaaaaaaaaa

FIG. 5B

(human GST-6, translation of ORF)

MPKGGAPPWIMALMFTGHLLFLALLMFAFSTFEESVSNYSEWAVFTDDIDQFKTQKVQDFRPNQKLKKSMLHPSLYFD
AGEIQAMRQKSRASHLHLFRAIRSAVTVMLSNPTYYLPPPKHADFAAKWNEIYGNNLPPLALYCLLCPEDKVAFEFVL
EYMDRMVGYKDWLVENAPGDEVPIGHSLTGFATAFDFLYNLLDNHRRQKYLEKIWVITEEMYEYSKVRSWGKQLLHNH
QATNMIALLTGALVTGVDKGSKANIWKQAVVDVMEKTMFLLNHIVDGSLDEGVAYGSYTAKSVTQYVFLAQRHFNINN
LDNNWLKMHFWFYYATLLPGFQRTVGIADSNYNWFYGPESQLVFLDKFILKNGAGNWLAQQIRKHRPKDGPMVPSTAQ
RWSTLHTEYIWYDPQLTPQPPADYGTAKIHTFPNWGVVTYGAGLPNTQTNTFVSFKSGKLGGRAVYDIVHFQPYSWID
GWRSFNPGHEHPDQNSFTFAPNGQVFVSEALYGPKLSHLNNVLVFAPSPSSQCNKPWEGQLGECAQWLKWTGEEVGDA
AGEIITASQHGEMVFVSGEAVSAYSSAMRLKSVYRALLLLNSQTLLVVDHIERQEDSPINSVSAFFHNLDIDFKYIPY
KFMNRYNGAMMDVWDAHYKMFWFDHHGNSPMASIQEAEQAAEFKKRWTQFVNVTFQMESTITRIAYVFYGPYINVSSC
RFIDSSNPGLQISLNVNNTEHVVSIVTDYHNLKTRFNYLGFGGFASVADQGQITRFGLGTQAIVKPVRHDRIIFPFGF
KFNIAVGLILCISLVILTFQWRFYLSFRKLMRWILILVIALWFIELLDVWSTCSQPICAKWTRTEAEGSKKSLSSEGH
HMDLPDVVITSLPGSGAEILKQLFFNSSDFLYIRVPTAYIDIPETELEIDSFVDACEWKVSDIRSGHFRLLRGWLQSL
VQDTKLHLQNIHLHEPNRGKLAQYFAMNKDKKRKFKRRESLPEQRSQMKGAFDRDAEYIRALRRHLVYYPSARPVLSL
SSGSWTLKLHFFQEVLGASMRALYIVRDPRAWIYSMLYNSKPSLYSLKNVPEHLAKLFKIEGGKGKCNLNSGYAFEYE
PLRKELSKSKSNAVSLLSHLWLANTAAALRINTDLLPTSYQLVKFEDIVHFPQKTTERIFAFLGIPLSPASLNQILFA
TSTNLFYLPYEGEISPTNTNVWKQNLPRDEIKLIENICWTLMDRLGYPKFMD

FIG. 6A

(mouse GST6 cDNA, ORF highlighted in capitals)

ATGGCGTTTATGTTTACAGAACATTTACTATTTTTAACATTGATGATGTGTAGTTTTTCTACTTGTGAAGAATCTGTG
AGCAATTATTCTGAATGGGCAGTTTTCACAGACGATATACAATGGCTTAAGTCACAGAAAATACAAGATTTCAAACTC
AACCGAAGACTTCATCCAAATTTATATTTTGATGCTGGAGATATACAAACATTGAAACAAAAGTCTCGTACAAGCCAT
TTGCATATTTTTAGAGCTATCAAAAGTGCAGTGACAATTATGCTGTCCAATCCATCATACTACCTACCTCCACCCAAG
CATGCTGAGTTTGCTGCCAAGTGGAATGAAATTTATGGTAATAATCTTCCTCCTTTAGCATTGTATTGTTTATTATGC
CCAGAAGACAAGGTTGCCTTTGAATTTGTTATGGAATACATGGATCGGATGGTTAGCTACAAAGACTGGCTAGTTGAG
AATGCACCAGGGGATGAGGTTCCAGTTGGCCATTCTTTAACAGGTTTTGCCACTGCCTTTGACTTTTTATATAATCTA
TTAGGTAATCAGCGTAAACAAAAATACCTAGAAAAAATTTGGATTGTTACTGAGGAAATGTATGAATATTCCAAGATT
CGATCATGGGGCAAACAACTTCTTCATAACCATCAAGCTACAAATATGATAGCTTTACTCATAGGGGCCTTGGTTACT
GGAGTAGATAAAGGATCTAAAGCAAACATATGGAAACAAGTTGTTGTTGATGTGATGGAAAAGACTATGTTTCTCTTG
AAGCATATTGTAGATGGCTCATTGGATGAAGGTGTGGCCTATGGAAGCTATACCTCAAAATCAGTTACACAGTATGTT
TTTTTGGCACAACGCCATTTTAACATCAACAACTTTGATAATAACTGGCTAAAAATGCATTTTTGGTTTTATTATGCT
ACACTTTTGCCAGGCTATCAAAGAACTGTAGGCATAGCAGATTCCAATTATAATTGGTTTTATGGTCCAGAGAGCCAG
CTAGTTTTCTTGGATAAGTTCATTTTACAGAATGGAGCTGGAAATTGGTTAGCTCAGCAAATTAGAAAGCATCGACCT
AAGGATGGACCAATGGTTCCTTCCACTGCTCAGCGGTGGAGTACTCTTCATACTGAATACATCTGGTATGATCCAACA
CTCACCCCACAGCCTCCTGTTGATTTTGGCACTGCAAAAATGCACACATTTCCTAACTGGGGTGTCGTGACTTATGGG
GGTGGGCTGCCAAACACCCAGACCAATACCTTTGTGTCTTTTAAATCTGGGAAACTGGGAGGACGAGCTGTGTATGAC
ATAGTTCACTTTCAGCCATATTCCTGGATTGATGGATGGAGAAGCTTTAACCCAGGACATGAACATCCAGATCAAAAT
TCATTTACTTTCGCTCCTAATGGGCAGGTATTCGTTTCTGAGGCTCTTTATGGACCAAAATTGAGCCACCTTAACAAC
GTATTGGTGTTTGCCCCATCACCATCAAGTCAATGTAATCAGCCCTGGGAAGGTCAACTGGGAGAATGTGCACAGTGG
CTCAAGTGGACTGGGGAAGAGGTTGGTGATGCAGCTGGGGAAGTTATTACTGCTGCTCAACATGGTGATAGGATGTTT
GTGAGTGGGGAAGCAGTGTCTGCTTATTCTTCTGCCATGAGACTGAAAAGTGTCTATCGTGCTTTACTTCTTTTAAAT
TCACAAACTCTGCTTGTTGTCGATCATATTGAAAGGCAAGAAACTTCCCCAATAAATTCTGTCAGTGCCTTCTTTCAT
AATTTGGATATTGATTTTAAATACATCCCATACAAGTTTATGAATAGATATAATGGTGCCATGATGGATGTGTGGGAT
GCACACTATAAAATGTTTTGGTTTGATCACCATGGCAACAGTCCTGTGGCTAATATACAGGAAGCAGAACAGGCTGCT
GAATTTAAGAAACGGTGGACACAGTTTGTTAATGTTACATTTCATATGGAATCCACAATCACAAGAATTGCTTATGTA
TTTTATGGGCCATATGTCAATGTTTCCAGCTGCAGATTTATTGATAGTTCCAGTTCTGGACTTCAGATTTCTTTACAT
GTCAACAGTACTGAACATAGTGTGTCTGTTGTAACTGACTATCAAAACCTTAAAAGCAGATTCAGTTACCTGGGATTT
GGTGGTTTTGCCAGTGTGGCTAATCAAGGACAGATAACCAGATTTGGTTTGGGTACTCAAGAAATAGTAAACCCTGTA
AGACATGATAAAGTTAATTTCCCCTTTGGGTTTAAATTTAATATAGCAGTTGGATTCATTTTGTGTATTAGTTTGGTT
ATTTTAACTTTTCAATGGCGGTTTTACCTTTCCTTTAGAAAGCTAATGCGCTGTGTATTAATACTTGTTATTGCCTTG
TGGTTTATTGAGCTTCTGGATGTATGGAGTACATGCACTCAGCCCATCTGTGCAAAATGGACAAGGACTGAAGCTAAG
GCAAATGAGAAGGTCATGATTTCTGAAGGGCATCATGTGGATCTTCCTAATGTTATTATTACCTCACTCCCTGGTTCA
GGAGCTGAAATTCTCAAACAGCTTTTTTTCAACAGCAGTGATTTTCTCTACATCAGAATTCCTACAGCCTACATGGAT
ATCCCTGAAACTGAATTTGAAATTGACTCATTTGTAGATGCTTGTGAGTGGAAAGTATCAGATATCCGCAGTGGGCAC
TTTCATCTTCTTCGAGGGTGGCTGCAGTCTTTGGTCCAGGATACAAAACTTCACTTGCAAAACATCCATCTACATGAA
ACCAGTAGGAGTAAACTGGCCCAATATTTTACAACTAATAAGGACAAAAAGCGAAAATTAAAAAGAAGGGAGTCTTTG
CAAGATCAAAGAAGTAGAATAAAAGGACCATTTGATAGAGATGCTGAATATATTAGGGCTTTAAGAAGACACCTTGTT
TATTACCCAAGTGCACGTCCTGTGCTCAGCTTAAGTAGTGGTAGCTGGACATTGAAGCTTCATTTTTTTCAGGAAGTT
TTAGGAACTTCAATGCGGGCATTGTACATAGTAAGAGACCCTCGAGCTTGGATCTATTCAGTGCTATATGGTAGTAAA
CCAAGTCTTTATTCTTTGAAGAATGTACCAGAGCACTTAGCAAAATTGTTTAAAATAGAGGAAGGTAAAAGCAAATGT
AATTCGAATTCTGGCTATGCTTTTGAGTATGAATCACTGAAGAAAGAATTAGAAATATCCCAATCAAATGCTATCTCC
TTATTATCTCATTTGTGGGTAGCAAACACTGCAGCAGCCTTGAGAATAAATACAGATTTGCTGCCTACCAATTACCAT
CTGGTCAAGTTTGAAGATATTGTTCATTTTCCTCAGAAGACTACTGAAAGGATTTTTGCTTTCCTTGGCATTCCTTTG
TCTCCTGCTAGTTTAAACCAAATGCTATTTGCCACTTCCACAAACCTTTTTTATCTTCCATATGAGGGGGAAATATCA
CCATCTAATACTAATATTTGGAAAACAAACTTGCCTAGAGATGAAATTAAACTAATTGAAAACATTTGCTGGACACTG
ATGGATCATCTAGGATATCCAAAGTTTATGGACTAAatgctgcaggtcggcaaaatttgcactaatgtgtcccaacct
actttgtggatatgaactagaaaactttgtttattcttgtacatgtatgtatgtgtgtagagtgagtgcgtgtgtcca
gtatgttatttgcacagagatattttcaaaataggcaccatatttggcctagcaggatttattttatgttaccactt
ttcttgcctttgtttctgaatttttttctgctaaaatgtttctgctacagaggtatatattctggggttctgaaatat
ggggtttaatggactttaactcaacttctttggaaactatttatctatcttaggacctcaaacactacaaacggcct
tgcaattgctgctgtatctagtcatctctcgctcttaatatggactacaaactttatgttttgaaaacgtctaacat
ttaccttgcacacaaaaacgagaaataaaaaaccaaaaattaaaaaaaaaaaaaaaaaaaaaa FIG. 6B
(mouse GST-6, translation of ORF)
MAFMFTEHLLFLTLMMCSFSTCEESVSNYSEWAVFTDDIQWLKSQKIQDFKLNRRLHPN
LYFDAGDIQTLKQKSRTSHLHIFRAIKSAVTIMLSNPSYYLPPPKHAEFAAKWNEIYGNN
LPPLALYCLLCPEDKVAFEFVMEYMDRMVSYKDWLVENAPGDEVPVGHSLTGFATAF
DFLYNLLGNQRKQKYLEKIWIVTEEMYEYSKIRSWGKQLLHNHQATNMIALLIGALVT
GVDKGSKANIWKQVVVDVMEKTMFLLKHIVDGSLDEGVAYGSYTSKSVTQYVFLAQR
HFNINNFDNNWLKMHFWFYYATLLPGYQRTVGIADSNYNWFYGPESQLVFLDKFILQN
GAGNWLAQQIRKHRPKDGPMVPSTAQRWSTLHTEYIWYDPTLTPQPPVDFGTAKMHTF
PNWGVVTYGGGLPNTQTNTFVSFKSGKLGGRAVYDIVHFQPYSWIDGWRSFNPGHEHP
DQNSFTFAPNGQVFVSEALYGPKLSHLNNVLVFAPSPSSQCNQPWEGQLGECAQWLKW
TGEEVGDAAGEVITAAQHGDRMFVSGEAVSAYSSAMRLKSVYRALLLLNSQTLLVVDH
IERQETSPINSVSAFFHNLDIDFKYIPYKFMNRYNGAMMDVWDAHYKMFWFDHHGNSP
VANIQEAEQAAEFKKRWTQFVNVTFHMESTITRIAYVFYGPYVNVSSCRFIDSSSSGLQIS
LHVNSTEHSVSVVTDYQNLKSRFSYLGFGGFASVANQGQITRFGLGTQEIVNPVRHDKV
NFPFGFKFNIAVGFILCISLVILTFQWRFYLSFRKLMRCVLILVIALWFIELLDVWSTCTQPI
CAKWTRTEAKANEKVMISEGHHVDLPNVIITSLPGSGAEILKQLFFNSSDFLYIRIPTAYM
DIPETEFEIDSFVDACEWKVSDIRSGHFHLLRGWLQSLVQDTKLHLQNIHLHETSRSKLA
QYFTTNKDKKRKLKRRESLQDQRSRIKGPFDRDAEYIRALRRHLVYYPSARPVLSLSSGS
WTLKLHFFQEVLGTSMRALYIVRDPRAWIYSVLYGSKPSLYSLKNVPEHLAKLFKIEEG
KSKCNSNSGYAFEYESLKKELEISQSNAISLLSHLWVANTAAALRINTDLLPTNYHLVKF
EDIVHFPQKTTERIFAFLGIPLSPASLNQMLFATSTNLFYLPYEGEISPSNTNIWKTNLPRD
EIKLIENICWTLMDHLGYPKFMD

GLYCOSYL SULFOTRANSFERASES GST-4α, GST-4β, AND GST-6

CROSS REFERENCE TO RELATED APPLICATIONS

This application claims the benefit of U.S. Provisional Patent Application No. 60/144,694, filed Jul. 20, 1999, which application is incorporated by reference herein in its entirety.

ACKNOWLEDGEMENT OF GOVERNMENT SUPPORT

This invention was made with Government Support under Grant No. GM57411, awarded by the National Institutes of Health. The Government has certain rights in this invention.

INTRODUCTION

1. Field of the Invention

The field of the invention is cell adhesion, particularly selectin mediated cell adhesion, as well as the treatment of disease conditions related thereto.

2. Background of the Invention

Sulfotransferases are enzymes that catalyze the transfer of a sulfate from a donor compound to an acceptor compound, usually placing the sulfate moiety at a specific location on the acceptor compound. There are a variety of different sulfotransferases which vary in activity, i.e. with respect to the donor and/or acceptor compounds with which they work. Known sulfotransferases include those acting on carbohydrate: heparin/heparan sulfate N-sulfotransferase (NST); chondroitin 6/keratan 6 sulfate sulfotransferase (C6ST/KSST); galactosylceramide 3'-sulfotransferase; heparan sulfate 2-sulfotransferase (Iduronic acid); HNK-1 sulfotransferase (3-glucuronic acid); heparan sulfate D-glucosamino 3-O-sulfotransferase (3-OST); etc., as well as those acting on phenols, steroids and xenobiotics: aryl sulfotransferase I & II, hydroxy-steroid sulfotransferases I, II & III, dehydroepiandrosterone (DHEA); etc. Sulfotransferases play a central role in a variety of different biochemical mechanisms, as the presence of a sulfate moiety on a particular ligand is often required for a particular activity, e.g. binding.

The presence of a sulfate moiety on selectin ligands has been shown to be important for selectin binding to occur. See Imai et al., Nature (1993) 361:555–557 and Imai et al., Glycoconjugate J. (1993) 10:34–39, as well as U.S. Pat. No. 5,695,752. Several selectin ligands have, to date, been identified. The L-selectin endothelial ligands in mouse that have been identified are: CD34, GlyCAM-1, MAdCAM-1 and sgp200. In addition, PSGL-1 has been identified as a leukocyte ligand for P-, E-, and L-selectin. Endothelial ligands for L-selectin in humans are still poorly defined, but include CD34 and podocalyxin.

Selectin mediated binding plays an important and prominent role in a variety of biological processes. Selectins are lectin like cell adhesion molecules that mediate leukocyte-endothelial, leukocyte-leukocyte, leukocyte-platelet, platelet-endothelial and platelet-platelet interactions. One critical biological process in which selectin mediated binding plays a role is the maintenance of immune surveillance.

Maintenance of immune surveillance depends on the constant recirculation of lymphocytes from the blood through the vascular wall into the tissues and eventually back into the blood. Lymphocyte recruitment from the blood into all secondary lymphoid organs (except the spleen) as well as into many sites of chronic inflammation is mediated by a specialized postcapillary venule called a high endothelial venule. These vessels are defined by the distinct, cuboidal morphology of their endothelial cells and their luminal presentation of ligands for the leukocyte adhesion molecule, L-selectin. This lectin-like adhesion molecule is expressed on all classes of leukocytes in the blood and is responsible for the initial tethering and rolling of a leukocyte on the endothelium prior to subsequent integrin mediated firm arrest and transmigration.

Although selectin mediated binding events play a critical role in normal physiological processes, disease conditions do exist for which it is desired to regulate or modulate, e.g. limit or prevent, the amount of selectin mediated binding that occurs. Such conditions include: acute or chronic inflammation; autoimmune and related disorders, tissue rejection during transplantation, and the like.

As the above conditions all result from selectin mediated binding events, there is great interest in the elucidation of the mechanisms underlying such binding events. There is also great interest in the identification of treatment methodologies for these and related disease conditions, as well the identification of active agents for use therein.

As such, there is continued interest in the identification of participants in the selectin binding mechanism, including enzymatic agents, and the elucidation of their role(s) in selectin mediated binding events, as well as the development of therapies for disease conditions arising from such binding events.

Relevant Literature

Chondroitin-6-sulfotransferase is disclosed in EP 821 066, as well as in Fukuta et al., "Molecular Cloning and Characterization of Human Keratan Sulfate Gal-6-Sulfotransferase," J. Biol. Chem. (Dec. 19, 1997) 272: 32321–32328; Habuchi et al., "Enzymatic Sulfation of Galactose Residue of Keratan Sulfate by Chondroitin 6-Sulfotransferase," Glycobiology (January 1996) 6:51–57; Habuchi et al., "Enzymatic Sulfation of Galactose Residue of Keratan Sulfate by Chondroitin 6-Sulfate by Chondroitin 6-Sulfotransferase," Glycobiology (January 1996) 6:51–57; Fukuta et al., "Molecular Cloning and Expression of Chick Chondrocyte Chondroitin 6-Sulfotransferase," J. Biol. Chem. (1995) 270: 18575–18580; and Habuchi et al., "Purification of Chondroitin 6-Sulfotransferase Secreted from Cultured Chick Embryo Chondrocytes," J. Biol. Chem. (1993) 268: 21968–21974.

References providing background information on selectin mediated binding include: Baumhueter et al., "Binding of L-Selectin to the Vascular Sialomucin CD34," Science (Oct. 15, 1993): 436–438; Boukerche et al., "A Monoclonal Antibody Directed Against a Granule Membrane Glycoprotein (GMP-140/PADGEM, P-selectin, CD62P) Inhibits Ristocetin-Induced Platelet Aggregation," Br. J. Haematology (1996) 92: 442–451; Celi et al., "Platelet-Leukocyte-Endothelial Cell Interaction on the Blood Vessel Wall," Seminars in Hematology (1997) 34: 327–335; Frenette et al., "Platelets Roll on Stimulated Endothelium In Vivo: An Interaction Mediated by Endothelial P-selectin," Proc. Natl. Acad. Sci. USA (August 1995) 52:7450–7454; Girard & Springer, "High Endothelial Venules (HEVs): Specialized Endothelium for Lymphocyte Migration," Immun. Today (1995) 16: 449–457; Hemmerich et al., "Sulfation Dependent Recognition of High Endothelial Venules (HEV)-Ligands by L-Selectin and Meca79, and Adhesion-Blocking Monoclonal Antibody," J. Exp. Medicine (December 1994) 180: 2219–2226; 262 Lasky et al., "An Endothelial Ligand for L-Selectin Is a Novel Mucin-Like Molecule," Cell (Jun. 12, 1992) 69:927–938; Rosen & Bertozzi, "The Selectins and Their Ligands," Current Opinion in Cell Biology (1994) δ: 663–673; and Sawada et al., "Specific Expression of a Complex Sialyl Lewis X Antigen On High Endothelial Venules of Human Lymph Nodes: Possible Candidate for L-selectin Ligand," Biochem. Biophys. Res. Comm. (May 28, 1993) 193: 337–347; as well as U.S. Pat. No. 5,580,862.

U.S. Pat. No. 5,695,752 describes methods of treating inflammation through administration of sulfation inhibitors.

SUMMARY OF THE INVENTION

Novel glycosyl sulfotransferases (GST-4 & GST-6) and polypeptides related thereto, as well as nucleic acid compositions encoding the same, are provided. The subject polypeptide and nucleic acid compositions find use in a variety of applications, including diagnostic applications, and therapeutic agent screening applications, as well as in treatment of a variety of disease conditions. Also provided are methods of inhibiting selectin mediated binding events and methods of treating disease conditions associated therewith, particularly by administering inhibitors of the novel sulfotransferases.

BRIEF DESCRIPTION OF THE FIGURES

FIG. 1 provides the cDNA sequence and amino acid sequence of human GST-4α. The full length cDNA sequence is SEQ ID NO:03, the coding DNA sequence is SEQ ID NO:04 and the amino acid sequence of the protein encoded by the open reading frame is SEQ ID NO:08.

FIG. 2 provides the cDNA sequence and amino acid sequence of mouse GST-4. The full length cDNA sequence is SEQ ID NO:01, the coding DNA sequence is SEQ ID NO:02 and the amino acid sequence of the protein encoded by the open reading frame is SEQ ID NO:07.

FIG. 3 provides the cDNA sequence and amino acid sequence of human GST-6 polypeptide fragment. The full length cDNA sequence is SEQ ID NO:05, the coding DNA sequence is SEQ ID NO:06 and the amino acid sequence of the protein encoded by the open reading frame is SEQ ID NO:09.

FIGS. 4A and 4B provide the cDNA sequence and amino acid sequence, respectively, of human GST-4β. The full-length cDNA sequence is SEQ ID NO: 12, the coding sequence is SEQ ID NO:21, and the amino acid sequence of the protein encoded by the open reading frame is SEQ ID NO: 13.

FIGS. 5A and 5B provide the cDNA sequence and amino acid sequence, respectively, of human GST-6. The full-length cDNA sequence is SEQ ID NO: 18, the coding sequence is SEQ ID NO:22, and the amino acid sequence of the protein encoded by the open reading frame is SEQ ID NO: 15.

FIGS. 6A and 6B provide the cDNA sequence and amino acid sequence, respectively, of mouse GST-6. The full-length cDNA sequence is SEQ ID NO:19, the coding sequence is SEQ ID NO:23, and the amino acid sequence of the protein encoded by the open reading frame is SEQ ID NO:17.

DETAILED DESCRIPTION OF THE INVENTION

Figure 7:
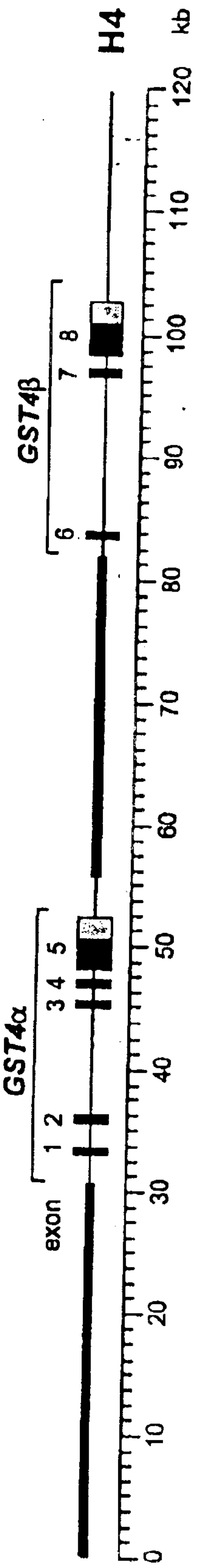
FIG. 7 is a schematic representation of the genomic structure of human GST-4α and GST-4β. Exons are indicated by rectangles, with exon numbers provided above each rectangle. Exons 1–5 encode GST-4α and are exons 6–8 encode GST-4β. Non-numbered shaded rectangles indicate non-coding regions containing regulatory elements.

Novel glycosyl sulfotransferases (i.e. GST-4α, GST-4β, and GST-6) and polypeptides related thereto, as well as nucleic acid compositions encoding the same, are provided. The subject polypeptide and/or nucleic acid compositions find use in a variety of different applications, including various diagnostic and therapeutic agent screening/discovery/preparation applications. Also provided are methods of inhibiting selectin mediated binding events and methods of treating disease conditions associated therewith, particularly by administering an inhibitor of the novel sulfotransferases.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a, an," and "the" include plural reference unless the context clearly dictates otherwise. Unless defined otherwise, all technical and scientific terms used herein have the same meaning as commonly understood to one of ordinary skill in the art to which this invention belongs.

Polypeptide Compositions

Novel glycosylsulfotransferases (i.e. GST-4α, GST-4β, and GST-6), as well as polypeptide compositions related thereto, are provided. The term polypeptide composition as used herein refers to both the full-length human protein as well as portions or fragments thereof. Also included in this term are variations of the naturally occurring human protein, where such variations are homologous or substantially similar to the naturally occurring protein, as described in greater detail below, as well as corresponding homologs from non-human species, such as other mammalian species. In the following description of the subject invention, the terms GST-4α, GST-4β, and GST-6 are used to refer not only to the human form of these novel sulfotransferases, but also to homologs thereof expressed in non-human species.

The novel glycosyl sulfotransferases of the subject invention are type 2 membrane proteins having a relatively short transmembrane domain and amino-terminal cytoplasmic tail of varying length. The subject glycosylsulfotransferases are capable of sulfating selectin ligands, particularly L-selectin ligands, e.g. GlyCAM-1. By sulfating selectin ligands is meant that the subject sulfotransferases are capable of catalyzing the transfer of a sulfate group from a donor compound to a position on a selectin ligand precursor as acceptor compound. Donor compounds from which the subject sulfotransferases obtain sulfate groups for transfer to acceptor ligand compounds include 3'-phosphoadenosine 5'-phosphosulfate (PAPS) and the like. Selectin ligands capable of being sulfated through the activity of the subject sulfotransferases include E-, P- and L-selectin ligands, particularly L-selectin ligands, such as GlyCAM-1, CD34, MAdCAM-1, Sgp200, podocalyxin, and the like. The subject human GST-4α and GST-4β sulfotransferases, and the subject mouse GST-4 sulfotransferase, have N-acetyl glucosamine-6-O-sulfotransferase activity.

Human GST-4α is a 390 amino acid protein having an amino acid sequence as shown in FIG. 1 and identified as SEQ ID NO:08. huGST-4α has a molecular weight based on its amino acid of about 40 to 50 kDa, more particularly 45 to 46 kDa. Since huGST-4α is glycosylated, its true molecular weight is greater, and is likely to be in the range from about 45 to 85 kDa, and more likely from about 50 kDa to 65 kDa. huGST-4α is expressed in human colon, small intestine, a variety of cancer tissues and perhaps HEC.

Mouse GST-4 is a 395 amino acid protein having an amino acid sequence as shown in FIG. 2 and identified as SEQ ID NO:07. Mouse GST-4 has a molecular weight based on its amino acid of about 40 to 50 kDa. Since mouse GST-4 is glycosylated, its true molecular weight is greater, and is likely to be in the range from about 45 to 85 kDa, and more likely from about 50 kDa to 65 kDa.

Human GST-6 polypeptide fragment is a 596 amino acid protein having an amino acid sequence as shown in FIG. 3 and identified as SEQ ID NO:09. This huGST-6 polypeptide fragment has a molecular weight based on its amino acid of about 59 kDa to 72 kDa. Since GST-6 is glycosylated, the true molecular weight of huGST-6 polypeptide fragment is greater, and is likely to be in the range from about 59 to 95 kDa, and more likely from about 60 kDa to 85 kDa.

Human GST-40 is a 395-amino acid protein having an amino acid sequence as shown in FIG. 4, and identified as SEQ ID NO: 13. HuGST-4 is 85.6% identical at the amino acid level to huGST-4α, as determined using the GAP program (see below) using default parameters. The molecular weight of huGST-4β, based on amino acid sequence, is about 45 kDa to about 55 kDa; a glycosylated molecular weight for huGST-4βis about 45 kDa to about 90 kDa.

Human GST-6 is a 1222-amino acid protein having an amino acid sequence as shown in FIG. 5 and identified as SEQ ID NO: 15. The predicted molecular weight of human GST-6, based on amino acid sequence, is from about 125 kDa to about 150 kDa; the glycosylated molecular weight is expected to be in a range of from about 125 kDa to about 200 kDa. HuGST-6 extends the sequence of human GST-6 polypeptide fragment (SEQ ID NO:9) by 626 amino acids at the N-terminus.

Mouse GST-6 is a 1207-amino acid protein having an amino acid sequence shown in FIG. 6, and identified as SEQ ID NO:17. The predicted molecular weight of mouse GST-6, based on amino acid sequence, is from about 125 kDa to about 150 kDa; the glycosylated molecular weight is expected to be in a range of from about 125 kDa to about 200 kDa.

In addition to the above specifically listed proteins, glycosyl sulfotransferases from other species are also provided, including mammals, such as: rodents, e.g. mice, rats; domestic animals, e.g. horse, cow, dog, cat; and humans, as well as non-mammalian species, e.g. avian, and the like. By homolog is meant a protein having at least about 35%, usually at least about 40% and more usually at least about 60% amino acid sequence identity to the one of the above specifically listed sulfotransferases, as measured by using the "GAP" program (part of the Wisconsin Sequence Analysis Package available through the Genetics Computer Group, Inc. (Madison Wis.)), where the parameters are: Gap weight:12; length weight:4. In many embodiments of interest, homology will be at least 75, usually at least 80 and more usually at least 85%, where in certain embodiments of interest homology will be as high as 90%. For example, of interest is mouse GST-6, which has a sequence identity with human GST-6 of at least 60%, and more particularly at least 70%.

Also provided are sulfotransferase proteins that are substantially identical to the above listed proteins, where by substantially identical is meant that the protein has an amino acid sequence identity to the sequence one of the above listed proteins of at least about 35%, usually at least about 40% and more usually at least about 60%.

The proteins of the subject invention (e.g. huGST-4α, huGST-4β, huGST-6, mouse GST-4 and the like) are present in a non-naturally occurring environment, e.g. are separated from their naturally occurring environment. In certain embodiments, the subject proteins are present in a composition that is enriched for subject protein as compared to its naturally occurring environment. For example, purified glycosylsulfotransferases are provided, where by purified is meant that the sulfotransferase is present in a composition that is substantially free of non-glycosylsulfotransferase proteins, where by substantially free is meant that less than 90%, usually less than 60% and more usually less than 50% of the composition is made up of non-sulfotransferase proteins. The proteins of the subject invention may also be present as an isolate, by which is meant that the protein is substantially free of other proteins and other naturally occurring biologic molecules, such as oligosaccharides, polynucleotides and fragments thereof, and the like, where substantially free in this instance means that less than 70%, usually less than 60% and more usually less than 50% of the composition containing the isolated protein is some other naturally occurring biological molecule. In certain embodiments, the proteins are present in substantially pure form, where by substantially pure form is meant at least 95%, usually at least 97% and more usually at least 99% pure.

In addition to the naturally occurring proteins, polypeptides which vary from the naturally occurring proteins are also provided, e.g. GST-4α, GST-4β, or GST-6 polypeptides. By GST-4α, GST-4β, or GST-6 polypeptide is meant an amino acid sequence encoded by an open reading frame (ORF) of the GST-4α, GST-4β, or GST-6 gene, described in greater detail below, including the full length GST-4α, GST-4β, or GST-6 protein and fragments thereof, particularly biologically active fragments and/or fragments corresponding to functional domains, e.g. acceptor binding site (postulated to be the most 5' consensus region A (see experimental section infra), the donor binding site, e.g. VRYEDL, and the like; and including fusions of the subject polypeptides to other proteins or parts thereof. Fusion proteins may comprise a subject polypeptide, or fragment thereof, and a non-GST polypeptide ("the fusion partner") fused in-frame at the N-terminus and/or C-terminus of the subject GST polypeptide. Fusion partners include, but are not limited to, polypeptides that can bind antibody specific to the fusion partner (e.g., epitope tags); polypeptides that provide a detectable signal (e.g., a green fluorescent protein); polypeptides that provide a catalytic function or induce a cellular response; and the like.

Fragments of the subject polypeptides, as well as polypeptides comprising such fragments, are also provided. Fragments of GST-4α and GST-4β of interest will typically be at least about 10 aa in length, usually at least about 50 aa in length, and may be as long as 300 aa in length or longer, where the fragment will have a stretch of amino acids that is identical to the subject protein of at least about 10 aa, and usually at least about 15 aa, and in many embodiments at least about 50 aa in length. Fragments of GST-6 of interest are about 10 aa, about 20 aa, about 50 aa, about 100 aa, about 250 aa, about 500 aa, or about 1000 aa, or more, but will usually not exceed about 1000 aa in length, where the fragment will have a stretch of amino acids that is identical to the subject protein of at least about 10 aa, and usually at least about 15 aa, and in many embodiments at least about 50 aa in length.

The subject proteins and polypeptides may be obtained from naturally occurring sources or synthetically produced. Where obtained from naturally occurring sources, the source chosen will generally depend on the species from which the protein is to be derived. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Nucleic Acid Compositions

Also provided are nucleic acid compositions encoding the subject novel glycosylsulfotransferases or fragments thereof. By nucleic acid composition is meant a composition comprising a sequence of DNA having an open reading frame that encodes one the subject sulfotransferases and is capable, under appropriate conditions, of being expressed as one of the subject sulfotransferases described above. Thus, the term encompasses genomic DNA, cDNA, mRNA, and vectors comprising the subject nucleic acid sequences. Also encompassed in this term are nucleic acids that are homologous or substantially similar or identical to the nucleic acids encoding the subject sulfotransferases proteins. Thus, the subject invention provides genes encoding huGST-4 and homologs thereof, mouse GST-4 and homologs thereof, huGST-6 and homologs thereof, etc.

The human GST-4α cDNA has the nucleic acid sequence shown in FIG. 1, where the full length cDNA is identified as SEQ ID NO:03 or SEQ ID NO: 10 and the open reading frame is identified as SEQ ID NO:04, infra.

The human GST-4β cDNA has the nucleic acid sequence shown in FIG. 4, the full-length cDNA is identified as SEQ ID NO:12, and the open reading frame is identified as SEQ ID NO:21. A genomic sequence which comprises both human GST-4α and human GST-4β coding sequences is identified as SEQ ID NO: 1. The mouse GST-4 cDNA has the nucleic acid sequence shown in FIG. 2, where the full length cDNA is identified as SEQ ID NO:01 and the open reading frame is identified as SEQ ID NO:02, infra.

The human GST-6 polypeptide fragment cDNA has the nucleic acid sequence shown in FIG. 3, where the full length cDNA is identified as SEQ ID NO:05 and the open reading frame is identified as SEQ ID NO:06, infra. The human GST-6 cDNA has the nucleic acid sequence shown in FIG. 5, where the full-length cDNA is identified as SEQ ID NO:18, and the open reading frame is identified as SEQ ID NO:22. A genomic sequence which comprises human GST-6 coding sequences is identified as SEQ ID NO:14 and SEQ ID NO:20. The mouse GST-6 cDNA has the nucleic acid sequence shown in FIG. 6, where the full-length cDNA is identified as SEQ ID NO: 19, and the open reading frame is identified as SEQ ID NO:23. A genomic sequence which comprises mouse GST-6 coding sequences is identified as SEQ ID NO:16.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 60% sequence identity, usually at least 75%, more usually at least 80% between nucleotide sequences. In many embodiments of interest, homology will be at least 75, usually at least 80 and more usually at least 85%, where in certain embodiments of interest homology will be as high as 90%. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings). The sequences provided herein are essential for recognizing related and homologous proteins in database searches.

Nucleic acids encoding the proteins and polypeptides of the subject invention may be cDNA or genomic DNA or a fragment thereof. The term gene shall be intended to mean the open reading frame encoding specific proteins and polypeptides of the subject invention, and introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a protein according to the subject invention.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. GST-4α and GST-4β nucleic acid molecules, encoding GST-4αand GST-4βpolypeptides or polypeptide fragments, may be from about 15 nt to about 18 nt, from about 20 nt to about 30 nt, from about 35 nt to about 50 nt, from about 50 nt to about 100 nt, from about 100 nt to about 500 nt, or from about 500 nt to about 1000 nt, up to the entire coding sequence. GST-6 nucleic acid molecules, encoding GST-6 polypeptides or polypeptide fragments, may be from about about 15 nt to about 18 nt, from about 20 nt to about 30 nt, from about 35 nt to about 50 nt, from about 50 nt to about 100 nt, from about 100 nt to about 500 nt, from about 500 nt to about 1000 nt, from about 1000 nt to about 1500 nt, from about 1500 nt to about 2000 nt, from about 2000 nt to about 2500 nt, or from about 2500 nt to about 3500 nt, up to the entire coding sequence.

GST-4α, GST-4β, and GST-6 nucleic acid molecules of the invention may comprise other, non-GST nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length.

The subject nucleic acid molecules may also be provided as part of a vector (e.g., a GST construct), a wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject genes are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", i.e. flanked by one or more nucleotides with which it is not normally associated on a naturally occurring chromosome.

Preparation of the Subject Polypeptides

In addition to the plurality of uses described in greater detail in following sections, the subject nucleic acid compositions find use in the preparation of all or a portion of the sulfotransferase polypeptides of the subject invention, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res*. (1980) 8:4057; EP 0 036,776; U.S. Pat. No. 4,551,433; DeBoer et al., *Proc. Natl. Acad. Sci.* (USA) (1983) 80:21–25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985)25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci.* (*USA*) (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

The subject proteins and polypeptides may be obtained from naturally occurring sources or synthetically produced. For example, the proteins may be derived from biological sources which express the proteins. The subject proteins may also be derived from synthetic means, e.g. by expressing a recombinant gene encoding protein of interest in a suitable host, as described in greater detail infra. Any convenient protein purification procedures may be employed, where suitable protein purification methodologies are described in Guide to Protein Purification, (Deuthser ed.) (Academic Press, 1990). For example, a lysate may prepared from the original source, (e.g. a cell expressing endogenous GST-4, GST-4, or GST-6, or a cell comprising the expression vector expressing the subject polypeptide(s)), and purified using HPLC, exclusion chromatography, gel electrophoresis, affinity chromatography, and the like.

Uses of the Subject Polypeptide and Nucleic Acid Compositions

The subject polypeptide and nucleic acid compositions find use in a variety of different applications, including research, diagnostic, and therapeutic agent screening/discovery/preparation applications, as well as therapeutic compositions.

General Applications

The subject nucleic acid compositions find use in a variety of different applications. Applications of interest include: the identification of homologs of the subject sulfotransferases; as a source of novel promoter elements; the identification of expression regulatory factors; as probes and primers in hybridization applications, e.g. PCR; the identification of expression patterns in biological specimens; the preparation of cell or animal models for function of the subject sulfotransferases; the preparation of in vitro models for function of the subject sulfotransferases; etc.

Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided nucleic acid sequences, e.g. allelic variants, genetically altered versions of the gene, etc., bind to the provided sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where the subject genes are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1: 194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to a gene in order to promote expression of wild type or proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of gene expression in the sample.

The sequence of a gene according to the subject invention, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual, CSH Press* 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of the subject proteins, or to alter properties of the protein that affect its function or regulation.

The subject nucleic acids can be used to generate transgenic, non-human animals or site specific gene modifications in cell lines. Transgenic animals may be made through homologous recombination, where the enodenous locus is altered. Alternatively, a nucleic acid construct is randomly integrated into the genome. Vectors for stable integration include plasmids, retroviruses and other animal viruses, YACs, and the like.

The modified cells or animals are useful in the study of gene function and regulation. For example, a series of small deletions and/or substitutions may be made in the host's native gene to determine the role of different exons in oncogenesis, signal transduction, etc. Of interest are the use of genes to construct transgenic animal models for cancer, where expression of the subject protein is specifically reduced or absent. Specific constructs of interest include anti-sense constructs, which will block expression, expression of dominant negative mutations, and over-expression of genes. Where a sequence is introduced, the introduced sequence may be either a complete or partial sequence of a gene native to the host, or may be a complete or partial sequence that is exogenous to the host animal, e.g., a human sequence of the subject invention. A detectable marker, such as lac Z may be introduced into the locus, where upregulation of expression will result in an easily detected change in phenotype.

One may also provide for expression of the gene, e.g. the GST-4α, GST-4β, or GST-6 gene, or variants thereof in cells or tissues where it is not normally expressed, at levels not normally present in such cells or tissues, or at abnormal times of development. One may also generate host cells (including host cells in transgenic animals) that comprise a heterologous nucleic acid molecule which encodes a polypeptide which functions to modulate expression of an endogenous the GST-4α, GST-4β, or GST-6 promoter or other transcriptional regulatory region.

DNA constructs for homologous recombination will comprise at least a portion of the human gene or of a gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on GST-4 and/or GST-6 activity.

The availability of a number of components in the leukocyte trafficking mechanism, such as GlyCAM-1, L-selectin and the subject enzymes, and the like, allows in vitro reconstruction of the mechanism, i.e. the production of an in vitro model.

Diagnostic Applications

Also provided are methods of diagnosing disease states based on observed levels of the subject sulfotransferase(s) or the expression level of the subject genes in a biological sample of interest. Samples, as used herein, include biological fluids such as blood, cerebrospinal fluid, tears, saliva, lymph, dialysis fluid, semen and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal sulfotransferase in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of the subject sulfotransferase genes. Biochemical studies may be performed to determine whether a sequence polymorphism in a coding region or control regions is associated with disease. Disease associated polymorphisms may include deletion or truncation of the gene, mutations that alter expression level, that affect the activity of the protein, etc.

Changes in the promoter or enhancer sequence that may affect expression levels of the subject genes can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express the gene may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in the gene may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity of the encoded protein may be determined by comparison with the wild-type protein.

Diagnostic methods of the subject invention in which the level of expression is of interest will typically involve comparison of the nucleic acid abundance of a sample of interest with that of a control value to determine any relative differences, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., Genome Res. (June 1996) δ: 492–503; Zhao et al., Gene (Apr. 24, 1995) 156: 207–213; Soares, Curr. Opin. Biotechnol. (October 1997) δ: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject polypeptides find use in various screening assays designed to identify therapeutic agents. Thus, one can use a cell model such as a host cell, e.g. COS7 cell, which has been cotransfected with a selectin ligand cDNA, e.g. GlyCAM-1 and a vector comprising a nucleic acid according to the present invention. One can then label the transfectants with a labeled sulfate, e.g. $^{35}$ S-labeled sulfate, and compare the amount of sulfate incorporation into GlyCAM-1 in the presence and absence of a candidate inhibitor compound. Alternatively, in a cell-free enzyme activity assay, recombinant polypeptide according to the subject invention may be combined with $^{35}$S-labeled sulfate donor such as [$^{35}$S]-PAPS, candidate inhibitor compound, and an acceptor molecule, which may be a synthetic carbohydrate mimicking structures found in mature and/or immature L-selectin ligands, or a simple nucleophile capable of accepting sulfate (such as phenolic compunds, and the like). The amount of [$^{35}$S]-sulfate transferred to the receptor by the candidate agent is then determined by counting the acceptor-associated radioactivity or product quantitation with an antibody specific for the sulfated acceptor, or in a suitable scintillation proximity assay format. Alternatively, the candidate inhibitor compound may also be combined with a selectin, a non-sulfated selectin ligand precursor, a polypeptide according to the subject invention and a sulfate donor compound under physiological conditions and the resultant amount of ligand which is capable of binding to the selectin is determined. Depending on the particular method, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4 and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound selectin-ligand complexes will then be detected.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Nucleic Acid and Polypeptide Therapeutic Compositions

The nucleic acid compositions of the subject invention also find use as therapeutic agents in situations where one wishes to enhance sulfotransferase activity in a host, particularly the activity of the subject polypeptides. The subject genes, gene fragments, or the encoded proteins or protein fragments are useful in gene therapy to treat disorders associated with defects in the genes encoding the subject sulfotransferases. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (i 992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Methods of Modulating Selectin Mediated Binding Events

Also provided are methods of regulating, including modulating and inhibiting, selectin mediated binding events. The selectin receptor of the selectin mediated binding event will generally be a receptor which binds to a sulfated ligand under physiological conditions and is a member of the selectin family of receptors that have an amino terminal C-type lectin domain followed by an EFG-like domain, a variable number of short consensus repeats known as SCR, CRP or sushi domains, and share greater than 50% homology in their lectin and EFG domains. Of interest is the modulation of selectin binding events in which the selectin is L-, P-, or E-selectin. Of particular interest are L-selecting mediated binding events.

Where the selectin mediated binding event occurs in vivo in a host, in one embodiment an effective amount of active agent that modulates the activity, usually reduces the activity, of the target sulfotransferase (e.g. GST-4 and/or GST-6) in vivo, is administered to the host. The active agent may be a variety of different compounds, including a naturally occurring or synthetic small molecule compound, an antibody, fragment or derivative thereof, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agents are antibodies that at least reduce, if not inhibit, the target activity in the host. Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey etc. The host animal will generally be a different species than the immunogen, e.g. human protein used to immunize mice, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of the gene encoding the target protein in the host. For example, antisense molecules can be used to down-regulate expression of the subject genes in cells. The anti-sense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S—S'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, an effective amount of the active agent is administered to the host, where "effective amount" means a dosage sufficient to produce a desired result.

Generally, the desired result is at least a reduction in the amount of selectin binding as compared to a control.

In the subject methods, the active agent(s) may be administered to the host using any convenient means capable of resulting in the desired inhibition of selectin binding. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with 9=7 appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the therapeutic DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving selectin binding interactions, particularly L-, E- or P-selectin, and more particularly L-selectin mediated binding events. Such disease conditions include those disease conditions associated with or resulting from the homing of leukocytes to sites of inflammation, the normal homing of lymphocytes to secondary lymph organs; and the like. Accordingly, specific disease conditions that may be treated with the subject methods include: acute or chronic inflammation; autoimmune and related disorders, e.g. systemic lupus erythematosus, rheumatoid arthritis, polyarteritis nodosa, polymyositis and dermatomyositis, progressive systemic sclerosis (diffuse scleroderma), =glomerulonephritis, myasthenia gravis, Sjogren's syndrome, Hashimoto's disease and Graves' disease, adrenalitis, hypoparathyroidism, and associated diseases; pernicious anemia; diabetes; multiple sclerosis and related demyelinating diseases; uveitis pemphiguis and pemphigoid; cirrhosis and other diseases of the liver; ulcerative colitis; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.; tissue rejection during transplantation; and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

Example 1

Cloning of GST-4

In order to identify novel members of the glycosyl sulfotransferase family, we used the cDNA sequences of HEC-GlcNAc6ST and KSGal6ST to probe the NCBI dbEST and LifeSeq (Incyte Pharmaceuticals, Inc.) human EST databases for related sequences. Two non-overlapping ESTs (corresponding to LifeSeq clone no. 1846903 & 3219891) were identified from two independent human colon libraries derived from the same donor. Using the LifeSeq EST #1846903 sequence from the database as a probe, we also identified a highly related sequence in the NCBI mouse dbEST database (GenBank accession no. AA261202). The Lifeseq #1846903 and Genbank AA261202 clones were fully sequenced and found to be partial cDNA's, each with 3' poly A tails. (882 and 869 bp in length, respectively). A 182 bp cDNA fragment of LifeSeq EST #3219891 was generated from human colon cDNA by RT-PCR.

BAC libraries from human and mouse (C57BL/6) were screened with the above EST-derived probes. Both human ESTs were found to hybridize to the same single BAC clone, while the murine probe hybridized to three different BACs from the mouse library. The genomic clone within the BAC from human contained an open reading frame (ORF) of 1173 bp. No introns were detected. Using sequence from the 5' end of the 1173 bp ORF as a probe, we rescreened LifeSeq for matching ESTs and identified ESTs #3372492 & 3373406 from a human skull ependymoma library & #3126392 from a human lung adenocarcinoma library. These three EST mapped to the 5' end of the ORF identified in the human BAC, with #3372492 & 3373406 both containing the longest 5' untranslated region. Further sequencing of the clones 3372492 & 3126392 extended the sequence to an internal Not I site at position 799 of the ORF. Using sequence from center of the ORF as a probe, we rescreened the NCBI human dbEST database and identified a matching EST (Genbank accesssion number AI282873) from a human colon adenocarcinoma. By further sequencing of the matching IMAGE clone this EST was shown to extend from the internal Not I site at position 799 of the ORF to a 3'poly A tail. The complete human GST-4 cDNA sequence (Sequence ID NO. 03) was compiled from the 5' EST (Lifeseq #3372492) and the 3' EST (Genbank AI282873) joined tail to head at the internal Not I site, with the entire ORF aligning completely with the BAC-derived sequence. The complete human cDNA contains two possible start codons following the 5' stop codon at position 218. Since the human genomic sequence as well as the homologous mouse cDNA rapidly diverge from the human cDNA upstream of the second start codon, we consider the ATG at position 344 as the true start of the open reading frame encoding the novel human sulfotransferase.

Chromosomal Localization of GST-4 Gene in Human and Mouse.

The bacterial artificial chromosome (BAC) containing the human GST-4 was used to determined the chromosomal localization of the human GST4 gene (H4) using fluorescent in situ hybridization technology. The H4 locus was found to be located on human chromosome 16 band q23.1. The chromosomal localization of the GST-4 gene was also determined in the mouse (C57b1/6) by FISH using the previously described BAC containing the murine GST-4 gene (M4). The M4 locus was found to reside on mouse chromosome 8E1.

Definition and Characterization of the Human GST-4 Gene.

The human GST-4 cDNA was split into two fragments, fragment A containing all 5'-untranslated sequence (5'UTR), and fragment B containing the GST-4 open reading frame (ORF) as well as all 3' untranslated sequence (3'UTR) except the poly A tail. Fragments A and B were used to screen (BLASTn screening algorithm) the human raw genomic sequences contained in the public Genbank HTGS database (NIH) on Apr. 8, 2000. This search yielded the following bundles of genomic sequence (listed by accession numbers): AC009105 (61 unordered fragments), AC009163 (58 unordered fragments), AC0011934 (15 unordered fragments), AC025287 (42 unordered fragments), and AC026419 (17 unordered fragments). These 193 fragments were fed into the contig alignment program Sequencher. 110 of these sequences assembled into 11 contigs. The largest of these contigs was comprised of 49 fragments spanning a total sequence of 160.6 kb. The entire consensus sequence of the contig after editing and trimming low-quality regions in the individual fragments is presented in sequence 2. 88.9% of the consensus relies on at least two overlapping fragments. Base-calls in the consensus were based on majority, in case that no clear call could be obtained, the consensus base is noted as ambiguous (S=G or C; Y=C or T; W=A or T; M=A or C; R=A or G; K=G or T). Only 117 out of a total of 160552 bases in the contig were ambiguous calls, and in accordance with pertinent estimates from the public human genome sequencing project the overall accuracy of the sequence is >99% but not perfect. Closer examination of this contig revealed, that it contained bases 327 through 2134 of the human GST-4 cDNA (Genbank accession no. AF176838), which includes the ORF, 17 bp of 5'UTR, and all of 3'UTR (5U0+ORF+3U) within one exon located at position 47939 through 49746 of the contig. The residual 5'UTR of the GST4 cDNA (bases 9–326) appear to be contained within four short upstream exons: 4a_5SU1 (bases 260–326 in GST-4 cDNA) corresponds to positions 46634–46700 in the contig; 4a_5U2 (bases 168–259 in GST-4 cDNA) corresponds to positions 45094–45185 in the contig; 4a_5U3 (bases 86–167 in GST-4 cDNA) corresponds to positions 35593–35674 in the contig; and 4a_5U4 (bases 9–85 in GST-4 cDNA) corresponds to positions 32847–32922 in the contig. The 30 kb of H4 upstream of 5U4 presumably contain 5' regulatory sequences controlling the transcription of the GST4 gene in the cell (GST-4 promoter). The overall structure of the human GST4 gene (H4) is depicted in FIG. 7

A Related GST-Gene is Present in the H4 Contig Downstream of the GST4 Encoding Exon.

Further examination of the H4 contig revealed that a long open reading frame encoding a novel member of the galactose/GlcNAc/GalNAc 6-O-sulfotransferase family of enzymes (GST family) is present in H4 at positions 98474–99661. The enzyme encoded by this long (1188 bp) ORF is predicted to be a typical type two transmembrane protein of 395 amino acids with 85.6% identity and 87.4% similarity on the amino acid level. The putative gene product was therefore termed GST-4α to highlight its similarity to GST4 the latter being referred to henceforth as GST-4β. In order to address the question, whether GST-4β is being expressed in vivo, we searched the Genbank and LifeSeq EST database for matching expressed sequence tags (ESTs). We found two matching ESTs (accession number AI824100 from Genbank, and clone #6869651 from LifeSeq). Plasmids containing both sequences were retrieved and sequenced in full. AI824100 was found to contain the GST-4β ORF from its start ATG through a Not I site (GCGGCCGC) at position 795 of this ORF. In addition, this plasmid contained 188 bases of GST-4β 5'UTR. Incyte clone #6869651 contained the GST-4β ORF from the Not I site at position 795 of the ORF through the stop-codon (TAG) and additional 307 bp of 3'UTR. A GST-4β cDNA constructed from these two ESTs is presented in sequence 3. This sequence was mapped back against the contig H4. It was thus found that the GST-4β ORF along with 17 bp of 5'UTR and all of the 3'UTR were contained within a single exon located within H4 at positions 98457–99968 (commencing 50.5 kb downstream from the start of the GST-4α ORF). The GST-4β 5'UTR was again contained in at least two small exons located upstream of the GST-4β ORF but downstream of the GST-4α ORF. Thus 4b_5U1 (bases 100–171 in GST-4β cDNA, sequence 3) corresponds to bases 96413–96484 in the contig. And 4b_5U1 (bases 9–99 in GST-4β cDNA) corresponds to bases 83257–83347 in the contig. 5' regulatory sequences controlling the transcription of GST-4β gene in the cell (GST-4 promoter) may be located somewhere upstream of 4b_5U2 but downstream of the GST-4α ORF and/or transcription of GST-4α and -β may be controlled by common regulatory sequences. Thus, as shown schematically in FIG. 7, the H4 gene is actually a tandem repeat of two highly similar GST genes GST4α and GST4β. The enzyme encoded by GST4α has been shown experimentally to catalyze 6-O-sulfation at GlcNAc in mucin-type acceptor glycoproteins (GlyCAM-1). GST-4β is 85.6% identical to GST-4α on the amino acid level.

Example 2

Cloning of GST-6

Screening of EST databases with the cDNA sequences of HEC-GlcNAc6ST and KSGal6ST yielded an additional unique contig at relatively low homology. A probe generated from a public EST (Genbank accession number AA421254) mapping to this contig was then used for hybridization screening of a human BAC library. One single BAC was found to hybridize to the probe. The genomic clone within this BAC from human contained an open reading frame (ORF) of 1791 bp. No introns were detected.

Full Length Open Reading Frames Encoding Human and Mouse GST-6.

The sequences for human and murine (C57B1/6) GST-6 described above were found to represent incomplete open reading frames. Complete open reading frames have were obtained by further 5'-sequencing of the pertinent BAC's (described above) as well as comparison with data generated by the human genome sequencing project (genomic clone Genbank htgs accession no. AC022662). SEQ ID NO: 18 provides the 3669 bp human GST-6 ORF and predicts a 1222 aa protein with a C-terminal sulfotransferase domain (SEQ ID NO: 15). The putative start ATG is preceded by an in-frame stop codon 18 bp upstream. The first ~770 N-terminal amino acids (GST6-NT) constitute a domain that is highly homologous (48.7% identity and 56.6% similarity) to a human squamous cell carcinoma antigen that is recognized by the HLA-A24-restricted cytotoxic T-lymphocytes (SART-2, Genbank accession no. AF098066). This is followed by a tandem repeat of a string (~25 aa) of highly hydrophobic residues that may represent one or two transmembrane domains (TM). The following C-terminal domain of ~400 residues (GST6-ST) exhibits significant though not high homology to the sulfotransferases of the GST-family. Thus the sulfotransferase domain of GST-6 (residues 851–1223) is 32.4% similar and 21.4% identical to the sulfotransferase domain in GST-3 (residues 41–386). The 1207 aa mouse protein (msGST-6, sequence 11) encoded by the 3624 bp mouse GST6 ORF (sequence 10) exhibits a very similar protein sequence (92.5% similarity and 89.8% identity to human GST-6) and domain structure. Both human and mouse GST6 are being expressed in vivo as evidenced by a number of matching expressed sequence tags (ESTs) in the appropriate databases. Two 3'-polyadenylated EST clones mapping to human GST-6 (Lifeseq EST #0182182) or mouse GST-6 (Genbank accession no. AI528511) were retrieved and sequenced in full length. These were found to contain 3'fragments of the human or mouse GST-6 ORF followed by a relatively short 3'UTR ending in a stretch of adenosine nucleotides (poly A).

Genomic organization of the human GST-6 gene. Genomic sequences containing the human GST6 gene were identified through an approach analogous to the one described above. The search, on Apr. 8, 2000, for sequences with significant similarity score to GST-3 (p<10–50) yielded a bundle of 23 unordered genomic sequences from the human genome sequencing project deposited in Genbank's HTGS database under the accession number AC022662. The ORF and 3'UTR of human GST-6 cDNA mapped to the same exon (positions 12899–16648 of reverse complement) contained in fragment AC010547-23 (total length: 27.15b kb).

It is apparent from the above results and discussion that novel glycosyl sulfotransferases, as well as polypeptides related thereto and nucleic acid compositions encoding the same, are provided by the subject invention. These polypeptide and nucleic acid compositions find use in a variety of diverse applications, including research, diagnostic, screening and therapeutic applications. Also provided are improved methods of treating diseases associated with selectin-sulfated ligand mediated binding events, since agents that selectively reduce or inhibit the activity of the subject enzyme are employed, so that other sulfotransferases whose activity is beneficial are not adversely affected.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid present in other than its natural environment, wherein said nucleic acid comprises a nucleotide sequence encoding a polypeptide, wherein said polypeptide comprises an amino acid sequence that is at least 85% identical to the amino acid sequence set forth in SEQ ID NO:08, and wherein said polypeptide has sulfotransferase activity.

2. A fragment of the nucleic acid according to claim 1, wherein said fragment encodes a polypeptide that has sulfotransferase activity.

3. The nucleic acid of claim 1, wherein the polypeptide catalyzes the transfer of a sulfate group from a donor to a selectin ligand.

4. The nucleic acid of claim 3, wherein the selectin ligand is an L-selectin ligand.

5. The nucleic acid of claim 4, wherein the L-selectin ligand is selected from GlyCAM-1, CD34, MAdCAM-1, Sgp200, and podocalyxin.

6. The nucleic acid of claim 1, wherein the polypeptide comprises an amino acid sequence that is at least 90% identical to the amino acid sequence set forth in SEQ ID NO:08.

7. The nucleic acid of claim 1, wherein the polypeptide comprises the amino acid sequence set forth in SEQ ID NO:08.

8. The nucleic acid of claim 1, wherein said nucleic acid comprises a nucleic acid sequence that is at least 85% identical to the nucleotide sequence of SEQ ID NOs: 03 or 04.

9. The nucleic acid of claim 1, wherein said nucleic acid comprises a nucleic acid sequence that is at least 90% identical to the nucleotide sequence of SEQ ID NOs: 03 or 04.

10. The nucleic acid of claim 1, wherein said nucleic acid comprises a nucleic acid having the nucleotide sequence set forth in any one of SEQ ID NOs: 03 and 04.

11. A nucleic acid present in other than its natural environment, wherein said nucleic acid comprises a nucleotide sequence encoding a fragment of a polypeptide that comprises an amino acid sequence that is at least 85% identical to the amino acid sequence set forth in SEQ ID NO:08, wherein said fragment comprises a functional domain selected from a donor binding site and an acceptor binding site, wherein said functional domain is at least 10 amino acids in length.

12. A composition comprising the nucleic acid of any one of claims 1, 2, 6, 11, and 9.

13. A nucleic acid according to claim 11, wherein said polypeptide comprises an amino acid sequence that is at least 90% identical to the amino acid sequence set forth in SEQ ID NO:08.

14. The nucleic acid of claim 11, wherein the polypeptide comprises the amino acid sequence set forth in SEQ ID NO:08.

15. The nucleic acid of claim 11, wherein said nucleic acid comprises a nucleic acid sequence that is at least 85% identical to the nucleotide sequence of SEQ ID NOs: 03 or 04.

16. The nucleic acid of claim 11, wherein said nucleic acid comprises a nucleic acid sequence that is at least 90% identical to the nucleotide sequence of SEQ ID NOs: 03 or 04.

17. The nucleic acid of claim 11, wherein said nucleic acid comprises a nucleic acid having the nucleotide sequence set forth in any one of SEQ ID NOs: 03 and 04.

18. The nucleic acid of claim 11, wherein said fragment comprises a donor binding site.

19. The nucleic acid of claim 11, wherein said fragment comprises an acceptor binding site.

20. The nucleic acid of claim 11, wherein said functional domain is at least 50 amino acids in length.

21. The nucleic acid of claim 2, wherein the polypeptide catalyzes the transfer of a sulfate group from a donor to a selectin ligand.

22. The nucleic acid of claim 21, wherein the selectin ligand is an L-selectin ligand.

23. The nucleic acid of claim 22, wherein the L-selectin ligand is selected from GlyCAM-1, CD34, MAdCAM-1, Sgp200, and podocalyxin.

24. An expression cassette comprising a transcriptional initiation region functional in an expression host a nucleic acid comprising a nucleotide sequence according to claim 1, claim 8, claim 11, or claim 2 under the transcriptional regulation of said transcriptional initiation region, and a transcriptional termination region functional in said expression host.

25. A cell comprising an expression cassette according to claim 24 as part of an extrachromosomal element or integrated into the genome of a host cell as a result of introduction of said expression cassette into said host cell.

26. The cellular progeny of the host cell according to claim 25.

27. A method of producing a glycosyl sulfotransferase polypeptide, said method comprising:

growing a cell according to claim 25, whereby said glycosyl sulfotransferase polypeptide is expressed; and isolating said glycosyl sulfotransferase polypeptide substantially free of other proteins.

* * * * *

SEQUENCE LISTING

```
<160> NUMBER OF SEQ ID NOS:  23

<210> SEQ ID NO 1
<211> LENGTH: 1989
<212> TYPE: DNA
<213> ORGANISM: mus musculus

<400> SEQUENCE: 1

ctcgagcact gttggcctac tggaccaccg actgagcggc tctttgtgtg cgccctgggt     60

gcgcagcgca gaagcgcagc gggcagcgca ggccctagcc agaggtatgc ggctaccccg    120

tttctccagc actgtcatgc tttcgctcct gatggtacag actggcatcc tggtcttcct    180

ggtctcccgg caagtgccat cgtccccagc aggccttggg gagcgtgtgc acgtgctggt    240

actgtcctcg tggcgctcgg gctcgtcctt cgtgggccag ctcttcagcc aacaccccga    300

tgtcttctac ctgatggagc cggcttggca cgtctgggat acgttgtcgc agggcagtgc    360

cccgcactc cacatggccg tgcgtgacct gatccgctca gtgttcctat gcgacatgga     420

cgtatttgat gcctacctgc cctggcgccg caacatctcg gatctcttcc agtgggcggt    480

gagccgcgca ttgtgctcac ctccggtctg cgaagccttc gctcgtggca acatcagcag    540

cgaggaggtg tgtaagcctc tgtgcgcaac gcggcccttc ggcctggctc aggaagcctg    600

cagctcctat agtcacgtcg tgctcaagga ggtgcgcttc tttaacctac aggtgctcta    660

cccgctgctc agcgaccctg cgctcaacct gcgcatcgtg cacctagtgc gcgacccgcg    720

ggccgtgctg cgctcccgag agcagacagc caaggcgctg gcacgggaca atggcatcgt    780

cctgggtacc aacggcacgt gggtggaggc ggacccccgg ctgcgcgtgg tcaacgaggt    840

atgccgcagc catgtgcgca tcgcagaggc agccttgcac aagccgccgc ccttcttgca    900

agatcgctac cgcctggtgc gctacgagga tctggcccgg gacccactca ccgtaatccg    960

tgaactctat gccttcaccg gcctgggtct cacgccgcag ctccagactt ggatccacaa   1020

tatcacgcat ggttcagggc caggcgcgcg ccgtgaagcc ttcaagacca catccaggga   1080

tgcgctcagt gtatcccagg cctggcgcca cacgctgccc tttgccaaga ttcgccgggt   1140

ccaggaactg tgcgggggtg cactgcagct gctgggttac cggtctgtgc attcggagct   1200

tgagcaaagg gacctctctc tggacctcct gctgccaaga ggcatggaca gtttcaagtg   1260

ggcatcgtcc acggagaagc aaccggaatc ttagaatttt agtggagaga cccagctata   1320

acattagggt ctattggagt atgataaaga aggggcttgg agaacccaaa agcaagtagc   1380

tgggagtgtg agtgatcttg tcctgtacta ggaaaggatg gagtccaaat cccacatctc   1440

tttctgtcca gattgtagtt ttcggttggg tcttttaggg tttggattcc caccaagtac   1500

tatcgaatgg aaagcaaaag ctgtgcccac ttccttcaga gaggcagcca gcctcctact   1560

aaagcacttc ctttctcgtt gactctctcc cctctttgat cataccatgc aatcgcagag   1620

aatggggtcc caggcctgct ctggagtgcg ggaaaggcgc ggctgtgggc tggctcctaa   1680
```

-continued

```
aatctgtgca cctgcctctc gttggctcac ccagacctct gctcactgcc acgccctagt   1740

atctcagtcc atcatagact tggacagtta tgggcctggt caaggaggaa aatgagacga   1800

tgcttccctc tgtgattctc tgcctgacct tctagaaggg aatccaggca cacacacaac   1860

catacctgag gaggatggct ttttaatgaa tctttgattt gtcctaaaat gaaagatcct   1920

aatttatgga aataaacata aatatgctgc gtgatcccaa aaaaaaaaaa aaaaaaaaaa   1980

aaaaaaaaa                                                           1989


<210> SEQ ID NO 2
<211> LENGTH: 1188
<212> TYPE: DNA
<213> ORGANISM: mus musculus

<400> SEQUENCE: 2

atgcggctac cccgtttctc cagcactgtc atgctttcgc tcctgatggt acagactggc     60

atcctggtct tcctggtctc ccggcaagtg ccatcgtccc cagcaggcct tggggagcgt    120

gtgcacgtgc tggtactgtc ctcgtggcgc tcgggctcgt ccttcgtggg ccagctcttc    180

agccaacacc ccgatgtctt ctacctgatg gagccggctt ggcacgtctg ggatacgttg    240

tcgcagggca gtgcccccgc actccacatg gccgtgcgtg acctgatccg ctcagtgttc    300

ctatgcgaca tggacgtatt tgatgcctac ctgccctggc gccgcaacat ctcggatctc    360

ttccagtggg cggtgagccg cgcattgtgc tcacctccgg tctgcgaagc cttcgctcgt    420

ggcaacatca gcagcgagga ggtgtgtaag cctctgtgcg caacgcggcc cttcggcctg    480

gctcaggaag cctgcagctc ctatagtcac gtcgtgctca aggaggtgcg cttctttaac    540

ctacaggtgc tctacccgct gctcagcgac cctgcgctca acctgcgcat cgtgcaccta    600

gtgcgcgacc cgcgggccgt gctgcgctcc cgagagcaga cagccaaggc gctggcacgg    660

gacaatggca tcgtcctggg taccaacggc acgtgggtgg aggcggaccc ccggctgcgc    720

gtggtcaacg aggtatgccg cagccatgtg cgcatcgcag aggcagcctt gcacaagccg    780

ccgcccttct tgcaagatcg ctaccgcctg gtgcgctacg aggatctggc ccgggaccca    840

ctcaccgtaa tccgtgaact ctatgccttc accggcctgg gtctcacgcc gcagctccag    900

acttggatcc acaatatcac gcatggttca gggccaggcg cgcgccgtga agccttcaag    960

accacatcca gggatgcgct cagtgtatcc caggcctggc gccacacgct gccctttgcc   1020

aagattcgcc gggtccagga actgtgcggg ggtgcactgc agctgctggg ttaccggtct   1080

gtgcattcgg agcttgagca aagggacctc tctctggacc tcctgctgcc aagaggcatg   1140

gacagtttca agtgggcatc gtccacggag aagcaaccgg aatcttag                1188


<210> SEQ ID NO 3
<211> LENGTH: 2044
<212> TYPE: DNA
<213> ORGANISM: homo sapiens

<400> SEQUENCE: 3

ggctcgaggt ccactgtgct gaatgtaagt ctccttatca gaaagctccc agtgaggaac     60

tggtcttctg gagactctgt gtggcataga gtgattcaac caccttaaga agacctctgg    120

ctttcctgga acacagatgt cgagacatct cccatggatt tgtgatcagc gttgcagctc    180

tcccagcagc cctggacggt ggcccccagc cgcccgcatg tggctgccac ggttctccag    240

caagacagtg acagtgctcc tcctggcaca gaccacctgc ctcctgctct tcatcatctc    300

ccggccaggg ccctcatccc cagccggcgg cgaggatcgt gtgcacgtgc tggtgctgtc    360
```

-continued

```
ctcgtggcgc tcgggctcat ccttcttggg ccagctcttc agccagcacc ccgacgtctt    420
ctacctgatg gagcccgcgt ggcatgtgtg gaccaccctg tcgcagggca gcgcggcaac    480
gctgcacatg gccgtgcgcg acctgatgcg ctctatcttt ttgtgcgaca tggacgtgtt    540
tgatgcctac atgccacaga gccgaaacct gtccgccttt ttcaactggg caacgagccg    600
cgcgctgtgc tcgccgcccg cctgcagcgc ctttccccga ggcaccatca gcaagcagga    660
cgtatgcaag acactgtgca cgcggcagcc attcagcctg gcccgggagg cctgccgctc    720
ctacagccac gtggtgctca aggaggtgcg cttcttcaac ctgcaggtgc tctacccgct    780
gctcagcgac cccgcgctca acctgcgcat cgtgcacctg gtgcgcgacc cgcgggccgt    840
gctgcgctcc cgggaggcgg cgggcccgat actggcacgc gacaacggca tcgtgctggg    900
caccaacggc aagtgggtgg aggccgaccc tcacctgcgc ctgattcgcg aggtgtgccg    960
cagccacgtg cgcatcgccg aggccgccac actcaagccg ccacccttcc tgcgcggccg   1020
ctaccgcctg gtgcgcttcg aggacctggc gcgggagccg ctggcagaga tccgcgcact   1080
ctacgccttc accggcctga ccctcacgcc acagctcgag gcctggatcc acaacatcac   1140
ccacgggtcg gggatcggca agccaatcga ggccttccat acttcgtcta ggaatgcgcg   1200
caacgtctcc caggcctggc gccacgcgtt gcccttcact aagatcctgc gcgtgcagga   1260
ggtgtgcgcc ggcgcgctgc agctgctggg ctaccggcct gtgtactctg cggaccagca   1320
gcgtgacctc accctggatc tggtgctgcc acgaggccca gaccacttca gctgggcatc   1380
gcctgactga gaactctggg ccttagagca agccccgaac tgtggtcgcc aggcccagga   1440
agcgactgca tggtggaaaa ggagctgggg cgcatgggga acaggtccct actatcaacc   1500
gggagtttgg ggtcctcccc tgaagtaagc aaggactgca cgtttctttc tctcctgatt   1560
ctcggttttc ctttgagtct tctggagctg ccttctcatc aggtgcactc ttcatggaaa   1620
agcaactctt gcccctacct cttctgggcg cagggagtaa gttactgcta aattaaatta   1680
aatgtgtgcc aggccgggtg cggtggctca tgcctgtaat cccagcattt tgagaggctg   1740
aggcgggtgg atcacctgag gtcaggattc aaaaccagcc tggccaacat agtgaaaccc   1800
cctctctact aaaaatgcaa aaattagtcc ggcgtggtgg cacactcctg taatcccagc   1860
tacttaggag gctgaggtgg gaaaatcact tggactccaa aggtggaggt tgcagtaagc   1920
tgaaatcatg ccactgcacc ctagcttggg tggcaaagca aaactctatc aaaaaaataa   1980
ttaataaatt tgttcaaaag tcctgccgaa aaaaaaaaaa aaaaaaaaaa aaaaaaaaaa   2040
aaaa                                                                2044
```

<210> SEQ ID NO 4
<211> LENGTH: 1173
<212> TYPE: DNA
<213> ORGANISM: homo sapiens

<400> SEQUENCE: 4

```
atgtggctgc cacggttctc cagcaagaca gtgacagtgc tcctcctggc acagaccacc     60
tgcctcctgc tcttcatcat ctcccggcca gggccctcat ccccagccgg cggcgaggat    120
cgtgtgcacg tgctggtgct gtcctcgtgg cgctcgggct catccttctt gggccagctc    180
ttcagccagc accccgacgt cttctacctg atggagcccg cgtggcatgt gtggaccacc    240
ctgtcgcagg gcagcgcggc aacgctgcac atggccgtgc gcgacctgat gcgctctatc    300
tttttgtgcg acatggacgt gtttgatgcc tacatgccac agagccgaaa cctgtccgcc    360
```

-continued

```
tttttcaact gggcaacgag ccgcgcgctg tgctcgccgc ccgcctgcag cgcctttccc    420

cgaggcacca tcagcaagca ggacgtatgc aagacactgt gcacgcggca gccattcagc    480

ctggcccggg aggcctgccg ctcctacagc cacgtggtgc tcaaggaggt gcgcttcttc    540

aacctgcagg tgctctaccc gctgctcagc gaccccgcgc tcaacctgcg catcgtgcac    600

ctggtgcgcg acccgcgggc cgtgctgcgc tcccgggagg cggcgggccc gatactggca    660

cgcgacaacg gcatcgtgct gggcaccaac ggcaagtggg tggaggccga ccctcacctg    720

cgcctgattc gcgaggtgtg ccgcagccac gtgcgcatcg ccgaggccgc cacactcaag    780

ccgccaccct tcctgcgcgg ccgctaccgc ctggtgcgct tcgaggacct ggcgcgggag    840

ccgctggcag agatccgcgc actctacgcc ttcaccggcc tgaccctcac gccacagctc    900

gaggcctgga tccacaacat cacccacggg tcggggatcg gcaagccaat cgaggccttc    960

catacttcgt ctaggaatgc gcgcaacgtc tcccaggcct ggcgccacgc gttgcccttc   1020

actaagatcc tgcgcgtgca ggaggtgtgc gccggcgcgc tgcagctgct gggctaccgg   1080

cctgtgtact ctgcggacca gcagcgtgac ctcaccctgg atctggtgct gccacgaggc   1140

ccagaccact tcagctgggc atcgcctgac tga                                1173
```

<210> SEQ ID NO 5
<211> LENGTH: 2546
<212> TYPE: DNA
<213> ORGANISM: homo sapiens

<400> SEQUENCE: 5

```
cttggcggag gaggttggtg atgcagctgg ggaaataatc actgcctctc aacatgggga     60

aatggtattt gtgagtgggg aagccgtgtc tgcttattct tcagcaatga gactgaaaag    120

tgtatatcgg gctttgcttc tttaaattcc caaactctgc tagttgttga tcatattgag    180

aggcaagaag attccccaat aaattctgtc agtgccttct ttcataattt ggatattgat    240

tttaaatata tcccatataa gtttatgaat aggtataatg gtgccatgat ggatgtgtgg    300

gatgcacatt acaaaatgtt ttggtttgat catcatggca atagtcccat ggccagtata    360

caggaagcag agcaagctgc tgaatttaaa aaacgatgga ctcaatttgt taatgttact    420

tttcagatgg aatccacaat cacaagaatt gcatatgtct tttatgggcc atatatcaat    480

gtctccagct gcagatttat tgatagttcc aatcctggac ttcagatttc tctcaatgtc    540

aataatactg aacatgttgt ttctattgta actgattacc ataacctgaa gacaagattc    600

aattatctgg gattcggtgg ctttgccagt gtggctgatc aaggccaaat aacccgattt    660

ggtttgggca ctcaagcaat agtaaagcct gtaagacatg ataggattat tttccccttt    720

ggatttaaat ttaatatagc agttggatta attttgtgca ttagcttggt gattttaact    780

ttccaatggc gtttttacct ttcttttaga aaactaatgc gatggatatt aatacttgtt    840

attgccttgt ggtttattga gcttttggat gtgtggagca cttgtagtca gcccatttgt    900

gcaaaatgga caaggacaga ggctgaggga agcaagaagt ctttgtcttc tgaagggcac    960

cacatggatc ttcctgatgt tgtcattacc tcacttcctg gttcaggagc tgaaattctc   1020

aaacaacttt ttttcaacag tagtgatttt ctctacatca gggttcctac agcctacatt   1080

gatattcctg aaactgagtt ggaaatcgac tcatttgtag atgcttgtga atggaaggtg   1140

tcagatatcc gcagtgggca ttttcgttta ctccgaggct ggttgcagtc tttagtccag   1200

gacacaaaat tacatttgca aaacatccat ctgcatgaac ccaatagggg taaactggcc   1260

caatattttg caatgaataa ggacaaaaaa agaaaattta aaaggagaga gtctttgcca   1320
```

-continued

```
gaacaaagaa gtcaaatgaa aggcgccttt gatagagatg ctgaatatat tagggctttg   1380
aggagacacc tggtttacta tccaagtgca cgtcctgtgc tcagtttaag cagtggaagc   1440
tggacgttaa agcttcattt ttttcaggaa gttttaggag cttcgatgag ggcattgtac   1500
atagtaagag accctcgggc atggatttat tcaatgttgt acaatagtaa accaagtctt   1560
tattctttga agaatgtacc agagcattta gcaaaattgt ttaaaataga gggaggtaaa   1620
ggcaaatgta acttaaattc gggttatgct ttcgagtatg aaccattgag gaaagaatta   1680
tcaaaatcca aatcaaatgc agtgtccctc ttgtctcact tgtggctagc aaatacagca   1740
gcagccttga gaataaatac agatttgctg cctactagct accagctggt caagtttgaa   1800
gatattgtgc attttcctca gaaaactact gaaaggattt ttgcctttct tggaattcct   1860
ttgtctcctg ctagtttaaa ccaaatattg tttgccacct ctacaaacct tttttacctt   1920
ccctatgaag gggaaatatc accaactaat actaatgttt ggaaacagaa cttgcctaga   1980
gatgaaatta aactaattga aaacatctgc tggactctga tggatcgcct aggatatcca   2040
aagtttatgg actaaatgct gcaggtcagc agaaatttgc actaataata cttaccaacc   2100
cactttgtgg atatgaatca gaagagtttg tttattcttt agtgtgtgtg tgtgtgtgtg   2160
cacgcgtgta tgtgttcagt gttgtttgca cagagagatt gttttaaaaa atggcaccat   2220
atttggccta gcaggattta tttttatgtc atcacctccc ttgcctttgt ttctgaaaat   2280
tttgtctgct aaaaagtttc tgctacagag tggtagatga agttatatca tggggtcagg   2340
ggagatggga aaattttaag tttttgtcta actccccttc atctgtaact gtgctaatct   2400
atctagagac ctcaaacact gctaaaggcc ttgcaattgc tgctttaccc acgcatctct   2460
tgctttcaag aaggactaca aaagttcctt atccttttga aaaggtcttc tgacacactt   2520
atcttgcaca aagaaaaaga aaattt                                        2546
```

<210> SEQ ID NO 6
<211> LENGTH: 1791
<212> TYPE: DNA
<213> ORGANISM: homo sapiens

<400> SEQUENCE: 6

```
atgaataggt ataatggtgc catgatggat gtgtgggatg cacattacaa aatgttttgg     60
tttgatcatc atggcaatag tcccatggcc agtatacagg aagcagagca agctgctgaa    120
tttaaaaaac gatggactca atttgttaat gttacttttc agatggaatc cacaatcaca    180
agaattgcat atgtctttta tgggccatat atcaatgtct ccagctgcag atttattgat    240
agttccaatc ctggacttca gatttctctc aatgtcaata atactgaaca tgttgtttct    300
attgtaactg attaccataa cctgaagaca agattcaatt atctgggatt cggtggcttt    360
gccagtgtgg ctgatcaagg ccaaataacc cgatttggtt tgggcactca agcaatagta    420
aagcctgtaa gacatgatag gattattttc ccctttggat ttaaatttaa tatagcagtt    480
ggattaattt tgtgcattag cttggtgatt ttaactttcc aatggcgttt ttacctttct    540
tttagaaaac taatgcgatg gatattaata cttgttattg ccttgtggtt tattgagctt    600
ttggatgtgt ggagcacttg tagtcagccc atttgtgcaa aatggacaag gacagaggct    660
gagggaagca agaagtcttt gtcttctgaa gggcaccaca tggatcttcc tgatgttgtc    720
attacctcac ttcctggttc aggagctgaa attctcaaac aactttttt caacagtagt    780
gattttctct acatcagggt tcctacagcc tacattgata ttcctgaaac tgagttggaa    840
```

-continued

```
atcgactcat ttgtagatgc ttgtgaatgg aaggtgtcag atatccgcag tgggcatttt    900

cgtttactcc gaggctggtt gcagtcttta gtccaggaca caaaattaca tttgcaaaac    960

atccatctgc atgaacccaa taggggtaaa ctggcccaat attttgcaat gaataaggac   1020

aaaaaaagaa aatttaaaag gagagagtct ttgccagaac aaagaagtca aatgaaaggc   1080

gcctttgata gagatgctga atatattagg gctttgagga gacacctggt ttactatcca   1140

agtgcacgtc ctgtgctcag tttaagcagt ggaagctgga cgttaaagct tcattttttt   1200

caggaagttt taggagcttc gatgagggca ttgtacatag taagagaccc tcgggcatgg   1260

atttattcaa tgttgtacaa tagtaaacca agtctttatt ctttgaagaa tgtaccagag   1320

catttagcaa aattgtttaa aatagaggga ggtaaaggca aatgtaactt aaattcgggt   1380

tatgctttcg agtatgaacc attgaggaaa gaattatcaa aatccaaatc aaatgcagtg   1440

tccctcttgt ctcacttgtg gctagcaaat acagcagcag ccttgagaat aaatacagat   1500

ttgctgccta ctagctacca gctggtcaag tttgaagata ttgtgcattt tcctcagaaa   1560

actactgaaa ggatttttgc ctttcttgga attcctttgt ctcctgctag tttaaaccaa   1620

atattgtttg ccacctctac aaaccttttt taccttccct atgaagggga aatatcacca   1680

actaatacta atgtttggaa acagaacttg cctagagatg aaattaaact aattgaaaac   1740

atctgctgga ctctgatgga tcgcctagga tatccaaagt ttatggacta a            1791
```

<210> SEQ ID NO 7
<211> LENGTH: 395
<212> TYPE: PRT
<213> ORGANISM: mus musculus

<400> SEQUENCE: 7

```
Met Arg Leu Pro Arg Phe Ser Ser Thr Val Met Leu Ser Leu Leu Met
 1               5                  10                  15

Val Gln Thr Gly Ile Leu Val Phe Leu Val Ser Arg Gln Val Pro Ser
            20                  25                  30

Ser Pro Ala Gly Leu Gly Glu Arg Val His Val Leu Val Leu Ser Ser
        35                  40                  45

Trp Arg Ser Gly Ser Ser Phe Val Gly Gln Leu Phe Ser Gln His Pro
    50                  55                  60

Asp Val Phe Tyr Leu Met Glu Pro Ala Trp His Val Trp Asp Thr Leu
65                  70                  75                  80

Ser Gln Gly Ser Ala Pro Ala Leu His Met Ala Val Arg Asp Leu Ile
                85                  90                  95

Arg Ser Val Phe Leu Cys Asp Met Asp Val Phe Asp Ala Tyr Leu Pro
            100                 105                 110

Trp Arg Arg Asn Ile Ser Asp Leu Phe Gln Trp Ala Val Ser Arg Ala
        115                 120                 125

Leu Cys Ser Pro Pro Val Cys Glu Ala Phe Ala Arg Gly Asn Ile Ser
    130                 135                 140

Ser Glu Glu Val Cys Lys Pro Leu Cys Ala Thr Arg Pro Phe Gly Leu
145                 150                 155                 160

Ala Gln Glu Ala Cys Ser Ser Tyr Ser His Val Val Leu Lys Glu Val
                165                 170                 175

Arg Phe Phe Asn Leu Gln Val Leu Tyr Pro Leu Leu Ser Asp Pro Ala
            180                 185                 190

Leu Asn Leu Arg Ile Val His Leu Val Arg Asp Pro Arg Ala Val Leu
        195                 200                 205
```

-continued

```
Arg Ser Arg Glu Gln Thr Ala Lys Ala Leu Ala Arg Asp Asn Gly Ile
    210                 215                 220

Val Leu Gly Thr Asn Gly Thr Trp Val Glu Ala Asp Pro Arg Leu Arg
225                 230                 235                 240

Val Val Asn Glu Val Cys Arg Ser His Val Arg Ile Ala Glu Ala Ala
                245                 250                 255

Leu His Lys Pro Pro Pro Phe Leu Gln Asp Arg Tyr Arg Leu Val Arg
            260                 265                 270

Tyr Glu Asp Leu Ala Arg Asp Pro Leu Thr Val Ile Arg Glu Leu Tyr
        275                 280                 285

Ala Phe Thr Gly Leu Gly Leu Thr Pro Gln Leu Gln Thr Trp Ile His
    290                 295                 300

Asn Ile Thr His Gly Ser Gly Pro Gly Ala Arg Arg Glu Ala Phe Lys
305                 310                 315                 320

Thr Thr Ser Arg Asp Ala Leu Ser Val Ser Gln Ala Trp Arg His Thr
                325                 330                 335

Leu Pro Phe Ala Lys Ile Arg Arg Val Gln Glu Leu Cys Gly Gly Ala
            340                 345                 350

Leu Gln Leu Leu Gly Tyr Arg Ser Val His Ser Glu Leu Glu Gln Arg
        355                 360                 365

Asp Leu Ser Leu Asp Leu Leu Leu Pro Arg Gly Met Asp Ser Phe Lys
    370                 375                 380

Trp Ala Ser Ser Thr Glu Lys Gln Pro Glu Ser
385                 390                 395


<210> SEQ ID NO 8
<211> LENGTH: 390
<212> TYPE: PRT
<213> ORGANISM: homo sapiens

<400> SEQUENCE: 8

Met Trp Leu Pro Arg Phe Ser Ser Lys Thr Val Thr Val Leu Leu Leu
 1               5                  10                  15

Ala Gln Thr Thr Cys Leu Leu Leu Phe Ile Ile Ser Arg Pro Gly Pro
            20                  25                  30

Ser Ser Pro Ala Gly Gly Glu Asp Arg Val His Val Leu Val Leu Ser
        35                  40                  45

Ser Trp Arg Ser Gly Ser Ser Phe Leu Gly Gln Leu Phe Ser Gln His
    50                  55                  60

Pro Asp Val Phe Tyr Leu Met Glu Pro Ala Trp His Val Trp Thr Thr
65                  70                  75                  80

Leu Ser Gln Gly Ser Ala Ala Thr Leu His Met Ala Val Arg Asp Leu
                85                  90                  95

Met Arg Ser Ile Phe Leu Cys Asp Met Asp Val Phe Asp Ala Tyr Met
            100                 105                 110

Pro Gln Ser Arg Asn Leu Ser Ala Phe Phe Asn Trp Ala Thr Ser Arg
        115                 120                 125

Ala Leu Cys Ser Pro Pro Ala Cys Ser Ala Phe Pro Arg Gly Thr Ile
    130                 135                 140

Ser Lys Gln Asp Val Cys Lys Thr Leu Cys Thr Arg Gln Pro Phe Ser
145                 150                 155                 160

Leu Ala Arg Glu Ala Cys Arg Ser Tyr Ser His Val Val Leu Lys Glu
                165                 170                 175

Val Arg Phe Phe Asn Leu Gln Val Leu Tyr Pro Leu Leu Ser Asp Pro
            180                 185                 190
```

-continued

```
Ala Leu Asn Leu Arg Ile Val His Leu Val Arg Asp Pro Arg Ala Val
        195                 200                 205

Leu Arg Ser Arg Glu Ala Ala Gly Pro Ile Leu Ala Arg Asp Asn Gly
    210                 215                 220

Ile Val Leu Gly Thr Asn Gly Lys Trp Val Glu Ala Asp Pro His Leu
225                 230                 235                 240

Arg Leu Ile Arg Glu Val Cys Arg Ser His Val Arg Ile Ala Glu Ala
                245                 250                 255

Ala Thr Leu Lys Pro Pro Pro Phe Leu Arg Gly Arg Tyr Arg Leu Val
            260                 265                 270

Arg Phe Glu Asp Leu Ala Arg Glu Pro Leu Ala Glu Ile Arg Ala Leu
        275                 280                 285

Tyr Ala Phe Thr Gly Leu Thr Leu Thr Pro Gln Leu Glu Ala Trp Ile
    290                 295                 300

His Asn Ile Thr His Gly Ser Gly Ile Gly Lys Pro Ile Glu Ala Phe
305                 310                 315                 320

His Thr Ser Ser Arg Asn Ala Arg Asn Val Ser Gln Ala Trp Arg His
                325                 330                 335

Ala Leu Pro Phe Thr Lys Ile Leu Arg Val Gln Glu Val Cys Ala Gly
            340                 345                 350

Ala Leu Gln Leu Leu Gly Tyr Arg Pro Val Tyr Ser Ala Asp Gln Gln
        355                 360                 365

Arg Asp Leu Thr Leu Asp Leu Val Leu Pro Arg Gly Pro Asp His Phe
    370                 375                 380

Ser Trp Ala Ser Pro Asp
385                 390


<210> SEQ ID NO 9
<211> LENGTH: 596
<212> TYPE: PRT
<213> ORGANISM: homo sapiens

<400> SEQUENCE: 9

Met Asn Arg Tyr Asn Gly Ala Met Met Asp Val Trp Asp Ala His Tyr
 1               5                  10                  15

Lys Met Phe Trp Phe Asp His His Gly Asn Ser Pro Met Ala Ser Ile
            20                  25                  30

Gln Glu Ala Glu Gln Ala Ala Glu Phe Lys Lys Arg Trp Thr Gln Phe
        35                  40                  45

Val Asn Val Thr Phe Gln Met Glu Ser Thr Ile Thr Arg Ile Ala Tyr
    50                  55                  60

Val Phe Tyr Gly Pro Tyr Ile Asn Val Ser Ser Cys Arg Phe Ile Asp
65                  70                  75                  80

Ser Ser Asn Pro Gly Leu Gln Ile Ser Leu Asn Val Asn Asn Thr Glu
                85                  90                  95

His Val Val Ser Ile Val Thr Asp Tyr His Asn Leu Lys Thr Arg Phe
            100                 105                 110

Asn Tyr Leu Gly Phe Gly Gly Phe Ala Ser Val Ala Asp Gln Gly Gln
        115                 120                 125

Ile Thr Arg Phe Gly Leu Gly Thr Gln Ala Ile Val Lys Pro Val Arg
    130                 135                 140

His Asp Arg Ile Ile Phe Pro Phe Gly Phe Lys Phe Asn Ile Ala Val
145                 150                 155                 160

Gly Leu Ile Leu Cys Ile Ser Leu Val Ile Leu Thr Phe Gln Trp Arg
```

-continued

```
                165                 170                 175

Phe Tyr Leu Ser Phe Arg Lys Leu Met Arg Trp Ile Leu Ile Leu Val
            180                 185                 190

Ile Ala Leu Trp Phe Ile Glu Leu Leu Asp Val Trp Ser Thr Cys Ser
        195                 200                 205

Gln Pro Ile Cys Ala Lys Trp Thr Arg Thr Glu Ala Glu Gly Ser Lys
    210                 215                 220

Lys Ser Leu Ser Ser Glu Gly His His Met Asp Leu Pro Asp Val Val
225                 230                 235                 240

Ile Thr Ser Leu Pro Gly Ser Gly Ala Glu Ile Leu Lys Gln Leu Phe
                245                 250                 255

Phe Asn Ser Ser Asp Phe Leu Tyr Ile Arg Val Pro Thr Ala Tyr Ile
            260                 265                 270

Asp Ile Pro Glu Thr Glu Leu Glu Ile Asp Ser Phe Val Asp Ala Cys
        275                 280                 285

Glu Trp Lys Val Ser Asp Ile Arg Ser Gly His Phe Arg Leu Leu Arg
    290                 295                 300

Gly Trp Leu Gln Ser Leu Val Gln Asp Thr Lys Leu His Leu Gln Asn
305                 310                 315                 320

Ile His Leu His Glu Pro Asn Arg Gly Lys Leu Ala Gln Tyr Phe Ala
                325                 330                 335

Met Asn Lys Asp Lys Lys Arg Lys Phe Lys Arg Arg Glu Ser Leu Pro
            340                 345                 350

Glu Gln Arg Ser Gln Met Lys Gly Ala Phe Asp Arg Asp Ala Glu Tyr
        355                 360                 365

Ile Arg Ala Leu Arg Arg His Leu Val Tyr Tyr Pro Ser Ala Arg Pro
    370                 375                 380

Val Leu Ser Leu Ser Ser Gly Ser Trp Thr Leu Lys Leu His Phe Phe
385                 390                 395                 400

Gln Glu Val Leu Gly Ala Ser Met Arg Ala Leu Tyr Ile Val Arg Asp
                405                 410                 415

Pro Arg Ala Trp Ile Tyr Ser Met Leu Tyr Asn Ser Lys Pro Ser Leu
            420                 425                 430

Tyr Ser Leu Lys Asn Val Pro Glu His Leu Ala Lys Leu Phe Lys Ile
        435                 440                 445

Glu Gly Gly Lys Gly Lys Cys Asn Leu Asn Ser Gly Tyr Ala Phe Glu
    450                 455                 460

Tyr Glu Pro Leu Arg Lys Glu Leu Ser Lys Ser Lys Ser Asn Ala Val
465                 470                 475                 480

Ser Leu Leu Ser His Leu Trp Leu Ala Asn Thr Ala Ala Ala Leu Arg
                485                 490                 495

Ile Asn Thr Asp Leu Leu Pro Thr Ser Tyr Gln Leu Val Lys Phe Glu
            500                 505                 510

Asp Ile Val His Phe Pro Gln Lys Thr Thr Glu Arg Ile Phe Ala Phe
        515                 520                 525

Leu Gly Ile Pro Leu Ser Pro Ala Ser Leu Asn Gln Ile Leu Phe Ala
    530                 535                 540

Thr Ser Thr Asn Leu Phe Tyr Leu Pro Tyr Glu Gly Glu Ile Ser Pro
545                 550                 555                 560

Thr Asn Thr Asn Val Trp Lys Gln Asn Leu Pro Arg Asp Glu Ile Lys
                565                 570                 575

Leu Ile Glu Asn Ile Cys Trp Thr Leu Met Asp Arg Leu Gly Tyr Pro
            580                 585                 590
```

-continued

Lys Phe Met Asp
595

<210> SEQ ID NO 10
<211> LENGTH: 2170
<212> TYPE: DNA
<213> ORGANISM: homo sapiens

<400> SEQUENCE: 10

```
ggctcgagag ttatacgtga acggagacct gaggctgcag cagaagcagc cgctgagctg     60
tggtggccta gatgcccgat acaacatatc cgtgatcaac gggaccagcc cctttgccta    120
tgactacgac ctcacccata ttgttgctgc ctaccaggag aggaacgaaa gctcccagtg    180
aggaactggt cttctggaga ctctgtgtgg catagagtga ttcaaccacc ttaagaagac    240
ctctggcttt cctggaacac agatgtcgag acatctccca tggatttgtg atcagcgttg    300
cagctctccc agcagccctg gacggtggcc cccagccgcc cgcatgtggc tgccacggtt    360
ctccagcaag acagtgacag tgctcctcct ggcacagacc acctgcctcc tgctcttcat    420
catctcccgg ccagggccct catccccagc cggcggcgag gatcgtgtgc acgtgctggt    480
gctgtcctcg tggcgctcgg gctcatcctt cttgggccag ctcttcagcc agcaccccga    540
cgtcttctac ctgatggagc ccgcgtggca tgtgtggacc accctgtcgc agggcagcgc    600
ggcaacgctg cacatggccg tgcgcgacct gatgcgctct atctttttgt gcgacatgga    660
cgtgtttgat gcctacatgc cacagagccg aaacctgtcc gcctttttca actgggcaac    720
gagccgcgcg ctgtgctcgc cgcccgcctg cagcgccttt ccccgaggca ccatcagcaa    780
gcaggacgta tgcaagacac tgtgcacgcg gcagccattc agcctggccc gggaggcctg    840
ccgctcctac agccacgtgg tgctcaagga ggtgcgcttc ttcaacctgc aggtgctcta    900
cccgctgctc agcgaccccg cgctcaacct gcgcatcgtg cacctggtgc gcgacccgcg    960
ggccgtgctg cgctcccggg aggcggcggg cccgatactg gcacgcgaca acggcatcgt   1020
gctgggcacc aacggcaagt gggtggaggc cgaccctcac ctgcgcctga ttcgcgaggt   1080
gtgccgcagc cacgtgcgca tcgccgaggc cgccacactc aagccgccac ccttcctgcg   1140
cggccgctac cgcctggtgc gcttcgagga cctggcgcgg gagccgctgg cagagatccg   1200
cgcactctac gccttcaccg gcctgaccct cacgccacag ctcgaggcct ggatccacaa   1260
catcacccac gggtcgggga tcggcaagcc aatcgaggcc ttccatactt cgtctaggaa   1320
tgcgcgcaac gtctcccagg cctggcgcca cgcgttgccc ttcactaaga tcctgcgcgt   1380
gcaggaggtg tgcgccggcg cgctgcagct gctgggctac cggcctgtgt actctgcgga   1440
ccagcagcgt gacctcaccc tggatctggt gctgccacga ggcccagacc acttcagctg   1500
ggcatcgcct gactgagaac tctgggcctt agagcaagcc ccgaactgtg gtcgccaggc   1560
ccaggaggcg actgcatggt ggagagggag ctggggcgca tggggaagca ggtccctact   1620
atcaaccggg agtttggggt cctcccctga agtaggcaag gactgcacgt ttctttctct   1680
cctgattctc ggttttcctt tgagtcttct ggagctgcct tctcatcagg tgcactcttc   1740
atggaaagca actcttgccc ctacctcttc tgggcgcagg gagtaagtta ctgctaaatt   1800
aaattaaatg tgtgccaggc cgggtgcggt ggctcatgcc tgtaatccca gcattttgag   1860
aggctgaggc gggtggatca cctgaggtca ggattcaaaa ccagcctggc caacatagtg   1920
aaaccccctc tctactaaaa atgcaaaaat tagtccggcg tggtggcaca ctcctgtaat   1980
cccagctact taggaggctg aggtgggaga atcacttgga ctccaaaggt ggaggttgca   2040
```

-continued

```
gtaagctgaa atcatgccac tgcaccctag cttgggtggc aaagcaaaac tctatcaaaa   2100
aaataattaa taaatttgtt caaaagtcct gccgaaaaaa aaaaaaaaaa aaaaaaaaaa   2160
aaaaaaaaaa                                                          2170
```

<210> SEQ ID NO 11
<211> LENGTH: 160552
<212> TYPE: DNA
<213> ORGANISM: homo sapiens

<400> SEQUENCE: 11

```
agaaatgtga gcgatggggg gcagccataa atacagatga aacttcaagt gctcacctgt     60
tacttatctc ctgctgtgtg accttgttcc tgacaggcca cagacaagta atggtctgtg    120
gctctggggc tgggggcccc tgccctaaag cttttagagg aagcagaagc cccaccaaca    180
acctgtttgg acttctagcc tccagaactg aaaggggata cagtcttttc ttcttatttt    240
ttgagatgga gtcttgctct gtcacccagg ctagagtgca gtggcacgat cctggctcac    300
tgcaacctcc acctcctggg tttgagagat tcttctgcct cagcctcctg agtagttggg    360
actataggcg tgcgccaata cacctggcta atttttgtat ttttagtaga aaggggcttc    420
accatgttgg ccaggatggt cttgatctcc tgacgtcgtg atctgcccac ctcggcctcc    480
taaagtgttg ggattacagg cgtgagccac tgcacccggc caggaataca tttctgttgt    540
cttaagccac ccagcttgtg gtacttcgtt aagaaacagc tctaggaaac tattacaggc    600
acaaaatttg tgatgaaaat gttctaaaat tgatggttgc acaactctgt ggatatacta    660
aaaaaatttt tttttttttt ttttgagaca ggatctcact ctgtcaccca ggctggagtg    720
caatggcatg atcttgactc actgcaacct ccgcctccca ggttcaagtg attctcctgc    780
ctcagcctcc caagtagctg ggactacagg cgtgcaccac catgcccggc taatttttgt    840
atttttagca gagacggggt ttcatcatgt tggccagact ggtctcgaac tcctgacctc    900
aggtgatctg cctgcctcag cctcccaaag tgttggaatt acaggcgtaa gccaccgtgc    960
ccggcctaaa aacttttaaa atgtatactt tagttgggtg aattttatgg tctgtgaatt   1020
atatctcaat acaactgtta tttaaaaata tttatagcca caaaatgctg aagaaccaat   1080
aaggaccttg agtaacccca acatgggagc ttccattttc agtcaatcat tcaaggtctg   1140
aagttgagtg ttaaacattc gatgttaaaa caggattggc tgctgggtct attgctgatt   1200
tgctgcaggg cctttggct tcttttttt ttttttttt tttttttgag atagggtctt   1260
gctctatcac ccaggctgga gtgcagcggt acgatctttg ctcaccacta cctccgcctc   1320
ctgggttcaa gcaattctcc tgcctcagcc tcccgagtag ctaggattac aggtgtgcgc   1380
caccatgccc ggctagtttt tgcattttta gtagagacag ggtttcacca ggttggccag   1440
gctggtcttg aactcctgac ctcaagtgat ctgcctgcct gggcttccca aagtgctggg   1500
attacaggcc tgagccacca agcctggcca ccttttggct ttttggacag aactctttca   1560
attgtaagtc agaaaaccaa cacaaacagg cttaatcaaa ataacaacag gaatctgtct   1620
cacataattg agacatctaa acagtgttac tagatctttg attctcttgg ctgtttcctt   1680
tgttgccttc attctttgct ggctttctct aggtagtagg aaaagatggc caccggcagt   1740
cccatgatta tgtgaccctt acagctccag atcaaaacag aaagcctttc ctgatacctc   1800
tgagaacaag tccaggcagt ccagggctgg ctcacaggct attcctagag ccagggagta   1860
aggttagctt cagccaagtc tgaggcacag agcaggatca ctgaagaatg ggaaaagaat   1920
```

-continued

```
ggctccctga agaaagaaag gctgggaata caaaatatat attcgctatg ctaggcaaag   1980
ctgtaaaact tgcagagcgt caaacatcat ttcagctcaa taaatatttg ctgaatcaat   2040
gtaggaaccc ataaaacaga gctgctgcag agtactttca aagcatcatg ttccaaactc   2100
tgatttcata ttttagagaa gcaataaaac acaatggaag tcagatagtg aggtcattag   2160
tgagatgcca ttttagcaga gagctacttc aatcaagtat agcttgctct aagttccaga   2220
ttccatctgt attacacaac agagatgcaa agctcagaaa gaatgttccc tgatttaact   2280
accaaaaaag ctaagacttg tcctgcgtgg aggaaggcag ttcaggatga agggtcctgc   2340
taccagagca aacatttcct tctcacttga actggtgata atccggtggg tttctgatcc   2400
aggatccaaa cacctgcttc cggagtgtgc tccaggcttc ctggtaagag gacgcagcct   2460
ccttgtactc ctggtaggta tccagcttct gcaccctaat gcacacaggc caccaaatac   2520
acaggttctc attgaatagc ccaccccagg ggccaccaga cacctgagca agcaactgga   2580
cagacttgta atgagactta ggtagagaag gagttcagta tgcttttgtg aaagttgatc   2640
atacaaacta cgttattctt gtcatactca actgaaacag agttgagaag ccaggggtaa   2700
aaaacactca gggcgcataa cattgctcca agaatgcatt ctctgcaagc ctggctgcta   2760
aaactgcctg ccagttttat ctaacagcta ctgaaccaac ctgctgcaga ctttaagaat   2820
agttttaccc agtgccatca cttggcagct cctcacttta ctcatgtcaa tgaaccttct   2880
tcaacaatat gttacatttc ttttttgaaa aataaaacct ctaaccttcc ctttgttctt   2940
cagacatatt gaagaccacc cagtctgtat gtcttgaatt tcttgtatcc caaataaaat   3000
attaaattta gagatttatc tttacatttt tattttgact tttgacactt tcctagagca   3060
actctgtctc ctttgtaggg aattcacgag aaagcaacat gaattaaaac agttaagaat   3120
gaacagaatt ctaggtttct atggtcctag tggaatcaga taaaataaaa acaactgtct   3180
actttttggt tttaaaagtt ttctaggcca ggcatggtgg ctcacacctg taaccccagc   3240
actttgggag gccgaagcag gcggatcacc tgaggtcagg agtttgagac cagcctggcc   3300
aacatggtga aaccccatct ctactaaaaa tacaaaatta gccgggcgtg gtggcaggca   3360
cctgtagtcc cagctacctg ggaggctgag gcaggagaat cacttgaacc caggaagcgg   3420
aggttcctgt aagctacgat tgtgccactg tactacacag actgggcgac agagcaagac   3480
actgtctcaa aaaaaaaaaa atacagtaac tactagttat caaaacccta ctacaaacca   3540
ggctcttggt cacatgcaac acttccctta attgtctcag ctaccctgtc tcaaaaacaa   3600
acaaacaaac aaacatacat acatgccagg cggtggctca cgcctgtaat cctggcactt   3660
tgggaggctg aggcaggtgg atcgcccgag gtcagtagtt caagaccagc ctggtcaata   3720
tggtgaaacc ccgtccctac taactatacc aaaaattagc cgggcgtggt ggcgggtgcc   3780
tgtaatccta gctactctgg agactgaggc aggaaaatca cttgaacctg ggaggcggag   3840
gctgcagtga gctgaaattg tgccactgca ctccagcctg gttaacaggg agcaaaactc   3900
tgccttagaa gtatctcctc acctaaattc agatttgaca tatagaatat atggaaaccc   3960
aagaaagaag ccaactgacc acagatccat cacttcagta tgcatgatgg cgatgcctct   4020
tcatatagaa gtttctagct actccttagt ttccccactg tcatataatg aaggattcac   4080
ttggtctttg tcaccagttc ccgggagcct ctaagctttg gagtttctgc aagtgtcttt   4140
gtcctgcatg gtagatctcg ctgatcacac gtgagtttct gtttaaccag gtgactcatg   4200
gtgggccccc gagatagttt caggatgata ccggccatgc cagaaagacc aaccatgtag   4260
agaattaggg ctctgagaca cgtgatatca gtttgaactc ttgggagagg aggaggttgg   4320
```

-continued

```
agattaagtt caatcacatc atgtggccaa taattcaatc agtcataata gttaatgaaa   4380
ctccaacaaa aactttggac actgatgtct gagtgagatt cctagttggt gatgcgcagc   4440
aatgtgctgg gaaggtgata tgtcctgagg acatggaagc tctgcctttg cgaccctccc   4500
atatcttacc ctatatctct ctccttttgg ctagtactga tctgtagcct tcataataaa   4560
actttaatgg caactatagt gcttttctga gttctgagag atgttctagt gaatgactga   4620
acgtgaaggg gagtggagac actcaaattt gtagccagtt ggtcagaagt atgggtggtt   4680
tggggctttc cttaacttgt ggtagttgtt tgaaatgaag acagtttagt gggaactgtg   4740
tccttcacct gtgaaacttc acctaaatct aggtggtcac tgtcagaatg tcactgcacc   4800
catctacctg ttcccaagag tggttttaaa gttctttgaa tttttgtttg aagagcaatt   4860
taagtcatgg agctgcaagt tcaaaaggaa aagaggagta acacttgtaa cagaatatat   4920
tgctcttaga gcactcccat ttccacagtg atctccatct agaggtggaa tcaaaggagg   4980
gcctggaatg gccaagcccc agttctatcc ttagtttttt ataactctat accaccaaac   5040
tacccatcct ctgcatctca gatcatgcac gtatctgcaa atagggctat ggggaaagaa   5100
gaacttgtgg tcaacaataa gtgccactgg cttgctgaac caccactcct gccaaagctt   5160
cttgctactc agaagccaga atcaaaacag ttgtctacct aaatatgaga aaacataggt   5220
caacagcatc acctgaggga gtgtggccac ttgtcccttg caattctgct tagcagcttc   5280
tggaatgatc tgaagagttc cactttgctg atttgggatc tgtttggaaa aagaaggcaa   5340
agatgattta ttaagtgttt agtatgttct aagcccctat caaagatgcc aggcttcatg   5400
tggtttttag gtttgaaggt gccagagccc ctcattttca cctgtacttg gtgaggagaa   5460
aatccagacc tggatgtctg attaggttga ggtataaaaa cgagtctaac cttaagaaat   5520
gccatcagcc atgggatcat taaagtaaca agcccaaacg ggtaccctga ggtgcaatta   5580
cgaaattttg ccccaggata tctgtaagac acttctggct aaatcctttc aagggtgctg   5640
gcccctatgg gtttacaaga aatggaaagc tttgtttcag agatctgagt gctgttccct   5700
gtgtgaactg tcattataaa atccacttgg acgagccacc tgaggcagaa tccctggact   5760
cctgccatgg gcatcacagg cctttggaga acaagcgttt gctcctaaac aacaaaattc   5820
tgggtggagg tcatggtttg gaatacttaa ggaggtgagt gttgactact ttataagccc   5880
acccagacct tcgtggttgc cttcttttcc ctcatgtata caattcatga gctgcatcta   5940
gaaattggga aatgctgtgt ataccaacaa tgtgcagtct cacttttaca caccacactc   6000
tgcatcatcc tagcagatca caccctcagc ttggacacag tgaccatcac tgctacatgt   6060
aaaataggga attatggagt ctgtccaaaa tctcccttac ctggctggaa cctagcctac   6120
ttcaggaatt gctgcttaaa ggggaaccct gagcactcag acactgctct cccagggcct   6180
tagctggagt ggctgctggc actcaggaag atgaggccac tttagcatga aaacaaagca   6240
aaaattaatg gaactctcat gaacaaatta aagaagaaca atgtaattag ggatggccaa   6300
acacagtggc tcatgcctgt aatcccagca ctttgggagg ctgaggtgaa tgagcagatc   6360
acctgaggtc aggagttcga gaccagcctg gctaacatgg tgaaacccca tctctactaa   6420
aaatacaaaa actagccggg cgtggtggca gtcgcctgta atcccagcta ctagggggca   6480
gaggcaggag aatcgcttga agctgggagg cagaggttgc agtgagctga gatcgcgcca   6540
ctgcctgggc actctagcct gggcgacatg agtgaaactc cgtctccaaa aaaaaaaaaa   6600
aagtcctgtc cttaaagagg tatttaccca gaaatgatca aagtgcttta agcacatttc   6660
```

-continued

```
taaataaagg atgattaagt gtggggtgag aagtcattaa ttgggcctga agggtcagga   6720
attggatttc tggttactct gtcctaaaat cctgacttgg gttactggta taatctgctt   6780
tagggtggat tctcagcaga atggaaaggc aaatgggact tggagagaaa atggccttga   6840
agcagtctct gttgccctga aaatcacttt tcatttccaa aacatcacaa cttcctttta   6900
ctgaagatct ctttaagatc cagaagcaaa taaacaccat attcttaaac agcacaggtt   6960
tcccaatgtc agttataata tctggccagg catggtgggt aacacccata atcccagcac   7020
tctgggaggc caaagcagga ggatcacctg tagccaggag tttgagacca acctggtgag   7080
gtaggaggac ttctcaagcc caggagttca aggctgcagt gagctatgac tgtgccactg   7140
cactccagcc agggtgacag agcaagacct tgtctcaaca acaataaaaa ataatatctt   7200
agagatatta tatttaatga tatactcctg tttctatttt aaacagggga ttaacaagac   7260
tcttatctat gttctaaaca aacaaagacc aaagaccatt cactgccagg tctgagttcc   7320
cctctaacgt catgactagg aaacttgtac actgatgttt tttctgaagt tctgtctgaa   7380
caaaggcatg gttccccatt ccgtttttgg cctgattctt gatgctggca cctaggcaga   7440
gaattcaact ttccaatgct aaatgggaaa aggccattgt gattccctct tttttaaatg   7500
aaacaagaac ttagaattta ggaagtaaaa cttagggact tgcctctgtc tctatttata   7560
gaatcaatat ttaatactaa ctactctaaa taaaaatcat gacactttac atggtgaccg   7620
cctgttttcc actccaaggc agaaataact gagaactcac tccccttcag cctcagacat   7680
aattgatctt catgcagacc agtcagtcac cggagaggga gggctcctgc aggcctgaat   7740
tcgtcccttc tctaatttcc ccagccactc tttgaagcca gcaagcactg catgaaggtt   7800
aagggaggct ccatgctccc ctaaggaagc tgaaaagacc tgaggaagag gctgctaaat   7860
tgtcttgggg aagagatggt gaagctgaat cacagccagc tttaggaagg accctgtagc   7920
actttttatg tttatgggtg atttatatat tgcataaagc ccaatgatgt cacacgcctc   7980
ttatgtttag aaacaaattt atatttttag cccggtgtgg tgacatgcac ctgtggtcct   8040
gtcccagtta ttagggaggc tgaggtgaga ggatcacttg aacctaggag gcagagattg   8100
tagtgagctc agattgcacc actgcactgc aatctgggca acagagtgag actctgtctc   8160
aaaaaaaaaa ttacttctga gaataaaacc ccaaaataaa cagttgcatt aagtgtaggg   8220
tgataagtca ttaactgggg ccaaagagct gacagcctgg gcaaaagggc cctagctggt   8280
gactctaaat cctgaagggt caggagctgg atttctggct actcggccct aaaatcctga   8340
cttgagttac cagtgtaatc tgctttaggg ttgattctca ccacactgga aaggcaaatg   8400
ggacttggag agaaaatggc ttgaaacagt ctctgctgcc ctgaaaaatc atttttcatt   8460
tccaattcta tttctatctc agggataacg gggagggga agttgataag acctgtagcc   8520
attttaattg ctagattact gtggagccat ctgagtaatc ttaaggtctc cagaagcctg   8580
cttcatttcc tttgagaaga accagagaat cagaattgag gaaaataaac tcaatgccat   8640
aggtcctagt cacttatttt ctcccactaa gccaacacct ccaggaagta caaaacacag   8700
agtcaccaag gctctgtaga agttgcagat gttatgaaag aagattacct ccccaaacac   8760
gttaaggaaa gcccagggta accacggatg cccaaggctt cctcccctgg tgaagacaca   8820
gcccagaggc ctgggaagga aggttagaag agccccatgg gtgacaagat ctcctcaagc   8880
aacaccacag cttccagagc tacagctgtg gcagaccaat ggcgtccagt gggcaggccc   8940
tggggtgtct cctcaggttg aatactggcc ttagggaagg agcttccatt tctcccctgc   9000
ctttctatca gacaccagga agtagaggtg gaggacactg ggaaagagga aatcagacca   9060
```

-continued

```
aaaaatggcc agagctttcc acctttaaca gaaataaggt ctggaatttg gcacaggcct  9120

cttctggagt cttcaaggat tttcaacagg aacctatttg gacaacattg ggctagttcc  9180

cagggcttct gagagccttc acttttagaa gtattacttc tgggagtggt aaatgaaacc  9240

tagattgggt cacaaagata agatgtggcc agaaactcac actcagggga gaggtggggg  9300

ctggaatctg gatcagggcc tacaactacc cactcagtaa cgggaaagga ctgaccagga  9360

ggttagacgg agcccatcca ctttcctttt tccacagggg actaaagctg ggctgtcaaa  9420

cacacagaaa acgggaattc taatgcctct gcctacattc aggccacaag ttacagtccc  9480

aaagattgct tccaggcagc acaatagtct gacagtcaaa gcaagtgcta ccaagggagg  9540

tataagtctg taaagagact tcagagccct ttactgtgcc gcagtcattt tgtcagactt  9600

gaggatcagg cagctataga ctcttacaat gtcaaagagt tgaccaagtt tgggagcaag  9660

caaactggat gattaactga gtgagcctca gcagggccca caggctccca gtggaggagc  9720

atgccaggac tgccttcagg gaagaaaacc tcatttcagg cctcagttct acctatagct  9780

taagactaaa taagttctca accgttttaa aagattcttg gagatcttag gctgagtttc  9840

atcattttt taaaagtcca ggccttgttc tattttctga atccaaaatg cactcttatg  9900

tattgcagcc attattttcc tggagcccct gatgtcaggg agcataaaat ccagatttct  9960

agtcaggacc cctaagagtt ttcagacttc caaagttttg gagttccgta agcagccaac 10020

cagatgtcta ataccagagg gcccatctag taaacacctc tcacctggac tgtgggactg 10080

tcttatccac aaacaggaag atcgcctttt cagaaggaag ctggatcctt ttcctgatga 10140

tccacatgaa ctgagccaca gtgatatcag atggaaccaa gtacttccgt ttgtcaatgt 10200

caacaatctg agagcctgag acctttttcca caatcacctg ggaaagtaaa gagaggtcag 10260

gactgtgttt cctaaagcga ggctctggcc tcacatggct gaggagctga tgaacagagt 10320

gtgggcaagg aggtgggtgg ggaactgcat agcaggagaa aatatgtctt tggcttaata 10380

aaccacacgc tctggaggtt aagaattgat ataaatgtgt tacagggaaa cagtaagtgc 10440

ttttctgtgg tcaattatgt aagagaaatg cagcccttac cactaagctt ttccacattt 10500

tatctgggca gacctaagaa tatctgggga gggtttcatc catggcccgt tactccagga 10560

ccccagaatg gatccacctt cacactacag gaaacactac tgtgttccca aggaacacag 10620

gagacaagaa tggatggact aattggaatg cctggaattt tagccagcca agaaccaagt 10680

tcttcatttg gcctgttgct cctctctgaa caagtttcaa atccgtccct cctactcctt 10740

tccccagaca aattattcac aagcaaagag ctacaataac aggccttaat gtccattaaa 10800

aattaataac gattacaaaa ctatctcccc aaccatggaa gaaatataac attatattta 10860

ttattgacta agaagaaaat atggcagaag gggttttcag cggcttttca cattattttg 10920

gtcaggcaag gatgacaggg tcaaggtgag ataacggagc tagaagttag gtaaagatgg 10980

agacaaagta aaagatgaac gtcctgagac tcaagtacca cttccaagac caaaatgaca 11040

gtctccctcc accaccattc ccaaaagtgg cagtgacctg ttgccctgtc ctagaacatc 11100

gttccttaca taattggcca gggagccccg aggctgcaga cggctcgctg gcctagatcg 11160

ggagattcag cactgaggca ccctgaacag caccagcccg agcccctcac gccccggccc 11220

tgggcggcct catcccggtc tggcccgtca gctactgtaa ctgggactgg aacctcaact 11280

tgtcaactgt tgaatggcct ggggcctatc acgggtccca gacgacagag gtgacagcga 11340

ggtgaggggg cggagagtcc actcaccgga accctgtcgg gatatttcgc tcgaatcttc 11400
```

-continued

```
gcggactcca cgcatctgtg ttctgtggga gaaacaaacg gggctgacgg ccgcgcctgc  11460
ccaccggtcg gttcccggcc cccggccctc ctcctcctgc gccctgcgta caacccaggc  11520
cctggttccg gcgtccccgg ggccgcggtc ctgtccccta ctagctccca gcaaggcccg  11580
cggagggtga catggggtca gggggccgct gcccgaggca ccagggcatg ggcgactcca  11640
gcccgcagca gggcatccgc cccgctccac tcggcccagg gccgcccgag tgggggaggg  11700
ggcccacccg ccgccccagc ccccagcagc cgggccgacg accaagtgct tacccagcga  11760
gtggtcctcc ttgaacatcc acttcatggc ggcggcggga aggggacgga accggctcgc  11820
ggagccgcgg agctcagcgc accgagcaca acaacaacga cggcggcagc ggcagcggca  11880
gcgacggcgg cgactacacg gcaggcggga cttccggctg tcggagccta gcaaccggcc  11940
gggggcgggg cttccggcgc catttgtcag ggcgccacgc caaggggcgg ggccgcacgt  12000
aaaggggcgg ggccgcggag gaccccttttg ggggctcctg ggctgcggtg gcgaagaagt  12060
tggttatggg gacgtctgtg agcagtatct gcgacattgc tcgcaggaat gttcggggaa  12120
ctggtgacag gagtggggtc tcgggagcgt tggtggcgga aaacgtctgg ctgatagtgt  12180
agggctctta ctgagggctg tttgggggtg tggctgatag ctgagggctc ttagagcggt  12240
tcatagggga agtctgggga attggtgaca agaacggtct ttaggggtaa gaatgacata  12300
aggagggctt tctagagctt ggcgataaca agggagctgt ttagggcgtt gacagtttgg  12360
ggagtattgc tcggagtggt gacaggttgg gggctcatta tgggagggga gggtgtttga  12420
ggacactgtt ggaagcggca ctgaggacaa cccggaggtc cgtattaggg acagccgtag  12480
taggttgtct tggacctaga aattgaattt aaacaaatcc cgttttcttc ctttattcgt  12540
gaataaatat ttgaataaac atttacgaaa aggtatcaca aatgcacatt tgaggcgggg  12600
tacggtggct cacgcctgta atcccaacac tttgggaggc cgacgcgggt ggatcacctg  12660
aggtcaggag ttgaagacca gcctggccaa catggtgaaa ccccgtctct actaaaaata  12720
caaaaattag ccaggcatgg tagtgggcgc ctgtagtccc agctcctcgg gaggctgagg  12780
caggagaatc gtttgaacca gggaggtgga ggtggcagtg agccgagatc acaccactgc  12840
actccagcct gggcaacaga gcaagactcc gcctcaaaaa aaaatgcaca tttgaggagt  12900
gtaacatcac tgatcacaga ccccttaatt ttaactggca gaggagttag aggtgactgt  12960
cagactcgga gaattcccct gagagctggt catgagatgg gtttccttat ttggctgtgg  13020
gagtggttta gcaatcacag cctgagctgt gtgtgtgtca cctgcccgga catatgcttt  13080
gaggttctcc aatcagtgat gtaatgcctt ttttccaagc agactcatca aggcagtctg  13140
gtctgggtca ccatctgttt ataagctgct gaacatgtag caggaatatt cacttaattg  13200
ggcacatgaa ccctgccacg tgcttgtgat tctgatgcac ctgtaaagcc tgtatgtttg  13260
aatgtggtag ttcatcattt cctacactgg aaattcctga tcgatgctgt ggaatctagc  13320
ttcattctat aagtattttt gttattttaa gactgtgtgt ctgagtaact agaataggtt  13380
tttttgtttc tttgtttttg tttttgtttt ttggagacag ggtctttctc tgtcacccag  13440
gctggagttc agtggcacaa tcttggctta ctgcagtctg cctcctgggt tcaagcgatt  13500
ctgctgcctc agcctcctga gtagctggga ctacagggac acaccaccac acccagctaa  13560
tttttgtatt tttggtagag atggggtttt gtcatgttcg ccaggctggt cttgaacttc  13620
tcacctcaag taagtgattt gcccgcctcg gcctcccaaa gtgctaggat tacaggtgtg  13680
agccactgca tctgtttgtt tgtttttaat gaagtggaaa aaatcctttg aatttcctac  13740
ttagaaatta ttgttacata caagagctct gtgctaggtg ctggggaaaa acagtgaaga  13800
```

-continued agacagatga catccctatt ctcatgggtg gcagcatgag atattcttgt ccccctgaca 13860
tattctagtg ggataagaca aaaaataagt atgttaggta atgataggtg ctatttcgaa 13920
aaataaagca cagtaggtga ctagagagtg tggtgggatg gaatgctaat tagataaagt 13980
gcctggcata ttctagggaa cccctgtggc tggagctgaa taaatgagag aggagagtgt 14040
gttatgagac aaattcaaag atatctagaa caaaactgtg ttgagctttg aattccatgc 14100
aaagagcttt ggattttatt tagaatgaga tgagaagtca gtgtaggggt ttaagcagag 14160
acgtaacaca atctgccttt ccttttcaaa aggctagctt agtagactgt aggcgctgag 14220
ggtggaagca gggaaatagt tgagacacta ttgtgataat cctggtgaaa gatgatgttg 14280
gctttggcca aggtggggtc tacagaggtg atgggaagca gttgtattct ggatatattt 14340
cgaaggtaaa actggtaaca gttgctgata gattggatgt aagacatgag ggacagatca 14400
aaatcaaggt ttttggaagg atggaattgc catttactga aatagggtgg agccagcttg 14460
gggagtgaaa aacaagagtt tggtttttga gatattaaat atgagatgtc caagggacat 14520
acacaagtga agatgtagag ttggtgaatg gtgctatgag tctcaaattt agagagaaat 14580
atttcaagct attaaactgg gtaagattag gtagacagtg agtttaaaaa tgaaaatact 14640
tggccgggtg cagtggcata tgcctgtaat cccagcactt tgggaggccg aggcaggtgg 14700
atcacctgaa gtcaggagtt catgaccagc ctgactaacg tgttgaaacc ccgtctctgc 14760
taaatacaaa acaattagcc aggtatggtg gcacatgcct gtaatcgcag ctacttggga 14820
ggctgagaca ggagaattgc ttttacttag gaggcagagg ttgcagtgag ctgagatcgc 14880
gccactccac tccagcctgg gcaacaagag cgaaactccg tctcaaaaaa agaaaatacc 14940
tattttacaa atagaattaa acactgaaga atgaagatgg ttgttcacca tctcctagtc 15000
agtgaaccag tggaggagtt agaaattgga ctcaacaccc ctgcttccct ttacagagct 15060
ggtcattgca tcctagtcca aaatatatgt atattgtctt gcatgtgaaa gagctgagaa 15120
cacttcttag gggaaaattt cactgcacac caattcatag acatgtcttt tgatggtctc 15180
aatgatgtgc aatgcatttt ggtcttccat ccttacctac tttcttggtg tgttttccca 15240
gttcaccatt ctaattgact tatttcatcc accttgatga tatgtaccac cttctttaca 15300
tattgggtca ttgtatttag ctatggaatg ttctaaggac actggatgcc ttccttgagg 15360
gagtggttag ttaaggacgt aagtcaggag gagaaatagg ataatgaata tatgcaacgt 15420
aattacacat taacaaatct ataaaacaca gagaatgaat ttcaaatgtt ggagaggtat 15480
gtgaacatgg atactgaggc attgctaggg caataggggc cagcacaaag ccaagtgaga 15540
attagcaagg aagacttcac agagaatgtg aatcttctgt tgtagagaga agggtacatt 15600
ttcattgggt aaacttttcc tttccagata aaaacaaagg ctggggttgg aagagggaac 15660
agaaaagcag tatagataag taaataaaat gttggaaagc tttgaagcaa acattcagaa 15720
gttctaacct aattcaggag accctgaata agagctccta taaaggagag aagaacatga 15780
ttaaaatgtg caatttgggg ctgggtgcag tggctcatgc ctgtaatccc agcactctgg 15840
gaggccgagg caggtggatc acctcaggcc aggagttcta gaccagactg gccaacatgg 15900
tgaaaccccg tctttactga aaatacaaaa attagccagg catggtggca cgcacctgtg 15960
gtcccagcta ctcaggaggc tgcaggcatg agaatcgcct gagcccagga ggtggaggtt 16020
gcagtgagcc aagatagtgc cactgcactc cagcctgagc gacagggtga gactccatct 16080
caagaaaaaa aaaatgtggc caggtgcggt ggctcacgcc tgtaatccca gcactttagg 16140

-continued

```
aggccaaggc aggcggatca tgaggtcagg agttcgagac cagcctgacc aataaggtga  16200
aaccccgtct ctactaaaaa tacaaaaaaa aaaaaaaaaa ttcaccaggc gtggtggtga  16260
gcgcctgtaa tcccagctac tcaggaggct gaggcaggag aatcgcttga acccgggagg  16320
cggaggttgc agtgagccga gatcgcccca ctgcactcca gcctgggcta cagaacaaga  16380
ctccatctca aaaaaaaaaa aaaaaaaaaa gtgcagtttt aagaggatga ctctttttgt  16440
cctcagaaat aaattgtatg aaaaacaaga acattgtgga agtggaaact gagaagtcag  16500
ttatcagtca tgggtgtatg gaaatgacac atatacacag atctttaaca tttttaaatc  16560
tatactttct cttaaagaat tgaaataaaa ctacaaaacg agctttctca aaccatggaa  16620
gcaaagagta aatagtatcc attattacta aatacttttg caaagttcat ggcatctcag  16680
ggaaggctga agcacttggt acacctaaat tcttagtagt cacctccttc tgtttcagga  16740
gtgactttgg tacagtatct gtttccttcc attgaaagaa ggagctttgg aggcaaacac  16800
ttccttcctc acaggatagt gactctcagg agtcgaccct agatccatct attccagaag  16860
acccctgtgg ttatataaat aaatgaaagt cggctgggcg tggtggctca cgtttgtaat  16920
cccagcactt tgggaggccg aggtgggcga atcatgaggt caggagtttg agaccagcct  16980
ggccaacatg gtgaaacccc atctctacta aaaatacaaa aaattagctg ggcgtggtgg  17040
caggtgcctg taatccgagc tactcaggag gctgagagag gagaatcgct tgaacctggg  17100
aggctgaggt tgcagtgagc cgagatcaca ccattgcact ccagcctggg caacaacagt  17160
gaaactctct ctctcaaaaa aagaaagtca tccacttaaa gcatagatat agtgtgtcag  17220
aatcaaacca tagatttaac cttaacaatt gctatattta agaactatgt tgaggctcag  17280
tgtggtggtc ccagcacttc aggaggccga ggcaggtgga tctcttaagc cccagaatat  17340
gagatcaacc tgctagcctg ggcaacatgg cgaaatccca tctccaccaa aaaaacaaaa  17400
acgaacaaaa acctatgttg aggccagata cagtggctca cacccgtaat cccagcactt  17460
tgggattact caagaaggat acttgagccc aggagttgga gaccagcctg ggcaacatga  17520
caagactttg tcacttaaaa acaaaatttt tttttagatg gaagcgccta ggctggagtg  17580
cagtggcacg atctcagctc gctgcaacct ctacctcccg ggttcaagtg attgtcctgc  17640
ctcagccaaa aatttttttta aaaattagcc gggaatagtg gcctcagcta ttcaggaggc  17700
tgaggcagga caagtacttg agcccaggag gtagacagag ggagaccctg tataaaaaca  17760
acaacaacaa caaactacat tgccacccca gaaaagcttt taatcaagaa caagtagtat  17820
tgaacctgat atttcaaaag cattttgtgg ctgatgacgt tgtcgtcttg gactgtagta  17880
aggaccctag gatggttttc ccaaatgggc agtcttgacc tctctattaa gtctgtgatg  17940
ttaggatgtc agctgttctc ttcatctaaa agccacttcg aggttgcttt caaagtagtg  18000
ggagtaacta ctggactcca cccagcacaa acctcacgcc atctcctgac actgcaatgt  18060
gatccttcag ggcttttttt tttttttccc tttcttcaga cagtctcgct ctcgctctgt  18120
cacccaggct agagtgcagt agtgcagtca ctgcttactg caacctctaa ctcttgggct  18180
caagcaatcc tcctttctta gcatcccaaa gtgttactgg aaaggggtcc caatccagat  18240
cccaagaaag ggttcctggc tctcaacaca ggaaagaatt tggggcaagt ccacagagta  18300
aaaaaaaatg gctactccat agacagagca gcagtatggg ctactcgact gagtaaattt  18360
atagttattt cttgatccat atggtaaaca aagggtagat tattcctgac ttttccagga  18420
aaggggcaga gatttcccca gaactgaggg tccctcccct ttttagacta tatagggtaa  18480
cttccggaca ttgccgtggc atttgtaaat tgtcatggca ccagtgggag tatcgtttag  18540
```

-continued

```
catgccaatg cattacaatg agcagatcat gagcagtgag gacgaccaga ggtcacactc  18600
aaggccatct tggttttggt ggcttttgac tggctttttt tctttttttct ttcttttttt  18660
tttttttctc tgagacagag tttcgttctt atcacccagg ctggagtgca atggcgtgat  18720
ctcggctcac tacaacctcc gcctcccggg ttcaactgat tctccctcct cagcctccag  18780
agtagctgag actacaggtg cccgccacca tgcccagcta atttttgtat ttttagtaga  18840
gacagggttc caggcatgag ccaccatgcc cggccttggc tggcttcttt ttaactgcat  18900
cctgttttat ccacagggtc tctgtaacct gtatcttgtg ccatccttct agctcatact  18960
gtgactaaga atgccttacc tcctgggaag acagctcagt aggtcccagc cttattttac  19020
ttagccccta ttcgagatgg agttgctttg gttcaaacac ctctgacaaa agtgctaaga  19080
tgagccactt cacccagcct caacagcctc ttgactggtc tccctgactt ctgtttttcc  19140
tcacccctca ctcaatgacc ccatcctggt atactgtaaa cctaaaataa aattctaagc  19200
tcccaaccat ctgaatggaa cccttgtctc agccaagggc attccaaagt taacctgaaa  19260
aactagtctg gccatcatgg gaagtgggga gtcagacgta actcattata ccctcctctt  19320
tttggaattc agacccagct gaccagtatt agcatcaaca catagatctt aagactgata  19380
ttaatagaac agactcttaa agtctgataa gaaacattta caatctgttc tctctgaagc  19440
ctggaggctt catctgcatg ataaaacatt agactccaca accccttatt gtttttttgtt  19500
tttgtttttt ttttgaaatg gagtctcact ttgtcaccca ggctgaagtg cagtggtatg  19560
atctcggctc actgcagctg ctgcctcccg ggttaaagca attctcctgc ctcagcctcc  19620
caagtagctg ggattacagg tggacaccgc cagatgcagc taatgttttt ttttttaata  19680
catatttttg gtagagacag ggtttcacca tgttggccag gctggtcttg aactcctgac  19740
ctcaagtgat ctgcctgcct tggcctccca aagtgttggg attacaggcg tgagccactg  19800
tgccccgccc acaaacccac acattccttt ctattgattc caggtcttta gataataacc  19860
agttgacaat tggaaaaatc tctgaatctg ccaattctgt ggtctggaag ccccacccca  19920
cctccacttg tctcatcttt cagtactgaa ccaatgtaca tcttacacgt attgattgat  19980
gtcttatgtc tccctaaatg tataaactca agttataccc tatccacctt gggcgtatgt  20040
catcaggacc tcctgaggct gtgtcacagg catgtcctta accttggcaa aataaatttc  20100
tacgttgatt gagacttgtc tcagatacat tttggtttac actactgaca tgctgtcatt  20160
agagtgactt ttccaaatca caaagcttat catgtctttc cacttaaatg tcattttact  20220
gacccttttaa caaatttact tatatttaaa tattttgtat ttattttttt agagacaagg  20280
tctccttctg tctcccagcc tggagtgcag tagtgcattc atggctcact gcagcctcct  20340
gggctcaagc cttcctcctg cccaggcctc ccgagtagct ggacctacag gcatgagcca  20400
ctgtgctcag ccactcagga ccttttttgtt gttgttgttg ttgtttgaga tggagtctcg  20460
ctgccaccca ggctggagtc caatgtgtga tctccgctca ctgtaatctg tgcctcccgg  20520
gttcaagcga ttctcctgcc tcagcctcca gagtagctgg gattacaggt gcccatcacc  20580
atgcctggct aatttttgta tttttagtag agatgagggt tcaccatgtt ggccaggctg  20640
gtcttgaacc cctgacctca ggtgatccgc ccaccttggc ctcccaaagt gttgggatta  20700
caggcgtgag ccaccgtgcc cagccattca gggccatttg atgaagaaat tggctgtgga  20760
ccatagattt ttttaaaaag tccttctacc atgttagaaa tattggttgg gggtggtggs  20820
gggggggtgt aggcattcaa ttaagcaata agccagtgat ctttggggag gaccatatat  20880
```

-continued

```
tcctgtaaaa ctcgcggctg agctgtaccc aacacagggt taacgaagtg catcagagct  20940
ttgtagtaat tccactctat ccgtggaaga gccaggggat ttgtgtttcc gtgtctgtct  21000
tgcatgggag catagtggaa gcaacagaaa atctgggggc aaaagcacct ggctttgatc  21060
tcagcccagg accaggtcca ggaccacggc caggcttgtg actgactgga cttcagtagg  21120
aaccacactg gggttaaca gatgacacaa aagcaggtgt tcgttctgtg cgggagacgc  21180
gctaggggag aagaaaaggc acacacacag tacctttaag ggtaagcaag ctttatccca  21240
cgtaaatggc aatgcagata ttataataag caaattaata taataagcag attgatataa  21300
taagcaaatt gcaatgggaa gaggagaagg aaaaagacat atatatatat atatttacac  21360
tcaccagact atggaggatt cacctccaga ctgggaagca acgacctggg ctccagagcc  21420
ggccactcgt cagtgcacag acgaggagag gtctcatgaa gctttttggc gtggtctggg  21480
accctagatc tttttgtaac atgttgtcta gcatgaggcc cagtcacgag ggccctttgc  21540
gactgggctc aaggaacaca aaaaggtcaa cttgtttttg cgattgttgt ttttcaataa  21600
ctgacgtata ggagtagact gaaatagaga tttctccgaa acagcgctgg atgaacgcct  21660
caaggggctc ccacaacctg tttagggact tggtgaccat tgtttgtgtc catgtcagtt  21720
gaaatttaaa tatttagttc ttcctcctca gtgttcaagt caacttttat gggcatctta  21780
ttttacacaa atgttaacac agacaacagc cacgactctg gtccacggaa acgttctatc  21840
gccgcccagc ctttacgcaa acgtacacag ctcgaaaagc taggccgacc gtccccggca  21900
gcgccacgcc cgctaacccc gcccccgcca ctggctcctt tcggtgcggc cttgctattg  21960
gctcctttct gtgagccgtc ggttgccgtg gagaccgagg cgatggcaac caggagaagc  22020
caaacttggt cccccggctc gcggagtgcc tgcgagcggt gctcatggcg ctctatgagc  22080
tcttctctca cccggtcgag cgcagttacc gcgcggggct ctgctccaaa gccgcgctgt  22140
tcctgctgct ggccgctgcg ctcacgtaca tcccgccgct gctggtggcc ttccggagcc  22200
acggtgagcc tgccccggcc gctgtgccac gaggctcccc gggcgcgctc ggccagggcc  22260
ggcctcccta accgcctccc taccgccctc tttaactcag ggttttggct gaagcggagc  22320
agctacgagg agcagccgac cgtgcgcttc caacaccagg tgctgctcgt ggccctgctc  22380
ggacccgaaa gcgacgggtt cctcgcctgg agcacgttcc ccgccttcaa ccggctgcaa  22440
ggggatcgcc tgcgcgtccc gctcgtttcg gtgcgtggtt cccgcctggg cctggggcag  22500
agtcggggat agggtgggga tggggactgg aatgaggatg tggggcgagc ggccccggcc  22560
ctggggagcc cagctttgat cctaaggact cgcgaacccg caaaggtggc gtttcatctc  22620
ctaggaccta gggaatcgat cttctgtttc attctgcttc tcccagatgt ccccggcccc  22680
cagaaagtta gccatgctgt cagcgtgtgc gccctgacac agagtccaga agtgtggggg  22740
cagcctgtgt ctgcccgggt cacacccgcg ggcctggcct gatggagggt gtttgtgaaa  22800
gtccatttag gagcctggaa ggccgcgcgc tgttaatgta gataacccca ttctgtcgcg  22860
gcgtttctgc atcacaccac tataggaacg gaaagggcag catttttatg cagacctgac  22920
ccctggaaac caaggcgctg attggttaag cggccttccc agaacgcgct gtggccgagt  22980
cacgcctccc tgggtttgtc ccattggaga ctgcgccatc ctgaagctgt cgggatgaaa  23040
tggaagcatg ttactgtctg taatttattt atttattttt aaattttttc aycagtagag  23100
cgctgagagg aatctgtaat ttagtatttg ctttgagata agcgaatgct tcctttgtag  23160
tcactccttt tcactcattt tctgaaaacg ttttccttta gaagtatgaa acttctggtt  23220
ttccttcttt caaattcgaa tctcttcaga catatctaag atgattgccc tacaagccaa  23280
```

-continued

```
ccttgtatag ctgaggagaa aagaaaatca gacttgttcc cagcaactaa ataaaattgt  23340
ttttaaaaat ccgattggtc gtataaataa ctgcaaaaaa aatagtaata ggttgatgca  23400
aaagtcattg cggcttttgc cattaaaagt aatgacaaaa aaccggaatt acttttgcac  23460
caacctaata tgattcaggt tacttttctc ctattacttt ataaatgttc ttatattctg  23520
attacaaaag tgcatgctca ttctaaaata tgatagagtt acaggtagat ataatgacag  23580
aaattgaagg ctcagttttg tatatgtatc aatacttatt aatcagctgt attctttttg  23640
aggtttgctt tgactttttc actatwaggg acaacatttc tttttttctt ttcttttttc  23700
ttttcttttc tttttttttt ttttttttga gacacagtct tgttctgttg cccaggctgg  23760
agtgcagtgc tgcaattctc tgctcactgc aactctgcct cctgggttca agcaattctc  23820
gtgccttagc ctcccgagta gctgggatta caggctaatt tttggatttt tagtagagaa  23880
ggggtttcac tatgttggcc aggctggtct cgaactcctg acctcaggtg atccacccgc  23940
cttggtctcc caaactgctg ggatcatagg tgtcagccac tgtgcccggc ctagggacaa  24000
tatttcaatg aacaaggttt tgactaaatc ttatgccttt aaacatcaaa ttttgaggaa  24060
ttggaatagc agctctttga tgaaatggta taagtacata gaaaactaag caaataatta  24120
ttaactgcag ggaaatgaaa agtaaggaaa actgagaacc aaaatgttat cagagttgtg  24180
aataggattg acatagtctt aattatatga acactgaatg tttactaaaa agagatttta  24240
actctattgg gggtaatgag aaaggtattg ggtatgtgat aggggatggt gggaggaatt  24300
gggggagaga agaagctaaa tcatctttcc ttgtgggaac tcaatagaga atgcctaaaa  24360
ctgagaaact gagaatttc aatgcaaatg ttatctcaag acctggagat acatttctaa  24420
atgatcaggt aaatgagata aaaatatttg ccgccagaaa tgatagctca cacctgtaat  24480
cctagcactt tggaaggctg aggcaggagg attgcttgag cccaggagtt caaggccagt  24540
gtgggcaaca tagcaagacc ccacatttca aaaaaataaa aaattaaaaa gaaatagaga  24600
agtggtacaa tttgccctag cttttcttct tttcttttt tttttttttt ttgcaacaga  24660
gtttcactct gtcagccagg ctggaatgca gtggcacaat ctcagctcac tgcaacctct  24720
gccttctggg ttcaagcaat cctctcgcct cagccttcca agtagctggg actgcaggca  24780
tgcaccacca ctccgggcta actttttgt gtttttagt ggaaacaggg tttcaccatg  24840
ttggccaggc tggtctagaa ctcctcaact ctggtaatac actcacctca gcctttcaaa  24900
gagctgggat tacaggtgtg attacaggtg tgagccactg ctttgaagtg aacagagtct  24960
ggactggaac tcagtatttc ttatgctata tcttaaaatc ttagccctta ttgcaacaaa  25020
ctacttttat tttctaactt tgaacataga gccagactga cgtcagtcta tccaggaaac  25080
tgtccagaag gcaaaggaaa cagtggttgt tgattaaggt tggaccaagt gctgggaggt  25140
ggctttgcag tggctaattg ggggaaatgc tgaagtcaca aacagccttg cttctgcttt  25200
ggtcagctca tcctggacag cgtctctaag ctccctacat gtttaatgct ttggaagtct  25260
agtttttgtt gtttttaatg agagaagaga aaagcagagt gactttttcc ccctcaagcc  25320
tcaaggaggc tgacatagct cttgaaggca tgtgtggacc cagagaatac agggactgaa  25380
ggttatagaa ggattccaga ggatgagtgg agagtaccgt gtttctaaga cacctgtttc  25440
ttctcatccc tgaaatcagt gtcttcctgt ctgtggttat caactgttgg caaggaggca  25500
ggtatggcat agttctcatt gcttacacct gtgccggcat caaaacatgc agaaggggca  25560
tcatttctgt gtaagaggta ggtgttagaa aaataaaaat gcaattaaaa agaaggggca  25620
```

-continued

```
tcagcaacct cagaggaaac cccagagaca gtagtagaac attttttaa cccctgaatt  25680
gaatggagag caagtaaggg aaagtttgag aggcttttaa aaacaggaaa gctctccata  25740
atttcaaagt ctgcttaagg gcccagacca atggctttta gtttctttta tgaattgttt  25800
gtttgtttgt ttgtttgttt tgagacaggg tctcactctg tcacccagac tggagttcag  25860
tggcgcaatc ttggctcact gcagcctccg ccccccaggt tcaagagatt ctcctgcctc  25920
agcctccgaa ggagctggat tacaggctcc tgccactacg cctggctcat ttttgtattt  25980
ttagtataga tgaggtttta ccatgttggc caggctggtc tcgaactcct gagctcaagt  26040
gatctgcctg cctcggcctc ccaaagtgct gggactatag gcatgagcca ccatgcccag  26100
ctgaattttt gtttttgtt tttgtttttc ttttaatgct gtatcaccaa catgtttgat  26160
ggcacaaagg acaaagttgc atagaaaagt atgggttgtt gactgagtta aagtgttact  26220
caaaaggatg aggatgtaaa gaagttttag gaatccctga atcaatttat tttgcctata  26280
tttttctttc ttttcttttc tttttttttt ttgagatgaa gtctcactct gttgcccagg  26340
ctggagtgca gtggcgcaat ctcttctcac tgcaacctcc gcctcctggg ttcaagcgat  26400
tctcctgcct cagcctcatg agtagctggg attacaggca ggcaccacca cggccggctg  26460
atttttgtat ttttagtaga gacgggattt catcatgttg gtcaggctgg tctcgaactc  26520
ctgacctcag gtgatccacc cacctcggct tcccaaagtg ctgggattac aggcgtgagc  26580
cactgccccg acctattttg cttatatttt tctaagtaaa taaacatatc tgtgtaaata  26640
tgtctaaatc taaaagctct tttagtaact ttttaaaaag taagtgatta gaaaagtgtc  26700
atagtttaat tggaaatgtt tttcttttat cagtggtata taaaataatg gttcatttta  26760
taagtaatgg tatcttagat tgaaatacaa ggctgagcac tgtggctcat gcctataatc  26820
tcagcacttt gggaggctag ccccttgagc tcaggagttc cagaccgcct aggcaacata  26880
gtgaggccct actataaaaa atttaaaaat tagccagggg tagtggtgaa tgcctatagt  26940
cccagctact caggaggctg aggtgggagg atcacttgag cctgagaggt caaggctgca  27000
atgagctgtg atcgtgccac tgcactctag cctttttga ccctgtatca agaaaaaaag  27060
aaatagaaaa aaaaagaaat acaggtagaa aggtggaaag gaaccacgaa gtggcagttt  27120
ctgctttgct agagacccac aactggtgcc aaagagtatt tttagcttaa aaagaaagga  27180
gcacccggtg atgacaagta tatggtgaaa tagacactgg tataaactag gaaattaacc  27240
tttaataaaa gaatatgggc cgggcgcagt ggctcacgcc tgtaatccca gcactttggg  27300
aggccgaggc ggatggatca cctgaggtag ggagttctag accagcctgg ccaacatggt  27360
gaaaccccgt ctctactaaa aacacaaaaa ttagccgggt gtgatggcag gttcctgtaa  27420
tcccagctgt ttgggaggct gaggcacgag aattgcttga acccgggagg cggagattgc  27480
agtgagctga gattgcacca cccatactcc aacctgggca acagagccag actgcatctc  27540
aaaaaaaaaa aaaaaagaat acgacttaaa tgaatgaaat gtacgcaaac aaaacagaaa  27600
ccaaacaaaa ttccaacaaa ccgtcagatg ctgggaattc ctgacgggga aaaaagtcac  27660
acatcaggat actctggaaa caatggcact tgaatttctg gcaattcctg cagtcaggtg  27720
gtgtgctggt tatgaggtat tgtctcagct ccaaacccac cctcctacgc tcagcttcca  27780
ggttcctgct gagatgctgg aaaccacctt cttcccctgc agcttcctgt taggttctgc  27840
cagtaggagg catgatgagc cttgttctgg gagtgcagaa aaaaagaaat gaaaccagtc  27900
accactgcca gggtgaagaa ccactgtgga tgccacaaac agggacaacc agcaaacagg  27960
aaggagcagg acgcctctcc taccggcttc aaggttccct ctagtgcatg cttcctccaa  28020
```

-continued

```
gctcagaggt cctggcccca tctgggccgc ggtcccttct tgaagtctga ggctcagctc  28080
ttcgaggcct cttccctgaa cctctaagtt ctatcagtcc cacccgcttc cccttcttct  28140
ctagtcctag gtgtgggaaa tgttccctgc agctactatc tctgtgttgc tgggatatcc  28200
ccttttttacg tcttcagtcc tctaatacct atgggactat ttattcccta tgttaaattc  28260
cctctggcca ggtgcggtgg ctcatgcctg taatcccagc actttgggag gctgaggcgg  28320
gcagatcacc caaggtcagg agtttgagaa tagcctggcc aacacggtga aaccccatct  28380
ctactaaaaa tgcaaaaatc agctgggcgt agtggcgcac acctgtaatc ccagctagtc  28440
aggaagctga ggcaggagaa tcactcgaac ctgggaggtg gaggttgcgg tgagtggcga  28500
ttgtgccact gcactccagc ctgggcaaca gagtaagact tcgtctcaaa aaaaaaacaa  28560
aaaaattccc tctgactctg ctcagtacat gcgtgtggat ttcatgtgta tctctaaagg  28620
gttatcctcc tttaaccatg agaaatcttt tcagttagag ttcttatgag ctattataga  28680
agagccctga atcaggagtc agcaaaccaa gatccttgtc ccacaaggtc ctagtcccaa  28740
ttctgtcact gggtttcata acctcaccct caatttatct atccatatac agggcatgag  28800
agtacccaca tctctcctgg gatatgcaga ggaatcacgt gggacaatga atggatataa  28860
aaattgttcc aaagcctgta tatacgttgt agatataagg tggtggtgtg atatgtgaat  28920
tctcttggct aagtaccagt tggaggttag atagcgacct agaatttgtg ttaaagaagt  28980
agtagccttt gaatgcctgc ctttgttagc tattgcacat atgttaaact tactttcaac  29040
taaatggaat taaataattg atttattcag tggtccaagt gataacagag gagcacagcc  29100
aaacttcgcc agccccagga gggtgagagt ccagcttggt gacaggtcat ttgtgggaga  29160
cacatccttt ccatcgaaac ttctctcccc cctctctcca ccctgctctc cttctcaccc  29220
actctgccag atgcattgat cccacgggta cccagagcac atgtacctga ttagcctgga  29280
tccctcctct ctgagatgtt cctgcacccc atcacttcac ttccttcagg actccaacaa  29340
gttgggtcat cctgaatatt taaaaatttc tgttaaattc tttttgggtt tttttgttgt  29400
ttgtttgaga tagagtcttg ctctgtcacc aggctggagt gcagaggcac gatctcggct  29460
cactgcaacc tccaccttct gggttcaagc gattctcctg cctcagcctc cctagtagct  29520
gggattacag gtgcacgcca ccatgcctag ctaatttttg tatttttaat agaggcaggg  29580
tatcgccatg ttgcccaggc tgctctcgaa ctcctgagcc caagcaatcc acccacctgg  29640
gcctcccaaa gtgctgggat tataggcata agccaccacg cctggccaat ttctgttaaa  29700
ttttaccttc attattctct aattttagcc tgcttcattt ctgtcagcgg cacttgtcac  29760
tgttttctac attgtccatc gggaatgtat gccccattag gatggggact ttgtctattt  29820
tgtttaccat tatagtctca ttatttgaaa tagtgcctgg cgtgtttcca aaaagtacgt  29880
aacagatcaa tgagtgaatt taacaagtag acactattga tggtgttgtg ccaaatctgt  29940
cccccgcgaa cttggaatgg aaggatgtgc acaggcaagt atacagacgt agatgcctgg  30000
tgctgctgtt tttcaggaag atttgtccaa cctgctgtct tcatttggaa tttttaaaat  30060
aattttagac attttggtcc taaaaagagg accagatttg aagtcacctg atctcaaatc  30120
ctgtcttcac cattacttgc tgtacctctg ataaatgccc taatctcact catccttgat  30180
tttgtcatct gtgtaatggg aaaatacctg ttctgcctgc ctggggcttt acatttattg  30240
taaagatcaa aggaaatgag cttttccccc tcccacagtg tgttggagtc tggattcttc  30300
tggcagttgt ctcctggcca ctatcctctg ttgcaagttg agaaatgtgc tcttttcttc  30360
```

-continued

```
ctgtccaacc ctaaagatct agaaggtgtg gatccatcac agagagttac ataagatttt  30420
ctacccagat cccaattgaa gaaaatccac aggagacaag gcaggctctt ttatttattt  30480
tttattttat ttttttgaga tggagtctcg ctctgtcacc aggctggagt gcagtggcaa  30540
gatcttggct cactgcaacc tccaactccc tggttcaagc gattctcctg cctcagcctc  30600
ctgagtagct gggattacag gcacgtgcca ccactcccag ctaatttttg tatttttagt  30660
agagacgggg tttcaccatg ttggccagga tggtctcgat cttctgacct catgatccgc  30720
aaggcaggct cttttcatcc tacctataat gactagtcca tcattgcctc agtaacttga  30780
tcatcagccc tggtagcaga tatccctccc cgaagctgat gaaacagggc agagaggaag  30840
tatccaagag aaaagggagg gaggtttctc taaaacaaga cctaagagaa ggaacattat  30900
tgtctagaaa gaaagaaata attgaaagtt tctgaaaatt gagatttctt catttcaaat  30960
gaccttatta ttagcctgaa aaagcacaca cacaaaaaat ctcttcctta cgtaatagta  31020
atggtgggaa tcaaaatgaa tccatagatg gtggatccag atgggaatgc tgctacacga  31080
tagtagaatt gttctgggaa tccacagtgg gaaaggatca gttgtagcaa aaagatccag  31140
agttgtgcag agggaccatg tccagcagtg atcacttttc agtaaccgtg ctttcctgat  31200
catcatttta gcatcactgt ttggcaagac tgtggatggt aggagtggat accagttttt  31260
tttcactgcc tacatatgct tcataagctg tattttgtct tttttcctct acagacctct  31320
gtcttctttc ctttcatgcc cgtaatttat caaatagata tggttttaat actttgctga  31380
tttgacatag cttccttttt catttcattg attgctacta aaagatgcac aaggctttca  31440
ggtcctcaca cgaatgatga gataagatcc aacatcaaga atctgaagca aagacactcg  31500
tggtttcaga atctataaac agagtttggt aaggccgggt gcggtggctc acgcctataa  31560
tcctagcact ttgggagcct gaggtgggcg gatcacccga ggtcaggagt tcaagatcag  31620
cctggccaac atggtgagac ccagtctcta ctaaaaataa aaaaattagc tgggcatggt  31680
ggtgggcact tgtaatccca gctcctcagg aggctgaggc aggacaattc cttgaccctg  31740
ggaggcggag gttgtagtga gccgtgattg cgtcactgca ctccagcctg ggcgatagag  31800
ttagaccccg gctcaaaaaa aaacaaaaaa aaatagagct tggtgatttt ctgttgagtt  31860
tgagtttgtt ggaggaatgc ataatgatta ggattaggtg tttttctatt ttaacaagtt  31920
gacttctaga gacatagaag actattctga catgctactt aaaatttcca tacaaattca  31980
ggcatatttg taaaaaagaa aaaaatatca gtgcaaaata agcaagatca catgagacaa  32040
ctgaaaggca caaatactat ccagatgttt tttgttattg cccatttatt ttggccagtg  32100
aacatttgaa aggcccagat atgaagttca gggaccatgc actttgtgtc tctccccagt  32160
attaatgcac ttacatctat ctgcttttct cttttagtgg aggagataat gcctgttgtg  32220
tacagcaaga cagtgggtca ttgtgtattt acagaagtga tgtggattcc tcccagactc  32280
attagtgacc agggctgctg ggcctgtttg ggtttcctag actagagaag aagacaggaa  32340
ccaggatggg aagacggaca tgttacattt taagctggag cttcccctgc agtccacgga  32400
gcacgttctc ggtgtgcagc tcatcctgac tttctcctat cgattacacg tgagtcagtc  32460
cgctgggagg ctgtcctctc ccttgtgtct ttttagtaga ccagagtcct tcttctgatt  32520
tctagaagac ccgcactcta gcgggccctc ttccccatgt agtttgggat ttaacttagg  32580
ccaatggaat ggttttcact agtcatatta actgacatgg gctattaata gctcagaagg  32640
ttctaggcag tgtttcctgc atggctacgc taggtatgtg agggcctctt aggtttcagc  32700
caagacaggt gactcttagc acccagagcc cttcagatct gatggcggtt ggtattgttg  32760
```

-continued

```
gtccttctaa tgatttcaga ggatggcgac cctcgtgatg cagagcatgg cgtttctcca  32820
gtcctccttt cctgtcccgg gatcccagtt atacgtgaac ggagacctga ggctgcagca  32880
gaagcagccg ctgagctgtg gtggcctaga tgcccgatac aacgtaagag cgcttctcat  32940
tgtccagctc ctttgtttct ctgtgttact gttcattaag ttctttaaag aggggaatga  33000
aaagtagaaa tgtcaggcca ggcgcagtgg ctcatacctg taatcccagc actttgggag  33060
gcggagatgt gcggatggat cacttgaggt ccggagtttg aaaccagtct ggccaacctg  33120
gtgaaaccct gtctctacta aaaatacaaa aaattagcca ggcgtgtggt gcgtgcctgt  33180
aatcctagct acttgggaga ctgaggcagg agaattgctt gaacccagga ggtggaggtt  33240
acagtgagct gagatctcgc cactgcactc cagcctgggc aacagagcaa gactctgtct  33300
caaaaaaaaa aaaaaaaaaa aaaaagaaaa agaaaagaaa agtagaaata tcatttcttt  33360
gtgggtggca ccaaagaggg tctctgtaga attcttgcca tgaatttttt caaactacag  33420
agaaggtaca cgcatagtta cacctagaag ggaagagaaa caaaatctgt gtttgtcgaa  33480
gaactaaatt gcttattgct tttaggtcca cgtgggtgca cacacacaca ttgtgtcttc  33540
catacacacg cttggtcaca cgcaggatgt actccgaagg acactgtaaa atgatgatgt  33600
maaatgttca tgtaaagtat ttcagaaata ttactagcca tagtttactg aactcataac  33660
atatgccacc cctgarkkca ggcgtttacc taatatcatc tcctttaatc atcakggsra  33720
cctctgagct gcctgcattg tcctttcccc gcactccagc cacttgtccc atcactgccc  33780
ccgcttgctc ccttccagcc cccctggcct ttttgctgtt cctcaaaccc aagaagcagc  33840
tgccacctca gggcttttgc ttttgccatt tcctctgcca ggcatccatg tggcttatcg  33900
gaccatgcca ttcaggtccc tgttcagata tccccaagcc cagtccttct ctgacctgct  33960
tctacagtag cagcccctcc ttccaccatt cctcagccag actctccctc ctgccgcctg  34020
gcctactcag gatatgtgtt tgtgtgttta tttgctgtct ccctcagcct tgacagcagt  34080
ggcatctcaa atactatcac atccgtgcct agcacactgc ctggcagatg gtaagctcac  34140
agagatactt gtttaaataa tgaactcatt ttgcagaaga cgtaactggg gcttaaagtg  34200
attaattttc ccaaaggctc aaatcttgaa agataacaga gcctgtctgt gtgcagaact  34260
catgcatcta atcactcatt cctcactttt attttatcac aatggggacc atagaagttg  34320
agctgaggta cttctgaaaa tgaaaaaggg atgttatcgg ttattacagc cataaaccca  34380
gacttgtaga tatatagtgg gttttactgt tgctctgact ataatcaata taagttgtaa  34440
agaataggaa gctgcaacat atgaaatgaa tatggcactt tttgtttgaa tgtctatata  34500
tcagattaca ttaacagcaa gcaattattt cctcctttaa gggattatat gcttatggtt  34560
tgcattttat ctatatctct atatttaaaa gtgataaaga acttagcacc cagaaaagac  34620
caagaaaatg acaaaggagt tggaagtatg gtttcttttt tttgtctttg tgtaggggtw  34680
twtatttgta ttttattttt atttttgaga cagagtcttg ctctgtcacc caggctacag  34740
tggagtggca tgatctcggc tcactgcaac ctctgtctcc caggcttaag agatcctctg  34800
atttcagcct cctgaatagc tgggattaca gccatatgcc accacgcctg gctaattttt  34860
gttttctttg tagtagagat ggggtttcac catgttggcc agactggtct cgaactcctg  34920
gtctcaagtg atccatctgc ctgggcttcc caaagtgttg ggattagagg cgtgagcttc  34980
catgcctggc tttttatttt tttttatttt tatttttttt tgagagatga agtctttctc  35040
tgtttcctaa actggagtgt agtgagtggc atgatcatca ttgactacgg ccttgaactc  35100
```

-continued atggcctcaa gtggtcctcc tgcctcagcc tcccaagtca ctgggattgt aggcatgagc 35160
caccacacct ggcgaaaata cggtctgtta aaataattta aggaattctt tctcccgctg 35220
agataaagag gggtatttta aaaatagctt taaaacctgt aaaacatgga cactgacccc 35280
ttatttccat ccacagaaag aaagactgag agtaaatggg cttaaattgt tgcaagagag 35340
tttattcatc tttgaagaga agattattga tactgcagta ggccaccaag aacaagaggg 35400
tgctctgtgg gaccagcctg ggtgggcagc agcctgtttt attcatcttt gaagaaaaga 35460
ttattgatac tgcagtaggc caccaagaac aagagggtgc tctgtgggac cagcctgggt 35520
gggcagaagg gtagaaggaa aaggggagga gtctcccagg tgctcacacc acatcctcct 35580
cccgtgtccc agatatccgt gatcaacggg accagcccct ttgcctatga ctacgacctc 35640
acccatattg ttgctgccta ccaggagagg aacggtgagt cacaggtaga gcccattcag 35700
ccgctgctca ggactttcaa ggttagtggg ggcaacagag acaagcagaa ctggaaccct 35760
tgtgatgaaa atgtcaaaac ccgtgaatgc tcaacgatgg gagcaaatat gctgtccagg 35820
atttgtcttt ttcgtcctga tcttcagacc tgggaccgcc cccacccctc cagcatccca 35880
tggtccagca ggctagtgat ggttaaatgc catcattatc ccaccactgg cttagtgggt 35940
ttctctttta aaaaatataa gcctaattga gttgttcccc ataccacacc tatccacacc 36000
tataacagat gccaaagaca aattgctgtt catgcttttc agagaaaaac agagaacgtg 36060
ggtgactctc cccacattag cagtccagca ggagaacagg agtgcccctg tttcctgcca 36120
gaaggcacag tgtgcttatt ccttacagag ctctaggcca tggcatgtgt ggactcggca 36180
cgtttgtctg gtcggtggct gaggttttct ctaaaagcat ctacagtgtt acttggcaag 36240
cagacatcat ggagactata cacagacgtc tcacaagggg gatgactgca aatccagtat 36300
tgcttactga ttttatggca tatactagtg gcattattgc aataatagag ggaattttaa 36360
aacaaaagta gaaaacattg ccctacaaat caactatttt ttcattcctt tcattcttta 36420
gccttctgca gatcttttta tacagccatt gtagtgtaga aacacattgg gatccaagtt 36480
acttttattt atttaaactt ggaatataaa tacttcccca cacagctaca aagctgtgat 36540
actactttta gtggcagtat agtattcctt cagttagcca ttcagcacat gtagaagaaa 36600
ctctttccaa gttttttatg tattttaaca aaagtatttt gactattatt ttaacaaata 36660
atgtgtgatc agctttgcac atgcaatttc tctttccttc cgaatgattt ctttcagttc 36720
tgaagcacag gataatttcc aggtatcaaa taatctttat agccttcaac tgccagagtc 36780
aaacagccat cgtggttaat ggttaatgat tgcattgcag ttaccaccgt cctgaatgat 36840
cccaacccca tctggctggt gggcagggcc gcagatgctc catttgtgat taatgctatc 36900
atccgatacc ctgtggaagt catttcatat cctttctgtt aaagagtcca tgttaaggct 36960
ggatgtggtg gctcctgcct ataatttcag cactttggga ggccaaggtg ggaggatcat 37020
ttgaacccag gagttcacaa ccagcctggc caagatagtg agtccctgtc tctaccaaaa 37080
aaaaaaaaaa aaaaattagc caggcatagt ggcgtacatg tgtagtccca gttacttggg 37140
atgccgaggc aggaggattg cttgagtcca ggaattcaag cttgcagtga gcgatgattg 37200
tgccactgta ctccagcctc ggtgacagag tgagaccctg cctcttaaag caaacaacaa 37260
tttaaaaaaa atcaatggta gctcagtttt caaagaggaa tgattcctta gttgtctcaa 37320
gtagtaacag acgtgggagg ttttctcttg gaaatcatga cagggttata gcctcataaa 37380
aatggctgcg tctttgacat cttaggctac atgtctcaga aaatgactgt atgtctgcta 37440
ttcatatagg aacaaataat tcatgtcttg gtcctatttg tttccaagca attcttctag 37500

-continued

```
gtaagaatca tccatattta tgtcttaata atcatatgat atccctttta tgctaaggtt  37560
atgtgaaaca ttcttgccag tccctgtctg acctaaactt tggtttaatt ttgacttagg  37620
tcgactaatg gaaaatgaaa ccaacaccaa cactgcagag aagcaaacaa aagagaaggc  37680
attttaactg gggtcttagg aattacaatt ccagagacac aaacctagga agcagctaaa  37740
ttgtgttccg tacaggtgca attaggcagg ggctaagggt gttccaagtt tacacaactg  37800
gaagatttta gaagatggat ggatggctgg ttaacagctc aggatatctc tagtccatga  37860
tcaatctagt ttggcatagt tgtctgttta ggaggttggt catcaggctt ggtatataaa  37920
tagctcaaat caaatgtggc tggttttacc atttggccaa gttcaggtca gcttccatct  37980
gggtgtgtac atgacagagg tcctgcctcc tttcgagata cctctgccac agccaattcc  38040
atcttggatt ttctcttcat acttaacacc atgtggccct tcactcctta actgtccata  38100
cttatcagcc aggattctgg gagatggtaa agttcgcctg ggtgcagtat gtcagcatcc  38160
tgcttatctt cctctgggtg tttgaaagaa tcaagatctt cgtgtttcag aatcaggtgg  38220
tgaccaccat tcctgtgaca gtgacgcccc ggggagactt gtgtaaggag cacttatcct  38280
agaaaggcca tttctgaaga ctcagcagga ccgtggctgc ctcattgtca tcttctggga  38340
acatcttagg accttttgaa agagcccagc ggacacctgc gggcttgtgt gcttttccct  38400
cagagacaac ggttctttcc ggttttgctc tacacagttc cgtatcttca gagctcctgc  38460
agaattgtca gggactagtt tgtggaaagg tctgagagtt cctggaggct ataattagct  38520
ttttgggttt tccttctttg ccttagcgtt gaatttcagg agaaaattgc agtcagttca  38580
gacatcttgg aaagagtccc atctctggtc aagcagagac ttttcctctg ttgaactgag  38640
gaacacactg tgcatttcta ccttctgttg tgagccactc ttactctttt cagggctctc  38700
ttgtgacaaa catgccaatc actagcactt tgcacccctg ggcttctcca tttcccattc  38760
acagctttga tttccagagc tgaggccttt aactggagac ctggaggggc agggcccaag  38820
ggcaagggcc gcattagcac aggcaatcag ggagggccgc tgaaggacac ttggaccgtc  38880
cacctgcccc agcccaacag tcagtcatct gtcatcagct cagctgagca gccctggatc  38940
tttgccgtac tgtgactggg ctctttgccc tatttttccc tctgtctgtg cccctggatg  39000
gcaggctgaa gtcagagggg ctgtttcatt ctcagccccc tcagcagcac tgggggaaga  39060
aagcattgtc acaacaggtt ctttctggcc ctcacccaac agcctgggca cttggccctc  39120
ctcctccttg acagccctcc cccttcctgc aaaggacagg ggcgacaggg gttggtgttg  39180
ggattggctc ccgctgcctg acaaccacaa gtttatttgg aaggctagcg ggaagcccag  39240
cggctggcgt ttcccttgac taaggaacag ggtgcccatc agagtggggc gggcagcttt  39300
gggaaggaca caagaagcag taagagtgta aagaggatgc tggcctgggc aggccagtcc  39360
agcctggcca ctagcagaat accaagcagt ccagtggatt accctcgtgg ctaagcaagt  39420
gtctgcagga gcagagatgg ctggaagggg cctctgcaca cggaagatgg cttgttcagc  39480
ccattcacct cctgaggatg tgggcagtct cctccaagaa cacatggagc tgcttcctga  39540
tcccaagcag gtcattgcca ctggaaggac atggccccgg tgatccatgc ttcatgccca  39600
cccagaaaca cacccctcag tgtgtgcctc agtttacttt ggagatcagt tgtcgttttt  39660
agtgctcctt taggcttact aaaacagttt tggaaacaaa gctattttga agtattcaag  39720
cagaggaatt ccctaacact gaccccccttg tcttttttta atattcaggc tgttttatat  39780
gcctaaattt ttttcttaag atctaaacga aaaatagttt cttgtttaaa ttcacataag  39840
```

-continued

```
gcaatgagat atggaaagat gacaagatac gtataaacat tggtttgcat tttattaaat  39900
tattctaatg caaatcttgt ataaagaacc catgatgttt tgtaactttc taattaaaat  39960
gttcaaaatg aggccgagca tggtggttca ttcctgtaat ctcaacactt tgggaggcca  40020
aggtgggagg atcacttgag cccaggagct tgaggctgca gtgtgctatg attgcaccac  40080
tgtactgtag cctgggtgac agagtgagac cctatctgtt aaaataaata aataaataaa  40140
taaaaaagtc aaaatggaag atcacatgta cctttttcga gggaaagggt ttggaatggc  40200
aaagaatagg gagggcagag gttgcacaca cctgtcttta ttactcatct acagccatgc  40260
tttacaaggc tctgcctaac gaccttggaa cttccatgag gtctttggtg aaagtcccct  40320
agttcttccc caggtagatg agttttcagt gggattcaca tgccatgtga aatctacgtg  40380
ttggataatt atgactgtgt ctggtgaata tgaaattatt tacagaccag atgttgatag  40440
tttctgactc tgaatcacag catagctgca agaggtaaat aaaaagcaag aggccgggag  40500
cggtggctca cgcctgtaat cccagcactt tgggaggccg aggtgggtga atcacaaggt  40560
caggagatcg agaccatcct ggccaacatg gtgaaacccc atctccacta aaaatacaaa  40620
aattggctgg gtgtggcgac acgtgcctgt catcccaact atttagtagg ctgaggcagg  40680
agaatcgctt gaaccctgga ggcggaggtt gcagtgagcc gagattgcgc cactgcactc  40740
cagcctggca acagagctag actccgtctc aaaaaaaaaa aaaaaaagaa atatagagga  40800
ttttattaac tcagctccga cccatagcta agttaaggtt tgatgttatt actgaatatt  40860
tggaggcaga aagactcctg attttgccaa atgattagta cagtttcggc ttaagtcaga  40920
tgaggccccc ctaatattcc atcatgtaag gctaataaag caattatttc tttttttttt  40980
ttccttccaa cttttattgt agactcatgg ggtatatgta tgggtttcgt atatagctaa  41040
attgtacaac ctggggkttt kgtgtacaga ttatttcatc acccacgtaa taagcatagt  41100
acccagtagg tggtttttct ktgtcttttt cttkttcttt tttttttttt tttytgagac  41160
agagtctcac tctgttaccc aggctggagt gcagcagcat gatctcagct cattgcagcc  41220
tctacctccc aggttcaagt gattctcctg ccttaccctc ccgagtagct gggattacgg  41280
gtgcccacca ccatgcccgg ctaatttttg tgtttttagt agagacaggg cttcaccctg  41340
gtggtcaggc tggtctcgaa ctcctgacct caagtgatcc atccgctttg gccacccaaa  41400
gtgctgggat cacagcagtt tgatcacaga agttattatg gttggcattc tggcacacat  41460
ctttctaatc ttttttgttg tatgtaacct ttttagtatc acaaacaaca cttttataaa  41520
ccttgtgtag aaatcattgt tgctggttta tttccttaag atacattcag aaaacttatg  41580
accattgtta aggatcttaa ttcattgcca aaccacagcc aggaaagact gctaatttct  41640
actcccagca gcagggactc ctcgtttcag ataccaccat ggattaaagg acctcccaat  41700
gctctatcct tttcagatta ctggactctg cccgtttgtt tctttgtttt tgagatggag  41760
tctcgctttg tcacccagtc tggagtgcaa tggccccatc tccgctcact gcagcctcca  41820
cctccggggt tcaagctatt ctcctgtctc agcctaccta gtagctggga ttacaggcat  41880
gtgctaccat gcgcggctaa attttgtatt ttcagtagag atggggtttt gccacgttga  41940
ccaggctggt cttgaactcc tgacctcaag tgatctgcct gccttgcctc ccaaagtgcc  42000
gggattacag tcatatgcca ccaggccagg ctgagctgtt atttgtaagg ggtgggtggg  42060
gagcttttat ttactgaaac atatcctgta ttcattggaa catgttatca agcctgcgcc  42120
tctgggcgga ggctagggca gggagggcac agctcctaag gccacctggt ctttcaactc  42180
ctcccagctg ggacactgca ccgggaggca gcacggattc ctgtgtcatc aaggtgcctg  42240
```

-continued ggtcttggct tagggctgag gttggggcct tgggaagggt ttggattcca agtcccttgg 42300
ctgcaaggat gcccccaaga gcgaggaggg ccaagattaa gattcgactt ccttcactag 42360
ggcctttgtc ctcccaggag ctcccaggtt ctctggcgat tggggggtg aggaagggtt 42420
acaacgttca tttgtggtca gttagatgag aagtgactct gccagcgtcc tttgacatcc 42480
ccggctaaaa ggtgcgcctc ttagagcccc agcccacctg ggccctcctg ctctgccctc 42540
ggccagcgcc cctccccgag acatggcccc tcggtcgggg gtggggagag ggagctgggg 42600
gcaaaacctg ctccttcctt ccttctccca tttccctggc tcccgccggc caccctggga 42660
ccgcagccac gtctgaaagc tcctcaccag gcagcgctga agattgcggg gcagcgccga 42720
gggttgttgg ccggcgcgcg gggagtagag ggcgcgggcc gcagtgccgg gctccggagg 42780
gagctctgcg ccgggtcctt ccctgtggta gccccaggac acccccatcc tcaacatccc 42840
attctgggac tcctgccctg ttcccagatt cgctctgcct cgagtctcca ggagcttcca 42900
gtggcttggt tacccccgac tcttcgtcca tgcctcttag agcccctttc ccagcctcac 42960
tgggtgtccc ttaatagtct tgggacctta aggagcaagt cagcccctgc ggaacctccc 43020
agtgaagaga aagagctggc tgtgcggtgg aacttggaag agacgacgtc tgggagcttt 43080
tgctgagccc agggggagag gcgtccctct ggctgctgct ccagctctgg cagacacgcc 43140
aagctttgag gtactttggt tcttcattct ccaccggagg tgtccccaca ctcggttggg 43200
ctgggggccg ggccagtggc ccagctgtga cgctcctctg tcctgcacca gagacctggg 43260
ttggcgggaa gagctggggg tggcttttcc atcagcaacg tggaaagttc atctcccctg 43320
ctagcgctgg tttggaagtg tcttgctggg gcttcggctg cacgcgggaa tcctcactgc 43380
gcagggcagg ggtcggggtg cgggttctta ttccatactt gggtctcaaa gggtgtggct 43440
ttcaaaagct ctccatgaaa ttcttgagaa aaaatagctt ggtgagttaa tttgcaacca 43500
gactcagggg aagtggagtc gtgcctcact gcctctaggg ccttgatgtt aggctttagg 43560
aaaggccctc tgggccccag gacagtacag gtgcctagga aatgtttttt tgtttgtttg 43620
tttgtttgtt tgtttcgaga cggagtctcg ctctgtcacc caggctgaag tgcagtggcc 43680
tgatcttggc tcactgcaac ctgtctcctg ggctcaggtg atttcctgcc tcagcctctg 43740
gagtaggtgg gattacagac gcccgccacc acacccagct aatttttgta tttttactag 43800
agacggtgtt tcaccatgtt ggccaggctg tccaattcct gacctcaggt gatccgcccc 43860
gctgaggctc ccaaagtgct gggatcacag gcgtgagcca tggcactggg cccaaatttt 43920
tgtttttgtt tttgtttttt cagatggggt ctcactctgt cacagagcct ggagtgcaat 43980
tgtgccatct cggctcactg taatctccac ctcctgggtt caagtgattc tcctgcctca 44040
gcctcccgag tagctgggat tataggcatg agccactctg cccagctaat tttagcgatg 44100
gggtttcacc atgttggcca ggctggtctt gaactcctga cctcaggtga tctacccatc 44160
ttggcctccc aaaacactgg gattacaggc atgagtcacc gcacctggcc taattttttt 44220
tttttttttt ttttttttga tatggagttt tgctcctgtt gcccaggcta gagtgcaatg 44280
gcacaatctc ggccactgta acctgtgtct cctgggttca agctactctc ctgcctcagc 44340
ctccaagtag ctgagattac aggcacctgc caccagacct ggcctaattt ttgtattttt 44400
agtagagata ggttttgcct tgttggccag gctggtcttg aactcctggc gtctggtgac 44460
cacccaccta ggcctcccaa agtgctggga ttacgggcgt aagccactgt gtccaatgtc 44520
tagcaaatgc aaatgttgac ttcctttctc tctcctttta cacagaggca aggcagtcaa 44580

-continued gaattgcatt ttggccaggc gctatggctc acgcctgtaa tcccaacact ttgggaggcc 44640
aagtctgcga tgccctcatc tctacttttt taatttcgtg tgacctgttt gtattatttt 44700
tctaaaaatt aaacatgtaa taaatatgtg cccccagaaa agaatcaaaa aacggaagaa 44760
tttagagggg aaggggacag tccttccagg atggaagagt tcactggaca aaggcttagg 44820
agtgtgaccc accacagggc cctgcactgg gagtctggct cttggactta agcccctgcc 44880
ctgcctcttt cttactgggt attaatgtct ctgagcccca ctgcttcaat taaaacagat 44940
agggatggtt atttctacct ccaagggact tgggaggata acattcaatc atgaagatga 45000
aagtgcatat cacagggcct ggctgactgg ttctccctaa ctttgcaccc ttggccaatt 45060
gtccactgtg ctgaatgtaa gtctccttat cagaaagctc ccagtgagga actggtcttc 45120
tggagactct gtgtggcata gagtgattca accaccttaa gaagacctct ggctttcctg 45180
gaacacaggt aacaaacacc ttagcttggg atcaagatcc tccctaccca gggaagggct 45240
gggctggcca ggacaactgt gtttgggcca gagcagcagg gtcctgcact ctgcaggggg 45300
caatcacagg tgggagaggc ccacagcctg ggatcagaag tgccaggagc ttcggaacag 45360
gagtcctgga gtcccagctt tcttgctgtc tctctaagcc ttgagtcttt cacctgaaaa 45420
attgacatca tcatgcccac ctcagggccc agagttaagt tatccagtgg actcgaagca 45480
cctagcactt gtgatcattg aagtcagcaa atatgagttc ccttcctttc tggcactctg 45540
ttggcaaggg agctcaccat ccatcagcca gcactggaaa aagtacagtt gcacttgtag 45600
cggaggtggg ggctactct cctcatcttc caggttttcc aggagtgggt gtggggatcc 45660
agaaggcagc tcgggagtca gcaggtgaca gaggtgttgg gcatcctccg ctcactcctg 45720
tccccgcatt gaggcgaagg agcagaggtg agatctgctc acaagttaga ccctggcttc 45780
tctcagtggg cagtgtggac aggggaaggg ggcaggcaag gagcaaagga tgcaggagca 45840
aggagaaaac ttccaggctc ctcccttcca aagtcaccca gccttgagat cattgcagat 45900
gcaacaggtg caaacagaag aacactttag gaccttggaa tgcgggaggc tggctcagtg 45960
ttccttccac cctgtgagaa atgcgtgaca ttcttaaggt ccactaaagg ctcagggtgg 46020
ttggacgcca gaggatggcc tgggagatac agggattgga agggtaggtg gcctgtgggt 46080
gtctcctctg tggggagact caccaggtgg agggggttct ttctctccag atgtagctca 46140
gcacagggac agtaacagta acaggggcat gtgtgtaagg aatgcttccc caggccctcc 46200
cctcataggt gtttgcagca gcatccatca caacagctct aagaggttaa atattgcaaa 46260
tcccattcta cagaggtgca aattgagcct cagagaagtt aagtcacttg ccccaggtct 46320
catagctccc cattggcagt gctgggattt ggagccagct ctctcgcttc catccatcag 46380
gagaccccgc cagttcccag ccatttggag aaatgcccta ctcagactta ttcaacctca 46440
gcaagcctgg tggtggtgtg acatccgcct aaaccgtcat caagcccttt agctccacaa 46500
cccaaaaggg tctctctacg agttatcctg aagcaaaagg caggcaggac agctctgttc 46560
ccaccctggg gagctttcta tgtacagggc tgtctctctg tagggctctg atctcctctc 46620
cttcctgctt tgccagatgt cgagacatct cccatggatt tgtgatcagc gttgcagctc 46680
tcccagcagc cctggacggt ggtgagtccc ctcagctggc caggacagta ctctgctctc 46740
acctctctgc ttcttgggct ccatcccagc tccccatcaa ctgatcttct tgcaaaccca 46800
cagggctcca ggacaccctc cttctggagc ccatgctgcc tacagcactt cactccccac 46860
cagtgatgac aacagttgct gttctttgtc cactttattt acttgtttat ctttaatgac 46920
aaaagttttt tttttgttgt tttttttttt ttttttgaaa cggagtctca ctcttcactc 46980

-continued

```
aggctgcagt gcagtggcgc aatctcagct cactgccacc tctgcctccc aggttcacgc  47040
cattctcctg cctcagcctc ccgagtagct gggactacag gcgcccacca tcacgcctgg  47100
ctaatttttt gtatttttag tagagatggg gtctcactgt gttagccagg atggtctcga  47160
tctcctgacc tcgtgatccg cccgcctcgg cctcccataa tgctgggatt acaggcgtga  47220
gccaccgcgc ctggctgaca aaagttttat acctgcctgt taaaaaaatt atataataca  47280
gaagcacacc ttgtaaaagg tgcaatcctc agttatgggc atgactgcgt gttcccttcc  47340
cccatcttca ttataataac cccccaatcc ccccagatcc tgtgagccag gtaccggaat  47400
tatccctctt tcacacacgg gtaaagtgat ccgtcacaga gagatttaag tgatcttcat  47460
aagcaagatc ataggctagg aagtggcaga gccaggattc aacctcggcg agcctggtgg  47520
tgctctgaca tccaccgaag cccccatcaa gccctttag ctccacaacc taaaagggtc  47580
tctctaagag gtatcctgaa gcaaaagaca ggagttctct ttgaaacata gtatttctct  47640
ctacagatag atagcctgta ggtatgtaag taggtgggtg ggtgggtagg tagacagttt  47700
gatgatatcc cacattattc tgcaactgga cttctgctgt gagcacagac tatattctgg  47760
cctatgtctt gactccgtat tcctgggaaa gtgctcgact gagaccttgg gagtcttggg  47820
aagtccaatg ggtagggtag ccgaatctga gggctgatcc ctgagggcac tgggcagtaa  47880
ttggggcatg ggatgggcat gagggcccgg gtccctaaag ttgcccactc cacccgaagg  47940
cccccagccg cccgcatgtg gctgccacgg ttctccagca agacagtgac agtgctcctc  48000
ctggcacaga ccacctgcct cctgctcttc atcatctccc ggccagggcc ctcatcccca  48060
gccggcggcg aggatcgtgt gcacgtgctg gtgctgtcct cgtggcgctc gggctcatcc  48120
ttcttgggcc agctcttcag ccagcacccc gacgtcttct acctgatgga gcccgcgtgg  48180
catgtgtgga ccaccctgtc gcagggcagc gcggcaacgc tgcacatggc cgtgcgcgac  48240
ctgatgcgct ctatcttttt gtgcgacatg gacgtgtttg atgcctacat gccacagagc  48300
cgaaacctgt ccgccttttt caactgggca acgagccgcg cgctgtgctc gccgcccgcc  48360
tgcagcgcct ttccccgagg caccatcagc aagcaggacg tatgcaagac actgtgcacg  48420
cggcagccat tcagcctggc ccgggaggcc tgccgctcct acagccacgt ggtgctcaag  48480
gaggtgcgct tcttcaacct gcaggtgctc tacccgctgc tcagcgaccc cgcgctcaac  48540
ctgcgcatcg tgcacctggt gcgcgacccg cgggccgtgc tgcgctcccg ggaggcggcg  48600
ggcccgatac tggcacgcga caacggcatc gtgctgggca ccaacggcaa gtgggtggag  48660
gccgaccctc acctgcgcct gattcgcgag gtgtgccgca gccacgtgcg catcgccgag  48720
gccgccacac tcaagccgcc acccttcctg cgcggccgct accgcctggt gcgcttcgag  48780
gacctggcgc gggagccgct ggcagagatc cgcgcactct acgccttcac cggcctgacc  48840
ctcacgccac agctcgaggc ctggatccac aacatcaccc acgggtcggg gatcggcaag  48900
ccaatcgagg ccttccatac ttcgtctagg aatgcgcgca acgtctccca ggcctggcgc  48960
cacgcgttgc ccttcactaa gatcctgcgc gtgcaggagg tgtgcgccgg cgcgctgcag  49020
ctgctgggct accggcctgt gtactctgcg gaccagcagc gtgacctcac cctggatctg  49080
gtgctgccac gaggcccaga ccacttcagc tgggcatcgc ctgactgaga actctgggcc  49140
ttagagcagg ccccgaactg tggtcgccag gcccaggagg cgactgcatg gtggagaggg  49200
agctggggcg catggggaag caggtcccta ctatcaaccg ggagtttggg gtcctcccct  49260
gaagtaggca aggactgcac gtttctttct ctcctgattc tcggttttcc tttgagtctt  49320
```

-continued

```
ctggagctgc cttctcatca ggtgcactct tcatggaaag caactcttgc ccctacctct  49380
tctgggcgca gggagtaagt tactgctaaa ttaaattaaa tgtgtgccag gccgggtgcg  49440
gtggctcatg cctgtaatcc cagcattttg agaggctgag gcgggtggat cacctgaggt  49500
caggagttcg aaaccagcct ggccaacata gtgaaacccc ctctctacta aaaatgcaaa  49560
aattagtccg gcgtggtggc acactcctgt aatcccagct acttaggagg ctgaggtggg  49620
agaatcactt ggactccaga ggtggaggtt gcagtaagct gagatcatgc cactgcaccc  49680
tagcttgggt ggcagagcaa gactctatca aaaaaataag taataaattt gttcaaaagt  49740
cctgcaatct agtgaactgt aacctcattt tttctctctt ttttctttaa ttgcatgatt  49800
ccatttattt aaagcagaaa aactagtcta tggtgataga ggtcagaata ggggatactt  49860
tgtagggagg atttgactgg gatgtaacct tatttattat gtaaacaaac tacaacttga  49920
ccaggcagta tattcttgta agaagaaagg agtcttctcc aatcatagca gccagccttc  49980
agccaggggc agactgcaga ctgaccagat gtgtccaaat tagacaaagg ttgagctgta  50040
accaatcagc ctatatccaa tgccacttcc tttttctgtt tataaacgct gcttgcccac  50100
tgttgctggg tggaggtctc tgaaacctct ctaatgtaga tctctcattt aatggggagg  50160
gtttggcctt taatcaccat catccctgaa caaagactga ccaattggac tcaaatgcta  50220
ttgaactatc tttattgcat ggactttgag ttatttgatt ttgactagtt gtttgttgaa  50280
actcctgata aggagtgtac ttcagtttct tggcattgtc cactcatagc catcataata  50340
gtctccctgg tcgggcacag tgactcacgc ctgtaatccc agcactttag gaggccaagg  50400
caggcagatc gcttgagctc agaagttcga gaccagcctg gccaacatag tgaaaccctg  50460
tctctgttaa agatacaaaa aatagccagt gtggttgtgc atgcctgtaa tcccagctac  50520
tcaggaggtt gaggcaggag aatctcttga atccaggagg tggaggttgc agtgagccaa  50580
gattgcacca ctgcactcca gccagggtga cagagcaaga ctccatctta aataacaata  50640
ataggccagg cacagtggct caagcctgta atcccggcac tttggaaggc caaggcgggt  50700
ggatcacttg aggtcaggag ttcaagacca gtctagccaa catggtgaaa ccctgtctct  50760
actaaaatac aaaaattagc cagtgtggtt gtgcatgcct gtaatcccag ccactcaaga  50820
ggttgaggca ggagaatcgc ttgaacctgg gaggtggagg ttgcagtgag ccaagattgc  50880
gccactgtac tccagcctgg gtaacagagc gagactccct ctcaaaaata ataataataa  50940
taaaataata ataataatag tctctctgat gtgttgactc ccctgggaag tcttacatac  51000
tcctatgcag ccattcttta taaatcaact ggtctgttag ggttagagta acaaaaacat  51060
gaagaaagca taaagaatca ttcaactaag gtgaaattgt gaagtcaata ctgaaacaaa  51120
acaagtccat tatgatggtg acaggaaatg gagtcagggc ccaaggtttt ggtcaatctc  51180
tcaaaattga gaggctgacc aaaaggcaga aatgtttaaa ttcaattaaa tttggcccaa  51240
agttcccagc actttgggag gccaaggtgg gcggatcatg aggtcaggag atcgagacca  51300
tcttggccaa catggtgaaa ccccatctct actaaaatac aaaaaattag ccgggcatgg  51360
tggcacatgc ctataatccc agctactcgg gaggctgagg cagaggaatc actagaaccc  51420
aggaggcaga ggttgcagtg agctgagatc gtgcactgca ctccagcctg gtgacagagc  51480
aagactccgt ctccaaaaaa aaaaaaagag aatttggccc aaagctgctg ccatacctgt  51540
tgaactgcaa cctaacttaa tatttaagta aactgcctcc caactgagac tatattcttg  51600
taacaaatag ttgaatctca gcaagtcaca gcagctgtgc tttaaccagt cacaggctgc  51660
caactgatca gaccaagtcc atataaggca aatgctgagc tgtaccccat cagactgttt  51720
```

-continued ctctgtgtta cttccaaaaa attcggcctg ccagtgtttc tgggtggagc actttgaacc 51780
tttactggtt cagggtgctg cccgattcat aaattttctt tgctcaaata aagtctgctt 51840
aatttgtcta atgtttttct attaacagtt cagatgactt ggcctctacc caaactcttt 51900
ctttcccta gactctcctc tcttggaatg catcctgaag cagctgaaaa ggggtgcccc 51960
gggcccagca gggagcaaaa tctggtgata ttgcttctga acatcccaca tgtgccacac 52020
acgtgcaccc ccccacacac acacatgcac actcacatgc acactcacat gcacactcac 52080
atgcacactc acatgcacac tcacatgctg cacactcaca tgcacacaca gcctggactc 52140
tgttcccctt atgcccctgg caccacactc catcaaagcc attgaccttt atatccccct 52200
gtgtcttcag taagaggtat atcaggccag acatggtggc tcatccctgt aattatcaat 52260
tacccggtct ctggtattct gttacagcag cacaaaaggg actaaaatag gctccttaac 52320
aaaaagattc acagacaaga agtttgtttg tttgtttgtt tgttttgaaa tagtgtcttg 52380
ctttgtggcc caggctggag tgcagtggtt ccatcttggc tcactgcaac ccccacatca 52440
ctgactcaag agattcgccc atcttaacct cccaagtagc tgggactaca ggcacatcac 52500
tatgccaggc taatttttgt attttggggg gctacatgtg tttcagtatg tagcccacgc 52560
tgatctgtaa ctcctgtgct cagccttccg aagtgctggg attacaggtg tgagccactg 52620
tgcctgccca agaacagttc attaatacat gcagcatata tcacacagga caaacctaaa 52680
tgaaaagtaa caacacagtg gctcagaaca ctgccttaca cagcagattc caaaagacac 52740
aataaatttg tagagaaata acaggaaaaa gaaagtttta ggcctccaaa ggtgagaaac 52800
tgtgcatagg taaatatctg agaggaagcc gatgcagcag gatttctctg cggtgcctct 52860
ggtaccgccg ctggctgggc aaagttaagg gttgtctcca gtgaaggaga gtttatattg 52920
tgcctttagg cagaaagggg agggaaacct gaacttttcc tgtattttct gcttcttaat 52980
tgccttaagc tgaaaatcat ttttatgtga aagaggcata atctgggatg acgcctctgc 53040
tttcctccac ctgaagagaa cctgtgtgct gctcctttgc tttggacctc tacctctgcc 53100
acggagaaag cccaggccaa cctgctggac aagcagggac cgtgagaagg agagttcagg 53160
tgtcccaatc caggccatcc tagaccagcc agcccctcac gagccccagc tgatcagcac 53220
gcagccactt ctgctatctt ctactggcca aagtgagtcc agggttcacc cagattcaga 53280
ggtggggaaa ctgagtccac cacttgagag gagtagctat aaagacatac gagcgagacc 53340
agctgagccc agcactgctg gccaagttga agactttagg accagccaca catgttccgt 53400
ggccacacgt ggccagtggc tccatattgg acaatgccaa tcagactcct cattctcatt 53460
acatttgtat acccttctgg ccctgagatc tttctatatc cgcatctgac taagatgctc 53520
tactagagaa cagcatctac ttcatatttc catcctttgg aaacccaaag agccagcaga 53580
agttttgact ttgcaattga tcctacacgt tcaaatttct agcatctatc agaccgtgta 53640
agatggaaga gagacttaca agggctccca ttacctagcc cagggtatgt gctcagggct 53700
cttggcactt ctcctcttgg ttacacatgg ttcagataat gttggccact tcttaacatt 53760
agtttctcat ggcttgattc ctaggaagca ttattcctcc cattttaaga gggcagccag 53820
ttgagtgatt caatgagtca ggcccagtac caggccccag ggacacagta agagacagag 53880
tacacatagc ccttgctctt gtctggggtg cagacactaa acaaataatc aaacagatta 53940
aacatgcaat tataggtttt aattatgccc taagaaaaaa caaagccggg ggcagtgaca 54000
caactgtaat cccagcactt cgggaggctg ggacaggagg attgcttgag gacatgagtt 54060

-continued

```
caagaccagc caggcaaatg aatcttgtgg gatagcactg tcaggctggg ctctgagcct  54120
gcatcaaagc agaccctgtg tctacaaaac atttttaaaa gttggtcaag catggtggta  54180
cacggctgta gtcctagcta cttgggaggc tgaggcgggg gtgttgcttg agcctagaag  54240
ttcgaggctg cagtgagcta cagtgagctg tgattcatcc cactacactc caacctgtgc  54300
gacacagcaa gacatcatct ctaatttaaa aaaaaaaaaa aaaaaaaaga aggaaagaaa  54360
gaaaaaagga tgatacaaaa taagccgagc gtggtggcac atgcctgtaa tcccagctac  54420
tcgggaggct gaggcaggag aatcgcttga acctgggagg cggaggttgc catgagctga  54480
gatcgcgcca ctgcactcta gcctgggcaa gaagagcgac actccatctc gaaaaaaaaa  54540
aaaaaaaaaa gaggcaggtg cagtggctca ctcctgtaat cccaggactt tggtaggcca  54600
tggcaggtgg atcacttgag gccaggagtt tgaaaccaac ctggctaaca tggcaaaacc  54660
tcagctctac taaaaataaa aaaaaattaa ccaggcgtgg tggtgcgcat ctgtaatccc  54720
agctacttgg gagactgagg caggagaatc acatgaacct gggaggtgga ggttgcagtg  54780
agccgagatc atgacattgc actctagcat gggtgacaga gggagactgc atctcaaaaa  54840
aaaaaaaaaa aaaatgaaga agcggctggg cacggtggct cacacctgta atcccagcac  54900
tttgggaagc caaggcgggt ggatcacgag gtcaggagtt ccagaccagc ctggccaaca  54960
tggtgaaacc cccatctcta ctaaaaatac aaaaattagc tgggcgtggt ggcagacgcc  55020
tgtaatccca gctacttggg aggctgaggc aggagaatca catgaacctg ggaggcagag  55080
gttgcagtga gtctagatgg tgtcattgca ctccagcctg ggcaatagag tgagactctg  55140
tctcaaaaaa aaaaaagaag caaatatgaa gactatgtag tcttgaagag gacacaatct  55200
tttgaacaag acacaaaatc cacaaactgt gaagaaagaa ttcactttca aaatataata  55260
aataggacaa aactttttgg aatttgcttg tggtgacgtg gtgatctgat ctcacaggtc  55320
tatacatcta attttatacc ttacatataa atattttata taaattatgt ctcaatactt  55380
ttttttacag aagcattggg ggaaaatacc ataaagtagg ttaaaaaaca gatgacaagc  55440
tagcagaaac catttgccat aaaaataaga gcaaaaccaa gaggaagcgg aaagtcaaca  55500
gaaaaatgag caaagccctt taacaaagaa aaaagaaggc caggccgggc gcagtggctc  55560
acgcctgtaa tcccagcact ttgggaggct gaggtgggtg gatcacctga ggtcaggagt  55620
ttgagaccag cctggccaac atggcaaaaa cccgtctcta ctaaaaatac aaaaattagc  55680
cgggtgtagt ggcacacgcc tgtagcccca gctacttcag aagctgaggc aggagaattg  55740
cttgaacccg ggaggcagag gttgcaatga gccgatattg ctccactgca ctccagcctg  55800
ggtgatagag caagactccg tctcaaaaaa taataataat aataatgata ataaaaagga  55860
gaaaaaggaa ggctgttgat taataagcat gaaaagatgc ttagctgccc agggaattaa  55920
agaaacgtag gttaaaacaa catcaagtaa catttttaac ccatcagcta tgcaaaagtg  55980
aaaatgatag atttagccat gtataggtgg tggtagcacc caccaccacg cctggctaat  56040
ttttatattt ttagtagaga cagggtttca ccacgttggt caggctggtc tcaaactcct  56100
aacctcaggt gatccacccg ccttggcctc ccaaagtgct gggattacag gcatgaagca  56160
ctgcgcccgg cctttttaat tttttttgga cagtcttgct ctgttgccca ggctggagtg  56220
caacggcaca atttcggctc actgcaacct ccacctccct ggttcaaacg attctcctga  56280
ctcagcctcc caagcagctg ggattacagg cacccaccac catgtccagg taatttttat  56340
gtttttattt tatttattta tttttaattt tattttttga gacagagttt cgctcttgtt  56400
gcctaggctg gagtgcaatg gtacgatctt ggctcataca acctctgcct cccaggttca  56460
```

-continued

```
agcgatttta ctgcctcagc ctcttgagta gctgggatta cagacattcg ccaccatgcc  56520
cagctaattt tgtattttta gtagagaagg ggtttctcca cgttggttag gttggtcttg  56580
aagtcccaac ctcaggtgat ccgcccgcct cagcctccca aagtgctggg attacaggtg  56640
tgagccactg tgcccagctc cagggctggt tatctttgta ttttcaggta gccagttctc  56700
cccacgccct ctactgaaag atctcatgca tcacattttc tccctttggg gtaagaccag  56760
agaacctggc ctgtcctgca agtcttgtgt tattctgatc ccagtcttca tgaactccac  56820
tcattcattc aacacacatt atgggttgag caccaaccag gcatcgggct tttggaggag  56880
ctggagatag agcaggacca agatagacaa aaagcaaaaa cccctgccct gtaggaactt  56940
gcattctgat ggtgggacac agccagtgaa tgagaagttt gataaatggc taaattattt  57000
agcatattag aaagtgccaa agattaaagt ggagagggat caggggatta ggaatgtatg  57060
tgtgtttagg ggtgtgagtt gttaattttt tttttaaga cagagtttca ctctgtcacc  57120
caggctggag tgtagtggca cgatcttggc tcactgcgat gtctgcctcc cgggttcaag  57180
ggatgctcct gcctcagccc cgctgagtag ctggaaatac aggcgttcgc caccatgtct  57240
ggctaatttt tatattttta gtagagatgg ggtttcacca tgttggccag ggtggtctcg  57300
aactcctgac ttcaggcaat ccgcctgcct cagcctccca gagttctggg attacaggcg  57360
tgagccattg tgcctggctt tttttttttt tttttttttt tttgagactg agtctggctc  57420
tattgcccag actggagtgc agtggcgcga tttcggctga ctgcaaactc tgcctcccag  57480
gctcaagtga ttctcctgcc tcagcctcct gagtggctgg gattacaggt gcctgccacc  57540
acctggctaa tttttttgta tttcaagacc aggctggtct caaactccta acctcaagtg  57600
atccacctgc cttggcctcc caaagtactg ggattacagg agtgagccac catgcctggc  57660
cttttttttg ttttttgttt ttttttgaga cagtgtctca ctttttcacc caggctgaag  57720
tgcagtggag tgcaatggca cgatctcagg tcactgcaac ctccacctcc cgggttcaag  57780
taattctcct gcctcagtct cccgagtagc tgggattaca ggtgcatgcc accaggctca  57840
gctaattttt ttgtatattt agtagagaca gggtttcacc atgttggcca tggctggtct  57900
cgaactcctg acctcaaatg atccacccgc ctcagcctcc caaagtgctg ggattacagg  57960
catgagccac tacgcccagc agtttcttcc acttctaata gactctgcta gtctaggaaa  58020
tgtaccaaaa agacagcatg gttaaaggtc agtatttcat gaccttttt atacttccta  58080
tttttatttt atttaggttt cttggttgat acaaaacgtc aattgtagtg gtagggaacc  58140
tgcataagga agcttcctaa acagaggctt caagagagaa cactaatagg ccgggcatgt  58200
tggctcatgc ctgtaatccc agcacttcgg aagcccaagg cgggtggatc acctgaggcc  58260
aggagttcaa agctggcctg gccaacatgg tgaaaccccc ctctactaaa aatacaaaaa  58320
ttagctgggc gtggtggcag gtgcctgtag tcctggctac tcgggaggct gaggcgggag  58380
aatcgcttga acccgggagg tagaggttgc agtgagccga gaacgtgcca ctacactcta  58440
gcctgggcca gagagtgaga ctctgtctca aagaaaaaaa aaaggtcggg ggaggcttga  58500
gagaatgggt tcactttctt cctccatgtg aggacccata ggtagtgcca gcagtgaggc  58560
acaggccctt tccagatacg caacctacag gcgcctatat cgtggacctc ccagcctcca  58620
gaaccatgag aaagtaaatt tctgttcttt ataaattacc cagtttactt aaaaaaaaat  58680
ttttttgag acagggtttc cctctcttgc ccaggctgga gttaaggagc accatctctg  58740
ctcactgcag tctccgcctc ccaggctcaa gcaatcatcc taccttagca tcctgagtaa  58800
```

-continued

```
ctgggattgc aggcatatgc caccacgtct ggctaatttt tctatttttt gtagagatgg  58860
gatcttgcta tattgcccag gctagtctcg aactcctggg ctccagtgat cctcctgccc  58920
tggcctccta aagtgctgcg attgcaggct tgagccacca cacctgacct tgcttattcc  58980
ttttcacaat ttctctgcct acattttaac gggatctctg aagggaggtg agtcaaaagt  59040
gtgatccagt tttgttgtat tgaatagaag gtctttaaat ttttattgta tttaaaactc  59100
ggtagcagct gggcaaggtg gctcatgctt gtaatctcag cactttgaga agctcaggca  59160
gggaggattg tttcaggcac aagttcgaga tcagcttggg gtaacacagt gagaccccat  59220
tcttttttta atttcttttc ttttcttttc ttttatcaga cagagttttg ctctgttgcc  59280
caggctggag tgcaatggtg ccaccttggc caactgcaac ctccacctcc caggttcaag  59340
cgattctcct gcctcagcct cctgagtagc tgggactaca ggcgcgcacc actacgccca  59400
gctaattttt gtatttttag tagagaggag atttcaccac gtaggccagg ctagtctcga  59460
actcctgacc tcaagtgata caccagcttc ggcctcccaa agtgctggga ttacaggtat  59520
gagccactgc gcccagccga gaccccattc ttagacacac acacacacac acacacacac  59580
acacatgaga gagagagaca gtgagagaga gaattagaga attagctggt catggtggtg  59640
catgcctgta atcccagcta ctcaggacgc tgaggaatga gaattgcttg aggcagaggc  59700
tgcagtgagc caagatcgtg ccactgcact ccagcctggg cgacagagct agaccctgtc  59760
tcaaaacaac aacaaaaaac aactactttg cactgtacag agactatata tccacaggcc  59820
aacctcctct cccattccgg tcccacacca gccttttaat aggtttttta caaggccggg  59880
cgcggtggct cacgcctgta atcccagcac tttgggaggc cgaggcgggc ggatcacaag  59940
gtcaggagat cgagaccatc ctggctaaca tggtgaaagc ccgtctctac taaaaaaaaa  60000
aaaaaaaaaa aaaatacaaa aaattaaccg ggcctggtgg caggcgccag tagtcccagc  60060
tacttgggag gctgaggcag gagaacggcg tgaacccggg aggcggagct tacagtgagc  60120
cgagatcgca ccactgcact ccagcctggg cgacagagca agactccgtc tcaaaaaaaa  60180
aaataggctt tttactatcc ggtttaaata gagaattttt ttttgcttgt tttttgtttt  60240
ctctcttttt tttttttttt ttttgttttt tgagacagag tctcactctg tcgcccaggc  60300
tggagtgcag gggcccgatc tcggctcact gcaacctcct cctcccggat tcaagcgatt  60360
ctcctgcctc agcctcccga ctagctagga tacaggcgcg caccaccacg cccggctaat  60420
ttttgtattt ttggaagaga cggggtgtca ccatgttggc caggatggtc tcaaactcct  60480
gacctcaagt gatccgcccg cctcggcctc cccccagagt gctgggagta caggcgtgag  60540
ccaccgcacc cggcctgaga atgttcgtat tctactcatg aagacttcgt aaatattggg  60600
gtccagacct agatactaca acgttacaaa tctgttctga tcactgcttt gccagatccc  60660
tggtaaatcc acagctctgg ccgggggcgg gggggccgca tgcaattccc ttctttccta  60720
caggggggcgc tgcagagaag ggcagagcag agcgcgcagt tcgcgggcag gggccgcttc  60780
tccaggatag cgcgcgtccg agggggtggg tctgtgctag ccctgcgcaa cctcaggggc  60840
gggaacaact ctggctctgc ccccgccggc tggagcgcct tctcattgga ggagggaacg  60900
gtcacttggc agcgccgttg ggattggagg aagagggtct cgggtggagt gacgctgagg  60960
cggcgagggg gctggtggct ggccgctgct gcccttcggt agctggtccc ttaactcagt  61020
ggtgaatggc gaccggatgg agctctaggg aagcgacagc agcggcgggt gggccgggtt  61080
atgggcgccc cgagtccggg cggcgtcccc ggtgtgccgc tgacctgctg ggtgggcgct  61140
gtcctcccgg agggggtcc ctttgctctc ccggacccct ttacccgtca cttcctcgcc  61200
```

-continued ggtccctgag gcaggtcccc ggagccccgc tgggcgtgag gtgcagggag cggccgcagg 61260
tggacccggg gctggagggc gctcggccac cacccgagcg ggtcttggcc ttgagcttcc 61320
gagcgcctca ggttcagagc tgcaccccac gagcccggga ggcggtggtc cgcgccctgc 61380
ctgggttgcc ccacggcgcc cggcctcctt cgaggggcct cggagcggcc cggcccggcc 61440
cggctgagga gtcagagctc gcgctcccct tgcccgggag ctgcagcccg gctcctccgt 61500
gcgggcgctc gttcgctgat cgcgggcacc tcgggccaaa tccaccccct ccgagacccg 61560
ctccgctttc taggagtctc tttcccagac ctggtgccac ctgttgctgg gtctcccact 61620
aagccttcga gatctttggc atagcttcct ttgaactctt cctccccgct gcggcttgag 61680
ctgggcctgc taggagggtt gctcagaatt ccaatgccag aaagaacgct ccgtgccctg 61740
aaagctggag ggaggagaga ggacttcacc tgggaaggag gagaaaagct ttgaggggag 61800
gcacagttat ttgtgtggtc cttgaaaggc aagaagactg ggcccgtgg ccctgaaagg 61860
ggaggtgggg ctcccagcag aggggactga ggtcttcata aacaatgagg gaccagagca 61920
gagggaagga ggacgagatt ccagactcta gttccaaaca aggcacctgt gatttctcat 61980
cccctgggca gtgactgcca ggcgcccttc agcggacacc tgggacttgc agtgttatgt 62040
gcccagggat tttcctggac gggattgtga agtagcgggt aaggtcatca ggcaggttgg 62100
ggtcagatgc agatgttcgc ttgtggtcat tcctgaaatg agaatctggc agctcacgtt 62160
atttcagaag gtgctaggat cacttttgac agtgatacca aaaaattgat ggtattctgg 62220
tgaccctgtg tgaaaaatga aatgttcgtg caatctggag acactactgg gaccagatta 62280
atctgttttt gtttccttat ttatttattt ttgagacgga gtttagctct tgttgcccag 62340
gctggagtac aatggcgcga tctcggctca ctgcaacctc cccctcctag attcaagcga 62400
ttctcctgtc acaggctccc gagtacctgg gattacaggc atgcaccacc acgcctggct 62460
aattttgtat ttttagtaga gacggggttt ctccatgttg gtcacgttgg tcgtcaactc 62520
ccaacctcag gtgatctgcc tgcctcggct tcccaaagtg ttgggattac aggtgtgagc 62580
ctgcccgccc agcctttttt ttttgaggcg gagtctcgct ctgtctccca ggctgcagtg 62640
cagtagctcg atctcggctc actgcaagct ccacctcctg ggttcacacc attctcctgc 62700
ctcagcctcc cgagtagctg ggattacagg catgcacacc atgcccagct attttttttt 62760
ttttttttta gtagagacag ggtttcacca tgttggctag gctggtctgg aactcctgat 62820
ctcaagtgac ccagccacct cggcctttca aagtgttggg attacaggct tgagccacca 62880
tgcctggcct atgccaattg tttcatagaa tgtttacaat ctagcttcct ctgattttct 62940
tcattattag attcagattt tttgttcaga atgccacctt cataggtgat gtacacttgt 63000
cagtggatca ccttaagaga tgtcagttta tacctttgtt gacaagtttg atcctttcgt 63060
gaagatgtgt ctgtcagctc tctccattgt aagggtacct gaaccctctc ttaattaaca 63120
gtcctatatg ggtgatactt ttggaactga atattctgtt gactcttctg gcttttagtt 63180
cacttttatt tcattaagaa aagattgaga taagtggatt taggatgata gttttaatgt 63240
accaaagtag aggatctgta tgcatgagaa ttgttttgat ctcagaaatt gttctgaaaa 63300
ttttaaactg cattgtgtac ttaagtttaa gattattttt atggatatat aacttcaagg 63360
tgttggatac cacggatcat tcattcaatg tgtatacatt tggccaagtg caggctctga 63420
cctggaggta taagcagata ggaggcgtgg ccccttgaccc caaatagatg agaatttggt 63480
ggtaaataca taacctgtgt attagtccat tttcatgctg ctggtaaaga catccctaag 63540

-continued

```
actgggcaac ttacaaaaga aagaggttta attggactta cagttccatg cggctgggga  63600
agcctcacaa tcttcatcgc ggaaggcaag gaggagcaag tcctgtcttc cgtggatggc  63660
agcaggcgaa gagagaatga ggaaaatgca aaatcagaaa cccctgataa aaccatcaga  63720
cctcttgaga tgtactacca cgagagcagt atgggggagg aaccgccgcc atgattcaat  63780
tatctcccac caggtccctt gcacaacaca tgggaattat ggragmtaga attcaatatg  63840
agatttgtgt gcggacacag agccagacca tatcaacccg catcccgtct ttagctggaa  63900
tgatggctgt attaggtaca tgaggtctga tcttgtttga ggcaccaaag cctgctttcc  63960
tgaagcatag ttaatatttt ggccccacag aaaaggttat ttgcagttta tgccaacttg  64020
ttattgcaaa atcattgctc tgaaatattc atttctacca ggaagctttg gattgatttt  64080
ttttacccgc aatatctgcc caaccctcct tattccagtt gtttagattt cttttgtcat  64140
ttttaatgaa tctgaatgtc aaggaaggca gatctttttc tggtatcagg attgatttta  64200
ttgtgtgata atacagattt cactaaacta aagtcctaga gggtcttgtg ataattaaag  64260
tacaacccaa taatattttt cttgtgtcat tgctggaatc aagactgggt cagatttgga  64320
ccactcattt attcactcaa caaacattta ctgagtgtca attgtgtgcc cccctttttt  64380
ttctctaggt accaggtcaa gatgccatgg tgaacaaaac aaagcccttt cccacatgga  64440
gctttaattc caatggaggg agggagaaaa caaccaacct gtgggctgga acagctggtc  64500
gtgagtgtca gggtgagggc agaaagtggt agggcctgtg tagctggggt ggagtgccat  64560
ttgtcgttgg gtgatgggga gaccctcgat ggtgatgata ttggagtcaa aatccgaagg  64620
aagtgaggaa tgagccaaca gctcttgggg taagagcaag tgttccagtc cagggagcag  64680
ccgattcaga ggccctgaaa caggagctta cagaagaaac attgaggggg ccagggtgcc  64740
tggagggact atgtgggcaa gggggagagg aggaggggag ggcaggtcct ggagggctct  64800
actggggggt tttgagcaga gatgagatga ttctgacttt tatttttatt tatttattta  64860
tttttttgag atggagtctt actctgtcgc ccaggctaga gtgcagtggc gcgatctcgg  64920
ctcactgcaa gttctgcctc ccgggttcac accattctcc tgcctcagcc tcctgagtag  64980
ctgggactac aggcgcccac caccacgccc gcctaatttt ttgtattttt akyagagatg  65040
gggtttcacg gtgttagcca ggatggtctc aatctcctga cctcatgatc cgccagtctc  65100
ggcctcccaa agtcctggga ttacaggtgt gagccactgc gcctggcctt tttttttttt  65160
ttttttgaga tggagtctca ctctgtcacc caggccggag tgcagtggca ggatctcagc  65220
tcactgcagc ctccgcctcc tgggttccag caattctctg cctcagcctc ccgagtagct  65280
gggattatag gcacccacca ccacacccgg gtaatttttg tattattagt agagacaggg  65340
tttcaccatc ttggccaggc tggtcttgaa ctcctgacct catgatccac ccaccttggc  65400
ctcccaaagt gctgggatta cagatgtggg ccaccatgcc cggccaatcc tgactttttt  65460
taaagtacac agtccagtgg tttttagtgt gttcagagag ttgtataact gttgccacaa  65520
tcaatttgag aatatttgca tcatcccgag aagaaatccc ttacccagtg gcattgactt  65580
actggctttg cgtggagaat agatggaaag cctgatcagg acaaagtctg ctcaggctag  65640
gatccagaga ccactgaggt aaggcaggcc aggggcacac ccacgaacca gggaggagca  65700
ggcaggcagt atccgagaga ggtggttgac tacagttggt agttcagtgg gcatgtcctc  65760
ttgttagaga ggagtggagg ggacagttgg acctccaggc agggaggtgg ggtttggcaa  65820
gagaggagtc tcccattgga caatgggtag agttgcaggc tgatgggcaa tgattagtat  65880
caaggcagct cagcacggag ttgaaggacc acataagact cttaatcccc aggaggaccc  65940
```

-continued

```
atgtggtctg cctagaaccc cagcttcaga ggaactggct gtgttgaccc agtcattcac  66000
tggaacacaa gatgaaagtg gggccagctg gaaggagggc tgagtgctga gcctcatgct  66060
gcccacttgg ctcagtttct ttgcattgct gccatttggg gccagggtgg tcttgaggcc  66120
ttggttggga gttaggtgac tctgctgtgg aggttagagg ctagggagcc agccattaca  66180
gaccgcttgt gtttatgttc tctatatctg ttctctttca ctgcaatatc tctctgaaaa  66240
tacatcctta aagaaataag ctctttgaga gcaggcatct tagacttttt tcaccaatgt  66300
tgccagcata tagaacgaac tctgtaaata ttcacagatg gactgggcac agtggctcac  66360
gcctgtaatg ccagcacttt gggagggtta ggtgggcaga tcacctgagg tcaggagttc  66420
gagaccagcc tggccaacat ggcaaaaccc cattgctact aaaaatgcaa aaaaaattag  66480
cttggcgtag tggcttgtgc ctgtaatccc agctactcag gaggctgaga cacgagaatc  66540
tcttgcaccc aggaggcgga ggttgcagtg agctgagatc gtgccactgc actccagcct  66600
gggtgacaga gtgagactca taaataaata aataaatatt catggatgaa tgaataaatt  66660
cttaatgttt gtataagttt gctattgtta ctgtaatcaa ttccccaaat tgagctactt  66720
aaaactatat tgattttatc atcttatagt tcttacttct ggtggtcaaa agtccaaatt  66780
ggatgtctct gggctaaaac caaggttcaa cgggactatg ttccttctag aggctctagg  66840
aagaatttgc ttccttgact ttaccagctt ctagaggcca cttgcattcc taggcccatg  66900
gtcccctcct cttctccaaa tccagcagtg taacatcttc aaatctttct gactcaacct  66960
cctgtctcct cacaaagaaa cttgtgatta ctttagaccc atcttgaaaa tttgcagtaa  67020
ccccctactg caagatcttt aatcacagct gattaaatat ccttaattta atcacaggtt  67080
ttttaaaatt attttcttca ttttgttaaa tagtctagca aaccatttct tcagcacctt  67140
ttgccttgta acctattcac aggttttggg gatgagaatt ttaacacctt ttggggccca  67200
ttctaccaca gtgcttagtc tcatttcccc ttatattctt ttattttttt attaatttga  67260
gacaaggtct tactctgttg cccagcctgg agtacagtgg tgctatcatg gctcactgta  67320
gcctccccct cctgggcgca agtgattctc acacctcagc ctcctgagta tctgggacca  67380
caggtgtgag ccaccgtgcc cagctagttt tttatttttt attttttgta gagacaggtt  67440
ctccctatgt ggcccagtct ggtcttgaac tcctgagctc acatgatcct cccacctcgg  67500
cctcccaaag tgctaggatt ataggcatga gccaccactc ccagccgctt tttgtttttg  67560
ttttcgtttt ttattttta aagacatggg gtcttgctct gttgtatagt gatttcgtgt  67620
cgtgtcatgc aatgatgtga tcatagctca ctgtaacctt gagcttctgg gctcacacaa  67680
tcctcctgcc tcagcctccc cagtagctag gactacagag aagccaagac ctcaggtaca  67740
tgttcccaca catggccagt agctggagac cagccatgga ctgggcacag tggctcacgc  67800
ctgtaatccc agcactttag gaggctgagg cgggcagatc acctgaggtc aggagtttga  67860
gaccagcctg gccaacatgg tgaaactccg tctctactaa aaatacaaaa aattagccgg  67920
ccgtggtggc acatgcctgt aatcccagct actcaggagg ctgagacagg agaatcgctt  67980
gaacccggga ggcggaggtt gcagtgagcc gagatggcgc cactgcacta cagcgtgggc  68040
aacaagagcg aaactctgtc tcaaaaaaaa agaaaaaaaa aacagacatt ggctggcctt  68100
gtggctcaca cctgtaatgc cagcactttg ggaggccaag gtgggaggat tgcttgaggc  68160
caggagttca agggtgcagt gagctatgat tgaacactgc attccagcct gggcaacgga  68220
gagggaccat gtctctaaaa cacacacaca cacacacaca cacacacaca cacacacaca  68280
```

-continued

```
cacaattgtt tcctcagttc tggaggctgg aagtctgaga taagggtgcc agcatggttg  68340
ggttctgact gggagttggg tgtcttctgt gtcctcacat agcagagaga gagagatcag  68400
gagattgaaa tctcttcctc ttgtaaggcc acagtcctat catatttaac ttgggaatct  68460
gtggtgcaca cagttcagcc cttagtagtt ggttggcaca cctgtgtcca gacccatttt  68520
tctggaagtt tccagcttca tgtgtttctg gcagatcagg gcgctgcctc ctaggtcact  68580
gccctgatgg ttatgggaca gtcagtaaga agctaggctc cggcagtgcc ttgaattact  68640
gcaaaaagca gtgcttatca cagcttcagc agaagccttc cacagcagga gtccggggtg  68700
tggtctcaca tcggtggggg cagacagcag ccagtggtga ctaatctgag ttctttgttt  68760
tctgagacgg agtctggctc tgttgcccag gctggagggc agtggtggtg tgatcttggc  68820
ttactgcaac ctccgcctcc cggattcaac caattctcct tcctcagcct cccaagtggc  68880
tgggattaca ggagtgtgcc actgtgccca gataattttt gttgttggct tttttttggt  68940
ggggaacaga gtctcagtct gtcacccacg ttccagtgca gtggcacaat ctcagctcac  69000
tgcaacctct gcctcccagg ttccagtaat tctcctgcct cagcctcccg agtaactggg  69060
attacagcca tgcaccacca cacctagcta atttttatta ttattattaa tagtagagat  69120
ggggcttcac catattggcc aggctggtct caaactcctg acctgaggtg atccacctgc  69180
ctcagcctcc caaagtgctg ggattacagg tgtgagccac catactggtc ttaatctgag  69240
ttcttggagg caggtttgca tctcatttgt tcacttggac cagtgaattc ctgatgccat  69300
catggaactt tgtgcagact agatgttcgg gtggtcagag ggtcagattg atttgggagt  69360
ggcaggtgag gacctgggat agaagatggt ctttctgctt tggaagagaa gcatggtgct  69420
gtgtgggggc ttggggatga gctggcggtg ggtggtggac agggggcctc agctcggagg  69480
ccaggctgct cttgactgag ccaggggcca cagtagctgc ccaggcagga gggatttgtg  69540
tgggcaccag agctctggca ggtgcacatt tgttagggag gagcagtatc cagatacagg  69600
cactgctccc tctggagttg ctgccagcca gggagggtgc gtctctgggc agcgaaaggc  69660
aggaatagct cctggcctaa tggcagctgg aaaagaagct gcaagaggat atgggtttgt  69720
tgtggaagag gtgggggctg aaaccctgag gaccaagaat cctgcccttc aatttctgat  69780
tgacactatt gactaaaggt agcttttttc attggtggag gaagggcagt agttcatttg  69840
ttcagcctca atttatctat ccatatcctg ggcatgagag tagccaactc tctcctggga  69900
tatatggagg gatcacatgg gacaatcaat agatataata attgtttcga atcctgcata  69960
taccttatag gtgtgaagtg gttgtgtcct ttgtgaattc tcttggccag gcaccagtgg  70020
gaggttagat agtgacctgg agtttgtgtt gaggaattag tagcctttga atgcctgcct  70080
ttgtagctgt tgcacatacg ttaggcttac tttcaactaa atggaatwag ctaattgatt  70140
tcttcagagg tccaagtgat aacagagcca aaccttgcta gcccataggg gtgagagtct  70200
agcttagtga caggttgttt ttgggagaca caccctttgt gtcttcactt ctctgtcccc  70260
tgtctccgtc ctgctctccc tctcacccat tctgccagct ctgctggccc catgggcacc  70320
tagagcacat gcacttggtg aatctagatc tttcttccct gagacattgc tgcaccacat  70380
cacctcatca cctcgcttcc ttcaggtctc caacaagtca ggtcatcctg aatattttct  70440
gtaaaacttt ctgttaaatt ctaccttcat tattctttca ttttagcctg ccttgttttt  70500
ctctgtggca ctcatcacta tttgatattg ttgcatattt atgaatctat tttctgtctt  70560
cttggtcggg aacataagct ccattaggat ggagactttg tctgttttgt ttagattata  70620
ttctcatcat ctgaaatagt gcctgtaggg cctcaaaaag ttcatagcag attaatgagt  70680
```

-continued

```
gaatttaaca agtagacact attgatggtg ctgagccaca tctgggccct ctctcagcgt  70740
ggagcggaat tatgcacaca ggcgagtata cagactttga tgcctggtgc tgccgttttg  70800
caaaaagact tctccaaccc actgtcttct ttttgaattt ttaaataaat ctggccgggt  70860
gtcgtggctc acacctgtaa tcccagcact ttgagaggcc aaggcgggcg gatcacgagg  70920
tcaggagttc gagaccagcc tggccaacat ggtgaaaccc catctctact aaatatacaa  70980
aaaaattagc tgggcgaagt ggcaggtgcc tgtaatccca gctactcagg agactgaggc  71040
aggagaattg cttgaaccca ggaggcggag gttgcagtga gctgagaccg tgccaccgca  71100
ctccagcctg ggcaacagag tgagactccg gctcaaaaat aaataaataa gtaagtaagt  71160
ctggatattt tagtcctgga aaggatacca catttgaagt caaagacctg atctgaaatt  71220
ctgtcttcac cattacttgc tgtacctctg ataaatgccc taacctccct cacccatgat  71280
tttctcatct atgtaatggg aaaatacttg ttctgcctac ctggggctta acatttattg  71340
taaagatcaa atgaaatgag tttctcccca cgcccccacag tgtattggag tctggcagtt  71400
gtctcctggc cactgtcctc tgttgcaagt tgagaaatgt gatctttact tcctgtccaa  71460
ccctaaagat ccggaaggcg tggatccgtc acagagagtt acacaacatt gtctacccag  71520
atcccaattg aagaaaatcc acaggaagac aaggcaggct cttttcatcc tacccataat  71580
gactaatcca tcattgcctc agtaacttga tcgtcagccc gggtagcaga tatccctccc  71640
cgaagctgat gaaacagggc agagaggaag tatccaagag aaaagggagg gaggtttctc  71700
taaaacaaga cctacaataa ggacattatt gtctaaagga aataaataat tgaaagtttc  71760
tgaaaactga gatttcttca tctcaaatga ctttattagc ccaaaaaagt acaaaaatta  71820
ttttcctcac ataatattaa tggtgggaat caaaatgaat cagtagatgg gggatccaga  71880
ttggaatgct gctacaccat agtagaatcc ttctgggaac ctacggtggg aaaggatcac  71940
ttgtagcaaa aagatccaga gttgtgcaga gggaccacgt cagcagtgat cacttttcag  72000
taaccgtctt tttctgctga tcattttagg gtcactatga ggtcagactg gatggtggga  72060
gtggatacca attttttttt tactgcctac atatgcttca tgagctataa tttgtctttt  72120
tttccaccac agatctctgt ttcttttcct tactttcatg cccataattt atcttacaga  72180
tgtggtttaa tgctttgctg atttgacata gctttctttt ccatttcatt gattgctact  72240
taaagatgca caaggctttc agggcctcac atgaatgatg agatgagatc caacgtcaag  72300
aatctgaagc aaagacactt gtggtttcag aacgtgtaaa tagagcttgg tgattttctg  72360
ttgagtttgt tgggggaatg cataatgatt aggattaggt gtttttctat tttaaaaagt  72420
tgcttctaga ggcatagaag acaattctga tacactattt aaattttcca tacaaatcca  72480
ggcatgttta tgcaaaagaa aaaaaaacac cagtacaaaa caaacaagat atgatctgac  72540
tgggcatggt ggctcacccc tgtaatctta gcactttggg aggccaaggc aggaggatcc  72600
cttaaccaca ggagttcaag accagcctag gcaacatagg gagaacctct ttaaaaaaaa  72660
aatttttttt taatttaaaa aaaaaaagat caaatgagac aaatgctatt cacatgtttc  72720
ttgtcttgtt atcgccactt caagttccca tttattttgt ccagtgaaca tttgaaagac  72780
tcagatatga agttcagggg ccatgcactt tgtgcctctt tccccagtat taatgcactt  72840
acacctgtct atttttctct ttcttttagt gggggagata atgcctcttt cttttgtgta  72900
cagcaggaca gtgggtcatt gtgtatgtac agaagtgatg tggattcctc ccagactcat  72960
tagtgaccag ggctgctggg cctgtttggg tttcctagac tagagaagaa gacaggaacc  73020
```

-continued

```
aggatgggaa gacggacatg ttacatttta agctggagct tcccctgcag tccacggagc  73080
acgttctcgg tgtgcagctc atcctgactt tctcctatcg attacacgtg agtcagtccg  73140
ctgggaggct gtcctctccc ttgtgtcttt ttagtagacc agagtccttc ttctgatttc  73200
tagaagaccc gcactctagc gggccctctt ccccatgtag tttgggattt aacttaggcc  73260
aatggaatgg ttttcactag tcatattaac tgacatgggc tattaatagc tcagaaggtt  73320
ctaggcagtg tttcctgcat ggctacgcta ggtatgtgag ggcctcttag gtttcagcca  73380
agacaggtga ctcttagcac ccagagccct tcagatctga tggcggttgg tattgttggt  73440
ccttctaatg atttcagagg atggcgaccc tcgtgatgca gagcatggcg tttctccagt  73500
cctcctttcc tgtcccggga tcccagttat acgtgaacgg agacctgagg ctgcagcaga  73560
agcagccgct gagctgtggt ggcctagatg cccgatacaa tgtaagggcg cttctcattg  73620
tccagctcct ttgtttctgt gtgttactgt tcgtcgagtt ctttgaagag ggggataaaa  73680
agtagaaata tttctctgtg ggtggctttc aagggacctt ctgaggaatt cttgccatga  73740
agtcttttca gactatgaag atacacctgt atttacacct agagggagag agagaaaaaa  73800
tctgtgtttg ttgaataact aaattgttta ttgcttttag gtacacatgt gcacgtgcac  73860
acacacgcac atacattctc tcttccatac acatacttgg agtatgtgtt tccaagagat  73920
catgtaaaat gttcatgtaa agtatttcag aaatactact agacagttta ctgaacccat  73980
aacatatgcc agccttgagt gcaggggttt atacgtatca tctcctttaa tcatcacagc  74040
aacctctgag ctgcctgcac tgtcctttcc cagcactcca gccagtggtc ccattgctgt  74100
ccccccttgct actttgcagc ccccctggcc tttttgctgt tccttgaacc caagaagcag  74160
ctgccacctg agggcttttg ctcttgccat ttcctctgcc aggcatccat gtggcttatc  74220
taaccatgcc attcaggtcc ctgttcagat atcgccaagc accatccttc cctgacctgc  74280
ttctagagta gcagcccctc cctccaccat ctctcagcca gactctccct cctgcccccct  74340
ggcctactca ggatatgtgt ttgtgtgttt atttgttgtc tccctcagcc ttgacagcag  74400
tggcatctca tacactatca tgtccatgcc tagcacactg cctatcactt ggtaagctca  74460
cagagaagct tgtttgaaga atgaactcat tttggagaag acaaaactgg ggcttacagt  74520
gattaatttt cccaaaggct caaatcttga aagtataaca gagccaggaa ctttctgtgt  74580
ccagaactca tgcatctaat cactcattcc tcacctttat tttatcacag tggggaccat  74640
agaagatgag ctgctgtact ttggaaaatg aaaaagggaa attatcagtt ataaggcatc  74700
ctcccacctc agcctccaag ggtactggga atacagacat gagccactgc acctaacctt  74760
ttttaaaaca atttcattta ttattttatt tattttttgt gacagagttt cactttgtca  74820
cccaggctgc agtgcagtgg cgcaatcatg gctcactgca gccttgacct ccccaggctc  74880
agatgatcct cctacctcag ccttctgagt agctagctgg gactacaggt gcatgctacc  74940
acgcctggct aatttttaca ttttttgtag agacggggtt tgccatgttt ctcagggtgg  75000
tgtcaaactc ctggacccaa gtgatccact caccttggcc tcccaacatg ctgggattac  75060
aggtgtgagc cactgtgcct gcccccgcac cccctttttta ataaaaaaac tagactctca  75120
ctctggccca ggctggagtg cagtggccta cctatgactc attgtgcctc atactcctgg  75180
gtacaagcag ttcacccacc tcaccctccc tggaagctag gactggaggc accacaatgc  75240
ctagtttatt gggatttttt tttttttttt ttttttggta gagatgggat ctttatgttg  75300
cccaggctgg tcttgaactt gtgtcctctc aagcagtcct cctgcctcag cctcccagat  75360
tgctgggatt acaggcatga gccatgacat ccagctgaga gagattttat aaatagcttt  75420
```

-continued

```
aaaatctatg aaacatggac actgaccact tattttcatc cccacagaag gaaggacaga  75480
gtaaatgaac ttaaattgtt gcaagagagt ttattcatct ttgaagaaaa gattattgat  75540
actgcagtag gccaccaaga acaagagggt gctctgtggg accagcctgg gtgggcagaa  75600
gggtagaagg aaaagaggag gagtctccca ggtgctcaca ccacatcctc ctcccgtgtc  75660
ccaagtatct gtgaccaacg ggaccagccc ctttgcctat gactacgacc tcacccatat  75720
tgttgctgcc taccaggaga ggaacggtgg gtcacaggta gagcccattc agccgctgct  75780
caggactttc aaggttagtg ggggcaacag agacaagcag aactggaacc cttgtgatga  75840
aaatgtcaaa acccgtgaat gctcaacgat gggagcaaat gtgctgccca ggatttgtct  75900
ttttcgtcct gatcttcaga cccgggacca cccgcacccc tccagcatcc cgtggtccag  75960
caggctagtg atggttaaat gccatcatta tcccaccact ggcttggtgg gtttctcttt  76020
taaaaaatat aagcctaatt gagttgttcc ccatagcaca cctataacag atgccaaaga  76080
caaattgctg ttcatgcttt tcagagaaaa acagagaacg tgggtgactc tccccacatt  76140
agcagtccag caggagaaca ggagtgcccc tgtttcctgc cagaaggcac agtgtgctca  76200
ttccttacag agctctaggc catggcatgt gttcactcgg catgtttggc tggtccgtgg  76260
ctgaggatgt ctgtgaaggc atctagagtg ttacttggca accagacatc atggagacta  76320
tacacaaaca tttcacaagg gggaacgact gcaaatccag tattgctttc tgattttatg  76380
tcatacatta gcagcatttt tataatagta aagggaattc taaaacaaaa ctaaaaagca  76440
cggcccaaga aatcgatgtt ttttctttac ttttttcact ctttattctt atgtggattt  76500
taaaaatata cctattatga tagtgttgaa acactttggc atccaaatta tttgtatttc  76560
catgtaataa aagtatttcc ccacactgct acaaagttct aatttttttt tttcttgaag  76620
agacacaggg tcttgctctg atgatcaggc tggagtgcag tgctgtaatc atagctgatt  76680
gtaaccttga actcctgtgg gctccgtgat cctctcacct cagcctcctg ggccgctagg  76740
actacaggca cgtgccacca tgcccagcta attttttttt attttttagt agagagaggg  76800
tctcaatatg ttagccaagc tgctctcaaa ctcctggcct caagtgaccc tcccaccttg  76860
gcctcccaga tccttgggat tacaagaatg cgcgactttg tccagacaaa catattattt  76920
agagtggcaa catgttattc tttcagttag ccattcagca attgtagatg atcacatgac  76980
catttccaag tttttgacgt attttaatat aaatatcgta ttagtccttt ctcacacagc  77040
tgtaaagaca tacctgagac tgggtaattt ataaagaaaa gaggtttaac tgacttagag  77100
ttctgcatgg ctgggtaggc ctcacaatca tggcagaagg cacctcttca cagggcggca  77160
gaagagagaa tgagagcaga gctaagtaag cagatctgat aaaaccatca gatctggtga  77220
gaactcacta tcatgagaat ggcatgggga aactgccccc atgattcaat tatctccacc  77280
tggtcctgcc cttgatccgt ggggattgtt acaattcaag gtgagatttg ggtcatagag  77340
ccaaaccata tcaaatgctt ttttgacaag tatcttaaca aattatttgt taatctactt  77400
tgtacatgca atttttaatg ctttcgaatg atttctttta gttctgaagt acagaatatc  77460
ccacaggaat aaaataatac ttttatagcc gagcgtggtg gctcatgcct ataatcccag  77520
cactttggga ggctgaggca agcagatcac ctgaggtcgg gagttcaaga ccagcctgac  77580
caacatggag aaaccccatc tctactaaaa atacaaattt agctgggcat ggtggcacct  77640
gcctgtaatc ccagctactt aggaagctga ggcaggacaa ttgcttgaac ccgggaggca  77700
gaggttgcag tgagccaaga tcactccatt gcactccagc ctgggcaaca agagcgaaac  77760
```

-continued

```
tccatcccaa aaacaataat aatattttta tagccctaat atattttgcc aataggctgc  77820
cccatcatgg attaatggtt aatgattgta ttgcagttgc caccatcctg aatgacccca  77880
acttcatctg gctggtaggc agagccatga aactccattt gtgattaatg ttgtcatcca  77940
gtaccctgtg gaaaccatat catatccttt ctgttacaga ggcagtggta actcaacttc  78000
caaaaaggaa agattccaaa gttgtcccca gcagaaacac atgtgggagc ctttgattgg  78060
aaattgctac agcactgtat ctccacataa atgactatgt ctgctcttta tacagggggg  78120
aagatcattt cctgttcgta tttctttctg agccattctt ctaagtcaga atcatccata  78180
tttatttttt aataatcttt tattattcct ttcatcttaa gagtatttga aatattcttg  78240
ccatatcctg tctggcctaa accttagttt actttgactt ataccatgtg gtccccaact  78300
ctttaactgt ctgtccttat cagccaggat tctgggcgat ggtaaagttc gcctgggtgc  78360
agtatgtcag catcctgctt atcttcctct gggtgtttga aagaatcaag atcttcgtgt  78420
ttcagaatca ggtggtgacc accatccctg tgacagtgat gccccaggga gaagtgtgta  78480
aggagcactt atcctagaaa ggccgtttct gaagactcag caggaccatg gctgcctcat  78540
tgtcatcttc tgggaacgtc ttaggacctt ttgaaagagc ccagcggaca cctgcgggct  78600
tgtgtgcttt tccctcagag acaacggttc tttccagttt tgctctacac agttccgtat  78660
cttcagagct cctgcagaat tgtcagggac tagtttgtgg aaaggtctga gagttcctgg  78720
aggctataat tagctttttg ggtttttctt ctttgcctta gcgttgaatt tcaggagaaa  78780
attgcagtca gttcagacat cttggaaaga gtcccatctc tggtcaagca gagacttttc  78840
ctctgttgaa ctgaggaaca cactgtgcat ttcttccttc tgttgtgagc cactcttact  78900
cttttcaggg ctctcttgtg acaaacatgc caatcactag cactttgcac ccctgggctt  78960
ctccatttcc cattcacagc tttgatttcc agagctgagg cctttaactg gagacctgga  79020
ggggcagggc ccaagggcaa gggccgcatt agcacaggca atcagggagg gccgctgaag  79080
gacacttgga ccgtccacct gccccagccc aacagtcagt catctgtcat cagctcagct  79140
gagcagccct ggatccctgc ccgactgtgg ctggctcttt gcccggtttt tccctctgtc  79200
tgtgcccctg gatggcaggc tgaagtcaga ggggctgttt cattctcagc cccctcagca  79260
gcactggggg aagaaagcat tgtcacaaca ggttctttct ggccctcacc caacagcctg  79320
ggcacttggc cctcctcctc cttgacagcc ctccccccttc ctgcaaagga caggggcgac  79380
aggggttggt gttgggattg gctcccgctg cctgacaacc acaagtttat ttggaaggct  79440
agcgggaagc ccagcggctg gcgtttccct tgactaagga aaagggtgcc catcagagtg  79500
gggcgggcag ctttgggaag gacacaagaa gcagtgaggg tgtaaagagg atgctggcct  79560
gggcaggcca gtccagcctg gccactagca gaataccaag cagtccagtg gattatcctc  79620
gtggctaagc aagtgtctgc aggagcagag atggctggaa ggggcctctg cacacggaag  79680
atggcttgtt cagccgattc acctcctgag gatgcgtgca gtctcctcca agaacacatg  79740
gagctgcttc ctgatcccaa gcaggtcgtt gcccctggaa ggacatggct ccggtgatcc  79800
atgcttcatg cccacccaga aacacacccc tcagtgtgtg cctcagttta ccttggagat  79860
catttttcat ctccagcatc cgtttccttt aggctgacta aaaacagttt tggaaacaaa  79920
gctattttga agtattcaag cagaggaatt ctctaacact gtccccccttg tcttttttta  79980
atattctggc tattttagat gcctaaattt ttttcttgag atttatttat ttttatagat  80040
ggggttttca ctatgttgcc caggctggtc ttgaactccc aacctcagga aatcctcctg  80100
tctcagcccc acaaagtgcc aggaatatag gcatgggcca gtgtgccccg tctcttgaga  80160
```

-continued

```
ctgaaatgaa aaattgcttg tggtttaaat ccccagaatt taatgaaaca tgggaagatg  80220
gctaaagata cgtataaact ttggtttgca ttttattaaa ttatttgaat gcaaaacttg  80280
tataaagaat ccattatgtt ctgtagcttt ctaattaaaa tgttcaacat ggaaggttgt  80340
attagctatt tttgaagcaa ggctttggag ggaggaagaa tagggagggc tgaagttgag  80400
cacacttctc cgagttactc accagtagcc ttgctttgcc acggctctgc ccaaagacct  80460
tggagctttt gttagctctt tggcaaaagt ttcctggtcc aaccccaagt atattagttt  80520
ttagtggaat ccacatggca tatgggagct gcgggttgga aaattacaac tgtgtctggt  80580
gaatatcaaa ttatttacgg atcatttatt ggtagtttct gaaactgaac cacacagcat  80640
agttgcagga ggaagaaagg taagaaatac acaggatttt atcaactgag ctgaagccat  80700
agataagtca tatttgagat aattattgaa tttgttttgt gggagagaaa tctctaattc  80760
ttccaaatga ttagtccagt ttctgccaaa gcaggtgagg tgtctaatgc cccactgagt  80820
gcccatcttg aagcttatta aagcaattct ctctctttgc gtccctctta ccttatcctc  80880
cacatccttg ccccctctcc ttattcatgc tttgtaaaga ggttttggag ctttctggcc  80940
agataacttc taaatactga ttaaggaaat gtaaattaca tgatcctaag gaaaataatg  81000
attgccggcc aatcccctac ccagagttat ggttggcctt ctggcacaca tctttctatc  81060
ccatacacta tttctaactt tttaaaaatc atgaacaggc cgggcacggt ggctcatgcc  81120
tgtaatccga gcactttggg agacagaggc gggcagatca catctgagct caggagttcg  81180
agaccagcct ggacaacatg gtgaaaccct gtctctacta aaagtacaaa aattagcctg  81240
gcgtggtggt gggcacctgt aatcccagct attcaggagg ctgaggcaag agaatcactt  81300
gaactcgaga ggcggaggtt gcagtgagcc tagatcctgc cattgcactc cagcctgggc  81360
tacaaaagtg agactccatc tgaaaaaaaa atcagtatca aaatcatgaa caacacttat  81420
atgaaccctg tacataaatc cttgtttctg gtttatttcc ttaagatagc tcctagaaag  81480
gaattaccaa tccgaaaagc ttacgaccat tgtcaagaat cttaattcat cttgccaaac  81540
cacaaccagg aaggactgct tatttcttct cccagcagca gggagttctt gattaagatc  81600
ccatcactaa tttgacaaga cctagaaatg cttcatcctt ttcaggtgcc tgggctctgt  81660
ccctgttatt tgtwaagggg attttttttt tttttttttt tgaaacagtt tcgctctgtc  81720
gccccaggct ggagtgcagt ggtgcaatct cagctcactg caacctccgc ttcctgggct  81780
caagcacgtt ctcctgcctt agcctcctga gtagctagga ttacaggtgc ctgccaccac  81840
gcccggctaa tttttgtatt tttagtagag acggggtttc accctgttgg ccaggctggt  81900
ctcgaactcc tgacctcgtg atccacccac tacggccccc caaagtgctg ggattacagg  81960
cgtgagacac cgcgcctggc cggatttttt tttttttttt ttgcgaggga gtctcgcttt  82020
gtcgcccagg ctggagtgca gtggtgcgat ctcggctcac tgcaagctcc gcctcccggg  82080
ttcacgccat tctcctgcct cagcctcccg agtagctggg actacaggtg cccgccacca  82140
ggcctggcta attttttgt atttttagta gagacggggt ttcactgtgt tagccaggat  82200
gatttcgatc tcctgacctc gtgatccgcc cgcctcggcc tcccaaagtg ctgggattac  82260
aggcgtgagc caccgcgccc agccctggcc ggaaatatct tatttattga aacgtatcat  82320
gtctttatct ggacctgcta tgaacctgcg cctctgggcc taggctaggg cagggaatgc  82380
gcaggaggag gggaaaagct gcggacccag ctcctaaggc cacctggtct ctccgctctt  82440
cccagttggg acactgcacc gggtccatgt gtcatccagg tgccgtggcc ttgggaaggg  82500
```

-continued

```
tttggattcc aagtcacctc gccgcaagga tgcccccgag agtgaggagg gtcaagatta  82560
agattcgact tccttcacta gggcctttgt cctcccagga gccccccttc tctggggatt  82620
tggggtgggg tggggtacaa cgttcctctg tagtcagatg agaggtgact ctgccagcgc  82680
cctttgacat tctgggctaa aagttgagcc tctcagagcc ccagcccacc tgggccctcc  82740
tgccccgccc tcggccggcg cccctccccc gaggcgtggc ccctcggtcg gggtgggcc  82800
aaccggctcc ttccttcccc cacggcgcta gctcccgctg gccacctcgg gaccgcagcc  82860
acgtctgaaa gcgcctcatt gtgtgcgctc gggcgggctg caccgggcag cgccgagggt  82920
tgccggccgg cgcgcgggga gtagagggcg cgggccgcag tgccgggttc cagagggagc  82980
tctgcgccgg gtccttccct gtggtagccc caggacaccc ccagcctcaa catcccattc  83040
tgggactcct gccctgttcc cacattcgtt ctacctcgag tctccaggag cttccagtgg  83100
cttggtcacc gccaactctc gtccatgcct cttagagccc ctttcccggc ctcaccgggt  83160
gtcgcttaat agtcttggga ccttaaggag caagtcagcc cctgcggacc ctcccagtga  83220
agagaaagag ctggctgtgc ggtggaattt ggaagagacg acgtttggga gcctttgctg  83280
agtccaggga gagaggcgtc ccccaccgtg ccgctgcagc tcgggcagag ccgccaagct  83340
ttggggtacg ttggttcttc attctccgcg ggggatgtcc ccacactcgg gtcggctggg  83400
ggccgggctg gtggcacagc tggggacgct cctctgtcct gcaccgggga cctggggtgg  83460
cgggaagagc tgggagtggc ttttccatca gcaacgtgga aagggcatcg ccgctgttgg  83520
cgccggtttg gaagtgtctt gctggggctt cggctgcgca ggagaatcct cactgcgagg  83580
ggagaacccc ttttgtctcg atacttgagt ttcaaaggac atgactttca aaagctctcc  83640
aagggctttt tcctatagaa ttattgagag cacgstagct tgrcgggttg actattggta  83700
accagaaccc aggggaattg gagtcctgcg tcactgcttc tgacggcttc atcttgggct  83760
tcaggacagg ccctctgggc cttcaggaac aggttgccta gcaaatgttg actttccttt  83820
ctcctccctt tttcacagag gcaaggcagt caagtttccc atttttgagg atgggaaaac  83880
tgaggcctga agagcagaaa ggagttggct gacttaaacc cacaagcgag taggccaagt  83940
accagggcct ctgagggtgc tatgctgctc cgggagctgg ggctgggctc ctctccagcc  84000
tgagaggccg gaacttttct ggctttgttc tacaaacaga gtcaactgga gtatagagag  84060
ccagagagtg acttgctcta agtcacaccc ctcactggta gtagagacag gatttgaacc  84120
caatccggct tcagaagcca agcttctaag gccagtcgca gtggttcacg cctgtaatcc  84180
cagcactttg ggaggccgag gcaggtggat cacctgaggt caggagttca agaccagcct  84240
ggccaacatg gtgaaacccc atctctacta aaaatacaaa aataagctgg gcatggtggt  84300
gagtgcctgt aatcccagct acttgggagg ctgaggcaga agaatcactt gaacccagga  84360
ggcggaggtt gcagtgagct gagattggcg gtacttcact ccagtctgga caacagcgag  84420
actccatctc agaaaaaaca caagccaggc ctctagccat gactttccag cgtcttctgt  84480
tttgtttgcc cttgtgggga ccctgtctgt gcctgccaca ttctgttgct ggggcactgg  84540
ggcacctgaa tctggtagag ccattgtcct tgggttttcc tcattcaaag actttccctt  84600
ggattcatag aatataagtg tggcccagga aggaagattg ctaagcaaat actcataagt  84660
gcactatgcg ccagactttg ttctgcttta caaatatyca ctcactcact ctttcaatca  84720
agcccatgag ttgggttata ttgtttcccc cactttacag attttttttt tttttttga  84780
tacggagtct cgctctgtca ccgaggctgg agtgcagtga aagtgacata atctcggctc  84840
actgcaacct ctccgcatcc caggttcaag cgattctcct gcctcaaatt cctgagtagc  84900
```

-continued

```
tgggattaca ggcacccgcc accacgcccg gctaattttt gtatttttag taaagatggg  84960
gtttcactat gttggtcagg ctggtctcaa actcctgacc tcgtgatccg ccctcctcag  85020
cctcgcaaag tgctgggatt acaggtgtga gccaccgcac ctgaccttcc agattttttt  85080
ttaaccaagc aggcacagaa ggaagtaact tgcacaagat cgctcagtaa atggtcaagt  85140
gggattcaca ctcttaacct cagtgctcta tacctactgt ctttaatgag acagacacca  85200
ttctgcttct agtgtcttgg gcggggaaat gggtccagaa atacatgaac aagattgttc  85260
tgggtagtga taatagtatt aataataatt tctcactatc acctattagt caatattgaa  85320
atatatctga ttacctctag ggtatctcct ggcagatgtt tttttcaaat cagaatccac  85380
acaaggtcca catgttgcat ttgactatgt gttttttggt tttggttttt gtttttgttt  85440
ttgtttgaga tggagtctct ctctgtcgcc cagactggag tgcagtggcg tgatctcagc  85500
tcactgcagc ttcggactcc tggctccagt gattctcctg cctcagcctc ctgggtagct  85560
aggattacaa gcacgtgcca ccacacctgg ctacttttg tgtatttagt aaagacaggg  85620
tttcaccatg tttggccagg ctggtctcca actcctgacc taaggtgatc tgcctgtctt  85680
ggcctcccag agtgctggga ttacaggcgt gagccaccgc gcccggccct gagttatttt  85740
cctataaaat agtctcttcc tttttctgtc atagatttgg aagtatgatt tacttttaaa  85800
aaataaggta attaaaataa atggttaata aaccagggaa cattccagat tatctctgta  85860
atgagagggc tctgtcaata cttagggaaa caggcaaatg tgctaaaagc acagtcccac  85920
tccgtaccct gtgtgtgttg ctgcacagaa gaagtgggga accctcagac tttatggcct  85980
ccagctgtaa ggtactacaa tttagaccaa ggcaggtgct gtttgaagtg ccctgtgaga  86040
atccctaaag ctcccagcca aggaaaaggg tttgtgtgtt gctatctgct tatctgctct  86100
gaaatgcccc agggcagtgg ctctgagcca gggaggcttg aggctccttt cccaggctaa  86160
ttagaattca tttcccagta gattttgaag gcagatctgt tttctccatc agcatctggg  86220
ccttgcagtc ccagcccct gcctctgggg gatgccatgc agctgcatca ccaggactgg  86280
cagagttggc agatgtggcc agggcttggg ggccaggcac agcttcagcc acagcctggc  86340
ccagcccaca gtcctggtgt tgagagtgtg catgggagct ctgacacctt ttagtgcaga  86400
gcgggtaatt catgcccctg gacttctctg gctaactggg tactcaggtc agctgggaga  86460
tggttttgca ggcacctgtc tctctgcagt gatagctgga caaagacaaa ctccacctaa  86520
gcctccttta accaactaga aatttctgat tttatcattg tagtaaaagt ctgatgtaga  86580
ctatctggaa aatagcagca aagcactaat aagaaaataa attaccagcc gggcacggtg  86640
gctcacgcct gtaatcccag cactttggga gactgaggca ggcggatcac gaggtcagga  86700
gatcgagacc atcctggcta acacggtgaa acccggtctc tactaaaaaa tacaaaaaat  86760
tagccaggcg tggcgtcggg cacctgtagt cccagctact caggaggctg aggcaggaga  86820
atggcatgaa cctgggaggc agagtttgca gtaagccgag atcgtgccac tgcactccag  86880
cctaggcgac agagcaagac tccgtctcaa aaaataaaaa taaaaaaaaa ttacctgtaa  86940
actggccata gaaaaataaa caccaaactt cagtgtgcat ctcccatact ttgtattttt  87000
ttaaataatg gctttattga gatagaattc atgtatgtta aagtttatat atattatata  87060
taagtatatt atattttata tatatatata tatatatata tatatttttt tttttttttt  87120
tttttttttt aagacggagt ttcactcttg tcacccaagc tggagtgcag tggcttgatt  87180
tcagctcact gcaaactctg ccttcctgac ctcaggtgat ccacccattt aatccaaagt  87240
```

-continued

```
gctgggatta catgcgtgag ccactgcgtc cggcccaaag tttatatttt aaaagtgtac  87300
agttcactgg cttatagtat attcagtgtt ttcacattga actttgtata tatcagtact  87360
ttattctttt ttattgcaga taattgtcta ctgtgtggtt acaccacatt ttgtttatct  87420
attcatcagc tgatagacat tagggatgtc tccacttttt ggctattacg aataatgctg  87480
ctgtgcaaat tcatgagcag gttttcatgt gggcttgtat gttcagttct ctagggtgtg  87540
tacccaggag tggatctgct gtatcatatg gtcactctat tcaacctttc gagaaaccac  87600
caaattgttt cttcaggaaa tgcaccatct gacatcccca ttttatgagg atccccacgt  87660
ctctgtcatc tcaccaacac ttgtaattat atattattta ttataattac ctttttaaga  87720
ttgtaacctt cttggtggat ggaaagtgac ttgtcactgt ggtttaattt gcatttcccc  87780
gctgcctaaa aatgttaagc atctttcctt tttttttgag acggagtttc actcttgttg  87840
cccaggctgg agtgcaatgg tgcgatctcg gctcaccaca acctctgcct cccaggttca  87900
agtgattctc ctgcctcagc ctcccgagta gctgggttta caggcatgcg ccaccatgcc  87960
tggctaattt tgtattctta gtagagacgg aatttctcca tgttggtcag gctggtctcg  88020
aactcccgac ctcaggtgat ccaccagcct tggcctccca aagtgctggg attacaggcg  88080
tgagccactg tgcccggcct tttttttttt tttttttttt ttgaggcaaa gtctcgctct  88140
tgttccccag gctagaatgc aatggcacaa ccttggctca ctgcaacctc tgcctcccgg  88200
gttcaagcga ttctccctcc ccgccgagta gctgggatta caggtgcctg ccaccacgcc  88260
tggctagttt ttggtatttt tagtagagac ggggtttcac catgttggcc aggctggtct  88320
cgaactcctg acctcaggtg atccacacac ctcggcctcc caaagtgctg ggattacagg  88380
catgggccac tgcgcctggt tgagcatctt tccatttgtg tatcttcttc agagaaactt  88440
ctcccaaatc ctttactcat tttaattttt ttctttattc attcttaaat ttatttattc  88500
ttatatttct taaatatgct tattcttaaa aaactaaata ggatatttgc ctattttgtg  88560
ttgagttgta agagctcttc ttatattctg ggtacaagtc ccattctgta gacatgattt  88620
gcaactgttt tctcccatct gtgagtgttc tttgatattc gtgtattttt aacacccagc  88680
caactgtgtg aaaaatacat gcacatctaa gaacacacac agatgggaga aatgtatata  88740
tgtatgtcag ctttgttact tctgttttcc acttgacact atgtagcgaa gagctccaag  88800
gttacactgc tagacttcca actctgactc agcagccact gtgtgaattc ttcccgcaag  88860
tccctttctt tttttctttt tttttttttt ttttttgag acagagtctt gctttgttgc  88920
ccaggctgga gtgcagtggc acaatctcgg ctcactgcaa cctccgcctc ctgggctcaa  88980
gcgattcttc tgcctcatct tcacgagtag ctgggattac aggcatgcac caccacgcct  89040
agctaatttt tgtattttta gtacagttgg ggtttcgtca tgttgtccag gctgktcttg  89100
aactcctgac ctcaggtaat ccgcccgcct cggcctccca aagtgctgtg attacaggca  89160
tcagtcacac atgccctgcc tcccttaatt tgtttctaca cctcactttc ctcactctat  89220
aaaataggga tgatcatcag gtmcawgtca targgttgct gtgaggatca aatcagaaaa  89280
tggatgggaa agactgsgca tgtaggaaac cctcatagat gatgtttrca ggggttcctk  89340
gttcctgccc cccatgaaca ctcaccttcc atctttatgt tttatgtttt gtttttggtt  89400
ttgtttttct ttgagacgaa gtttcactct tgttgcccag gctggagtgc aatggcgtga  89460
tctaggctca ctgcaacctc cacctcccgg gttcaagcga ttctcctgcc tcagcctccc  89520
attacagacc tcatgtgatc cacccacctt ggcctcccaa agtgctggga ttacaggcat  89580
gagccaccgc acctggcctg ttttatgttt tatgttccct gctttatgtt ttgtctcatt  89640
```

-continued

```
ttctgttttc ttctctcttc tttcttcctc tttcttttgc tccttgttag ccttccccct  89700
tccaaatgcc cagggctcca ctagagcagt ttggccccag ttgtagctct tgatgcctca  89760
aggccactga ctcctcattg ggtatgtttt ttccagcctt tgggattctt tttttttttt  89820
ttttctcctt gtgacggggc tttgctcttg ttgcccaggc tggaatgcaa tggctcatga  89880
tctctgctca ctgcaacctc cacctcccag actcaaacaa ttctcctgcc tcagcctctg  89940
gagtagctgg ggttacaaat aggcacctgc caccatggtg gctaattttt gtatttttag  90000
tagagacgag gtttcaccat gttggccagg ctggtctcaa actcctgacc tcaggtgatc  90060
cacctgcctc ggcctcccaa agtgctggga ttatagacat gagccaccgt gcccaggtgg  90120
ctttgggatt ctcgaacagg gatgacctcc agccaactct aaacagagaa atctaaacct  90180
gggatctata cctagtgtta cattttgttc ccttagattc tatgaacagg gctggaacag  90240
gctggtaaca agaagagctg ctgtgtcttg ttgttgtttt ggttttgttt gtttgtttgt  90300
tttttgaggt ggagtgttac tctgttgcca ggctagagtg cagtggcatg atctgagctc  90360
actgcaacct ctgcctcctg ggttccagcg attctcctga ctccgcctcc cgagtagctg  90420
ggattacagg tgcccaccac cacacctggc taatttttgt atttttctc tttttttttt  90480
tttttttttt tttagggggg acggagtctc actctgtctg tcacccaggc tggagtgcag  90540
tggcacgatc tcagctcact gcaagctctg cctcccagat tcacgccatt ctcccacctc  90600
agcctcctga gtagctggga ctacaggtgc ccgccaccac gcccggctaa tttttgtat  90660
tttttaggta gagacagggt ttcactgtgt tagccaagaa gatgtcgatc tcttgacctt  90720
gtgatccacc ctactcagcc tcccaagtgc tatgattaca ggcgtgagcc accacgcctg  90780
gccaaatttt tgtattttta gtagagatgg ggtttcaccg tgttggtcag gcttgtccca  90840
aactcctgac ctcaggtgag ccacctgcct cagcctccca aaatgctggt attacaggtg  90900
tgagccacca ctcccggcct ggagctgctg tgtcgagggt aggcagagct tggctggaag  90960
tgagtgctgc ccagagagcc aggactcctg ggctccagct caaccctgct atggaaaacc  91020
atccttggtc aatgtcttgc ttttcctatt tgcaaatcag gcagaaccat agctccttcc  91080
taggtctctc aggccaggcc aagaaatggt aagggatgtt tagaagatcc tgtgacttta  91140
aggtgctcgg cagaaagcca tgtgggctay tggggaattc ctccctctgg atgtggacca  91200
cagagtatct gagtgcaatg gcaagtattt gttcatgtcc tctactcatt tgttgtttgg  91260
gacattcctt gacatgactc ttactatctt cttcagtcag gattctttac tttttattga  91320
agtatgccat tcttcagagt acatataatg aaagtacagc ttggtgaact ttcacaaact  91380
gaacacaccc atgtaattag cactgtcaga gagaaacaac gcagggccag cccccagaag  91440
ctctgcccct gcacccttcc cacctcaccc caccaagggt ttcactgtca ctatctaatc  91500
accactcttg ggtgtaagtg acagaaactc atctcccarg gacttaagca gaaagtgaat  91560
gcttccctca gctgaggggt ccatgggtaa gccttgcaca actggatcca aatgcttaga  91620
tggtgctgtc agcttgcctg tgaactttct ctgctgagtt ctcttctgtt gttgatttta  91680
aacctaggca gtttcctctt cccttgtgat caacaaaact ccagaattgc agttgagcag  91740
atgtcccatt cctaggccaa tagttctgtg tgggctgggg gggcagggtc agtgtgtgga  91800
atatagaggt gggtctgtct tgggacacat gacccttagg agccgggagt ggtggatcag  91860
ccccatctga gccacatgca cttttgagtg ggtgagggtg attccccagg gaaaagccta  91920
gagactgtta tcagaaggaa aaacgggtac tgagtggaca gaaccaagca tgtccagtgc  91980
```

-continued

```
acctgtgcag tgctgatcct cacactagtc accggagaac aggtgttcgc ttgcgaaaaa  92040
ccacaatcca aagttccggg ttgctcacag gcaagaaggg aaagcaaagt acaatgcagg  92100
gcagagtggg gcatgccttg acaggcacag aggaggtggc tgcaggcgag gctgaaatgc  92160
ctcccagtgg gagtcagggc tgcgcactca tagcatgggt gagggagttg ggagagatgg  92220
agcttgtttg atgaacactg attattcccg gccatctgaa gcctgggata tgggagataa  92280
ggytggaaag ctgaaggtta ctgaaaagga gaatgacagg atcagatgtg tggtgtaggc  92340
acctctgggg gcaactgtac aagatggact gaagggaggc caggtgggga ctttgctgga  92400
atccaggaga taaggatgca gccaggacca gcatgaccct cccgcggctg gatgtccagg  92460
ccatccactg ggacaccatc aggtcccttg accgtcacat agccagatgt gtcttcagtg  92520
tccccaactt gattgtcagc tctgccagga tcgggatcct gagcactggc tttcctggat  92580
gaatcttttg ctgatcttat ctcttctcta ttttccaacc tttatctgtc atttatgttt  92640
tttgttctac ttttcacatc ttttaaattt ttctttcaac gtttctaata tctaatgcaa  92700
ttagccccaa ggaaaactaa gggaaacaag aaaaaacaag aaaggaaatg tactctcagt  92760
acttcagctg tgagctgtga gcttcagctg tgagctggag tgttttgcts tggttttagg  92820
tttttgattt tttttaagaa agagggtcac actctgttgc ccaagctggt gagcagtaga  92880
atgatataac tcactgcaac cttgaactcc tgggctcaag agatcctccc accttggcct  92940
cccaaagtgc taggattaca ggcacgagcc accgtgcctg gcctccaggc atattttatc  93000
ctttctcaag ctatgtgtag tgttttgaca aaaataaatt ttaaaaagag ttaatgtcaa  93060
aaaaagtttc tgtgacttaa gaaggaccac tgcttagggt gctcctcctg ggtaccaaaa  93120
caagaaacag aactttctat tccctttatg gcctcttgta ctttttagtt ccaccctcct  93180
cctgaaaaaa tatgatcatt ttcatcatca tcatcaccat catcaccatt aattacttgt  93240
tggaaattta aagcagaatt gcctctgagg ttggaaggct ggagagggca tgagagatag  93300
gaaacgtcac tttcttctgc ctgactggcc ttgtgctctg gtgtggggct gtgtctgccc  93360
agggggtgtg gcctcttttc ctgtcttcac atatgaaaca tgagctggca atgccctcat  93420
ctttaccttg agtttttttg tttgtttgtt ttgtttttga gatggagtct cgctctgtcg  93480
cccaggctgg agtacagtgg cgcaatctca gctcactgca acctccatct cccgggttca  93540
aatgattctc ctgcctcagc ttcccaagta cctgggacta caggcactca ccaccacacc  93600
cggctaattt ttgtattttt agtagggttt tgtcatgttg gtcaggctgg tctcgatcta  93660
ctgacctcta gtgatctgcc cgcctcagcc tcccaaagtg ctgggattac aggcgtgagc  93720
caccatgcgt ggcttagaat tttatacaac acctatgtgt taacttttcc aaaaagtaaa  93780
catataataa atatgtgccc ctcatcaagg gaagactttc aagggggaga taggccttcc  93840
aggatgggaa agggcactgg acaaaggctc aggactgcga cacccaccac agagccctgc  93900
agtgagagtc tggttcttcg atgtatttat gtatgtttgt ttgtttattt atttatttac  93960
tttttgagac ggagtctcgc tctgtcaccc aggctggagt gcagtggtgt gatcttggct  94020
cactgcaacc tccacctcct ggattcaagc aattctcctg cctcagcctc ccgagtagct  94080
gggactacag gtgcctgcca tcatgcctgg ctatttttat atttttagta gagacggggt  94140
ttcaccatgt tggtcaggct agtctcaaat tcctgacctt aggtgatcca cccgcctcag  94200
cctcccgaag tgctgggttt acaggcgtga gtcaccgcac acccggccta tttatttatt  94260
tattatttat ttatttttga gacagggtct ttctccgttt tccaggctgg agtgcagtca  94320
cacagtctct gctcactgca acctgtgcct cctaggctca agcaatcctc ccacctcagc  94380
```

-continued ctcctgagta gttgggacta caggtccgcg ccactgcact gggctaattt ttgtattttt 94440
agtagagatg gggtttggcc atgttgccca ggctggtctt gagcttctgg gcccaagcaa 94500
ttcacccgcc tcagcctccc aaagtgccct aattacaggc atgagttacc gtacccggct 94560
ggctcttgga tttaagcccc tgcccttcct ccttcttact ggatattcat gtctctgagc 94620
cccactgctt caattaaaac agagaggtat ggtcatttct gcctcccagg gacttgggat 94680
gatagcattt aatcatgaag acagaagtac ctatcacagg gcctgcctga cttgttcttc 94740
ctaatgtcaa aaccttggcc caaatgtcta ctgtgctgaa cgtaaggctc ctatcagaat 94800
gctctcagct aggaactggt cttctggaga ctctgtggcg taggatgatt caaccacctt 94860
cctagttctt gagtttcagt aataggatct catagcagtt cctgtagtgt gtgagtcact 94920
taagaagacc tctggcttcc ctggaacaca ggtaacaaat accttggctt gggatcaaga 94980
tcctccctac ccagggaagg gctgagctgg ccaggacaac tgtgtttggg ccagagcagc 95040
agggtcctgc actctgcagg gagcaatcac aggtgggaga agcccacagc ctgggatcag 95100
aagtgccaga agcttaggaa caggagtcct ggggtcccag ctttctcgct gtctctccaa 95160
gccttgagtc tttcacctga aaaattgaca tcatcgtgcc cacctcaggg cccgttgagt 95220
taagtcatcg cgtggacttg aagcacctag cacttgtgat cattgaagtc agaaaatgag 95280
ttcccttctc tttcggcgcc ccattggcag gaagccaacc atcgtcagcc cactggcact 95340
ggaggagcgt tgatcatgtg cagagcagat gagtggctac tctccctgtc ttccaggttt 95400
tcccagagtg gctgtgggat ctggagtcgg ctggtgacag agctgctggg catcctccac 95460
ccacccctgt tgcctcctga tgagggaaat gggcagagag gagatctgct cacaagttag 95520
accctggctt ctctcagtgg gcgatgtgga caggggaagg gggcaggcaa ggagcaaagg 95580
atgcaggagc aaggagaaaa cttccaggct cctcccttcc aaagtcaccc agccttgaga 95640
tcattgcaga tgcaacaggt gcaaacagaa gaacactttg ggaccttgga atgcgggaag 95700
ctggctcagt gttccttcca ccctgtgaga catgtgtgac atttttgttg ttgttgctgt 95760
tttgagacgg agtttccccc ttgttgccca ggctggagtg cagtggcatg atctcggctc 95820
accacaacct ctgcttccca ggttcaagtg attttcctgc ctcagcctcc ctagtacagg 95880
catgtgccac aacgcctggc taattttgta tttttaggag agatagggtt tctccatgtt 95940
ggtcaggctg gtctcaaact cccaacctca ggtgatctgc ctgccttggc ctcccaaagt 96000
gctgggatta ccagcatgaa cctccatacc cgacctatgt gacattctta aggtccacga 96060
aagggctggt ggttggaggc cagagggtgg cctgtgagat actgggattg gaagagtagg 96120
tggcctgtgg gtgtctcctc tggggggaga ctccccaggg ggaggggttc ctcctctcca 96180
aacagtagct cagcacaggg acagtaacag taatgggggc atgtgtgtaa ggaatgcttt 96240
cccaggcccc ctcttcatag gtgtttgcag cagcatctca cagccctaag aggttaaatg 96300
ttgcacatcc catcctacag aagtggaaat cgagcctcag agaagttgtg tcgcttttgg 96360
ggctatcttc ccctgtagag tgtgactcca tcgccctcct gctttaccag gtgctgagga 96420
acctctaatc atctcccatg gatttgtgat cagcgttgca gctctcccag cagccctgga 96480
cagtggtgag tcccctcagc tggccgggac agtcctctgc tctcacctct ctgcttctct 96540
ggctccatcc cagctccgcc tcagctggtc tccttgcaaa cccacagggc tccaggacat 96600
cctccctctg gagcccatgc tgccttcagc acttcacccc ctaccggtga tggcaacaat 96660
tggtgttctt tgtccacttt atttattggc tcattttttt gtttttgaga aagagtctca 96720

-continued

```
ctctattgcc caggctggag tgcagtggca taatctcagc tcactgcaac ctctgcctcc  96780
cgggttcaag cgattttcac gtctcagcct accaactagc tgagactaca gacatgcacc  96840
accatgccca gctaattttt gtattttttt tggtagagat ggggttttac catgttggcc  96900
aggttggtgt cgaactcctg acttcaggtg atctgcccac ctcaacctcc caaattgcta  96960
ggattacagg catgagccac tgtgcctgga cttatttgct cattttgata ttgtactgta  97020
tgttttgagt cagagtctca ctctatcgcc caagctggag tgcagtggca tgatcaaagc  97080
tcactgcaac ctcaaactcc tgggctcaag cagtcctccc acctcagcct cccgaatagc  97140
agggaccaca ggcgcactcc accacacctg gctttccttt ttttgttttt tttaatgttt  97200
ttgtagagac aggcaggcta tccatatgtt gcccaggctg gtctcaaact tttcgcctca  97260
aggtatcctc ccacctcagc ctcctaaagt gctgggatta caggcttgaa tcccaggctc  97320
gcatcctgcc tatttgcttc ttttcttttc ttttcttttt tttttttttt ttttggaatg  97380
aagttttgct cttgcccagg ctggagtgca atggcgcgat ctcgtctcac tacaacctct  97440
gcctcccggg ttcaagcgat tctcctgcct cagcctcctg agtagctggg gattacaggt  97500
gcccgctacc acgcccggct aatttttgta tacttagtag acatgatgtt tcaccatgtt  97560
gaccaagctg gtcttgaact tctgacttca ggtgatccac ccacctcggc ctcccaaagt  97620
gctgggatta caggcgtgag ccaccacgcc cagcgcctat ttgcttattt tcaataagaa  97680
aagttatttt ccataagaaa agttatacct gtctatttaa aaaaaaaaaa atcatacact  97740
gcagaagcac acgctgtagc aagggcactc ttcagttagg gacattacta catgtctctc  97800
ctgtccatcc aggatattca aacatgttcc catttccaa taatccactt aaatcctgta  97860
ttatgtgctg gtatcatctc ccttttgcag atgggtaaac tgagtcacgg ggcgatccaa  97920
tattttgttc aagatcacag gctatgtatg tcagtgtagt gtgggagatt aaaaaaggaa  97980
aaagaccaca ggctacggag tggaagagcc tcagggagcc tggccgtgct gtgacatcca  98040
ccagagcgcc catcagttca acaacctaaa agagtttcct tacaggaatt cttaagcaaa  98100
agacaggaat tccgtttgaa atatatttcc ctctccaaat agacaatggt aatgtgggta  98160
ggtagaacta agaaggtagg actcacatta agaaggtagg actcacatta agaaggtagg  98220
actcacatgt agacagattt ccgaccgcat tctgcatttg tacttttgct ctcagctaga  98280
ctggatcctg agttatgtct taaggccaca tttccgggag agctccccac tgagaccatc  98340
atgttcatgg gatgctcggg tctggtggta gaatctgccc cctgcgggca ctgggcagtg  98400
gggtacggga tgggcgtgca ggctgcagcc cctaaccgct gcgctctcct ccctaaggcc  98460
cccagcagtc agcatgtggc tgccgcgcgt ctccagcaca gcagtgaccg cgctcctcct  98520
ggcgcagacc ttcctcctcc tctttctggt ttcccggcca gggccctcgt ccccagcagg  98580
cggcgaggcg cgcgtgcatg tgctggtgct gtcctcgtgg cgctcgggct cgtccttcgt  98640
gggccaactc ttcaaccagc accccgacgt cttctaccta atggagcccg cgtggcacgt  98700
gtggaccacc ctgtcgcagg gcagcgccgc aacgctgcac atggctgtgc gcgacctggt  98760
gcgctccgtc ttcctgtgcg acatggacgt gtttgatgcc tatctgcctt ggcgccgcaa  98820
cctgtccgac ctcttccagt gggccgtgag ccgtgcactg tgctcgccac ccgcctgcag  98880
tgcctttccc cgaggcgcca tcagcagcga ggccgtgtgc aagccactgt gcgcgcggca  98940
gtccttcacc ctggcccggg aggcctgccg ctcctacagc cacgtggtgc tcaaggaggt  99000
gcgcttcttc aacctgcagg tgctctaccc gctgctcagc gaccccgcgc tcaacctacg  99060
catcgtgcac ctggtgcgcg acccgcgggc cgtgctgcgc tcccgggagc agacagccaa  99120
```

-continued ggctctggcg cgtgacaacg gcatcgtgct gggcaccaac ggcacgtggg tggaggccga 99180
ccccggcctg cgcgtggtgc gcgaggtgtg ccgtagccac gtacgcatcg ccgaggccgc 99240
cacactcaag ccgccaccct ttctgcgcgg ccgctaccgc ctggtgcgct tcgaggacct 99300
ggcgcgggag ccgctggcag aaatccgtgc gctctacgcc ttcactgggc tcagtctcac 99360
gccacagctc gaggcctgga tccataacat cacccacgga tctggacctg gtgcgcgccg 99420
cgaagccttc aagacttcgt ccaggaatgc gctcaacgtc tcccaggcct ggcgccatgc 99480
gctgcccttt gccaagatcc gccgcgtgca ggaactgtgc gctggtgcgc tgcagctgct 99540
gggctaccgg cctgtgtact ctgaggacga gcagcgcaac ctcgcccttg atctggtgct 99600
gccacgaggc ctgaacggct tcacttgggc atcatccacc gcctcgcacc cccgaaatta 99660
gtggaggcca cagttgtagc aggcgctagg cccgggagga gagtgcatgg tgcagagggg 99720
gctggggcgc acggagaagc aggtccctat attgaccaag gagtttgtgg tacgacccct 99780
cccccctccc aagtaggcaa ggactgcacg tttctttctc tcttgattct tggttttcct 99840
ttgagtcctc tggagctgcc ttctcatcag gtgcactctt catggaaagc aactcttgcc 99900
cctcctcctc tgggcacagg gtgtgcgttc agatgacttg gctcctactc aagggctttc 99960
ttcccctttta actctctcct tctggtgaca catcctgcag cagctgaggg ggtgccctgg 100020
cactggctgg gagtggagag gcactgtggt gaaatggctc cagaggtctg tacatcacat 100080
acatatgcac acaggcacac atggcaaaac tcggaagtga aaggacttgt ctgaaatcac 100140
atggtgagaa ggaggatgaa gggaggagag agcttttgct ctgggtctcc agtggatagg 100200
agaggacctg cctcctgggt gagaagggtc agattttcct attttaattg ctttagggaa 100260
gagcaagcag agtcatgacc agggacacag ctgagagata gaggaggctg tgaatgctga 100320
gaccagagtt tatcatgctg gacaagcctg gaaggaggca ataagtggga aaggtaggag 100380
gagagaaggc tggggagggc tgggcagcaa gccaggcaca gtgagtggca gagccagagg 100440
gggaaagcag gatcagtgcc tggaaggcag gtgtgcccgt cagcggggag tggaactcat 100500
caggcttgcc aagaggttgg aagggaaatg gctctgggct ggaactgtct tcccttggtc 100560
cttctggtcc aggccttgga ggaaagcaga ggatgatccc tgcctgtgag ccacacctcc 100620
tagctctggg ggcaaagggg cttagtaaag gaatgctgga tgtgtagagg gtttagtccc 100680
gagctcagga aatgagagcc tataagtgcc cagtacatgt ttaaaagaag agctcatgga 100740
acctctggaa aggacaggga agttgagtta gccacataaa tgaacccaag tcacattgga 100800
acacagagct ggtctgggaa ctgtgttggc tgccaacaga acttctgacc ctgttacctg 100860
tgaaatgagg cagtttccct cacgttgcca tcagctacca ggagcgatgc tggtggtcac 100920
tagcttctga tcctcatcct gggtgtggcc acagattggg ggaacctgga ttgtggagtc 100980
acatcctccc tgcaaagcaa gcagggcaag ggagatctgg cattttctgc tttacgtgga 101040
gggagaacag gcacattagc cttgaagctg aagctcattt taggttcctt ccaggtttag 101100
aagcttcaac caaatgaaac ttgaatctgt ccctcgtgac aattatagga ggaaggtatt 101160
taaaacccca gatttatgaa tgtgtactac atggcttaga gaatgtcttt gttcttgttc 101220
aggtggttat aacaaaatac cttaagagtg ggtaacttgg ctggatgcag tggctcatgc 101280
ctgtaatccc agcactgtgg gaggccgagg gggatgaatc acctgaggtc aggcattcaa 101340
gaacagcctg gccaacatgg cgaagcccct cctctactaa aaatacaaaa ttagcgaggc 101400
atggtcgcac atacctgtaa tcccagctcc tcgggaagct gaggcaggag aatcgcttga 101460

-continued acccaggagg cggaggttgc agtgagccaa gatcacgcca ttgcactcca gcctgggtga 101520
cagagcaaga ctccatctca aaaaaaaaaa aaagactggg taacttataa acaaatgttc 101580
ttctcacaag tctggagact gggaagtcca agatcaagcc accagtgctg tctgatgagg 101640
gcccactttt tcaaagacag tgccttctag ctgtgtcctc ttatcgtaga agatgggaga 101700
cagctctcca gggccatttt tttttttttt tttttttttt tgagatggag tctggctctg 101760
tcgcccaggc tggagtgcag tggcacaatc tcggctcact gcaacctctk gcctctctct 101820
kgcctcctga gttcaagcaa gttctcctgg cctctagcct cctgtaggag ctggactaca 101880
gggggatggc accaccagtg tgcccaagct aaattttttg tatttttgta gacactggag 101940
ttttcaccaa tattaggcca ggttggtctc aaactcctga cctcaagtga tctgcccacc 102000
tcagcytccc aaagtgctga gattacaggc atgagccact gtacccagtc tccagggcct 102060
tttaaagaat gtcactaatc ccattcttga ggtctccacc ttcattatct aatcacctcc 102120
caaaggctcc acatcccaac accatcatat tgtgggttaa gatttcaacc acaagccagg 102180
cgtggtggct catgcctgta atcccagcat tttggaaggc tgaggcaggt ggatcacttg 102240
aggtcaggag tttgagacca gcctggccaa catggtgaaa ccccatctct actaaaaata 102300
aaaaaaatta gccgggtgtg gtggtgcaca cctgtaattc cagctactca ggaggctgag 102360
gcaggagaat cccttgaatc caggaggcgg acagtgcagt gagccgagat aatgccactg 102420
cactccagcc tggatgacag agcaagactc catctcatgc ccagccagca tgcccaacaa 102480
gcttcatttg cccctgttta ggtcacaaat tttattgatg gctgcaatta atggcctctt 102540
ggtatccaag tcctttgttg tatgacccat ccattctccc ctgactccca aggtgtcagg 102600
acatgcttga ctggctcctg aatttgctct ctgcgcatgg gcagtacagt caagcctcac 102660
agtgaaccca ggtcagcttt caggacaaag aaagtggcct ggctgactag gcacagtaaa 102720
gccagggctg ggtaggtaca tacttgtgct gatcacgtat gtcttatatc tctgtgagag 102780
tgcagtccca acaggaaggt ttaatcactg gggactgccc aatgctgtga cagggcacag 102840
agctctgggt tgctgtgggg gtgactgcat tgaccactgt tagtggtttg ctgtgttgac 102900
actctgtgct gtgtgaccat ggctcctgcc atcaagaagt agagtctgtt tctccacctc 102960
tgaatccagg ctggtcctgt gacttgcttt gtcctgtaga caagtgtagt gcaacttcct 103020
gtgagccagt ttgaagcata ggccttggaa gcaaaacttt acctccacct gtcttaggtt 103080
ttcagctggg gctctgctgt gatttgattg tgtctcccaa agttggaacc ttgatcccca 103140
gtgttgtgag gtgaggcttg atggaaagta aattacgccg tgcgggttat gcccttgtga 103200
atgggtagag aacattattt ctgggcgcag gcatggtagc tcatgtctgt aatcccagca 103260
ttttgggagg ttgaggtgtg cggattactt gaggtcagga gtttgagacc agcctggcca 103320
acaaggtaaa acaccatttc tagttaaaat acaaaaatta gccaggtgtg gtggcacatg 103380
cctgtaaggc cagctacttg ggaggctgag acaggagaat cgcttgaacc caggaggcag 103440
agattgcagt gagctgagat cgcaccactg tactccagcc tgggcaacaa agcgagagtc 103500
tgtcttaaaa aaaaccacca ttatttcagg agtgagttgg ttatcctgag agtggtgcct 103560
tttaaatgaa ggagttcatt ctttgtcttt ctctcgccct cactttgccc ttctgccata 103620
tgatgccttc catcatgcta ggacacagca agaaggctct cgctagatgc tggctccttg 103680
atcttgggct tcccagcctc cagaactgta agccaataca cttctattta ttatatatga 103740
cccttgctgg gttcagtggc tcacgcctgt aatcccaata ctttgcaagg ctgaggcagg 103800
aggatcactt gagaccaggc actcaagacc agcctgggca acatagtgag accccatctc 103860

-continued tacaaagtta aaaaaaaatt agcagggcat ggtgtcgtgc acctgtagtc ctagctactt 103920
gggaggctga gttgggagga ctgcttgacc ctgggaggtt gaggctacat tgaaccatga 103980
tcatgccagt gcactccagc ctgagtgaca gagcaagaca cctatctcta aataaatgac 104040
cccayctgtg gtattgttat agcaaaacaa aacagattaa gagagacttt ttaatgaaaa 104100
gacagattca caaagaaaaa caatgttttt gtttctgttt ttttgaggca gagtcttgct 104160
cttgtccccc aggctggagt gcagtggcgc catcttggct cactgcaacc tccgcctccc 104220
agtttcaagc gattctcctg cctcagcctc ccgagtagct gggattacag atgtacacca 104280
ccacgcccgg ctaatttttt ttgtattttt agtagagatg gggtttcacc atgtcgatca 104340
ggctgggctg gaactcctga cctcaggtga tccacctgcc ttggcctccc aatgtgctag 104400
gattacaggc atgagccact gtacctggcg aaaaacagtt tgttaacaca ggcagccaac 104460
atcactcagg ataagcctca atgaaaagta acaaagtgat ggcttggaac actgtcttac 104520
acagcatttt taaaaaatac aataaatttg tagagatagg atgaccaagg acaacagttt 104580
taggcttcca aaggtggtaa actatgggat ggtaaatatc cgagaggaag ctgatgcaac 104640
aggatttgtc tgcagcagcc tctggtacca cctctgagtc aagggttgtg tccagtgatg 104700
gagagtttat atcgtgcctt taggcagaaa aggggaggga aacctgaact tttcctgcac 104760
tttctgcttc ttaattgcct tcagctgaaa atcatttttt atgtgaaaaa ggcatagtct 104820
gagctgacgc ctctgctttc ctccacctga agagaacctg cgtgctgctc ctttgcttcg 104880
gacctccgcc tctgcccggg agaaagccca ggccagcctg ctggacaagc agagaccatg 104940
agaaggagag ttcaggggtc ccaaaccagg ccatcctaga ccagccagct ccagctgatc 105000
cgcacgcagc cacttcggct accttctact ggccaaaggg agtcccaggg ctcacccaga 105060
ttcagaggtg gggaaactga gtccaccact tgagaagagt agctataaag acatatgagc 105120
gaggccagct gagcccagca ctgcggccaa gtcgaagact ttaggagcaa taaaagtgct 105180
tattgtgttt cagtcatttg agtgttgtgg tggtttgtta cgtagcattg cctaaccgat 105240
acacttgaga acggagggct cctggcacct gcagcttcca atttccacca gggtccaggc 105300
tccctccctg ctggtagggc tgtaattagt gtctcccctt acctgtaggc cctgtgatgc 105360
agctagaagt gtctaggccc agcagtcacc cacaattagg ggcaggcacg cttgctgcct 105420
ctgctctggc tgtgggagct cagaaggggc aatcaaagca ctagatgggc tgatgggtgc 105480
atagaaacag tgttgcctgg aataggtcag agaacccacc tatcaagagg ctgttgggga 105540
atcaatggtg ggccttattt ttgttatttt gcatcaagaa gatatattat ccacatcaac 105600
actgtatcaa ctcctcatgg ccaccacaga ccctgtgtcc cctagstttg tctttgatgt 105660
gcctttgtca cccactccta cagactgcgc ccccaccactg ccacaactgc cccatcacct 105720
ctacagggtt aaatcaatgg ttttaatttt tgcctacctg atgggtgaaa aatgttactt 105780
gatgtttcag tctgcacttc tttaattcct ggggcagctg aacatctttt catgcttatg 105840
actcaactgt attccttttt cattgttcaa ggctgtgccc atgttgctgt tgacttacca 105900
cagcctcttt tgaatatgct ttgttatttt tgttgtgcaa atggtttctc ctagcttgtc 105960
atctgttttt tgttgttgtt gttttgttaa cttactttat ggcattttcc cctcaggctt 106020
cttaaaaaaa aagaagcttc attgagctat aattgatata caacatctgc acataaagtg 106080
taaagtttga ttaaacattt gtatatacct gtgaaatcaa atcaccacct catcacaatc 106140
aaatttcaaa aagtttcacc tagtttatca tattgttgaa tgtgaatcct ttccttatgg 106200

-continued

```
ccagtggatt ttatgtcttg ttgaaacgac tttgtcctgc tacagtgata aaaatggtct 106260
tcacgcttgc ttccagtact ttagtagtct agtgttttac gcttggatct aaattgcatg 106320
caatattcct gatcggtgcg agtcatcagt tctcccagcg ccctctactg aatgatctca 106380
ctcatcacac actgaaacca ccatgggctg gaatctgtcc ctcacccaca ggcccactcc 106440
acaccagtgg atcaggcgag caatttcttt aggtcgagtg acccctatgc tgaggtccag 106500
tgggttatcc csactacctt cacaagttaa tggatttaga tttaagcacc acctgccccc 106560
agcagattct cttacaattt aaatatcctc tcacagtgca aatccttatt ctgtgaatga 106620
ctctattcag accatgttcc ttaagaacca sagctaggct gggtgcagct gtaatgctag 106680
caatttggga ggccaaggtg ggcagattgc gtgagctcag gagttcgaga ccagcctggg 106740
caacttggcg aaaccctgtc cctactaaaa aaaatacaaa aacgtagcca agcgtggtgg 106800
tatgtgcctg aaattccagc tacttgggag gctgaggcat gagaattgct tgaacccagg 106860
aggtagaggt tgcagtgagc caagatcgcc ccactgcact ccagcctggg taatagagcg 106920
agactctgtc tcaaacaaac aaaaaacgaa agaaccagag ctaaagtctt gatgaaatgg 106980
aaaggattgg cctactatcc atttttccaa gatggcaatt cattccagcc aatcgagcat 107040
tttctccttt gggagtaaga ccagaaaacc tggcctgtcc tgcaagtctt gtgttattct 107100
gctcccagtc ctcaagaact ccactcattc attcaacaca cattatgggt tgagcaccaa 107160
ccaggcactg grctattata ggagctggag atacagcagg accaaaaaca gacaaaaagc 107220
aaaaacccct gccctaggct gggtgcagtg gttcacacct ctaatctcag cccttagtga 107280
ggccgaggca ggtggatcac ctgaggtcag gagttcaaga ccagcctgac ccatatggtg 107340
aaacccagtc tctactaaaa atataaaaat tagctgggca tcgtggcatg cacctgtagt 107400
cccagctact caggaggctg aggcaggaga attgcttgaa cccgggaggc ggaggttgaa 107460
ttgagccgag atggcgccaa aggactccaa cctgggcgac agagcgagac tccatctcaa 107520
aaacaaacaa aacaaaacaa aacaaaacaa aaaccagcca ggcgcagtgg ctcacgcctg 107580
taatcccagc actttgggag gccgaggcag gcagatcatg aggtcaggag ttcgagacca 107640
gcctggccaa catggtgaaa ccccatctct actaaaaata caaaaattag ccaggcgtgg 107700
tggtggtggt gcacgcttgt aatcccagct aatcaggagg ctgaggcagg agaatcgctt 107760
taaacctggg aggcggaggt tgcagtgagc tgagatcgcg ccactgcact ccagcctggg 107820
cgatagagtg tgactctctc aaacaacaac aacaacaacc ctgcccttca ggaacttgca 107880
ttctgatggt ggggagatag ctgatgaata agcttaataa atggctacat tatttagcat 107940
attagaaagt gccaaggatt aaagtagaga aggatcgggg gatgaggaat atatgtgtgt 108000
agaggtgtga gttgtaattt ttaatggggt gatcagggta ggtctcagtg agaaagcgac 108060
atttgaagga aagtcttaca ggaggtgagg gagtatgtta agggcaatca tgggtagcct 108120
gtctgggagc aggaaagagc taacacaaaa gccctaagga ggggaggcat ctggcttgtt 108180
gaaagagcag caaggggcca gggggtctgg tgtgctggac cgcctccttg gcttccttag 108240
acagggccca ggaaacctcc attttctgag tcctgcaagg ctaaatgtct ttttttaacc 108300
tgtcaattca taaatgaact aaagatcgaa ttctaaattc aaaataatgt ttcctaatgt 108360
aatacataat tgattatgta accctacaat aattgatttc ttccactttt tttttttttt 108420
ttttttttgag acggagtctc gctctgttgc ccaggctgga gtgcagtggc gcgatctctg 108480
ctcactgcaa gctccacctc ccgggttcac gccattctcc tgcctcagcc tctccggtag 108540
ctgggattac aggcgcccac caccacgccc agctgatttt tttttttttt tttttttttt 108600
```

-continued gagacagagt ctcattttgt tgcccagact ggagtgcaat ggcacgatct cggctcctgc 108660
aacctctgcc tcccgggttc aagtaattct cctgtctcag cctcccaagt agctgggatt 108720
acaggcgcat gccaccaggc ccggctaatt tttgtatttt tagtagagat ggggtttcac 108780
catgttggtc aggctgttct ggaactcctg acctcgtgat ctgcctgcct cggcctccca 108840
aagtgctggg attacaggtg tgacctacca cacctggccc tttttctttt tttttttttt 108900
tttttgagac agagtcttgc tctgtcgccc aggttggagt gcaatggtgc gatctcggct 108960
caccgcaacc tccacctccc aggttcaagc aattctcctg cctcagcctc ctgagtagct 109020
gggattacag gcacatgcca ccatgcccgg ctaatttttg tatttttagt aaagacgggg 109080
tttcaccatg ttggtcaggt tggtctcaaa ctcctgacct cgtgatccac ccgccgcagc 109140
ctcccaaagt gctgggatta caggcatgag ccaccacgcc cagcggtttc ttccacttct 109200
aatagactct gctagtctgg gaaatgtacc aaaaagacag catggttaaa aggtcagtat 109260
ttcctgaccc tttttatact tcctattttt attttagata ggtttcttgg ttgatgcaaa 109320
acgccaattg tagtggtagg gaactggcag gaggaagctt cctaaacgga ggtttcaaga 109380
gagacttctg tttctttttt tttttttttt tttttttgag acggagtctc gctctgtcgc 109440
ccaggattga gtgcagtggc gcaatctcag ctcactgcaa gctccacctc ctgggttcac 109500
accattctcc tgcctcagcc tcccgagtag ttgagactac aggcacctgc caccacgccc 109560
ggctaatttt tttgtatttt cagtagagac ggggtttcac cgtgttagcc agggatggtc 109620
tcgatctcct gacctcgtga tccgcccgtc tctgcctccc aaagtgctgg gattacaggt 109680
gtgagccacc acgcccggcc ttttttcttt ttgagatgga gtctggcttt gttgcccacg 109740
ctggagtgca gtggctcccg ggttcaagca atgctcttac ctcagcctcc tgagtaactg 109800
ggactacagt cacacaccac cattcccagt taattttttc tattttagta gagatggggt 109860
ttcaccatgt tgctcaggtt ggtctggaac tcctgagctc agacaatttg cctgcttcag 109920
cctcccaaag tgccagaatt acaggtgtga gccaccgcgc ccggctcagg agaaaattct 109980
aataaacagt cttgctaatg ttcttgaatt aaraggaaaa tatgggttgg gtgtggtggc 110040
ttatgcctgt aatcccagca ctttgggagg tcgaggtggg tggatcacra agtcaggggt 110100
tcgagaccag cctggccaag atggcaaaac cctgtctcta ctaaaaatac aaaaattagc 110160
agagcatggt ggtgggcacc tgtaatccca gctactcagg aggctgaggc aggagaattg 110220
cttgaacctg ggaggcggag gttgcaatga actgagatcg tgccattgat ctccagcctg 110280
ggtgactgag caagattctg tctcaaacaa acaaacaaac aaacaaaaat ggaaaatatg 110340
tattttgcac acaatacttt tgagtgtaaa ataggttaat gaccgggtgc agtggcttac 110400
atctgtaatc ccagaacttt gggaggccaa ggcgggagga ttgcttgagc ccacaagttt 110460
gagaccagcc tgggcaacat agtgagaccc tgtctcttaa aaaaatttaa aaacaaaaaa 110520
gctttaaaaa aaatcatttt ctctgcaaat actgaaggtg ttggtacatt gtcatccagc 110580
cttcttcttc atttggctac tgaaccattt gattctcatt tctttgtagg tgacctatag 110640
attccctctg ttttaggaat ttcttttttta tttctttctt ttttttttgag atggagtttt 110700
gcccttgttg cccaggctga agtgcaatgg caagatctcg gctcactgca acctcttcct 110760
cccaggttca agtgattccc ccgcctcagc ctcttgagta gctgggatta caggcacccg 110820
ccaccacgct cggctaattt ttgtattttt agtagagaca gtcttcacca tgttggccag 110880
gttggcctcc aactcctgac ctggtgatcc acccaccttg gcctcccaaa gtgttgggat 110940

-continued ttcaggcgtg agccactgtg cttggtagaa tttcttattt ctatcttttt cttcttgttc 111000
tatttatttt tcttttcctt tctttattat gattaatttg gtggagcaac accatttatt 111060
tccagggcca gcattggata tagcacaatt atggaaaaag gctgtcagcc actgtcacaa 111120
aaaaatccta cagaatctga aatgccaaca agaagtctag ctgcgccaga aaatacctgt 111180
gaatcacagg tttttccatt tcaacttata tgacaaaaag tttcagcttt aattatttac 111240
taaattcctg agccatcttt aaattcttgt ggggtttttt gtttgtttat ttgtgtgttt 111300
gttttttgag acagggcctt cttctgttgc ccaggctgga gtacaatgga gcaatgatag 111360
ctcactgcag ccttgacctc tggggctcaa gggatcctcc cacctcagcc tctggagtta 111420
gctgggacta taggtgtgtg ccactacacc cgactaattt ttgaattttt agtagagaca 111480
aggtttacct atgttgccca ggctggtctc aaactcctgg gctcaagcaa tcctscagcc 111540
ttggcctccc aaaagtgttg ggtttacagg catgagccac cttgcttggc agatcggtga 111600
attggtcact ttttaaaaag attttaaaag gtatgattta tgtagcataa aattcattta 111660
ttttaactgt acaattcaat gatttttaaa gaagttttca ggctgggcac ggtggctcac 111720
gcctgtaatc ccagcacttt gggaggccaa ggtagatgga tcacctgacg tcaggagttt 111780
gagacaaacc tgaccaatat ggtgaaattc catctctgct aaaaatacaa aaattacctg 111840
ggcatggtgg cacggagcta taatcccagc tacttgggag gctgaggcag gagaattgct 111900
tgaacccggg aggcgaaggt tgcagtgagc cgagattgcg ccactacact ccactccact 111960
ccagcctgga cgacagaaaa agactgcgtc tcaaaaaaaa aaaaaaaaaa aaaaaaaaaa 112020
aaaaaaaatt taccagtcag gtgcagtggc tcacgcctgt aatcccagca ctttgggagg 112080
ccaaggcagg tggatcgctt gaggtcagga acgagaccaa catggataac atggcaaaac 112140
cctatctcta ctcaaaatac aaaaattagc tgggcctggt ggcacgcgcc tggaatccca 112200
gctactgggg aggctgaggc aggagaatcg cttgaaccag ggaggcggag gttgcggtga 112260
gctgagattt cgccactgca ctccagcctg ggcaacaaag tgagactctg tctcaaaaca 112320
aaccaaccaa ccaaacaaaa acattattat tcgtcacaag cctcttcatc acctggaacc 112380
ttgtggacat tacttatcct tggtaacttc ccttccagaa cactattgtt aatggctgct 112440
atggtctgaa cgtgttcccc caaattcatg tcctgaaact tcgtgggaat gcgatagtac 112500
tgagaggagg ggcctttagg agacgattaa gtcagaagag tggagccccc gttatgggat 112560
taggaccctt ataaaaggga tttggagagt gggctccctt tgttaccgtg tgaggacgcc 112620
cgggcggtgc tatcagtgag gaacgggccg tccttagaca tggaacctgc tgcgaccttg 112680
atcttggacc tcccagcttc cagaactgtg agaaaataaa tttctgttct taataaattg 112740
cccactctca ggtactttgt tacagcagtg caaacaaact gaacattagc ttattccttt 112800
ttacgatttc tctgccttca ttttaacagg ctttctgaag ggaggtgaga caaaaatgtg 112860
tgatccacga ggacaggaaa tcgagaccat cctggctaac acgatgaaat cccgcctcta 112920
ctaaaaatac aaaaaattag ccgggcgtgg tggcgggcgc ctgtagtccc agctactcgg 112980
gaggctgagg caggagaatg gtgtgaaccc gggaggcaga gcttgcagtg agcagagatc 113040
gcgcggccgc actccagcct gggtcacaga gggagactcc gtctcaaaaa aaagaaaaaa 113100
gtgtgatcta attttattgc tctgaaccga atctctgtac attttatttt atttaaaact 113160
aagtcgagct ctatagaggc tacatagcct ccctcccatt ctggtcccac accagacttt 113220
gcatgggctc tttctactat cagctttaaa tagagaacgt tcttgttctg ttcatgaagg 113280
tttcataaat gctggagtcc agtcataact agaactttac atatccgttc catcactgta 113340

-continued

```
tttttccaga tccctggtaa ctccatagcg cggctctgtt ggggcgcatg caattcccta 113400
ctttctcaca gggggcgctg cagagaaggg cagagcagag cgcgcggtcc cagagcgcgc 113460
cgtccaggag gggcgcgtc cgtggggctg tgtctctgcg agccctgcgc aacgttgggg 113520
gcgggaacaa ccctggccct gcgcccgagc gctgcggcgc cttgtgattg gaggaggcaa 113580
cggtcacttg gcagcgccgt tgggattggg ggaagaggac cccggctgga ggtgacgctg 113640
aggcggcgag ggtgagtcgg cgccggccgc taccgcactt cgggcgctcg tccctcattt 113700
ctctgtggtg aatggcgacg ggatggagcg cgaggggagc ggcggcagcg gcgggtcggc 113760
cgggctcctg cagcagatcc tgagcctgaa ggttgtgccg cgggtgggca acgggaccct 113820
gtgccccaac tctacttccc tctgctcctt cccaggtacg gcccgccccg cgcctgcgca 113880
ctgcgcgccc cgccgtcgcc kctgccgtgc tgtgggcgcc ccgagtctgg gcggggtccc 113940
gggtgcgcag cctgctggcg gcgtgggcgc tgtcctccgg gagggggcc gtgctgctcg 114000
cccggagcsc ctttccccat cacttcttcg gcggtccctg aggcggagcc ccggagtccc 114060
gctgggcgtg agatgcagag agcggccgca ggtgggcccg gggctggagg gcgctcggcc 114120
gccacccgag cgggtcttgg ccttgagctt ccgagcgcct caggttcaga gctgcacccc 114180
acgagcccgg gaggctgtgg tccccgccct gcctgggttg ccccacggcg cccggcctcc 114240
ttcgaggggt ctcggagcgg cccggccgcg ctgaggagtc agagctcgcg ctccccttgc 114300
cccggggctg cagcccggcc cctccgcgca ggcgctcgtt cgctgatcgc gggcgcctgg 114360
ggctaaatcc tccccctccg agacccgctc cgctttctag gaatctttcc cagacctggt 114420
gccacctgtt gctgggtctc ccactaagcc ttcgagatct ttggcacagc ttcctttgaa 114480
ctcttcctcc ccgctgcggc ttgagctggg cctgctagga gggttgctca gaattctaat 114540
gccaggaaga gcgctccgtg ccctgaaagc tggagggagg agagaggact tcacttggga 114600
aggaggagaa aagctttgag gggaggcaca gttatttgtg tggtccttga aaggcaagaa 114660
gactagagcc cgtggccctg gaaggggagg tggggctccc agcagagggg actgaggtct 114720
tcataaacaa tgagggacca gagcagaggg aaggaggacg agattccaga ctctagttcc 114780
aaacaaggca cctgtgattt ctcatcccct gggcagcgac tgccaggcgc cgttcagcgg 114840
acacctggga cttgcagtgt tatgtgccca gggattttcc cggacgggat tgtgaagtag 114900
cgggtaaggt catcaggcag gttggggtca gatgcagatg ttcgcttgtg gtcattcctg 114960
aaatgagaat ctggcagctc acgttatttc agaaggtgct aggatcactt ttgacagtga 115020
tatcaaaaaa ttgatggtat tctggtgacc ctgtgtgata catgaaatgt tcgtgcaatc 115080
tggaggcact actgggacca gattaatctt tgtttcctta attttcccct ttcctgaaaa 115140
atgtcaagcc tgccaaacag ttgagagaac agtataacaa atacccatgt accctttact 115200
tagactcagt aatattttga ttctttggct ttctgtttct ctttctctct ctctgctstc 115260
tttctctctc tctatatrta taaccacatg tattacatac gtatcacact tagrtgtagg 115320
tcacatgtcc catttcaact cgagtcattc aataggaagt tgcagaagtc ataacacttg 115380
cttgatgcct gataatctta acatgtatct tctaaaaacc attttctats catgaaacca 115440
tatcacatcc aagaaactga acatcataga ataatgttac ctaatgtgtg ggccttgttt 115500
acatttcccc aattgtccac atagattttt ttccttaaaa aaatatatat attccatgat 115560
ctraggttca cacattgcat taagttgtcc gtctctttag tttcatttag ctaaaacagt 115620
tacttccttg tttgaatttt ttaagatgga cattttggaa gagtccatgt gaattgttkt 115680
```

-continued

```
atagactgtt ttacaatcta ggttcattag atggtcttca tgattagatt tagattaaac 115740
atttttggtc agaacgctac ctacctaggt gacgtccact caccagtaca tcacatcaag 115800
agacactgaa tgtcagcctg gctcagtggc tcacacctgt aatcccagca ctttgggagg 115860
ctgaggcagg cgtatcacct gaagtcagga gttcaagacc agcctggcca acatggcaaa 115920
accttgtctc tactaaaaag tcaggcgtag tggtgtgtgc ctgtaatccc agctactggg 115980
gaggctgagg cacgagaatc tcttgaaccc aggaggcaga ggttgcagtg agccaagatt 116040
gcgccactgc actttagcct gggtgacaga gcgaggcttt gtctcaacaa aaaaagagac 116100
attgaatgtc aatttgtatc ttcattgata atactaagtt tgatcatttg gtgaagatgg 116160
tgtctatgaa aactctactg taagggtatc tgcatcctct ctttactacc aagtttgatc 116220
atttggtgaa gatgatgtct atcagaactc tctactgtaa gggttcctgc atcctctgtt 116280
aattaaacgt catatgtagg gtcataagtt ggaactgaat agtctgttga gtctctggct 116340
tttagttccc tttcattaag aaaagattga gataagtgga tttgggatag gtttaataca 116400
tcacagtagg taatctgtag ccatgtgaat tgttttactt tcagaacttt tttctgaaaa 116460
tattaaactt cagtatgttc ttgagtttat gattactgtt atgggtatgt aacttgtgat 116520
gtcgattacc agagatcgtt tattcagtaa gtatacattt ggccaagtgc caactctggt 116580
ctggtgttat gagcaggtat gaggcatagc ccttgacccc aagtagatca gaatttggta 116640
gtaaacacat aacctccctg ctgtgtctca tctttggcag gaataatggg tgtaataaat 116700
acatgaagtt atatcctatt tgagacacca aaatctgctt aacaggagtt gcattcattg 116760
tcctgaatct gttgtattga tattttggcc ccacagaaaa ggttacttgc agtgtatgcc 116820
aactcattat ggcagaatca ttgttctgaa gtattctgac atatttatgt ataccaggaa 116880
gtactgaatt gattttttct ttattacctg tatttgcagt ttagccattt acctacggag 116940
ggttaggtag acatctaaat gactaaattg gccggttgcc gtggctcacg cctgtaatcc 117000
cagcactttg ggaggccgaa gcgggcggat catctaaggt caggagttca agactagcct 117060
ggccaacgtg gtgacacccc atctctacta aaaatacaaa aatttgcggg gcgtggtggt 117120
gcatgcctgt aattccagct actcgggagg ctgaggcagg agaatcgctt gaacctggga 117180
gggggaggtt gcagtgagct gacatcatgc cactgcactc cagcctgggc cacagagcga 117240
gactgtctca aaaataaata aatgagtata agtaaatggc taaactgcaa atgcagttta 117300
aaatttttc ctttattgtt gtcattttta acaaacctca aaaccaagaa actgagatct 117360
ttatcttgta tcaagaatga cattcatctt cagaagatac agatttcact aaatcagtgt 117420
caaattagat ctagtgataa ttaaaaaccc agtaatgttt ttgtgtcatc cttgcaggaa 117480
tcaagactgg tcacacttgg accagtcatt tattcattca ctcaaaaaat atttgctcag 117540
tgttgattgt gtgcctgttg ttttctaggc accaagtcaa gatgccatag taacaaagca 117600
aagccccttc ccacgtggaa ctttcattcc aatggggaga gagaaaaaca aaacagctgg 117660
tggtgagggg cctgggaagg ggcagggcct gtgtggtggg ggtggattgc tgtttgctgt 117720
aaagtgatgg ggaggccctg gatggtgatg atattggagt caaaatctga agaaagtgag 117780
taatgagcca acagctactt ggggaagagc atgtgttcta ggccagggag cagcagattc 117840
agaggccctg aaacaggagc ttgcagaaga aacactgagg agcccagggt gcctggaggg 117900
actgtgtcgg caacgcacag aggaggaggg gagggtagat cctggagggc tctactgggg 117960
aattttgaac agagatggga tgattctgac tttttaaaaa agtgtacaat ccagtggttt 118020
ttagtatatt tacagagtta tacaactatc acaattaatt tgagaatatt tgcatcatcc 118080
```

-continued tgagaagaaa cgttctttgt acaaagaaga aacttaaaga aacttaccgg ctttgcatgg 118140
agagtagatg gaaggcccca tcaggacaga caaggtctgg tcaggctagg atgcagagac 118200
cactgaggtg aggcaggcca ggggcacacc caggaaccag ggaggagcag gcaggcagta 118260
tccagagaga ggtggttgac tacagttggt agttcagtgg gcacatcatc ttgttaggga 118320
ggagtagaga ggacagttgg acctccaggc caggaggtgg ggtttggcaa gagagggtgc 118380
agggctgcag gctgatgggt gattagtatc aagatagccc aacttcagca tggagttgca 118440
ggactacgta agactttttt ttttttgag atggagtttc gctctgtccc ccaggctgga 118500
gtgcaatggt gtgatcttgg ctcactgcaa cctctgcctc gcaggatcaa gtgattctcc 118560
tgcctcagcc tcctgagtag ctgggattag aggcagacac caccaaaccc ggctaaattt 118620
tgtagtttta gtagagatgg ggtttcactg tgttggccag gctggtcttg aactcctgac 118680
ctcaggtgat cctcctacct cggcctccta aagtgctggg attacaggtg tsagccacca 118740
cgccctgcca agactacata agagtgttaa tccccaggag gactcatgtg gtctgcttag 118800
aaccccagct tcagaggaac tggctgtgtt gacccagttg ttcactgaaa cacaagatga 118860
gagtggggcc agctggaagg agggctgagt actgagcctc atgctgccca cttggctcag 118920
gttgtttgca ttgctgccat ttggggccag gttggtcatg aggccttggt tgggagttag 118980
gtgactctgc tgtggaggtt agaggccagg gagccagcca ttatagaccg cttttgttaa 119040
tacagaatcc actagaggat tctgctctct gtgtctgttc tttcactgca gtatctctct 119100
gaatatgtat cttaaagata tgtctgtcta ggctgggcac agtggctcat gcctgtaatc 119160
ccagcacttt gggaggccaa ggcgggtgga tcacctgagg tcaggagttc gagaccagcc 119220
tggccaatat ggtgaaaccc catctctact aaaaatacaa aaattacctg ggcgtggtgg 119280
catgcacctg tagtcctagc tacttgggag gctgaggcag aataattgct tgaacccagg 119340
aggcagaggt tgcagtgagt cgagatcacg ccgctgcact ccagcctggg caacagagtg 119400
agactgtctc aaaaaaaaga aaaaaaaaga tatgtctctg taaaaatata tcctcaagga 119460
aatcctcaaa tatcttttag ggtagggatc ttagtctttt tactgatatg tcagcatata 119520
gaatgagatc aatgtatatt tatttgattg atcagtgatt aactttttag tgtttttatg 119580
actgctattg ctactgtaat taattccaca aatttagcag cttaaagcca tacagatttt 119640
attgtcttac agttatgaag gtcagaagtc caaattgggt gtgtgtgggc taaaaccaag 119700
gtttagcagg gctgtgttcc ttctggagct tgtaataaga actttgcttg ccttttccag 119760
catttagagg ccacgtacat tccctgatgc ttggcctgct cttcttcttc atagccagcg 119820
gcataacatc ttcaaatctc tctgactctt atctcctacc ttggtcttac aaagaccctg 119880
tgattacatt agacctaact ggaaaatcca agacaatctc cttttggaag atccttactt 119940
tagtcaccac aatgtccctt ttcccatgtg ggttaatctg ttcacaggtt ttggagatgg 120000
agatgcgaac acctttggga gcccattcta ccacaatgct taatctcatt ttccaatatc 120060
atattgtatt acagattaat tacctgattt accttcacca tagggagatg atgtgccttt 120120
agctgccaaa gtaaacaaag ccgaagtaat atacttgctt taaagcagtg aacaaataaa 120180
tactgtaaga tatgtagaca aagatttgag agagttttga gccagcgaaa tgaaaagtac 120240
tgtatgacaa tcgataaata gctattaaat agatggcaaa ttaaggtgca gtagattaaa 120300
gggaaatcac ttagtttttt aaaaagcgtt ttagattcag gtttgccttt gctatttaga 120360
gtcctgtaat aacctcatgt gaaagtgttt tataagctgt actcctctac tcatctataa 120420

-continued taaacctttt tttcctactt gaaatgactt tagtgatgct atataaaata catagtgaag 120480
gagctaatgg atgtggctca gggttgtagg gggtgcggtg tgcctcctcc ctttctcaga 120540
acctcagaga ggtgttggcc tgctgtgtat kccggacgct gtttacaaat tggcctttaa 120600
gctttttgga aaattgagat gtgggttggt gacttagcag gcctcctggg gcaggggctg 120660
tgctcctagg gaagtgggga tgggtgacat ttttgtctca gcatgggccg ccataacaaa 120720
ataccacaga ctagctgtct taaataacag acattatctc ctcagttctg gaggctggaa 120780
ggctgggatt agggtgccag gatggttggg ttctggtgaa gaccctcttc ctgacttgca 120840
gatggctgcc ttctcaccat gtcttcacat ggcagagaga gagaggtatc aagagattga 120900
gaatctcttc ctctcctaag accacagtcc tgtagggttt aacacaggaa tagtaggggc 120960
acataattca gcccttagca cttggatggc atacctgtgt tccaacctgc tttcctggaa 121020
attaccagct tcgtgtgttt ctgggatatt aaggctttgc ctcccagttc aaggcctcag 121080
tggttctgyg gcagctggta ggaagccagg ctccagcagt gccttgagtt actgcagaaa 121140
gcagagcttc tctctaaaac tctggcagct ccagcagaag ccctggatag cagggaccca 121200
gggctgatct caggtcagta tggggcagac agcagccagg tgaagattgt tctgagttct 121260
tggaggcagg tttgcatccc atttgtccac tttggaccag tgaattcctg atgccatcat 121320
agaattttct gtagactagg tgttggggta gtcaggatca gattgatttg ggagtggcac 121380
gtgaggactc gggatagaag atggtctttc tgctttggaa gagaagcatg gtgctgtgtg 121440
ggggcttggg gatgagctgg cggtgggtgg tggacagggg gcctcagctg ggaggccagg 121500
ccactcttga ctgatccagg ggccacagta gctgcccagg caggagagat ttgtgtgggc 121560
accagagctc tggcaggtgc acatttgtta gggaggagca gtatccagat gcaggcactg 121620
ctccctctgg agttgctgcc agccagggag ggtgcgtctc tgggcagcga aaggcaggaa 121680
tagctcctgg cctaatggcg gctagaagag aaactgcagg aggatatggg ttygttgtgg 121740
amgaggtggg ggctgaaacc ctkrggacca agaatcctgc cctcratttc tgattgacac 121800
tattgactaa ggstgacttt tttcattggt ggaggaagac tcctgagtcg ccaggattac 121860
aggcttgcgc caccccacct agctaatttt tatatttttt ggtcgagacg gtttcgccgt 121920
gttggcctgg ctgttctgga actcctaacc tcagatgatc cacccgcctc agcctccaaa 121980
gtgctggtat tacagatgtg acccactgtg cccggcctca tttgttattt ttaataagca 122040
ttgagaccta attggggcat ccttgatgtt ttcaccgaga accatttatc caaaacaaga 122100
cctgagcact ctcactggaa gtgttcagaa tatgctctga attgaagctt tattaactca 122160
aaatgggcaa agaatttgag cagtcatctg tgacaatgtc aaggktgggt taaggggatt 122220
tggctccacc cctatctcca atagcccctt aaatccagct tctcaacaag attaagaagc 122280
ctgtgtaaag ggaataaaaa taccttcata aaactgtggt tttcattgat ctgggggaaa 122340
aaacacacac actaacagtg tgcttacagt gctaatacag cttcagtaaa gcttctggtc 122400
ctcctctcct ccccctttct aatcccctca agcggattga tgcccctgac tggtctcttt 122460
taaattgttt atcccaataa gctcattctt cctgagcagt tcttgtgaaa acaaaagctt 122520
tgttttttct taccttgttt ttctttttaa agtctagctc tcttgccctc ggctcattgc 122580
gacctctgcc tcctgggttc aagcgattct cgggcttcag cctcctgagt agctgggatt 122640
acaggcattt gccaccacgc ccggctaatt tttacgtatt tttaggagag acagtgtttc 122700
accatgttgg ctaggctggt cttcaactcc tggcttcaag tggtgggatt acaggcacga 122760
gcaccatgcc tggcctatct aataawtatt tattaaataa acatgctcag tacatagaag 122820

-continued catttccaca tgagtgttta ttgtgtttgt tttctcaaaa acaggatctt attctacatg 122880
caactggctt ttgttacttc acaatgtggc ttgggcatct tgccccttca gtatatatac 122940
atctattgca tttttttttt ttttttgag acagtgtctc gctctgtcac ccaggctgga 123000
gtgcagtggc gtgatctcgg ctcactgcaa gctccgcctc ccgagttcac actattctcc 123060
tgcctcagcc tcccaagtag ctgggactac aggtgcccgc tgccttgccc agctaattct 123120
ttgtattttt agtagagacg gggttttacc gtgttagcca ggatggtctc aatcttctga 123180
cctcgtgatc tgcctgcctc agcctcccag agtgctggga ttacaggcgt gagccactgt 123240
gcccagccca tctattgcat attttaatgg gactttgtag tattacgtgg gtgcacagaa 123300
tgtgttttcc aaattctgca gtgatagcca tgcaggtgac ttctagtttt tgatattatg 123360
gacaatgctg ttgggacctt cttgttacct ctgtccttgc ctacctatgc ttttctgtgg 123420
ggtgtatccc cggaagtaaa attgttgcag caagggccat gcacatttga cttccaaatt 123480
accctgcaaa aaggtggttt tccagtttgt attccaacta ggagtgtcag gtggggcctg 123540
tggaataatg tcatgacaac cgttactgct caaaacctat actggcactt tagatctttt 123600
gtgaagtcct tagtctggtg tcaaattccc caaagggttt ccctcatctg tctttatagc 123660
tttaactgtc attgctcttt tatttttttg agacggagtg tcattctgtc tcccaggctg 123720
gagtgcagtg gtgtgatctg agctcactgc aacctctgcc tcctgggttc aagcgattct 123780
cctgcctcag cctcccaagt agctgggact acaggtgcct gccaccatgc ccggctaatt 123840
ttgtgtgtgt gtgtatgtgt gtgtattttt agagagacag ggtttcacta tgttggccag 123900
gctggtcttg aactcctgac ctcgtgatta gcccacctcg acctcccaaa gtggtgggat 123960
tacaggtgtg agctaccacg cccggccatc atggctctta taaagcctct gtgctttggt 124020
aaagcccgtg gtttttaatc agggtagttt tgccccccttg gggacatttg acaatgtctg 124080
gaaatatttt tggttgacac aactgggaat agagtgctgc aggccagagg tgcctctcca 124140
tatcctgcag tgcacagtgc agcccccaca atgaaaagtt atctggtcca aatgtcaata 124200
gggcggaggg cggtggtcaa gaaaccctgc tgagctaagc tcttcactga tctcaaaaat 124260
cacttgctac ttacctgcct ctagccaagg atggacagtg ggttttatct aatgtgtcac 124320
cgccagtccc tccctgtggg tagctggaga gctaccttga ggattctaag gccttgcctt 124380
gggttcactg gggggaaatg ctacatgggc catttaacaa attgtaaagt cacattccag 124440
caggatggtt ttgttttctt tatatgggtg cctcatgcat agtttttcat acatagttga 124500
tgattatatg tatcttaatg ttgcctgagt tacagacacc ttaagagtga ttagagttct 124560
gtaggagcca gctctcctaa cctgcactgt tgtttacctg ccatttgtct tcaagccaaa 124620
catttatatt ttctggtatt tatttcatat cctaaagagc tttgaaatcc taataggagg 124680
tgatggcttg atatttactg cattgtcttt caaatgattg tggaatgaat ataattgtat 124740
agctgtccat tttagaagac tgagtgatca aaaggtcagg aaagatcaac aggcattgat 124800
tgcatagtac cgtatcaatt ggctctttgg cttgtgcctc ttatggggga attatttttg 124860
tttgggtttt ttggtttttg ggggagtttt ttgagaccgt ctcaccctgt tgcccaggca 124920
ggagtgcagt agcatgatct tgacttactg caacctctgc ctcccaggct caagcaatcc 124980
tcccacctca gcctctcgag tagctaggac tacaggtatg caataccatg ccaggctaat 125040
ttttgtattt tttgtagaga cagggtttcg ctgtattgcc caagctagtc tcaaactcct 125100
gggctcaagc gacctgccca ccttggccac ctgaagtgtt gggattacag tcgtgagctg 125160

-continued ccgtgcccag ttatggtcgg ggacattatt taggtcaatt ttgaaatcta gatgaacctt 125220
ttttttcagt ttgagggtac agagattggt cagctttttc tgtgaagggc cagatagtaa 125280
atatgttagg ctttatgggt catgtggtct gtgtcactgt tatcagcttt gcccttgaag 125340
ctggaaggca gccataaaca atacttaaat gaaagggcat gggttgaata agtatgtgtg 125400
tgcaaaactc ttgtaaatgg tttcagataa gtgtgtatgt ataaaagtat tatgaatggg 125460
ttcagataag tgtgtaaaaa acaggtggtg ggtctgtagg cagtaatttg ttgaacacac 125520
taaaaccgtc aatatttgga tatttgactg atgaacccta ctttgcaagt aaatgatgtt 125580
gaaggccggg tgcggtggcc tcacacctgt aatccctgcc ctttaggagg ccaagttggg 125640
cggattgttt gagccgaggc attcaagacc agcctgggca acacggtgag accccatctc 125700
taaagaaaat acaggccaag cgcagtggct catgcctgtt atcctagcac tttgggaggc 125760
caaggcgggc agatcacctg aggttgggag tttgagacca gcctggcgaa actcccactg 125820
cactccatcc tgggcaacag agtagtgaga ccctgtctca taaaaaaaga aaattaaaaa 125880
aaaaagaatt ttgccaggcg tggtagcaca catctgtagt tccagccact ccggaggctg 125940
aggcgggaga acacccagac ctaggaggtc aaggctgcag tgagccatga tggtgccatt 126000
gcactgcagc ctgggtgacg gagtgagacc ccgtctttaa aaataaaaat ttttgactgg 126060
gcgcggtggc tcacgcctgt aatcccagca cttgggaggc cgaggcgggc ggatcatgag 126120
gtcaggagat cgagaccatc ctggttaaca tggtgaaacc ccgtctctac taaaaataca 126180
aaaaattagc caggcgcggt ggcgggtgcc tgtagtccca gctactcggg aggctgaggc 126240
aggagaatcg tgtgaaccca ggaggcagag cttgcagtga gccgagatca cgccactgta 126300
ctccagcctg ggtgacagag cgagactccg tctcaaaaaa aaattaaaaa taataaaaat 126360
ttttcaaaaa aaaggaaaaa agaaacggtg ttgaaaatga aatgacgggt atgatgagta 126420
ccctctgcaa tgattgtcct gggaagggca gtgattcaca acttttcttt gtcttccctc 126480
atagagatgt ggtatggtgt attcctgtgg gcactggtgt cttctctctt ctttcatgtc 126540
cctgctggat tactggccct cttcaccctc agacatcaca aatatggtag gttcatgtct 126600
gtaagcatcc tgttgatggg catcgtggga ccaattactg ctggaatctt gacaagtatg 126660
ttagacatta aaataccagt caaaaatgtt taatatgact agtcaatttc aggacctatt 126720
ctagaaaaca tatctgagta ggatgaagga aagagtgcct tttaactgca agtccagaca 126780
gggtctccct atgtcaccaa ggccggagtg cagtggttgc aatattggct cactgcagcc 126840
tccacctctt gggctcaagt aatcctcctc catcagcctc ccaagaagct tggactacag 126900
gggtgtgcca ccatggcccc gctaattttt tttgtatttt ttgtagagac agggtttcgt 126960
catgttgccc gggtctcgaa ctcctgagct caagcaatct gcccaccttg gcctcccaaa 127020
atgctgggat tacaggcgtg agccactgtg cctggcccag ttttttttaat gtattgattt 127080 ttttttttcca cccccaaggt cctattactt ggctaacctc tttgacttct tgagtcagat 127140
ttcatctcag tggcttcagg gaagtcatgt taaactttgt gagatatatc tcgtgagaga 127200
ggccaccagc aagaggaaaa tttatctttt tggaagctac ttctcctctc tgatcagcta 127260
tcacttgagc attggccctg caagatggtt ggtgaattac ttccactcat gtgggtgtgg 127320
ttgctgtaaa gatagaagac aaattttgat gacaagaatt ctttgccagg tgtagtggct 127380
catgactgta atcccagcac tttgggaggc agaggtggga ggcttgctga agcctaggaa 127440
attgagacta gcctcagcaa catagcaaga ccccatctct acaaataaaa ataaaaaatt 127500
tagctgagtg tggtggtgtg tacctgtggt tccaactacg tgggaggctg aaatgggagg 127560

-continued attgctggag ccaggaggtc caggctgggc tgcagtgagt cgtgatcaca ccacagcact 127620
ccagcctggg ccacagagca agacccgggg gaaaaaaaaa gaattcttgc ttagaaaagt 127680
acccgattag tgctctagtt attttttttcc ccttaggact ttctgaataa gaattggagt 127740
aacatgatgt tatgaattat tttcaggctt gtttttgggg cgtttggttt gttatggctt 127800
ttgcttatgg gataagaaac agttacagaa atgagaacaa taagtttaaa tcatttcaaa 127860
gctcatgcat aaatataaat gtgtatttta tataaactga aaattctaag taattaaaat 127920
gtaaaatcct ccattttctc atccctaaat aatagccaca gtttacatct tggtgtgtat 127980
ttcttttttt aggtatagat gtaaacataa atacattttt ataatataga aatgtaatat 128040
tcctactgat ttgtaacttt ttttcactgt gaattgaaac cttagcatca agcagaaatc 128100
gccctctatg tctttgactt gaggtgtttt tttttttttt ttttgagaga aagtggccta 128160
gtttctctgt gttctaactg tatcacctac tgctgctttg gagaccctct gccccaggat 128220
gactggctgc tagggcctgt cttagtttgt tcctcagtaa aataggggta atactaccca 128280
acctcatacc cttgcatgat tgagctaatg tgtatatgat gtaatacctg acacatagta 128340
attgtcgaat aaatgttgta ttcatttctg tctttaaggc tctatgaata gtctgttccc 128400
tttccatttg ctgctctctt ggatatactt tttcctttct tcgcttcatt atcccaatcc 128460
cactttaggg cccagttcaa gttccttaag cttctttcta tccaacccag tctttcttgt 128520
gtacctaaat tttggagggg cccaatgaaa catgtctttc agatgttagt aacaaaatgt 128580
acgcattgcc agtggagctg ggcattttaa atcactaaat gttcaaggca gccaaccttt 128640
ggttaatatt gttctttctt cttgttaaaa tatgttaata taccttcaca tcacatttgt 128700
gaaatgtgcc aggcatggtg gcttatgcct gtaatcccag cactttggga agccagcttg 128760
ggaggattgc ttaagtccaa gagttcaaaa ccagccttgg caacatagtg agaccctgtc 128820
tctacaaaaa ataaataaat aaaatagcca ggtgtggtgg cgtgtgcctg tagtcccagc 128880
tgctcgggag gatcacttga gcccaggagg ttgaggctgc agggagccat gatcatgcca 128940
ccgcattcca gcctaggtga aagagtgaga cactgtctca aaaaaaaaaa aaattgtaaa 129000
cgtgattgag acactgtatg ttattttgca ttattgcaaa tctgtttctg tcttgtgtcc 129060
ccagctagat tccaagtacc ttgagaatag cgatcatacc ttataaaaca cagaagtgtt 129120
ctgcagatga aaattggagt gaatgaacac actatgacaa aggagaattt tgttggagca 129180
ttttgtgggg agggtcatct gggaaatctg gatctattct tttcttttta aaatttttat 129240
tatttattta tttattttta tttgagaaca gggtcttgtt ctgtcaccca ggctggagtg 129300
cagtggcata gtcacagctc actgcagcct tgacctccct agctcaagtg atccccctac 129360
ctcagccacc caagcaacta ggattacagg cacgttcact acacccagct aatttttgta 129420
ttttttgtaa agacaaggtt tggtcatgtt acccaggatg gtctcaaact cctgggctca 129480
agcgatcctc ctgcctcggc cttccaaaat gatgggatta taggcttgag ccactgtact 129540
tggccggttc tttttttttt tgagacagga tcttgttctg ttgcccaggc ttgagtgcag 129600
tgtcgcgatg tgagctcaca acaacctcca cctcctgggt tcaagcagct ctcctgcctc 129660
agcctcccga gtagtaggga ttacaggcac gtgccaccac acttggctga ttttttgtat 129720
ttttagtaga gatggggttt caccatgttg cccaggctgg tctcaaactc ctgagctcag 129780
atgatccacc catctcggcc tcccaaagtg ctgggattac aggcgtgagc caccgtgccc 129840
ggccggatct attcttttca aacgaatgaa atgttaactt tcttggtaca cttccttggt 129900

-continued ataatgctga actcgtatag taactcaaat gggtatctgc atagatacag gggttttcgt 129960
tttgtttttc caatttgcag gaaattatag tgactagcgt aataaaaaca atcaatgact 130020
tgggagacaa aggaatccct gagtatctct cctctcatgc cctgtgaatg aataacaact 130080
ttatggctta gagtcctcct gtcttccctt ttcacccctc tagtccctcc tccgtccatt 130140
tcttgaaggg aactatgagt gtgatagaag gtggagtggg gattccctgt ggcctgaaac 130200
atttcttgct tagtctaact caaaagatcc tttttcattt gttaccaaaa atgtattagg 130260
tccctgttga aggctaggca tggggtaact ggtaggggaa tacagatatt tttgagttca 130320
taatctggtc atgtgggaat tgctatcttt gtgattttga ttatttcttc cagattattt 130380
tattcaataa atctaggaga ctctgggttt taaggagtca gcatctaaaa gtgatcttgc 130440
aagccatgca atgaatactc aaagtgtaga gtagtccaca gaaagaatag ggaaaaccta 130500
acatttctgt aagatttaaa tttcagtata aaatctggaa cattctactc gcagtagtat 130560
tttaaatgtt gtattttcgt gagtttgtta accttcgttt tttgtttttg tttaacattc 130620
ttgcatttta aatcaggtgc agctattgct ggagtttacc gagcagcagg gaaggaaatg 130680
ataccatttg aagccctcac actgggcact ggacagacat tttgcgtctt ggtggtctcc 130740
tttttacgga ttttagctac tctatagcat acatccttat gctgagatgt tgaacttaaa 130800
ctttatggaa tcctccaaaa gaatacatta tggagtgtag tgttttctta gttcttcaaa 130860
gggaagcaac ttggatgaac aggaacatga aggacaacac atctcagcct tttcttcatt 130920
ttgaagctcc tagaattgaa gacttatgtg gactcctatt gttctcaacc aaaacaagtc 130980
ttttggcttt cttttttgta gatatttrat ttaagcagtt ttcatgtgta cctttacsca 131040
agccaagtca acagtgtctc tggggtggca tcctttgcac tgaaatttac agtattctgt 131100
gagatgtcgc atattttgaa gaaaccgtgg aagatactgg tttatttcaa atgagcagag 131160
tatgttgtat taaaatctta tctaatcttg attaaaattt ggcaaactct tttctttgct 131220
acatcttagt gacaataaat gccaaatagg ttttggttga gtatagtttt gaaaacaaat 131280
ttggtgaaat aaagcaggaa aaaaaattta agtataactc aagtagtggc tttggttcca 131340
ctgtttataa ataaaaagta gataacaatg aataatgtga cattttctgg acaactgtct 131400
tgacttctga ttaagatatt ttaagagatg tgaatttgtt attttgtatg ttttatcaaa 131460
ataagctagc taatttagac tttttagatt ttctgtacca cctttcccct atcactttta 131520
attytcttaa ttttatttca tttaattgga aamatacata ccctattaaa tggcttgagt 131580
tggaaatttt aagccagatt tgtttggaca ttgagrcaca cataagatac tttaggcatt 131640
ctgtcatagt ttttcttagt gactttggta tactaatgac ccttgagaaa ctatagaagt 131700
gcatctgaaa ctagagttag tggttattga ttttttagct taatgtgttt acctagtggt 131760
aactcttcag cccactttta cagtattggg tatcaactcc cagaaagtgc ctaaagttta 131820
atgttcagat atgtacccac tctcccottt acatttttat tcaaaagaat ttatatcttt 131880
aaagagattt aaatatcaag agttttttta aaacttaatt ttagctattt aaatttttat 131940
tctactgcct aactttcttt ttcattaaaa ggcctgaaaa ctgtgactct ttgagaggga 132000
aagaatcgca gaaattaagt atttaatgtg atcctttcca cctaaactgt tttgtatgga 132060
atacaatcag tgtggtggta gtggtggtgg ttatctgcaa aatagtttct ggtgattaaa 132120
tctgactttt tttttttttt ttcttttaaa tgagacgkag cctcactgtg ttgcccaggc 132180
tggagtgcag tggtgcaatc tcagctcact ccaacctctg ccacccgggt tcaagcgatt 132240
ctcctgcctc agtttcctga gtagctggga ttacaggcac ctgccaccgt gcccggctaa 132300

-continued

```
tttttgtatt tttagtagag ataggtttca ccatcttgcc caggctggtc ttgaactcct 132360
gaccttgtga tccacccgcc tcggcctccc aaagtgctgg gattacaggc gtgagccacc 132420
gcgcctggcc ataaatctga catctttaaa ggaaagtttt cattgtgaga ttaacggctt 132480
aacagcccat gaggtcatat acacatgaac gtatctattc catttaaagc aatacacact 132540
ctggcttctg attaaaaata gccaggagga gagtctctga atctactgtg attctggagt 132600
ctgcccaatt tggaaaaaaa aaaaaaagaa aaaagtcagg aggaccaatt tgccagggaa 132660
actcatagaa aagaattaca aagagatcac aaaaactgga catattcttt tgactaatta 132720
gaccacttat ggctgggcgc agtggctcac acctataatc ccagcacttt gggaggtcga 132780
tgtgggagga ttgcttgagc cacaagagtt caagactggc ctgggcaaca tagtgagacc 132840
ttgtctctac tacaaaataa aaaaaaatta gctgggcgtg gcctcagcta cccaagaggc 132900
taaagtggga ggatcacttg tgcctgggag gttcaggctg ctgtgagccg agaccacgcc 132960
actgaactcc agcttaggcc acagggcaag accctgtctt aaaataatat tactaatttt 133020
ggtaattaac ttatcaaaac tatagtgaca tatacacggg cagaaactta taagtagagt 133080
tgtaatgcag ccaaatattc ttacaaattc cctaacaaga agctcaaatc tttctcacag 133140
gcaaattgta aaaattctag ttttttgttt aaagagctgt gattttcaaa agtatccctt 133200
cagtttaaga aatctgggga attggtaact tttcttatgg gaaatgattg ccatcatctc 133260
tactgaagga tgcctcttac tgaaaaatgt cttttgaagg agttcttgcc taaagcattc 133320
tttggatgta atttcataca ctaaacatat agaccagtag ttagtgggcc cctcctctta 133380
aacagtaact tttgaagtac tgatacatga ttaaaatgtt agatattttt cactggagct 133440
aagacttaaa attagggcat tttgaaaggt gtatttgttt ctgtttcttg tttgatatat 133500
tttggttatc tactctttta aaaaactaaa cgtataaaag gtatcttcaa attactgagt 133560
gtttcatcca tcccagtagg tgaagtattc tccagtgaat aaatctatat atatatatag 133620
attttaaata gcttgagcgg tgtagcttga aatgttttca gggaaagact atttgaatca 133680
taaggaatag ctttgatttt ctttttttatg tctcaaatat agaattattt gggggtggtc 133740
actcagatgg aagaatattg gcaattgtgt tgaacatttt accttatata gttttgagaa 133800
tttttgccaa aaactgattt cttagaaata tcctccccca gctgtgcttt ggttttttgg 133860
tttttttgtt ttgagacgga gtcttgctct gtcgcccagg ctggagtgca gtggcatgat 133920
ctcggctcac tgcaagctct gcctcccggg ttcacgccat tctcctgcct cagcctcccg 133980
agtagctggg actacggacg tccaccacca tgcccagcta attttttgta tttttagtag 134040
agacggggtt tcaccgtgtt agccaggatg gtctcaatct cctgacccgc ctccacctcc 134100
caaagtgctg ggattacagg catgagccac cacacccggc ctctgctttg ttttttaaaa 134160
aaaaagaaat gcaagagagg gagggaggca gcctcctgac cataaaagct gatttcttga 134220
ttttttttttc ttttttttttt gaaatggagt cttgctctgt ctccaaggct ggagtgcagt 134280
ggcatggtct cagctcactg cagcctccgt ttcctgggtt caagtgattg tcctgccttg 134340
gccgctgagt agctaggatt actggcaccc gccacaaggc ccagctaatt tttgtatttt 134400
tagtagagac agggtttgat tatgttggac aggctggtct caaactcctg acttcaagtg 134460
atccacccgc ctcggcctcc caacgtgatg ggactataga catgagccat catgcttggc 134520
cttcttgatt cttgaatacg gggttttgag gtgaaagcat ttcatgaaaa cttaagttca 134580
tacacaagag catcatgaat attctaaaag aggtatctgt gcttttttttg tgaccacaaa 134640
```

-continued atattacttc ttatgaaatg tttacactag gtgaggaaaa gttcattaat tacctttaaa 134700
ccgttcctta ttttttttaa gattttaaat tgtattttgg cttttgcctc cagtatcctt 134760
tctggttgct ctggtttgaa ttaagttcct attatgctgc agcacatatc aaccttccct 134820
aagtaaccat ttcctggaat gtgaagcatc ggtgccatta gcagaccata tgcagaaatg 134880
tcgtgtactt gcatttcttt tttgtgcact ctataaggct ggttgtgact cagatcagct 134940
taacttttta tattatgtta tttcactaac tgctacagtc aaaatgatca aatctttgta 135000
caatagaaaa ttatttaaat tttatttttc tactgacatt tctaattcta gtgtaaatgt 135060
ttatcaataa aaaattactt tcaattctga gttggaatta tatttctttt tggtggctaa 135120
tgagtttaat cttttgtaat aaaattgact tcagttttca ttttttaaat aacttaatat 135180
ctagcatgtg taactttttt tatgttctac ttcttactaa tttatgataa aattcttgtt 135240
caaagttgtg attaaaccgt acttaacatg tgaacttgaa attcttatta actctacttg 135300
ctgggccata tattcccatc aagaaacttt tgtttgattc tgtgcaggaa taggtgagta 135360
ttgatacagt gtgtgaaaat gtattatttt aatagtaagt ccacatgaag agaagcttcg 135420
tcgtgtttgg ttaatttaat acccttggtg acatcataaa tctcactgtt ctgccatttt 135480
taacaaatgg gactaagttg ggtagtttac ctcatggtca caagattgct gcagttccag 135540
ccattgcaga cacatacaga gaatgtctgg caggagattg cccattcatt ccttctaatt 135600
ttctaaagtt gaggtttaac atgcagtaaa gtgtacaaat cttaaaatgt atagcttaat 135660
gaattttaca tatatatata tatatatata tatatactta atgtgactaa tagatcaaga 135720
gacagaatgt ttctagcacc ccggaaagat acgtacacag ttcagacaga agaccccaag 135780
actgtatatg tatctgggag taaaggtgct gagatcggca gggaggacac cctaaattat 135840
taccgagaaa acagaacagt gaaccaggaa tctttaggga gttggaggga tttgtgctgt 135900
ggccaagtgg agagccctgt ccgaaggagt cagctattgc ttggctccag cctgtttctg 135960
ctttattcga tgattaaccc aatcttgcca gatacttatt ttcaagagaa gctggaaatc 136020
taggttactg tttgaaatct ctccattttt aagtgttagc aactaattta aacttgcgta 136080
aaacactttt attatttatt tatttattta gagacacagt ctcgctctgt tgctcaggct 136140
ggagtatagt ggcgcgatct tggctcactg caatcttcac ctcccaagtt caagtgattc 136200
tcctgcctca gcctcccaag tagctgggat tacagatgtg cgcccccaaa cctggctaat 136260
ttttgtattt ttagtagaga cgaggtttca cggtgttggc caggatggtc tcgaactcct 136320
gacctcaaat ggtccgccca ccttggcttc ccaaagtgct ggaattacag ccgcgagcca 136380
cctgtaattg tgcgccttgc cgtaaaacac ttttaagtca ttacaataca tgattttaag 136440
ctggatttgg cctgctcacc accaattttt tttccatctc aactattaga aagtaattcc 136500
cactctgatt acccttaaag cggtcaggaa ctctagttgt aaatctgaac aatcacatgg 136560
agtgctagga gaaatgggtg ctggggagtg tctgccagag aacgcagtgg ctcctgttcc 136620
ccagactcac ccccagtgat agggcaaaag ggtacatcct gatttgtggc tgtaggacac 136680
catttatgct gtccaaggta aatgacgcca agaatggtca acttccaaat actgggttca 136740
aattttacat ctattttttct attactctcc cataagaaaa gtgtgcttag gccgggtgca 136800
gtggctcatg cctgtaatcc cagcacttcg ggagcccgag gcgggcagat cacctgaggt 136860
caggagttcc agatcagcct gaccaacatg gagaaaccct gtctatacta aaaatacaaa 136920
attagccaca cgtggtggtg tatgcctgta atcccagcta cttgggaggc tgaggcagga 136980
gaatcgcttg aacccaggaa gcagaggttg cagtgagccg agatcacgct attgcgctcc 137040

-continued agcctgggca acaagagcga aactccatct caaaaaaaaa aaaaaaatgt gcttaaatgg 137100
atcataaacc taaacgcaag aactacaact cttagaaaaa aataagcgta aattttatga 137160
tcttggctta ggtaaagctt tcttagatac aattccaaaa gcacaaggga aaataaacaa 137220
aaaatagata aattggactt catcaaaatt aaaaacgact ttgaaggaca ccttcaagaa 137280
agtatgaata gccagacacg gtggctcatg cctgtaatcc cagcaatttg ggaggcccgg 137340
gtgggaggac tggtttaggt catgagtttg agatcagcct gggtaacaca gcaagaccct 137400
atctttacaa aatatgtgta tttttaaaag ttagctgggt gtggttgtgt gcacctgaag 137460
ttctagttac tcaggaggct gaggtgggag gattgcttga acccaggagt tggaggctac 137520
agtggggcta tgcaccactg cactccagcc tgggcaatag agcaggatgc tgtctttcaa 137580
aaaaagtgga aacctcacaa aatatgagga aatatgttca agtcacaaag gactggacca 137640
gcctggtggt ggaccaactg gaccaacatg gtgaaacccc gtctttacaa aaggtataaa 137700
agttagctag gcgtggccag gcgcggtggc tcacacctgt aatcccagca ctttgggagg 137760
ctgaggcggg cggatcacaa ggtcaggaga tcgagactag cctggccaac atggtgaaac 137820
cctgtctcta ctaataatac aaacattagc cgggtgtggt ggtgcatacc tgtaatccca 137880
gctactcagg aggctgaggc aggagaatcg cttgaacctg ggaggtggag gttgtggtga 137940
gccaagatca tgccattgca ctccagcctg ggcaacaaca gcaagactca gtctcaaaaa 138000
aaaaataata ataatgataa taataattag ctaggcatga tggtgcgccc ctgtagtccc 138060
agctactcag gaggctgagg tgggacgatt gcctgagacc agggaggttg aggctgcagt 138120
gagccgtgat ggcactacta cagcgtgagc aacagtgaga acccatttca aaacaaacaa 138180
aaaaacttaa acatcaacaa aaagaaccca attttaaaat gggcaaaggc cagacgcagt 138240
ggctcacgcc tgtaatccca gcactttggg aggccgaggt gggcagatca cgaggtcagg 138300
agatcgagac catcgtgggt aacacagtga aaccccgtct ctactaaaaa tacaaaaaaa 138360
ttagccggtt gtggtggcgg gcgcctgtac tcrggaggct gaggcaggag aatggcgtga 138420
acccgggagg tggagcttgc agtgagccga gatcacacca ctgcactcca gcctgggcga 138480
caaaacgaga ctctgtctta aaaataaaat aaaataataa aataaaaaat aagtaaaata 138540
aaataataaa ataaaataaa atgggcaaaa caggcacagt ggctcacacc tgtaatccca 138600
gcactttggg aggctgaggt gggtggatca cttgaggtca ggagttcgag accagcctga 138660
ccaaaatgat gaaaccccat ctctactaaa aatacaaaaa ttagccatgc ctggtggctc 138720
acacctgtgg tcccagctac tcgggaggct gaggcaggtg aatcgctgga acccgggagg 138780
cagagcttgc aatgagctga gatcacgcca ctgcactcca gcctgggcag cagagcaaga 138840
ctccatctca aaaaaataaa ataaaaaggg caaaacatct caaaagatat ttctccaacg 138900
aacatwtaca atggccaatt aggacatgaa aagatgctta actccattag tcatcaggaa 138960
aatgcaaatc aaaactacag tgagatgcca cttcacacca actaggaagg ctagaataaa 139020
agagggtatt ggaggccggg cgcggtggct cacgcctgta atcccagcat ccctgggagg 139080
ccgaggcggg cggatcacct gaggtcagaa gttcaagacc agcctggcca tggtgaaacc 139140
ccgtcttcta ctaaaaatac aaaaaattag ccgggcgtgg tggtgtgtgc ctgtaatccc 139200
atctactcgg gaggctgagg caggagaatc gcttgaaccc gggaggcgga agttgcagtg 139260
agccaagatg acgccattgc actccagcct gggcaacaag agtgaaactc tgtctcaaaa 139320
aaaaaaaaaa aaaaaaagag ggtattggca aggggataaa gaaattgtaa ccatcacatg 139380

-continued ctgctggtga gaatataaca tggtacaact gctttggaaa acactttggc agttcttcaa 139440
aaggttttgt tttttgcttt gagacggagt cttgctatgt tgcccaggct ggagtgcagt 139500
ggcgcaatct cggcttactg cagcctctgc ctcctgggtt ccagcaattc tcctgcctca 139560
gcctcctggg tagctgggat tacaggcgca caccaccaca cctggctaat ttttgtattt 139620
ttagtagaca tggggtttca ccatgttggc caggctggtc tcaaactcct gacctcaggt 139680
gatctgcctg cctcggcctc ccaaagtgct gggattacag gcgtgagcca ccgcgcctgg 139740
cctccaaagt ttttttttta aagttattat atgatcacgc aatcccactt aggatatacc 139800
taagagaaat gaactttgaa aatgtgaaat gtgaaatgtg aaagaagcca gaccccaaag 139860
accacatgtt gtctgattcc atttatatga aataaatgtt cagaataagc aaatctatag 139920
aagttggtct ttgaggagaa acaaagaatg agcatgaatg gggaatgaga aagggtttat 139980
tttgggggca ataaaaatgt tctaaatgga tttcgtgatg attgtgcaag tctgaatata 140040
ccaaaaacta ttgaattgtg catttttaaa ttttatttta ttgagacgga gtcttactct 140100
gtcacccagg ctagagtgca atggcaagat ctcggctcac tgcaacctct gcctcctggg 140160
ttcaagcaat tctcccacct cagcctcctg agtacctggg attacaggca catgctatca 140220
tgcccagcta atttttgtat ttttgtagag atggggtttc actatgttag ccaggctggt 140280
cttgaactcc tgacctcagg tagtccacct ccctcagcct cctaaagtgc tgggattaca 140340
ggcgtgagcc actacgcctg gcctgagttg tgcacttaaa tgggtacatt ttatggtgtg 140400
tgaattgtgt ctcaataagg cttttttttt tttttttttt tgagacggag tctccctctg 140460
ccacccaggc cggagtgcag tggcgcgatc tcggctcact gcaagctccg cctcccaggt 140520
tcatgccatt ctccggcctc agcctcccga gtagctggga ctacaggcgc ctgccaccac 140580
gcccggctaa ttttttatat tttttagtac agacggggtt tcaccgtgtt agccaggatg 140640
gtctcgatct cctgaccttg tgatccgcct gcctcagcct cccaatcaat aaggctattt 140700
ttaaaagttt gctggtatag agccattgca atgtcttatt aatcacatgc atgtctcatc 140760
tattccttga ttcacaaaag atttatttct tgatttcctg gatttacaga cccagtctag 140820
tccagagtgt caatgaggag caatttcagc tgacaaaaac tcatatttgt atacaagata 140880
aacaaatagt tgccgggcac ggtggctcac gcctgtaatc ccaacatttt gggaggtcga 140940
ggcaggcgga ttgcctgagg tcaagagttt gagaccagtc tagctaacat grtgaaaccc 141000
cgtctctact aaaaatacaa aaaaaaaaaa tagccgggcg tggtggcgtg cgcctgtaat 141060
cccagctact tgggaggctg aggcagggga attgcttgaa ccagggaggt gggggttgca 141120
ttgagccgag atcgcgccac tgcactccag cctgggcgac agagagagac tccatctcaa 141180
aaacaaacaa aaccaaatag tgtggtagtc attggtgtct cttctgaatt tgcttctgat 141240
tgttacctca taaatagatc attaaaatgt tttaatctga agaaatggta aagattatat 141300
atggttgtac ttccatatgg tttaacttga agggttcctg tggatgatgg ctgcattcct 141360
gaatagtcaa ttctttgtat tcacagtagt tatggctata aagttgtcga gaacattgaa 141420
ttagcaaaaa ccgaaccatg ggtcctggga gaaatacagg gttaggttcc tgtgaacctc 141480
tggtcaacac ttttgtcaac tgatcggtat gtaactttgt tttatgtgtg tttctgttca 141540
aagacacctt atttaatatg tatttcttaa aaataatctg cagtatttac aataaaattt 141600
caatgacagt agtttggtgt aatgtactct agtgtactga gattgcacta cttttttttt 141660
ttgagtcagt cttgcccttt tgtctaggct ggagtgcaat ggcatggtct tggctcactg 141720
ccacctccga cccccaggtt caaacgattt tcctgtttca gcctcctgag tmgctgggat 141780

-continued tacaggcgcc caccaccaca cccagctaat ttttctattt ttagtagaga cagggtttca 141840
ccatgttggc caggatggtc ttgaactcct gaccttgtga tccgcccacc tcagcctccc 141900
aaagtgctgg gattacaagt gtgagccacc gcgtccagcc tgtacaacct tttcattggc 141960
acacacagag tacacacata tagttcccat atacagtcaa cagtataaca tactgtacag 142020
ttcccacagt aaacacatac actactttgc acacatactg tataccctac agtacagcaa 142080
tacaaataaa gggaaaaagt tcaaagatgg agcatcctaa gttttataaa aatatcaact 142140
aaaatcttac ggttgatgga gctgcacaat gtggttaaac ctctcgacct tggcttgccc 142200
cacagaaacc aggggagggg tgagtgaaat ttattctgca gaagaggaag agggtggcag 142260
gtcaacctct ggcatttcta ccttaggagt ctggctcttg acacttgttg aaggagtggg 142320
caatcttccc tcccaaactg gcttgagaaa ttgcattagc cttgcctgcc tggcttttct 142380
gcctgaaatc tttaagcatc tcggtataag gggcaaacgc agtggaggcc agccatttaa 142440
atttgaggct tcgatcaagc gtagggtcac actcttccat gtcgctaaaa attttttcca 142500
aggcagaact ccattctgat attttggcgc tgtgagaggg acaattctgg aagtcttggg 142560
ccgactttca tggccatcaa ctccaatgcc ttsttttgcc atctcatcca ggtcttcgtt 142620
ggttggttcc actgccttct ctgccaaaat gtactccaca tctccttcct tcacgtcatc 142680
aaagccctct ccacttacct gctgtgccat atgcattatg tctctgacag tgttctttat 142740
attttctgta acaccttcaa acccttcaaa attctccacg cagtctggcc aaacattttc 142800
ccaacagtta ttggtagtag cctgaccaat gctctcccag gctgtactga cataatcaat 142860
aacgttgcat gtagtgaccg acttccaata gtccagcatg gtggtttcct tgttggtcct 142920
gagagcctca caggccttca tataaagctc ccttgtgtag tgtgccttga atgcttttat 142980
tatgccccga ttgaggggtt ggatgagaga cttagtgttt gggggcataa aaagaactcc 143040
tatgttggcg tgtgcatttt cgagttcttt gcagcaatgg attgtagcat tatccaaaat 143100
taacaaaacc ttgaaggtgc ccggcgcggt ggctcacgcc tgtaatccca acactttggg 143160
aggccgaggc aggcggatca tgaggtcagg agatcaagac catcctggct aacacggtga 143220
aaccccgtct ctactgaaaa tacaaaaaat tatccaggcg tggtagtgga cgcctgtagt 143280
cccagctact cgggaggctg aggcaggaga atgacgtgaa cccgggaggc ggagcttgca 143340
gtgagccgag attgcgccac tgcactccag cctgggcgac agagcgagac tccgtttcaa 143400
aaccaaacca aaacaaaaca aacccaaaca aacaaaaaac aaaacaaaac aaaacaaaaa 143460
acccttgaag gcaaggtttc tgccctggag acagtgttca gcttctggga tgaagcagtt 143520
gtggaaccaa tcagacatca tccacacttt tttgttccac ctccaataga ctggcagatg 143580
gttcacgtat ttcccgttaa gtgcttgtgg attttgggtt ctttacacca ttaggagttt 143640
gcactttagt cgctcttggc attggcgcac aataacaagg gtgcatgatc ctggcatgat 143700
ttaaagccag ggctttggag gccgtttgca ttatataggt tcgtttgcca acatccttgt 143760
aaaataagcc agtctcatcc gcattgaaaa cctgctcttt cacataaccc ttttcctgta 143820
taacacttag caagtatttt taaaattctt ccgcagcctc ctgatctgca gagctcgcct 143880
cacctgcaag tttaacattt ttcaccccgt atcgcctttt gaaacgcgcg agccggccag 143940
cactcgccga gaagggctta gcatttcttt gactctgggt aacgtgacca cagatatctt 144000
tggctttcag cctcaccaca atgctgtcca ctatgttttt tttaatcgat tgacatctca 144060
tgaatccaca aatttagccg cttttccatc ttttccatct ttgtcatagc ttcatcacgc 144120

-continued acgatggagg tcacttcagc actatccgga gcggcctcac ggacagatcg gtgaatttcc 144180
ttttcctttt tcttgatgta ccggattgtc gactcgttaa cattgagctc atggccaaca 144240
gcactgtaac tcatgcctga ttggagctta tccaacacgc ggactttctc cgtaaggcac 144300
atcacggtct tctttcgctt aggaacactg ggcagagctt aagcactacg cttgggggcc 144360
attttagaaa gcaaaaccac ccacaaaaag cagaaaaaaa agtgtcagta aacagactgc 144420
ggaaaggact ctttgtttac agcacaggag ctgcgactag aaggcggcgc ttctcccagt 144480
tcaaacttca gctgggaacc ttacctccgc caactccaaa ttttcaccct ctgcgcatgc 144540
ccgggaagaa ccccagacag taccgtgatg attgatttta gggttacaaa tacattttag 144600
caagtaagtg aatttggcat tacgaattaa tgattaatga aggtcacctg tatttccata 144660
gatatgtaat tttatttaag caggtttatt atattaaggc ggcgaggcag cgccgaagac 144720
tacaagttcc agcatgcacc gcgtccgggc gggttcgggc tcccagcgag ggcttcaggg 144780
acgccagccc ggaggcatcg gccggaagtg tcgtagggca accacgtagt actctctgcg 144840
catgtgcaaa gcgctgtcgg gggccgccct agctgccgtc gccgccgccg gggctctatg 144900
gtctctccct agagctttgc cgttggaggc ggctgctgcg gtcttgtgag tttgaccagc 144960
gtcgagcggc agcaacatgg aggaattcga ctccgaagac ttctctacgt cggaggagga 145020
cgaggactac gtgccgtcgg gtgagcgatt ccgcctgagg cgagaagcga attgccccgc 145080
cccacgcctc acgtgaggcg cgctctgccc ccgcgggcgt ctgccctgtg gcccaggtgg 145140
tccagggggg ctcctgttct cgarcgtccg ctccctcagg cccctcatcc tcggccgctc 145200
cggcccgagg cgtgtgcgcg tggcggttct gtgctcccct cccgttgggc agctccggcc 145260
gccgcccccct cttgcagcgc gggaaccggc acatggacac ggccccttgt cgctagggac 145320
gctcgtcggt cagccccgaa cgacaccgct gcttcagaag tcggggcggc agtccgagcc 145380
ttggaggttt ttttcagccc tggcccgaga gagctgctgg ccaccacccc gtccaagata 145440
gagctgtccg ctctccgcct ggttgttaga aagttctgat agaaagttcc ccctttgatg 145500
ctttttgcct cattgtgacg tccacccatc ctctcctctc agaactttct ttccttaggg 145560
atctcaaccc gaacggggtg agaatgaatc ttactgaaga aatctttctg ttccccccttc 145620
ttggtcttcc ccagacaaac cgtctcgttg aaagtatctt cacccattca catcttcagt 145680
tgaaagacta gacaaacaag aaacaaacag actaacaaaa cacaacccag gagtcgtccc 145740
tattctcttt gttttacttt gttctgttct gttttattta aagacagggt cttgctgttg 145800
tctaggctgg agtgcagtga tgcgatcttg gctcactgca acctcagact cctgggctca 145860
agcgatcctc ccgtctcagc ctctggagta gctgggactg caggtgcagg ctgccacgcc 145920
cgctaatttt ttaaattttt tttttttttt tttttttag aaatggcatc ttgctatgtt 145980
gcccaggctg gtctcgaact cgtgggctca agtgatcctc ccacctcagc cacccaaagt 146040
gctgggatta caggcatgag ccaccgcgcc ccggctagtg aagtatttct aaaaggcacg 146100
ttgaaaacta gccattccat tcctggcgcg gtggctcatg cttgtaatcc caacactttg 146160
ggaggctgag gtgggtggat cacaaggtct ggagatcgag accatcctgg acaacatggt 146220
aaaaccccgt ctgtactaaa aacacaaaaa ttagctgggc atggtggcac gcgcctgtag 146280
tcccagctcc tcaggaggct ggagcaggag aatcgcttga actcgggagg tggaggttgc 146340
agtgagccga gatcacacca ctgcactcca gcctgggtga cagagcgaga ctccgtctca 146400
aaaaaaaaaa aaaaaaagtt agccagtccc atcaccctca tccctatttt atttaatatt 146460
cctcaggaga aacttctttc caccttttga atttggtatt atatttctgt tgtctattga 146520

-continued

```
tttaacccat gtatagtagg tatcattttt agtagcccct gacctccttc ccctcatccc 146580
aaacacacac acaaacactt ccaccttcgg ggcctcccca actccgtagt ctgccgttga 146640
acctgtgtcc agttttagtt agatcagtat tcagtgtttt tttttctttc gagacagtgt 146700
ctcgctctgt ggctcaggct ggagtgcagt ggcacagtct ctgcttaatg cggcctctgc 146760
cttcccggtt caagcagttc tgcctcagcc tcctaagtag gtgggattac aggcgcccgc 146820
cagcacaccc gatcgatttt cttttctttt cttttttttt tttttttttt ttttgagaca 146880
agagttttgc tctgtctccc aggctggagt gcagtagcgg gatctcgtct cactgcaagc 146940
tctgcctccc gggttcacgc cattctcttg cctcagcctc ctgagtagct gggactacag 147000
gtccccgcca gcacacccga atgatttttt tgtattttta gtagagacga agttacacca 147060
tgttggccag gcttgtttca aactcctgac ctcaaatggt ctgcccgcct cggcctccct 147120
gagtgctggg attacaggcg tgagccaccg tgccaggccc agtgtttttt ttttctaatg 147180
acagtgtgaa taaacatcat gttgacagct gaaccgtatg ttatacagat tacttttcct 147240
gcacttcttg ttttctctgg tgctaataat tgccattttt tgttgctact tagctgtcta 147300
tgtacttaac tgctgtaaac caaaaataaa attctaaggc gcccccaacc atctgaatgg 147360
acttcctcct tagccagggc tctttaacat ttaacctgag agactgtttt gggcccatgc 147420
atgggaagtg gggctgaac ctgcctcatt gtatgtctct gacattaaca tcgatgcaga 147480
ctttaagtct gataataaac attttgcaac ctattctctc tgaagcctgt ctgctaaaag 147540
cttcatctgt atgataaaac tgtgttctca gccgagcagt ggctcgagcc tataatccta 147600
tcacttargg aggcagaggc tggtggatca tttgaggtca ggagttcaag accagcctgg 147660
ccaacgtggt gtaaccccat ctctactgaa aatatgaaaa ttagccaagt gtggtgacgg 147720
gcgcctgtaa tcctatctac tggggaggct gaggcacgag atctcttgaa cccaagaggt 147780
gggggttgca gtgagtgaag atcatgcttc tgcactccag cctgggtaac agagcaagac 147840
tccatttaaa aaaaaaaagt ggccaggtgc ggtggctcac acctttaatc ccagcacttt 147900
gggaggctgt ggtgggcgga ttgcctgagg tcaggagttg gagaccagtc tggccaacat 147960
agtgaaaccc tgtctgtact aaagatataa aaaaatagct gggtgtggtg gcgtgtgcct 148020
gtaatcccag ctactccgga ggctggggca ggggaattgc ttgaaccagg ggcgtggggt 148080
tgcagtgagc tgaggttgcg ccactgcact ccagcctggg caacagagtg agactccatc 148140
tcgaaaaaac aaacaaacaa acaaaaaaaa cctctggtct ccacaacctc tatcttaacc 148200
cagacattcc tttctgttta grcaaactca acctgttgcc aacaagaaaa tttttaaatt 148260
tacctgtagc ctggaagcac tcccaccccg agttgtcctg gtcttaatgg accaaaccag 148320
tatatttctc aaatgtattt gattgatgtc tcatgcctcc ctaaaatata taaaaccaag 148380
ctgcacccca accaccttgg gcgcgtgctc tcaggacctc ttgagggctg catcatgggc 148440
tgtggttact catatgtggc acagaataat tctcttcaaa tacttgacaa gagtttgact 148500
cttttcgtcg acactgctaa tttgactcta aacttttaga attgtataaa tcatctccca 148560
aaatatttac attcattaga ttttcacttt aatcttctga aacagtcttt gccttctggc 148620
ctccactttg tcttggttac cttctatgag tactccagtg tatttactta tttatttaga 148680
gatagagkct ygctcttgwy scccargctg gagtgcagta scgtgatctt ggctsactgc 148740
aacctmcacc tcccsggttt gagcgattct cttgcctcag cctcccaagt agcttggata 148800
caggtgccca ccaccacacc cagctaattt ttgtattttt agtagagacg gggtttcacc 148860
```

-continued

```
atgttggcca ggctgatatt gaactcctga cctcaggtga tccgccctcc tcagcctccc 148920
aaactgctgg gattacaggc gtgagccacc acgcctggtc aggaacattc ttatgagacc 148980
attgaatgca ctaaaagtaa ccatgcacca ctcaggcgta attgattgtc tgtttgaatt 149040
ctaggttgga aataattttc catcagaatt ttaaagtgtt acttcattac tttctagatt 149100
cccatgttgc tattaataaa tattttgtta ctgatttctg ctcaatgtat aagatctgtt 149160
tgtctccgga agctggtaga atattctctt tgttcccatk ttcttttttc ttttttttcg 149220
agacagactc tgtctctctt gtccaggcta gagtgcagtg gtggcatcta ggctccctgc 149280
aacctccact tcccgggttt aagcaactct cccacctcag cctccggagt ggctgggact 149340
acaggttcat gccaccacgc ctggctaatt tttgtatttt tatagtagag acgggatttc 149400
accatgttgg ccagcctggt ctcgaactcc tgacctcatg atctgcctgc ctcggcctcc 149460
caaagtgctg ggattacagg cgtgagcctc tacgcctggc ctgttcccat tttctaatat 149520
gtcaccatga tatatcttgg tatgagtgtt ttcagccatt ttgctgagcc ttctgagaac 149580
ttttttttcc tataattttt tttccttttc cttttccttt ctttcctctc tcactctttc 149640
ttttcctttc cttcctttct ttttttttctt tctctccctc tccgcccttc tttttctctc 149700
tctctattta tttatttttg agacggagta tagctctgtc acccaggctg gagtgcagtg 149760
gcgcaatctc ggcccactgc aacttccgcc ttccgggttc aagcgattcc cctgcctcag 149820
cctctcgagt agctgggata caggcgcgtg ccaccacatc tggctaattt ggtctatgta 149880
tcttaataga ttacggggct tcacttgttg gtcaagatgg tctcgatctc ctgaccttgt 149940
gatccacttg cttcggcctc ccaaagtgct gggattacag gtgtgagcca ctgagcccag 150000
ccaactttga atatttttat agcattatgt tcttcttttg taaatgcagt atcagcattt 150060
aacatacaat ttttaactta catacaataa aatttactgt tttcaatgta ctgttctctg 150120
atttttgtta aatgcctagc gttgtgtaac ctccaccaaa atgaacagtt tcaagccgtc 150180
aaccctctta aaaaaaaaaa aaaacaaatt tcccctgcta ctctttgtag tcaaacaact 150240
ctccctcacc cccggcccca gccattagca acctctggtc tgttttccat ctttatagtt 150300
ttgccttttt cagaatataa tctaaatgga accataacag taggcagctt tttgtatctg 150360
gcttcttccg cttagcataa tgcatttgag attcacctgt gttgttgcac atgtcagtaa 150420
ttagctcctt ctgttgttgg gtggtagtcc attatatgga tataccacag tttattctgc 150480
atttgaaaga cactgggttg tttccaattt tttatgatta caaataaagc tgtttataaa 150540
tatttacaca cagctttttc tgtgaacatg ggttttcatt tcacttgagt caatatctag 150600
gagtgggatt actgggtttt gtagtatgtg tatgtttaac tttacaagaa gctgctaaat 150660
ttttttgtgg cttgattgct gttggtaaca agtttgagag ttcragttgc tcttcatcct 150720
caacaacact tggggtggtc agattttttt gtttttgttt ttgttttaaa tattagctaa 150780
tttggggccg agcgcggtgg ctcatgcctg tawtcccacc actttgggag gccaaggcag 150840
gcagatcaca aggtcaggag tccaagacca gcctggccaa tatgttgaaa ccctgtctct 150900
actaaaaaat acaaagaatt agccgggcat ggtggtgcat gcctgtagtc ccagctactt 150960
gggaggatga ggaaggagaa tcgcttgaac ccaggrgstt ggagtgttgc rgtgagccgg 151020
aattgtgcca ctgcactcca gcctgggcaa gagagcgaga cactgtctcg aaaaaaaaag 151080
aaaaaaaatt agctaatttc tcctttagtt tgcatttccc taaggatgtt gatgctctty 151140
tcatgttcct gtttgccatc attttatctt ctttggtgtg tcttttgaat tctttgtcca 151200
tttaaaacat tgggttgttt tcagttttgg aattatatat tctggatata gtcctttgtc 151260
```

-continued agatatttgt tttgtttttt tttttttgag acagtctcgc tgtcccccag gctggagtac 151320
agtggcataa tcttggctca ccacaacctc cacctcccgg gttcaagcga ttctcctgcc 151380
tcagcctccc aagtagstgg gattacaagc actcgccacc acacccagct aatttttgta 151440
ttttcagtag agatggggtt tcaccatgtt tgccaggctg gtctccaact cccaacctca 151500
agtgatccac ccaccttggc ctcccaaagt gctgggagta caggcctgag tcaccacccc 151560
cggctccttt gtcacatact tgttttgcag tgttttgtct ctgtgcttgt cttttcattc 151620
tcttaatagt gtttgcacag caattttttt tggtgttttt ttgaaacaga gtcttgctct 151680
gttgccccag gctggaatgc agtggcacga tttcacctca ctgcaacctt tacttcctgg 151740
gctcaaacaa ttttcctgcc tcagcctctg tagtaactgg gactacaggc atgagacacc 151800
atgcctggcc tgcagagtaa aatttttaaa cttgrataaa atccagtttg tcaaattttt 151860
ctattatggg ttgtgctttt ggaatcatat ctaagaactc ttttttgcct aactcgggat 151920
tacaaagata gtgtattttc ctatgtaaaa gttacatagt tttactttgt tgttgtttty 151980
gtytttttga gatrgagttt cgctcttgtt gcccaggctg gagygcaatr kcrtgatcty 152040
ggctcactgc aacctcygcy tcctgrgttc aagggattct cctgcctcag cctcctgagg 152100
tarctgggat tgcaggcatg tgccaccacg cctggctaat tttgtatttt tagtagagac 152160
aggggtttct ccatgttggt caggctggtc ttgaactccc aacctcaggt gatccgccca 152220
cctcggcctc ccaaagtgtt gggattatag gcataagcca cagtgcctgg cctttacttt 152280
tktttttttt tkkttttttt tttttgagac agagtgttgc tctgttgccc aggcttgagt 152340
gcagtggcat gatctcagct cgctgcaacc kccgcctccc aggttcaagc gattctcctg 152400
cctcagcttc ccgagtagtt gggattatag gcgcctgcca ccacgcctgg ctaattttg 152460 tatttttagt ggagatgggg tttcaccatg ttggccaggc tggtcttgaa ctcctgacct 152520
ctcaggtaat ccgcccaccc cggcctccca aagtgctggg attacaggag tgagccaccg 152580
tgcccggcca gcatttactt ttttawaaaa tcagttatca ttatttattt tcagttaatt 152640
tttgcataag atatgagtta tggattcttt tttttttttt cttttgcatc tggatgtcca 152700
gtattttcat tatttgttga aaagattatt ctttctccat cgaattccct ttgtatttct 152760
gtaaagtgaa ctggccatac ttgtataggt ttatttctgg gcctctgttt ccacagtttc 152820
atttactgtt tttgatttaa gtgttgaaat caggtagaga gagtactcca acttttattc 152880
ttgtttcaaa atagttttgg ctgctcttgt tcctttgcct ttccatatag tttttttttt 152940
tttttttttt tttgaggggg atggagtgtc actctgttgc ccaggctgga gtgcagtggc 153000
gcgatctctg ctcactgcaa cctctacctc ccaggttcaa gtgattctcc ttcctcagcc 153060
tcctgtgtag ctggtactac agacgtgtgc caccaggcct ggccaccata tgcattgtaa 153120
aatcactttg ttcatctctc gaaaaagtat cctactttga ttttgtttgg aattgcattg 153180
aatctgtaga ccgttttggg aagaattgac aatttaacga tcttatattt tagtctatga 153240
atacagtctg tatctttttt ttttaggtgt aaaaagtttt tatttctaat tgtttgtaac 153300
tagtatatgg aaatacaata caggttctgc atactaacct tgtattctac aaccttgcta 153360
aactcattta ccagttctgg aggtttttgt agattctgtg ggattttcca cacagacagt 153420
gatgtcaaat gtgaatagaa acagttttat ttcttccttt ccaatatgtt taccttttat 153480
atttattttg cttgccttgt tgtactttat acttccagta tgatgttgaa tgctagtggt 153540
gagaggggac atctttgcct tttcccaat cttttttttt ttttttttga gacggagtct 153600

-continued ccctctgttr cccaggctgg agtgtgcagt ggcacgatct tgggtcactg tgacctctgc 153660
ctcctgggtt cacgccattc ttctgcctca gcctcccgag tagttgggac tacaggcgcc 153720
cgccaccacg cccgctaagt ttttgtattt ttagtagaga ctgggtttca ccgtgttagc 153780
cagaatggtc ttgatctcct gacctcgtga tccgcccgcc tcagcctccc aaagtgctgg 153840
gattataggc gtgagccacc gcgtctggca gcctttttcc caatcttaag gggaaaaaga 153900
aactagtgtt ttaccacttg atgtggtgtt agctataggt ttttcacaga tgccgtgtgt 153960
gtctgtctgc ctgccgttta aaccctttag cattgagtaa cttattacca actcagtcac 154020
ctaacactgt acgtgctaat tgtgttctgc attttactga tgaaaaaact gaggcacaaa 154080
gtctaagcaa atggctgaaa ttcatccagt tagatagtaa cttagctgga atgttaacct 154140
tggcagtctg catatattgt ccctcagaga ttccttttat catgttagat aagttcccct 154200
ctgttcctaa ttttcagaga ggtgaatttt gtcaaatgct tttctccat ctattgattt 154260
aattacatgt ggtttttctt tttttttgtc tgttaatatg gtggattaca gtgtttgatt 154320
ttcaaatttc tgacagactt atttctggga gacagctcac ttggtcagga tatatttata 154380
cattgctgaa tttggtttgc taatatagtc agccttctgt atctgtggtt tccacagcca 154440
tggattcaac caactgcaga tagaaaatat ttggaaaaag gctgggtgca gttgctcacg 154500
cctgtaatcc cagcactttg ggaggccaag gagtgcagat cacttgaagc caggagttaa 154560
agaccaacct gggaggccga ggtgggcgga tctcaaggtc aggagatcga gaccatcctg 154620
gctaacgtgg tgaaaccccg tctcaactaa aaatacaaaa aattagccgg gcgaggtggc 154680
gggtgcctgt agtcccagct gctcgggagg ctgaagcagg agaatggcgt gaacccaaga 154740
ggcggaggtt gcagtgagcg gagatcgcac cactgctctc cagcctgggc gacagagtga 154800
gactccgtct caaaaaacaa aaaaaaacca acctcgccaa cgtggtgaaa cccagtctct 154860
actaaaaata caaaaattag tcccagctac tgggctgagg cacgagaatc gcttgattac 154920
ccagactgga gtgcagtggc gcaatcagct cactgcagcc taaaactcct gggctcaagt 154980
gatcctccca cctcagcctc ccaggtacct gggactacag atgcacacca tcatgcccat 155040
ctaatttttt tttttttttt tttgagacgg aagtcttgct ctgtcaccca ggctggcgtg 155100
cagtggcacc atctcggttc actgccagcc ctgcctcccg ggttcacgcc attctcctgc 155160
ctcagcctcc cgagtagctg ggactacagg cacccaccac aaggcccggc taattttttt 155220
gtatttttag tagagatggg gtttcaccgt gttagccagg atggtctcga tctcctgacc 155280
ttgtgatccg cccacctcgg cctcccaaag tgctgggatt acaggcgtga gccactgcgc 155340
ccggcctaat tttttatttt ttgtagagat gaggtctctc accatgttgc ccaagctggt 155400
ctcaaacacc tggctttgag caatcttcct gccttagcct cccaaagtgc tggcattaca 155460
ggtgtgagaa aacctggatt tgtttgtttg tttttaaaag aaacagggtt ttgctccgtc 155520
acccaggctg gagtgcagtg gcaagatcac agctcagtga cacgttgaac tcctggcctc 155580
aagcgatcct tctgccttaa cctctaaaaa cktgtttttt ttttgatcac agttttaaga 155640
ctctctaaga ggctggatgt ggtggctctg acctgtaatc ccagcacttt gggaggctga 155700
agtgggtgga tcacttgagg ccaggagttc aagactagtc tgacgaacat ggtgaaaccc 155760
cgtctctacc aaaaatgcaa aaatcagctg ggagtggtgg tgcatacctg tagtctcagg 155820
tattcgtgag gctgaggcag gagaatcact tgaacccggg aggatcgtag tgagccaaga 155880
tcatgccact gcactctagc ttgggcaaca gagcgagact ctgtctcaaa aaaaaaaaaa 155940
aaaaaaaaga ggccatacgc agtggctcac gcctgtaatc ccagcacttt gggaggtcga 156000

-continued ggcaggtgga tcacgaggtc aagagatcga gaccatcctg gcaacacggt gaaaccctgt 156060
ctctactaaa aatacaaaaa attagccggg tgtggtggca agcgcctgta atcccagcta 156120
cttgggaggc tgaggcagga gaatagcttg aacacgggag gcagaggttg cggtgagccg 156180
agatcgcacc attgcactcc agcctgggca aaaagagcga aactccgtct caaaaaaaag 156240
agagagagag agaaagtatt tgggaaaaca aatgggtggt tatgtctgta ctgaatgtgt 156300
acaaactttt ttccttgtca ttatttccta aacaatacag tataacaact attcatatag 156360
cacttatatt gggtgttgta agtaatctag agatgactta aagtatgcaa gaggatgtac 156420
atagtttata tgtaaatatg acatcatttt atatcaggga cttgaacatc tgtgggtttt 156480
ggtgtggggt gggggagatc ttggaaccac ttccccagaa atatggaggg acagccgtat 156540
tttgtcgagg atttttgcat ctgtgtttat gagggatatc gatctgtagt tttttggtaa 156600
tttccttgtg tgattttagt atcagataat gcaggcctca taaaatgagg aaatacaggc 156660
tttgtttctt ccagggtgat tttttattca ccttgtatgc ttgtttaggg ttttattatg 156720
taagaggctt tctcggattt atactgattc ttagttggtt tggctcatat ttatgcttgg 156780
ggcactagaa aggttattgg aagctctgag tctttggaca agatttgttc cttttgtgcc 156840
tacattgtct acagggatgt tattctgatt cttactatct ttttttccct catagtaact 156900
gcatggaatt tgatattgag gttttggggg gttttgtatg tataatttaa aattttctta 156960
tctcttactg atgaaggact tttccatagt ttagctaaag atggagtcct tgtcccacag 157020
ccatgataat ttaggctcac agacaatttg aagcttgagt aaatcagggt tttattgggt 157080
gaaaagggaa aaaaggggga acagggactc tgcaaggcca gagttcctgc tgctgtgctt 157140
cctgccttgc agctttgaat cccaggttgc acacaggaag aagaggggcc gggctcctcc 157200
ccgctgcaaa cagcaggaac ctctgtggct ccaccccagt gcgcatgcct cctagtctgc 157260
tggctggccg gagattctcc agggaccccc tcccacatgg ctgtctcatt attaatgaga 157320
ttaagcatct ttttacatgt ttaagatcca gagtcatgtg catctacttg tctgaactgt 157380
ctacaacatt tgcctgtttt tatgatgaaa acaggcaaaa gttttcaaaa gtagtgcaga 157440
gctttataga aaattagaaa atgcagacag ttaaattaaa aatcacttaa aaataaaaaa 157500
aatagttgaa ctacctagag actatcatgt caatccttta gtgaaaactc actctgattt 157560
ttttctacac ctaggtatag atatttgtat tttttcctca gcctgcaatt gtatttactc 157620
acatcgcttt tcaacctact ctttttagtg gatgatttct acccatttat tttagtaaat 157680
gttttatctt atatatagat catactcaaa ttttccaaaa tggttatagc ttgtgtgtcc 157740
aaatcacagt tgagttcaat actacacata ttatccagtt gttccatcct tgagtctctt 157800
ttaatctagc acactcccct ttctataatg gcatagatag ctgaaaagat caaagccata 157860
catcctgcag catgtctcac ctcttggatt tgtctggtta ttccctcatg gcgttgtttt 157920
agttcctttg ttccttcagt tctctgtaaa tcagaagtta gatctaaatg cttgatgggt 157980
tccaatgaaa tactttggcc agaatgcatt atcaatggac atctgatgtt tgaatagcat 158040
cagaagacac aatatctggt tgataactat agtggtgact attaaaatca gggtgataac 158100
agtctgatcc ctctcttgta tacttgtttt ttcctttgga aacttttaag aaactggaaa 158160
agtattccct gtggcagtaa taacttaatg gttaaaactt aaattgcttt ttaatttttt 158220
tttttttttt ttttttttga gatgaaggtc tcactgtgtt gttcagtctg gactcaaatt 158280
cctgggctca agagagcttc tgaggtagct gagactacct gttacctgaa aggggatcca 158340

-continued

```
gacccagacc ccaagagagg gttcttggat ctcgaacaag aaagaattcg agggaaatcc 158400
atacagaaaa gtaaaaacaa gtttattaag aaagtagagg aataaagaat gtctactcca 158460
tagacagagc agacccaagg gctgctggtt gcccattttt atggttattt cttgattata 158520
tgctaaacaa ggggtggatt attcatgcct ccccttttca gaccatttag agtaacttcc 158580
tgatgttgcc atggcatttg taagctgtca tggcgctggt tttggtgggt tttagccagc 158640
ttctttacgg cagactgttt tatcagcaag gtctttatga cctgtatctt ctgccaacct 158700
tctagcttat cgtgtgactt agaatgcctt aacctcctgg gaatgcatcc cagcaggttt 158760
cagccttgtt ttacccagtc gctattcagg atggagttgc tctggttcag atgcctctgg 158820
cacacccagc ttcttaaatt gctttttggc attacttaat aacccttgcc taaactacta 158880
ctgtcattag agtttgagaa gtgatgtctt tctaattctg tggttcttct gtatttattg 158940
gttgacattt ttctgtaaag tatagctttc ctttatcaat tggaacaata taaatattta 159000
attcttttcc ctcaattttc aaaataggta gtaattttaa atagcagtct aaaatggtac 159060
aaattttttt ttctgtcttt ttaatatcat gaggggctca cagattttta ttcagtgtgt 159120
tttcattttc taacaattac ctgttttaat gttcaggtct tcactgcttt ggccagtagg 159180
agctctttca ggctggatct tgtatccttt taatttgatc tttttttatt attatttatt 159240
ttttatgagt cggcgtcctg cttactgtag ccttcaattc ctgggctcaa gtgatcctcc 159300
tgcctcagcc tccccagtag atggaactac aggtgcgtgc caccatgcct gactaatttt 159360
ttaaaaatct tttatagaaa caggctcttg ctctgttgcc caggctggtc tcgaactcat 159420
gggctcaagc attccccccc atactcaccc accttggcct cctaaggtgg taggattaca 159480
ggcatgagcc actgcacctg gccttgatct gttattttta aatagcttcc tgacttcctg 159540
gcacagaaaa atgtcctggt tttaccttgt gctttctttg cctcagacct gaaatgagtt 159600
tttttttttt tttttttagg gagccttttt gtggtaaatg gtctcaactt tgaactttag 159660
agatgcttga tgttaccaga atgatgtagt ttatatgccg tttgtgtagt ggacaaaact 159720
aggaaatact taaaaagggt tagccgggcg cgttggctca cgcctgtaat cccagcactt 159780
tgggaggccg aggtcggcgg atcacaaggt caggagttcg agaccatctt ggctaacatg 159840
gtgaaacccc atctctacta aaaatacaaa aaaaattagc caggcatagg tggtgcacgc 159900
ctgtagtccc acctacacgg gaggctgagg caggagaatg gcgtaaaacc cgggaggcgg 159960
agcttgcagt gagccgagat cgtgccactg cactctagcc tgggcgacag agcgagactg 160020
cgtctcaaaa aaaaaaaaaa aaagggttag agttcatatt gatattctta attctttttt 160080
tttttttttt tttttttgag acagagtttc actcttgttg cccaggctgg agtgcagtgg 160140
tgtatctcag ctcatcgcaa cctccgcccc ccaggttcaa gcaattctcc tgcctcagct 160200
ccctgagtag ctggtattac aggcatgcat caccacaccc agctaatttt gtatttttag 160260
tagagatggg gtttcactgt gttggccaga ctggtctcga actcctggcc tcaggtgata 160320
cacccacctc agcctcccaa agtgctggga ttacagacat gagccaccgc tcccagccaa 160380
tttctttgat tttataattg tgtcatttct cttattctga agatctagat tcctaacgtg 160440
attaattact tgctttaacc tatgatataa aggaaatagt ttcaaaatac cagcattgat 160500
gttactacac agaaagactg tgggatcctc tagagtgact acagcagcag cc         160552
```

<210> SEQ ID NO 12
<211> LENGTH: 1694
<212> TYPE: DNA
<213> ORGANISM: homo sapiens -continued

<400> SEQUENCE: 12

```
ggcacgagga cgacgtttgg gagcctttgc tgagtccagg gagagaggcg tccccccaccg     60
tgccgctgca gctcgggcag agccgccaag ctttggggtg ctgaggaacc tctaatcatc    120
tcccatggat ttgtgatcag cgttgcagct ctcccagcag ccctggacag tggcccccag    180
cagtcagcat gtggctgccg cgcgtctcca gcacagcagt gaccgcgctc ctcctggcgc    240
agaccttcct cctcctcttt ctggtttccc ggccagggcc ctcgtcccca gcaggcggcg    300
aggcgcgcgt gcatgtgctg gtgctgtcct cgtggcgctc gggctcgtcc ttcgtgggcc    360
aactcttcaa ccagcacccc gacgtcttct acctaatgga gcccgcgtgg cacgtgtgga    420
ccaccctgtc gcagggcagc gccgcaacgc tgcacatggc tgtgcgcgac ctggtgcgct    480
ccgtcttcct gtgcgacatg gacgtgtttg atgcctatct gccttggcgc cgcaacctgt    540
ccgacctctt ccagtgggcc gtgagccgtg cactgtgctc gccacccgcc tgcagtgcct    600
ttccccgagg cgccatcagc agcgaggccg tgtgcaagcc actgtgcgcg cggcagtcct    660
tcaccctggc ccgggaggcc tgccgctcct acagccacgt ggtgctcaag gaggtgcgct    720
tcttcaacct gcaggtgctc tacccgctgc tcagcgaccc cgcgctcaac ctacgcatcg    780
tgcacctggt gcgcgacccg cgggccgtgc tgcgctcccg ggagcagaca gccaaggctc    840
tggcgcgtga caacggcatc gtgctgggca ccaacggcac gtgggtggag gccgaccccg    900
gcctgcgcgt ggtgcgcgag gtgtgccgta gccacgtacg catcgccgag gccgcccacac    960
tcaagccgcc accctttctg cgcggccgct accgcctggt gcgcttcgag gacctggcgc   1020
gggagccgct ggcagaaatc cgtgcgctct acgccttcac tgggctcagt ctcacgccac   1080
agctcgaggc ctggatccat aacatcaccc acggatctgg acctggtgcg cgccgcgaag   1140
ccttcaagac ttcgtccagg aatgcgctca acgtctccca ggcctggcgc catgcgctgc   1200
cctttgccaa gatccgccgc gtgcaggaac tgtgcgctgg tgcgctgcag ctgctgggct   1260
accggcctgt gtactctgag gacgagcagc gcaacctcgc ccttgatctg gtgctgccac   1320
gaggcctgaa cggcttcact tgggcatcat ccaccgcctc gcaccccccga aattagtgga   1380
ggccacagtt gtagcaggcg ctaggcccgg gaggagagtg catggtgcag agggggctgg   1440
ggcgcacgga gaagcaggtc cctatattga ccaaggagtt tgtggtacga cccctccccc   1500
tccccaagta ggcaaggact gcacgtttct ttctctcttg attcttggtt ttcctttgag   1560
tcctctggag ctgccttctc atcaggtgca ctcttcatgg aaagcaactc ttgcccctgc   1620
ctcctctggg cacagggtgt gcgttcagat gacttggctc ctactcaagg gctttcttcc   1680
ccctggagaa gaga                                                     1694
```

<210> SEQ ID NO 13
<211> LENGTH: 395
<212> TYPE: PRT
<213> ORGANISM: homo sapiens

<400> SEQUENCE: 13

```
Met Trp Leu Pro Arg Val Ser Ser Thr Ala Val Thr Ala Leu Leu Leu
1               5                   10                  15

Ala Gln Thr Phe Leu Leu Leu Phe Leu Val Ser Arg Pro Gly Pro Ser
            20                  25                  30

Ser Pro Ala Gly Gly Glu Ala Arg Val His Val Leu Val Leu Ser Ser
        35                  40                  45

Trp Arg Ser Gly Ser Ser Phe Val Gly Gln Leu Phe Asn Gln His Pro
```

-continued

```
    50                  55                  60

Asp Val Phe Tyr Leu Met Glu Pro Ala Trp His Val Trp Thr Thr Leu
65                  70                  75                  80

Ser Gln Gly Ser Ala Ala Thr Leu His Met Ala Val Arg Asp Leu Val
                85                  90                  95

Arg Ser Val Phe Leu Cys Asp Met Asp Val Phe Asp Ala Tyr Leu Pro
            100                 105                 110

Trp Arg Arg Asn Leu Ser Asp Leu Phe Gln Trp Ala Val Ser Arg Ala
        115                 120                 125

Leu Cys Ser Pro Pro Ala Cys Ser Ala Phe Pro Arg Gly Ala Ile Ser
    130                 135                 140

Ser Glu Ala Val Cys Lys Pro Leu Cys Ala Arg Gln Ser Phe Thr Leu
145                 150                 155                 160

Ala Arg Glu Ala Cys Arg Ser Tyr Ser His Val Val Leu Lys Glu Val
                165                 170                 175

Arg Phe Phe Asn Leu Gln Val Leu Tyr Pro Leu Leu Ser Asp Pro Ala
            180                 185                 190

Leu Asn Leu Arg Ile Val His Leu Val Arg Asp Pro Arg Ala Val Leu
        195                 200                 205

Arg Ser Arg Glu Gln Thr Ala Lys Ala Leu Ala Arg Asp Asn Gly Ile
    210                 215                 220

Val Leu Gly Thr Asn Gly Thr Trp Val Glu Ala Asp Pro Gly Leu Arg
225                 230                 235                 240

Val Val Arg Glu Val Cys Arg Ser His Val Arg Ile Ala Glu Ala Ala
                245                 250                 255

Thr Leu Lys Pro Pro Pro Phe Leu Arg Gly Arg Tyr Arg Leu Val Arg
            260                 265                 270

Phe Glu Asp Leu Ala Arg Glu Pro Leu Ala Glu Ile Arg Ala Leu Tyr
        275                 280                 285

Ala Phe Thr Gly Leu Ser Leu Thr Pro Gln Leu Glu Ala Trp Ile His
    290                 295                 300

Asn Ile Thr His Gly Ser Gly Pro Gly Ala Arg Arg Glu Ala Phe Lys
305                 310                 315                 320

Thr Ser Ser Arg Asn Ala Leu Asn Val Ser Gln Ala Trp Arg His Ala
                325                 330                 335

Leu Pro Phe Ala Lys Ile Arg Arg Val Gln Glu Leu Cys Ala Gly Ala
            340                 345                 350

Leu Gln Leu Leu Gly Tyr Arg Pro Val Tyr Ser Glu Asp Glu Gln Arg
        355                 360                 365

Asn Leu Ala Leu Asp Leu Val Leu Pro Arg Gly Leu Asn Gly Phe Thr
    370                 375                 380

Trp Ala Ser Ser Thr Ala Ser His Pro Arg Asn
385                 390                 395
```

<210> SEQ ID NO 14
<211> LENGTH: 4599
<212> TYPE: DNA
<213> ORGANISM: homo sapiens

<400> SEQUENCE: 14

```
cacaaatgct catacatgtg tggtgagctt atcaccagtg atggttttct gtgctagaaa      60

tgactcttaa tttgaatttt ggagtgcttt ttctcttttt ttacaatgtg tgttccaact     120

ctttgtgtta aatagattta agtaaaggag gtaaatgcta aattcatagt gtttttttacc    180
```

-continued

```
tgtatcactt ccctgtgtat tatggaaaaa ttagagattt taacgttatt caaagtttta    240
ctggaagcaa aactgtgcca gggacagaga tatacaattt aagttttctc tttttggcaa    300
ctgcacttgc ttaaaatgta ctgaatgtca gctggatttc acagcatatc agatttacag    360
tctttgtctt atcaaggcct ttactgtatg ttttatacta accagatggg aaacacattg    420
agcatcatat ctgacatgta tgcctaaggg aggagctccc ccatggatca tggcgttaat    480
gtttacagga catttactat tcttagcatt attgatgttt gctttctcta cttttgagga    540
atctgtgagc aattattccg aatgggcagt tttcacagat gatatagatc agtttaaaac    600
acagaaagtg caagatttca gacccaacca aaagctgaag aaaagtatgc ttcatccaag    660
tttatatttt gatgctggag aaatccaagc aatgagacaa aagtctcgtg caagccattt    720
gcatcttttt agagctatca gaagtgcagt gacagttatg ctgtccaacc caacatacta    780
cctacctcca ccaaagcatg ctgattttgc tgccaagtgg aatgaaattt atggtaacaa    840
tctgcctcct ttagcattgt actgtttgtt atgcccagaa gacaaagttg cctttgaatt    900
tgtcttggaa tatatggaca ggatggttgg ctacaaagac tggctagtag agaatgcacc    960
aggagatgag gttccaattg gccattcctt aacaggtttt gccactgcct ttgacttttt   1020
atataactta ttagataatc atcgaagaca aaaatacctg gaaaaaatat gggttattac   1080
tgaggaaatg tacgagtatt ccaaggtccg ctcatggggc aaacagcttc tccataacca   1140
ccaagccact aatatgatag cattactcac aggggccttg gtgactggag tagataaagg   1200
atctaaagca aatatatgga aacaggctgt agtggatgtc atggaaaaga caatgtttct   1260
attgaatcat attgttgatg gttctttgga tgaaggtgtg gcctatggaa gctacacagc   1320
taaatccgtc acacagtatg tttttctggc ccagcgccat tttaatatca acaacttgga   1380
taataactgg ttaaagatgc acttttggtt ctattatgcc accctttac ctggcttcca   1440
aagaactgtg ggtatagcag attccaatta taattggttt tatggtccag aaagccagct   1500
agttttcttg gataagttca tcttaaagaa tggagctgga aattggttag ctcagcaaat   1560
tagaaagcac cgacctaaag atggaccgat ggttccttca actgcccaaa ggtggagtac   1620
tcttcacact gaatacatct ggtatgatcc ccagctcaca ccacagccac ctgctgatta   1680
tggtactgca aaaatacaca cattccctaa ctggggtgtg gttacttatg ggctgggtt    1740
gccaaacaca cagaccaaca cctttgtgtc ttttaaatct gggaagctgg ggggacgagc   1800
tgtgtatgac atagttcatt ttcagccata ttcctggatt gatgggtgga gaagttttaa   1860
cccaggacat gagcatccag atcagaactc atttactttt gcccccaatg gacaagtatt   1920
tgtttctgaa gctctctatg gacccaagtt gagccacctt aacaatgtat tggtgtttgc   1980
tccatcaccc tcaagccagt gtaataagcc ctgggaaggt caactgggag aatgtgcgca   2040
gtggcttaag tggactggcg aggaggttgg tgatgcagct ggggaaataa tcactgcctc   2100
tcaacatggg gaaatggtat ttgtgagtgg ggaagccgtg tctgcttatt cttcagcaat   2160
gagactgaaa agtgtatatc gtgctttgct tctcttaaat tcccaaactc tgctagttgt   2220
tgatcatatt gagaggcaag aagattcccc aataaattct gtcagtgcct tctttcataa   2280
tttggatatt gattttaaat atatcccata taagtttatg aataggtata atggtgccat   2340
gatggatgtg tgggatgcac attacaaaat gttttggttt gatcatcatg gcaatagtcc   2400
catggccagt atacaggaag cagagcaagc tgctgaattt aaaaaacgat ggactcaatt   2460
tgttaatgtt acttttcaga tggaatccac aatcacaaga attgcatatg tcttttatgg   2520
gccatatatc aatgtctcca gctgcagatt tattgatagt tccaatcctg gacttcagat   2580
```

-continued

```
ttctctcaat gtcaataata ctgaacatgt tgtttctatt gtaactgatt accataacct   2640
gaagacaaga ttcaattatc tgggattcgg tggctttgcc agtgtggctg atcaaggcca   2700
aataacccga tttggtttgg gcactcaagc aatagtaaag cctgtaagac atgataggat   2760
tattttcccc tttggattta aatttaatat agcagttgga ttaattttgt gcattagctt   2820
ggtgatttta actttccaat ggcgttttta cctttctttt agaaaactaa tgcgatggat   2880
attaatactt gttattgcct tgtggtttat tgagcttttg gatgtgtgga gcacttgtag   2940
tcagcccatt tgtgcaaaat ggacaaggac agaggctgag ggaagcaaga agtctttgtc   3000
ttctgaaggg caccacatgg atcttcctga tgttgtcatt acctcacttc ctggttcagg   3060
agctgaaatt ctcaaacaac ttttttttcaa cagtagtgat tttctctaca tcagggttcc   3120
tacagcctac attgatattc ctgaaactga gttggaaatc gactcatttg tagatgcttg   3180
tgaatggaag gtgtcagata tccgcagtgg gcattttcgt ttactccgag gctggttgca   3240
gtctttagtc caggacacaa aattacattt gcaaaacatc catctgcatg aacccaatag   3300
gggtaaactg gcccaatatt ttgcaatgaa taaggacaaa aaaagaaaat ttaaaaggag   3360
agagtctttg ccagaacaaa gaagtcaaat gaaaggcgcc tttgatagag atgctgaata   3420
tattagggct ttgaggagac acctggttta ctatccaagt gcacgtcctg tgctcagttt   3480
aagcagtgga agctggacgt taaagcttca ttttttttcag gaagttttag gagcttcgat   3540
gagggcattg tacatagtaa gagaccctcg ggcatggatt tattcaatgt tgtacaatag   3600
taaaccaagt ctttattctt tgaagaatgt accagagcat ttagcaaaat tgtttaaaat   3660
agagggaggt aaaggcaaat gtaacttaaa ttcgggttat gctttcgagt atgaaccatt   3720
gaggaaagaa ttatcaaaat ccaaatcaaa tgcagtgtcc ctcttgtctc acttgtggct   3780
agcaaataca gcagcagcct tgagaataaa tacagatttg ctgcctacta gctaccagct   3840
ggtcaagttt gaagatattg tgcattttcc tcagaaaact actgaaagga tttttgcctt   3900
tcttggaatt cctttgtctc ctgctagttt aaaccaaata ttgtttgcca cctctacaaa   3960
cctttttttac cttccctatg aaggggaaat atcaccaact aatactaatg tttggaaaca   4020
gaacttgcct agagatgaaa ttaaactaat tgaaaacatc tgctggactc tgatggatcg   4080
cctaggatat ccaaagttta tggactaaat gctgcaggtc agcagaaatt tgcactaata   4140
atacttacca acccactttg tggatatgaa tcagaagagt ttgtttattc tttagtgtgt   4200
gtgtgtgtgt gtgcacgcgt gtatgtgttc agtgttgttt gcacagagag attgttttaa   4260
aaaatggcac catatttggc ctagcaggat ttatttttat gtcatcacct cccttgcctt   4320
tgtttctgaa aattttgtct gctaaaaagt ttctgctaca gagtggtaga tgaagttata   4380
tcatggggtc aggggagatg ggaaaatttt aagtttttgt ctaactcccc ttcatctgta   4440
actgtgctaa tctatctaga gacctcaaac actgctaaag gccttgcaat tgctgcttta   4500
cccacgcatc tcttgctttc aagaaggact acaaaagttc cttatccttt tgaaaaggtc   4560
ttctgacaca cttatcttgc acaaagaaaa agaaaattt                           4599
```

<210> SEQ ID NO 15
<211> LENGTH: 1222
<212> TYPE: PRT
<213> ORGANISM: homo sapiens

<400> SEQUENCE: 15

```
Met Pro Lys Gly Gly Ala Pro Pro Trp Ile Met Ala Leu Met Phe Thr
 1               5                  10                  15
```

-continued

```
Gly His Leu Leu Phe Leu Ala Leu Leu Met Phe Ala Phe Ser Thr Phe
            20                  25                  30

Glu Glu Ser Val Ser Asn Tyr Ser Glu Trp Ala Val Phe Thr Asp Asp
        35                  40                  45

Ile Asp Gln Phe Lys Thr Gln Lys Val Gln Asp Phe Arg Pro Asn Gln
    50                  55                  60

Lys Leu Lys Lys Ser Met Leu His Pro Ser Leu Tyr Phe Asp Ala Gly
65                  70                  75                  80

Glu Ile Gln Ala Met Arg Gln Lys Ser Arg Ala Ser His Leu His Leu
                85                  90                  95

Phe Arg Ala Ile Arg Ser Ala Val Thr Val Met Leu Ser Asn Pro Thr
            100                 105                 110

Tyr Tyr Leu Pro Pro Pro Lys His Ala Asp Phe Ala Ala Lys Trp Asn
        115                 120                 125

Glu Ile Tyr Gly Asn Asn Leu Pro Pro Leu Ala Leu Tyr Cys Leu Leu
    130                 135                 140

Cys Pro Glu Asp Lys Val Ala Phe Glu Phe Val Leu Glu Tyr Met Asp
145                 150                 155                 160

Arg Met Val Gly Tyr Lys Asp Trp Leu Val Glu Asn Ala Pro Gly Asp
                165                 170                 175

Glu Val Pro Ile Gly His Ser Leu Thr Gly Phe Ala Thr Ala Phe Asp
            180                 185                 190

Phe Leu Tyr Asn Leu Leu Asp Asn His Arg Arg Gln Lys Tyr Leu Glu
        195                 200                 205

Lys Ile Trp Val Ile Thr Glu Glu Met Tyr Glu Tyr Ser Lys Val Arg
    210                 215                 220

Ser Trp Gly Lys Gln Leu Leu His Asn His Gln Ala Thr Asn Met Ile
225                 230                 235                 240

Ala Leu Leu Thr Gly Ala Leu Val Thr Gly Val Asp Lys Gly Ser Lys
                245                 250                 255

Ala Asn Ile Trp Lys Gln Ala Val Val Asp Val Met Glu Lys Thr Met
            260                 265                 270

Phe Leu Leu Asn His Ile Val Asp Gly Ser Leu Asp Glu Gly Val Ala
        275                 280                 285

Tyr Gly Ser Tyr Thr Ala Lys Ser Val Thr Gln Tyr Val Phe Leu Ala
    290                 295                 300

Gln Arg His Phe Asn Ile Asn Asn Leu Asp Asn Asn Trp Leu Lys Met
305                 310                 315                 320

His Phe Trp Phe Tyr Tyr Ala Thr Leu Leu Pro Gly Phe Gln Arg Thr
                325                 330                 335

Val Gly Ile Ala Asp Ser Asn Tyr Asn Trp Phe Tyr Gly Pro Glu Ser
            340                 345                 350

Gln Leu Val Phe Leu Asp Lys Phe Ile Leu Lys Asn Gly Ala Gly Asn
        355                 360                 365

Trp Leu Ala Gln Gln Ile Arg Lys His Arg Pro Lys Asp Gly Pro Met
    370                 375                 380

Val Pro Ser Thr Ala Gln Arg Trp Ser Thr Leu His Thr Glu Tyr Ile
385                 390                 395                 400

Trp Tyr Asp Pro Gln Leu Thr Pro Gln Pro Pro Ala Asp Tyr Gly Thr
                405                 410                 415

Ala Lys Ile His Thr Phe Pro Asn Trp Gly Val Val Thr Tyr Gly Ala
            420                 425                 430
```

-continued

```
Gly Leu Pro Asn Thr Gln Thr Asn Thr Phe Val Ser Phe Lys Ser Gly
        435                 440                 445

Lys Leu Gly Gly Arg Ala Val Tyr Asp Ile Val His Phe Gln Pro Tyr
    450                 455                 460

Ser Trp Ile Asp Gly Trp Arg Ser Phe Asn Pro Gly His Glu His Pro
465                 470                 475                 480

Asp Gln Asn Ser Phe Thr Phe Ala Pro Asn Gly Gln Val Phe Val Ser
                485                 490                 495

Glu Ala Leu Tyr Gly Pro Lys Leu Ser His Leu Asn Asn Val Leu Val
            500                 505                 510

Phe Ala Pro Ser Pro Ser Ser Gln Cys Asn Lys Pro Trp Glu Gly Gln
        515                 520                 525

Leu Gly Glu Cys Ala Gln Trp Leu Lys Trp Thr Gly Glu Glu Val Gly
    530                 535                 540

Asp Ala Ala Gly Glu Ile Ile Thr Ala Ser Gln His Gly Glu Met Val
545                 550                 555                 560

Phe Val Ser Gly Glu Ala Val Ser Ala Tyr Ser Ser Ala Met Arg Leu
                565                 570                 575

Lys Ser Val Tyr Arg Ala Leu Leu Leu Leu Asn Ser Gln Thr Leu Leu
            580                 585                 590

Val Val Asp His Ile Glu Arg Gln Glu Asp Ser Pro Ile Asn Ser Val
        595                 600                 605

Ser Ala Phe Phe His Asn Leu Asp Ile Asp Phe Lys Tyr Ile Pro Tyr
    610                 615                 620

Lys Phe Met Asn Arg Tyr Asn Gly Ala Met Met Asp Val Trp Asp Ala
625                 630                 635                 640

His Tyr Lys Met Phe Trp Phe Asp His His Gly Asn Ser Pro Met Ala
                645                 650                 655

Ser Ile Gln Glu Ala Glu Gln Ala Ala Glu Phe Lys Lys Arg Trp Thr
            660                 665                 670

Gln Phe Val Asn Val Thr Phe Gln Met Glu Ser Thr Ile Thr Arg Ile
        675                 680                 685

Ala Tyr Val Phe Tyr Gly Pro Tyr Ile Asn Val Ser Ser Cys Arg Phe
    690                 695                 700

Ile Asp Ser Ser Asn Pro Gly Leu Gln Ile Ser Leu Asn Val Asn Asn
705                 710                 715                 720

Thr Glu His Val Val Ser Ile Val Thr Asp Tyr His Asn Leu Lys Thr
                725                 730                 735

Arg Phe Asn Tyr Leu Gly Phe Gly Gly Phe Ala Ser Val Ala Asp Gln
            740                 745                 750

Gly Gln Ile Thr Arg Phe Gly Leu Gly Thr Gln Ala Ile Val Lys Pro
        755                 760                 765

Val Arg His Asp Arg Ile Ile Phe Pro Phe Gly Phe Lys Phe Asn Ile
    770                 775                 780

Ala Val Gly Leu Ile Leu Cys Ile Ser Leu Val Ile Leu Thr Phe Gln
785                 790                 795                 800

Trp Arg Phe Tyr Leu Ser Phe Arg Lys Leu Met Arg Trp Ile Leu Ile
                805                 810                 815

Leu Val Ile Ala Leu Trp Phe Ile Glu Leu Leu Asp Val Trp Ser Thr
            820                 825                 830

Cys Ser Gln Pro Ile Cys Ala Lys Trp Thr Arg Thr Glu Ala Glu Gly
        835                 840                 845

Ser Lys Lys Ser Leu Ser Ser Glu Gly His His Met Asp Leu Pro Asp
```

-continued

```
    850                 855                 860

Val Val Ile Thr Ser Leu Pro Gly Ser Gly Ala Glu Ile Leu Lys Gln
865                 870                 875                 880

Leu Phe Phe Asn Ser Ser Asp Phe Leu Tyr Ile Arg Val Pro Thr Ala
                885                 890                 895

Tyr Ile Asp Ile Pro Glu Thr Glu Leu Glu Ile Asp Ser Phe Val Asp
            900                 905                 910

Ala Cys Glu Trp Lys Val Ser Asp Ile Arg Ser Gly His Phe Arg Leu
        915                 920                 925

Leu Arg Gly Trp Leu Gln Ser Leu Val Gln Asp Thr Lys Leu His Leu
    930                 935                 940

Gln Asn Ile His Leu His Glu Pro Asn Arg Gly Lys Leu Ala Gln Tyr
945                 950                 955                 960

Phe Ala Met Asn Lys Asp Lys Lys Arg Lys Phe Lys Arg Arg Glu Ser
                965                 970                 975

Leu Pro Glu Gln Arg Ser Gln Met Lys Gly Ala Phe Asp Arg Asp Ala
            980                 985                 990

Glu Tyr Ile Arg Ala Leu Arg Arg His Leu Val Tyr Tyr Pro Ser Ala
        995                 1000                1005

Arg Pro Val Leu Ser Leu Ser Ser Gly Ser Trp Thr Leu Lys Leu His
    1010                1015                1020

Phe Phe Gln Glu Val Leu Gly Ala Ser Met Arg Ala Leu Tyr Ile Val
1025                1030                1035                1040

Arg Asp Pro Arg Ala Trp Ile Tyr Ser Met Leu Tyr Asn Ser Lys Pro
                1045                1050                1055

Ser Leu Tyr Ser Leu Lys Asn Val Pro Glu His Leu Ala Lys Leu Phe
            1060                1065                1070

Lys Ile Glu Gly Gly Lys Gly Lys Cys Asn Leu Asn Ser Gly Tyr Ala
        1075                1080                1085

Phe Glu Tyr Glu Pro Leu Arg Lys Glu Leu Ser Lys Ser Lys Ser Asn
    1090                1095                1100

Ala Val Ser Leu Leu Ser His Leu Trp Leu Ala Asn Thr Ala Ala Ala
1105                1110                1115                1120

Leu Arg Ile Asn Thr Asp Leu Leu Pro Thr Ser Tyr Gln Leu Val Lys
                1125                1130                1135

Phe Glu Asp Ile Val His Phe Pro Gln Lys Thr Thr Glu Arg Ile Phe
            1140                1145                1150

Ala Phe Leu Gly Ile Pro Leu Ser Pro Ala Ser Leu Asn Gln Ile Leu
        1155                1160                1165

Phe Ala Thr Ser Thr Asn Leu Phe Tyr Leu Pro Tyr Glu Gly Glu Ile
    1170                1175                1180

Ser Pro Thr Asn Thr Asn Val Trp Lys Gln Asn Leu Pro Arg Asp Glu
1185                1190                1195                1200

Ile Lys Leu Ile Glu Asn Ile Cys Trp Thr Leu Met Asp Arg Leu Gly
                1205                1210                1215

Tyr Pro Lys Phe Met Asp
            1220
```

<210> SEQ ID NO 16
<211> LENGTH: 5084
<212> TYPE: DNA
<213> ORGANISM: mouse

<400> SEQUENCE: 16

-continued

```
tctgagaatg acagtacttt atcatcttct tttggggaac atacagaaac ataccattta     60
tgtgtggtaa gttaatcact acagatggtt tcttgtgcta cgtggtcaaa tggcttcatt    120
tgaattttgg aattttaaaa aattttttct ttttcacatg ttaattagat ttacacacag    180
ggagtaaatg ttggatttgt tgtattttct gactagacca ctgttttctg tgcattggag    240
acattggagg cattaatatt ccttgaaatt ttattttatt ggaagcaaac ctgtgccagg    300
gacacagaca tgctatataa tttcctaact tttcttgctt tgaataagct gaatgtcacc    360
tggatttcac agcctatgag gtatagtctg ttttttgttt ttgttttttt gctacatctt    420
taatatataa tttacaataa ccagatggga aacactgtgc ttaacacata tgcctaagga    480
aaagatcttc cccatggatc atggcgttta tgtttacaga acatttacta tttttaacat    540
tgatgatgtg tagtttttct acttgtgaag aatctgtgag caattattct gaatgggcag    600
ttttcacaga cgatatacaa tggcttaagt cacagaaaat acaagatttc aaactcaacc    660
gaagacttca tccaaattta tattttgatg ctggagatat acaaacattg aaacaaaagt    720
ctcgtacaag ccatttgcat atttttagag ctatcaaaag tgcagtgaca attatgctgt    780
ccaatccatc atactaccta cctccaccca agcatgctga gtttgctgcc aagtggaatg    840
aaatttatgg taataatctt cctcctttag cattgtattg tttattatgc ccagaagaca    900
aggttgcctt tgaatttgtt atggaataca tggatcggat ggttagctac aaagactggc    960
tagttgagaa tgcaccaggg gatgaggttc cagttggcca ttctttaaca ggttttgcca   1020
ctgcctttga ctttttatat aatctattag gtaatcagcg taaacaaaaa tacctagaaa   1080
aaatttggat tgttactgag gaaatgtatg aatattccaa gattcgatca tggggcaaac   1140
aacttcttca taaccatcaa gctacaaata tgatagcttt actcataggg gccttggtta   1200
ctggagtaga taaaggatct aaagcaaaca tatggaaaca agttgttgtt gatgtgatgg   1260
aaaagactat gtttctcttg aagcatattg tagatggctc attggatgaa ggtgtggcct   1320
atggaagcta tacctcaaaa tcagttacac agtatgtttt tttggcacaa cgccatttta   1380
acatcaacaa ctttgataat aactggctaa aaatgcattt ttggttttat tatgctacac   1440
ttttgccagg ctatcaaaga actgtaggca tagcagattc caattataat tggttttatg   1500
gtccagagag ccagctagtt ttcttggata agttcatttt acagaatgga gctggaaatt   1560
ggttagctca gcaaattaga aagcatcgac ctaaggatgg accaatggtt ccttccactg   1620
ctcagcggtg gagtactctt catactgaat acatctggta tgatccaaca ctcaccccac   1680
agcctcctgt tgattttggc actgcaaaaa tgcacacatt tcctaactgg ggtgtcgtga   1740
cttatggggg tgggctgcca aacacccaga ccaatacctt tgtgtctttt aaatctggga   1800
aactgggagg acgagctgtg tatgacatag ttcactttca gccatattcc tggattgatg   1860
gatggagaag ctttaaccca ggacatgaac atccagatca aaattcattt actttcgctc   1920
ctaatgggca ggtattcgtt tctgaggctc tttatggacc aaaattgagc caccttaaca   1980
acgtattggt gtttgcccca tcaccatcaa gtcaatgtaa tcagccctgg gaaggtcaac   2040
tgggagaatg tgcacagtgg ctcaagtgga ctggggaaga ggttggtgat gcagctgggg   2100
aagttattac tgctgctcaa catggtgata ggatgtttgt gagtggggaa gcagtgtctg   2160
cttattcttc tgccatgaga ctgaaaagtg tctatcgtgc tttacttctt ttaaattcac   2220
aaactctgct tgttgtcgat catattgaaa ggcaagaaac ttccccaata aattctgtca   2280
gtgccttctt tcataatttg gatattgatt ttaaatacat cccatacaag tttatgaata   2340
gatataatgg tgccatgatg gatgtgtggg atgcacacta taaaatgttt tggtttgatc   2400
```

-continued

```
accatggcaa cagtcctgtg gctaatatac aggaagcaga acaggctgct gaatttaaga   2460
aacggtggac acagtttgtt aatgttacat ttcatatgga atccacaatc acaagaattg   2520
cttatgtatt ttatgggcca tatgtcaatg tttccagctg cagatttatt gatagttcca   2580
gttctggact tcagatttct ttacatgtca acagtactga acatagtgtg tctgttgtaa   2640
ctgactatca aaaccttaaa agcagattca gttacctggg atttggtggt tttgccagtg   2700
tggctaatca aggacagata accagatttg gtttgggtac tcaagaaata gtaaaccctg   2760
taagacatga taaagttaat ttcccctttg ggtttaaatt taatatagca gttggattca   2820
ttttgtgtat tagtttggtt attttaactt ttcaatggcg gttttacctt tcctttagaa   2880
agctaatgcg ctgtgtatta atacttgtta ttgccttgtg gtttattgag cttctggatg   2940
tatggagtac atgcactcag cccatctgtg caaaatggac aaggactgaa gctaaggcaa   3000
atgagaaggt catgatttct gaagggcatc atgtggatct tcctaatgtt attattacct   3060
cactccctgg ttcaggagct gaaattctca aacagctttt tttcaacagc agtgattttc   3120
tctacatcag aattcctaca gcctacatgg atatccctga aactgaattt gaaattgact   3180
catttgtaga tgcttgtgag tggaaagtat cagatatccg cagtgggcac tttcatcttc   3240
ttcgagggtg gctgcagtct ttggtccagg atacaaaact tcacttgcaa aacatccatc   3300
tacatgaaac cagtaggagt aaactggccc aatattttac aactaataag gacaaaaagc   3360
gaaaattaaa aagaagggag tctttgcaag atcaaagaag tagaataaaa ggaccatttg   3420
atagagatgc tgaatatatt agggctttaa gaagacacct tgtttattac ccaagtgcac   3480
gtcctgtgct cagcttaagt agtggtagct ggacattgaa gcttcatttt tttcaggaag   3540
ttttaggaac ttcaatgcgg gcattgtaca tagtaagaga ccctcgagct tggatctatt   3600
cagtgctata tggtagtaaa ccaagtcttt attctttgaa gaatgtacca gagcacttag   3660
caaaattgtt taaaatagag gaaggtaaaa gcaaatgtaa ttcgaattct ggctatgctt   3720
ttgagtatga atcactgaag aaagaattag aaatatccca atcaaatgct atctccttat   3780
tatctcattt gtgggtagca aacactgcag cagccttgag aataaataca gatttgctgc   3840
ctaccaatta ccatctggtc aagtttgaag atattgttca ttttcctcag aagactactg   3900
aaaggatttt tgctttcctt ggcattcctt tgtctcctgc tagtttaaac caaatgctat   3960
ttgccacttc cacaaacctt ttttatcttc catatgaggg ggaaatatca ccatctaata   4020
ctaatatttg gaaaacaaac ttgcctagag atgaaattaa actaattgaa aacatttgct   4080
ggacactgat ggatcatcta ggatatccaa agtttatgga ctaaatgctg caggtcggca   4140
aaatttgcac taatgtgtcc caacctactt tgtggatatg aactagaaaa ctttgtttat   4200
tcttgtacat gtatgtatgt gtgtagagtg agtgcgtgtg tccagtatgt tatttgcaca   4260
gagatatttt caaaataggc accatatttg gcctagcagg atttattttt atgttaccac   4320
ttttcttgcc tttgtttctg aatttttttc tgctaaaatg tttctgctac agaggtatat   4380
attctggggt tctgaaatat ggggttttaa tggactttaa ctcaacttct ttggaaacta   4440
tttatctatc ttaggacctc aaacactaca aacggccttg caattgctgc tgtatctagt   4500
catctctcgc tcttaatatg gactacaaaa ctttatgttt tgaaaacgtc taacatttac   4560
cttgcacaca aaaacgagaa ataaaaaaac aaaaattatt ttacgttgta tagtgtttat   4620
tgaaatcact tggtgaggct gggggagga gcttatgata aagttccctt aagaaactag   4680
aaaataaaga tgaaaacata gaattaaggt ttttttgttt ctttcttcct ttttttttt   4740
```

-continued

```
tttttgtact aagaaataag attgaacagt ggatactgaa atttggtgaa ttattttgga   4800

agtgattctc tcatttgtct ttctgaagct acagctgttc atcatcacac taccccttacc   4860

ctgtctatcc attctgtcat tgtcaccaaa aaaaaaaagt cagtaattac tagctacaaa   4920

actatctaac aagcccttct ctggatgatt tactttgtgt taaagactta cacagattta   4980

taatcacatt tagttgtgtg gcattaccac aatatgactc aaagcaaaag cagacttctg   5040

tctgttgtag tgtttttaag tgtgtgttgt ggggtggggg aggg                    5084


<210> SEQ ID NO 17
<211> LENGTH: 1207
<212> TYPE: PRT
<213> ORGANISM: mouse

<400> SEQUENCE: 17

Met Ala Phe Met Phe Thr Glu His Leu Leu Phe Leu Thr Leu Met Met
 1               5                  10                  15

Cys Ser Phe Ser Thr Cys Glu Glu Ser Val Ser Asn Tyr Ser Glu Trp
            20                  25                  30

Ala Val Phe Thr Asp Asp Ile Gln Trp Leu Lys Ser Gln Lys Ile Gln
        35                  40                  45

Asp Phe Lys Leu Asn Arg Arg Leu His Pro Asn Leu Tyr Phe Asp Ala
    50                  55                  60

Gly Asp Ile Gln Thr Leu Lys Gln Lys Ser Arg Thr Ser His Leu His
65                  70                  75                  80

Ile Phe Arg Ala Ile Lys Ser Ala Val Thr Ile Met Leu Ser Asn Pro
                85                  90                  95

Ser Tyr Tyr Leu Pro Pro Pro Lys His Ala Glu Phe Ala Ala Lys Trp
            100                 105                 110

Asn Glu Ile Tyr Gly Asn Asn Leu Pro Pro Leu Ala Leu Tyr Cys Leu
        115                 120                 125

Leu Cys Pro Glu Asp Lys Val Ala Phe Glu Phe Val Met Glu Tyr Met
    130                 135                 140

Asp Arg Met Val Ser Tyr Lys Asp Trp Leu Val Glu Asn Ala Pro Gly
145                 150                 155                 160

Asp Glu Val Pro Val Gly His Ser Leu Thr Gly Phe Ala Thr Ala Phe
                165                 170                 175

Asp Phe Leu Tyr Asn Leu Leu Gly Asn Gln Arg Lys Gln Lys Tyr Leu
            180                 185                 190

Glu Lys Ile Trp Ile Val Thr Glu Glu Met Tyr Glu Tyr Ser Lys Ile
        195                 200                 205

Arg Ser Trp Gly Lys Gln Leu Leu His Asn His Gln Ala Thr Asn Met
    210                 215                 220

Ile Ala Leu Leu Ile Gly Ala Leu Val Thr Gly Val Asp Lys Gly Ser
225                 230                 235                 240

Lys Ala Asn Ile Trp Lys Gln Val Val Val Asp Val Met Glu Lys Thr
                245                 250                 255

Met Phe Leu Leu Lys His Ile Val Asp Gly Ser Leu Asp Glu Gly Val
            260                 265                 270

Ala Tyr Gly Ser Tyr Thr Ser Lys Ser Val Thr Gln Tyr Val Phe Leu
        275                 280                 285

Ala Gln Arg His Phe Asn Ile Asn Asn Phe Asp Asn Asn Trp Leu Lys
    290                 295                 300

Met His Phe Trp Phe Tyr Tyr Ala Thr Leu Leu Pro Gly Tyr Gln Arg
305                 310                 315                 320
```

-continued

```
Thr Val Gly Ile Ala Asp Ser Asn Tyr Asn Trp Phe Tyr Gly Pro Glu
                325                 330                 335

Ser Gln Leu Val Phe Leu Asp Lys Phe Ile Leu Gln Asn Gly Ala Gly
            340                 345                 350

Asn Trp Leu Ala Gln Gln Ile Arg Lys His Arg Pro Lys Asp Gly Pro
        355                 360                 365

Met Val Pro Ser Thr Ala Gln Arg Trp Ser Thr Leu His Thr Glu Tyr
    370                 375                 380

Ile Trp Tyr Asp Pro Thr Leu Thr Pro Gln Pro Pro Val Asp Phe Gly
385                 390                 395                 400

Thr Ala Lys Met His Thr Phe Pro Asn Trp Gly Val Val Thr Tyr Gly
                405                 410                 415

Gly Gly Leu Pro Asn Thr Gln Thr Asn Thr Phe Val Ser Phe Lys Ser
            420                 425                 430

Gly Lys Leu Gly Gly Arg Ala Val Tyr Asp Ile Val His Phe Gln Pro
        435                 440                 445

Tyr Ser Trp Ile Asp Gly Trp Arg Ser Phe Asn Pro Gly His Glu His
    450                 455                 460

Pro Asp Gln Asn Ser Phe Thr Phe Ala Pro Asn Gly Gln Val Phe Val
465                 470                 475                 480

Ser Glu Ala Leu Tyr Gly Pro Lys Leu Ser His Leu Asn Asn Val Leu
                485                 490                 495

Val Phe Ala Pro Ser Pro Ser Ser Gln Cys Asn Gln Pro Trp Glu Gly
            500                 505                 510

Gln Leu Gly Glu Cys Ala Gln Trp Leu Lys Trp Thr Gly Glu Glu Val
        515                 520                 525

Gly Asp Ala Ala Gly Glu Val Ile Thr Ala Ala Gln His Gly Asp Arg
    530                 535                 540

Met Phe Val Ser Gly Glu Ala Val Ser Ala Tyr Ser Ser Ala Met Arg
545                 550                 555                 560

Leu Lys Ser Val Tyr Arg Ala Leu Leu Leu Leu Asn Ser Gln Thr Leu
                565                 570                 575

Leu Val Val Asp His Ile Glu Arg Gln Glu Thr Ser Pro Ile Asn Ser
            580                 585                 590

Val Ser Ala Phe Phe His Asn Leu Asp Ile Asp Phe Lys Tyr Ile Pro
        595                 600                 605

Tyr Lys Phe Met Asn Arg Tyr Asn Gly Ala Met Met Asp Val Trp Asp
    610                 615                 620

Ala His Tyr Lys Met Phe Trp Phe Asp His His Gly Asn Ser Pro Val
625                 630                 635                 640

Ala Asn Ile Gln Glu Ala Glu Gln Ala Ala Glu Phe Lys Lys Arg Trp
                645                 650                 655

Thr Gln Phe Val Asn Val Thr Phe His Met Glu Ser Thr Ile Thr Arg
            660                 665                 670

Ile Ala Tyr Val Phe Tyr Gly Pro Tyr Val Asn Val Ser Ser Cys Arg
        675                 680                 685

Phe Ile Asp Ser Ser Ser Ser Gly Leu Gln Ile Ser Leu His Val Asn
    690                 695                 700

Ser Thr Glu His Ser Val Ser Val Val Thr Asp Tyr Gln Asn Leu Lys
705                 710                 715                 720

Ser Arg Phe Ser Tyr Leu Gly Phe Gly Gly Phe Ala Ser Val Ala Asn
                725                 730                 735
```

-continued

```
Gln Gly Gln Ile Thr Arg Phe Gly Leu Gly Thr Gln Glu Ile Val Asn
            740                 745                 750

Pro Val Arg His Asp Lys Val Asn Phe Pro Phe Gly Phe Lys Phe Asn
        755                 760                 765

Ile Ala Val Gly Phe Ile Leu Cys Ile Ser Leu Val Ile Leu Thr Phe
    770                 775                 780

Gln Trp Arg Phe Tyr Leu Ser Phe Arg Lys Leu Met Arg Cys Val Leu
785                 790                 795                 800

Ile Leu Val Ile Ala Leu Trp Phe Ile Glu Leu Leu Asp Val Trp Ser
                805                 810                 815

Thr Cys Thr Gln Pro Ile Cys Ala Lys Trp Thr Arg Thr Glu Ala Lys
            820                 825                 830

Ala Asn Glu Lys Val Met Ile Ser Glu Gly His His Val Asp Leu Pro
        835                 840                 845

Asn Val Ile Ile Thr Ser Leu Pro Gly Ser Gly Ala Glu Ile Leu Lys
    850                 855                 860

Gln Leu Phe Phe Asn Ser Ser Asp Phe Leu Tyr Ile Arg Ile Pro Thr
865                 870                 875                 880

Ala Tyr Met Asp Ile Pro Glu Thr Glu Phe Glu Ile Asp Ser Phe Val
                885                 890                 895

Asp Ala Cys Glu Trp Lys Val Ser Asp Ile Arg Ser Gly His Phe His
            900                 905                 910

Leu Leu Arg Gly Trp Leu Gln Ser Leu Val Gln Asp Thr Lys Leu His
        915                 920                 925

Leu Gln Asn Ile His Leu His Glu Thr Ser Arg Ser Lys Leu Ala Gln
    930                 935                 940

Tyr Phe Thr Thr Asn Lys Asp Lys Lys Arg Lys Leu Lys Arg Arg Glu
945                 950                 955                 960

Ser Leu Gln Asp Gln Arg Ser Arg Ile Lys Gly Pro Phe Asp Arg Asp
                965                 970                 975

Ala Glu Tyr Ile Arg Ala Leu Arg Arg His Leu Val Tyr Tyr Pro Ser
            980                 985                 990

Ala Arg Pro Val Leu Ser Leu Ser Ser Gly Ser Trp Thr Leu Lys Leu
        995                 1000                1005

His Phe Phe Gln Glu Val Leu Gly Thr Ser Met Arg Ala Leu Tyr Ile
    1010                1015                1020

Val Arg Asp Pro Arg Ala Trp Ile Tyr Ser Val Leu Tyr Gly Ser Lys
1025                1030                1035                1040

Pro Ser Leu Tyr Ser Leu Lys Asn Val Pro Glu His Leu Ala Lys Leu
                1045                1050                1055

Phe Lys Ile Glu Glu Gly Lys Ser Lys Cys Asn Ser Asn Ser Gly Tyr
            1060                1065                1070

Ala Phe Glu Tyr Glu Ser Leu Lys Lys Glu Leu Glu Ile Ser Gln Ser
        1075                1080                1085

Asn Ala Ile Ser Leu Leu Ser His Leu Trp Val Ala Asn Thr Ala Ala
    1090                1095                1100

Ala Leu Arg Ile Asn Thr Asp Leu Leu Pro Thr Asn Tyr His Leu Val
1105                1110                1115                1120

Lys Phe Glu Asp Ile Val His Phe Pro Gln Lys Thr Thr Glu Arg Ile
                1125                1130                1135

Phe Ala Phe Leu Gly Ile Pro Leu Ser Pro Ala Ser Leu Asn Gln Met
            1140                1145                1150

Leu Phe Ala Thr Ser Thr Asn Leu Phe Tyr Leu Pro Tyr Glu Gly Glu
```

-continued

```
        1155                1160                1165

Ile Ser Pro Ser Asn Thr Asn Ile Trp Lys Thr Asn Leu Pro Arg Asp
    1170                1175                1180

Glu Ile Lys Leu Ile Glu Asn Ile Cys Trp Thr Leu Met Asp His Leu
1185                1190                1195                1200

Gly Tyr Pro Lys Phe Met Asp
                1205
```

<210> SEQ ID NO 18
<211> LENGTH: 3733
<212> TYPE: DNA
<213> ORGANISM: homo sapiens

<400> SEQUENCE: 18

```
atgcctaagg gaggagctcc cccatggatc atggcgttaa tgtttacagg acatttacta     60

ttcttagcat tattgatgtt tgctttctct acttttgagg aatctgtgag caattattcc    120

gaatgggcag ttttcacaga tgatatagat cagtttaaaa cacagaaagt gcaagatttc    180

agacccaacc aaaagctgaa gaaaagtatg cttcatccaa gtttatattt tgatgctgga    240

gaaatccaag caatgagaca aaagtctcgt gcaagccatt tgcatctttt tagagctatc    300

agaagtgcag tgacagttat gctgtccaac ccaacatact acctacctcc accaaagcat    360

gctgattttg ctgccaagtg gaatgaaatt tatggtaaca atctgcctcc tttagcattg    420

tactgtttgt tatgcccaga agacaaagtt gcctttgaat ttgtcttgga atatatggac    480

aggatggttg gctacaaaga ctggctagta gagaatgcac caggagatga ggttccaatt    540

ggccattcct taacaggttt tgccactgcc tttgactttt tatataactt attagataat    600

catcgaagac aaaaatacct ggaaaaaata tgggttatta ctgaggaaat gtacgagtat    660

tccaaggtcc gctcatgggg caaacagctt ctccataacc accaagccac taatatgata    720

gcattactca caggggcctt ggtgactgga gtagataaag gatctaaagc aaatatatgg    780

aaacaggctg tagtggatgt catggaaaag acaatgtttc tattgaatca tattgttgat    840

ggttctttgg atgaaggtgt ggcctatgga agctacacag ctaaatccgt cacacagtat    900

gtttttctgg cccagcgcca ttttaatatc aacaacttgg ataataactg gttaaagatg    960

cacttttggt tctattatgc cacccttta cctggcttcc aaagaactgt gggtatagca   1020

gattccaatt ataattggtt ttatggtcca gaaagccagc tagttttctt ggataagttc   1080

atcttaaaga atggagctgg aaattggtta gctcagcaaa ttagaaagca ccgacctaaa   1140

gatggaccga tggttccttc aactgcccaa aggtggagta ctcttcacac tgaatacatc   1200

tggtatgatc cccagctcac accacagcca cctgctgatt atggtactgc aaaaatacac   1260

acattcccta actggggtgt ggttacttat ggggctgggt tgccaaacac acagaccaac   1320

acctttgtgt cttttaaatc tgggaagctg gggggacgag ctgtgtatga catagttcat   1380

tttcagccat attcctggat tgatgggtgg agaagtttta acccaggaca tgagcatcca   1440

gatcagaact catttacttt tgcccccaat ggacaagtat ttgtttctga agctctctat   1500

ggacccaagt tgagccacct taacaatgta ttggtgtttg ctccatcacc ctcaagccag   1560

tgtaataagc cctgggaagg tcaactggga gaatgtgcgc agtggcttaa gtggactggc   1620

gaggaggttg gtgatgcagc tggggaaata atcactgcct ctcaacatgg ggaaatggta   1680

tttgtgagtg gggaagccgt gtctgcttat tcttcagcaa tgagactgaa aagtgtatat   1740

cgtgctttgc ttctcttaaa ttcccaaact ctgctagttg ttgatcatat tgagaggcaa   1800
```

-continued gaagattccc caataaattc tgtcagtgcc ttctttcata atttggatat tgattttaaa 1860
tatatcccat ataagtttat gaataggtat aatggtgcca tgatggatgt gtgggatgca 1920
cattacaaaa tgttttggtt tgatcatcat ggcaatagtc ccatggccag tatacaggaa 1980
gcagagcaag ctgctgaatt taaaaaacga tggactcaat ttgttaatgt tacttttcag 2040
atggaatcca caatcacaag aattgcatat gtcttttatg ggccatatat caatgtctcc 2100
agctgcagat ttattgatag ttccaatcct ggacttcaga tttctctcaa tgtcaataat 2160
actgaacatg ttgtttctat tgtaactgat taccataacc tgaagacaag attcaattat 2220
ctgggattcg gtggctttgc cagtgtggct gatcaaggcc aaataacccg atttggtttg 2280
ggcactcaag caatagtaaa gcctgtaaga catgatagga ttattttccc ctttggattt 2340
aaatttaata tagcagttgg attaattttg tgcattagct tggtgatttt aactttccaa 2400
tggcgttttt acctttcttt tagaaaacta atgcgatgga tattaatact tgttattgcc 2460
ttgtggttta ttgagctttt ggatgtgtgg agcacttgta gtcagcccat ttgtgcaaaa 2520
tggacaagga cagaggctga gggaagcaag aagtctttgt cttctgaagg gcaccacatg 2580
gatcttcctg atgttgtcat tacctcactt cctggttcag gagctgaaat tctcaaacaa 2640
ctttttttca acagtagtga ttttctctac atcagggttc ctacagccta cattgatatt 2700
cctgaaactg agttggaaat cgactcattt gtagatgctt gtgaatggaa ggtgtcagat 2760
atccgcagtg ggcattttcg tttactccga ggctggttgc agtctttagt ccaggacaca 2820
aaattacatt tgcaaaacat ccatctgcat gaacccaata ggggtaaact ggcccaatat 2880
tttgcaatga ataaggacaa aaaaagaaaa tttaaaagga gagagtcttt gccagaacaa 2940
agaagtcaaa tgaaaggcgc ctttgataga gatgctgaat atattagggc tttgaggaga 3000
cacctggttt actatccaag tgcacgtcct gtgctcagtt taagcagtgg aagctggacg 3060
ttaaagcttc atttttttca ggaagtttta ggagcttcga tgagggcatt gtacatagta 3120
agagaccctc gggcatggat ttattcaatg ttgtacaata gtaaaccaag tctttattct 3180
ttgaagaatg taccagagca tttagcaaaa ttgtttaaaa tagagggagg taaaggcaaa 3240
tgtaacttaa attcgggtta tgctttcgag tatgaaccat tgaggaaaga attatcaaaa 3300
tccaaatcaa atgcagtgtc cctcttgtct cacttgtggc tagcaaatac agcagcagcc 3360
ttgagaataa atacagattt gctgcctact agctaccagc tggtcaagtt tgaagatatt 3420
gtgcattttc ctcagaaaac tactgaaagg atttttgcct ttcttggaat tcctttgtct 3480
cctgctagtt taaaccaaat attgtttgcc acctctacaa accttttta ccttccctat 3540 gaaggggaaa tatcaccaac taatactaat gtttggaaac agaacttgcc tagagatgaa 3600
attaaactaa ttgaaaacat ctgctggact ctgatggatc gcctaggata tccaaagttt 3660
atggactaaa tgctgcaggt cagcagaaat ttgcactaat aatacttacc aacccaaaaa 3720
aaaaaaaaaa aaa 3733

<210> SEQ ID NO 19
<211> LENGTH: 4121
<212> TYPE: DNA
<213> ORGANISM: mouse

<400> SEQUENCE: 19
atggcgttta tgtttacaga acatttacta tttttaacat tgatgatgtg tagtttttct 60
acttgtgaag aatctgtgag caattattct gaatgggcag ttttcacaga cgatatacaa 120
tggcttaagt cacagaaaat acaagatttc aaactcaacc gaagacttca tccaaattta 180

-continued

```
tattttgatg ctggagatat acaaacattg aaacaaaagt ctcgtacaag ccatttgcat    240
atttttagag ctatcaaaag tgcagtgaca attatgctgt ccaatccatc atactaccta    300
cctccaccca agcatgctga gtttgctgcc aagtggaatg aaatttatgg taataatctt    360
cctcctttag cattgtattg tttattatgc ccagaagaca aggttgcctt tgaatttgtt    420
atggaataca tggatcggat ggttagctac aaagactggc tagttgagaa tgcaccaggg    480
gatgaggttc cagttggcca ttctttaaca ggttttgcca ctgcctttga ctttttatat    540
aatctattag gtaatcagcg taaacaaaaa tacctagaaa aaatttggat tgttactgag    600
gaaatgtatg aatattccaa gattcgatca tggggcaaac aacttcttca taaccatcaa    660
gctacaaata tgatagcttt actcataggg gccttggtta ctggagtaga taaaggatct    720
aaagcaaaca tatggaaaca agttgttgtt gatgtgatgg aaaagactat gtttctcttg    780
aagcatattg tagatggctc attggatgaa ggtgtggcct atggaagcta tacctcaaaa    840
tcagttacac agtatgtttt tttggcacaa cgccatttta acatcaacaa ctttgataat    900
aactggctaa aaatgcattt ttggttttat tatgctacac ttttgccagg ctatcaaaga    960
actgtaggca tagcagattc caattataat tggttttatg gtccagagag ccagctagtt   1020
ttcttggata agttcatttt acagaatgga gctggaaatt ggttagctca gcaaattaga   1080
aagcatcgac ctaaggatgg accaatggtt ccttccactg ctcagcggtg gagtactctt   1140
catactgaat acatctggta tgatccaaca ctcaccccac agcctcctgt tgattttggc   1200
actgcaaaaa tgcacacatt tcctaactgg ggtgtcgtga cttatggggg tgggctgcca   1260
aacacccaga ccaatacctt tgtgtctttt aaatctggga aactgggagg acgagctgtg   1320
tatgacatag ttcactttca gccatattcc tggattgatg gatggagaag ctttaaccca   1380
ggacatgaac atccagatca aaattcattt actttcgctc ctaatgggca ggtattcgtt   1440
tctgaggctc tttatggacc aaaattgagc caccttaaca acgtattggt gtttgcccca   1500
tcaccatcaa gtcaatgtaa tcagccctgg gaaggtcaac tgggagaatg tgcacagtgg   1560
ctcaagtgga ctggggaaga ggttggtgat gcagctgggg aagttattac tgctgctcaa   1620
catggtgata ggatgtttgt gagtggggaa gcagtgtctg cttattcttc tgccatgaga   1680
ctgaaaagtg tctatcgtgc tttacttctt ttaaattcac aaactctgct tgttgtcgat   1740
catattgaaa ggcaagaaac ttccccaata aattctgtca gtgccttctt tcataatttg   1800
gatattgatt ttaaatacat cccatacaag tttatgaata gatataatgg tgccatgatg   1860
gatgtgtggg atgcacacta taaaatgttt tggtttgatc accatggcaa cagtcctgtg   1920
gctaatatac aggaagcaga acaggctgct gaatttaaga aacggtggac acagtttgtt   1980
aatgttacat ttcatatgga atccacaatc acaagaattg cttatgtatt tttatgggcca  2040
tatgtcaatg tttccagctg cagatttatt gatagttcca gttctggact tcagatttct   2100
ttacatgtca acagtactga acatagtgtg tctgttgtaa ctgactatca aaaccttaaa   2160
agcagattca gttacctggg atttggtggt tttgccagtg tggctaatca aggacagata   2220
accagatttg gtttgggtac tcaagaaata gtaaaccctg taagacatga taaagttaat   2280
ttcccctttg ggtttaaatt taatatagca gttggattca ttttgtgtat tagtttggtt   2340
attttaactt ttcaatggcg gttttacctt tcctttagaa agctaatgcg ctgtgtatta   2400
atacttgtta ttgccttgtg gtttattgag cttctggatg tatggagtac atgcactcag   2460
cccatctgtg caaaatggac aaggactgaa gctaaggcaa atgagaaggt catgatttct   2520
```

-continued

```
gaagggcatc atgtggatct tcctaatgtt attattacct cactccctgg ttcaggagct   2580
gaaattctca aacagctttt tttcaacagc agtgattttc tctacatcag aattcctaca   2640
gcctacatgg atatccctga aactgaattt gaaattgact catttgtaga tgcttgtgag   2700
tggaaagtat cagatatccg cagtgggcac tttcatcttc ttcgagggtg gctgcagtct   2760
ttggtccagg atacaaaact tcacttgcaa aacatccatc tacatgaaac cagtaggagt   2820
aaactggccc aatattttac aactaataag gacaaaaagc gaaaattaaa aagaagggag   2880
tctttgcaag atcaaagaag tagaataaaa ggaccatttg atagagatgc tgaatatatt   2940
agggctttaa gaagacacct tgtttattac ccaagtgcac gtcctgtgct cagcttaagt   3000
agtggtagct ggacattgaa gcttcatttt tttcaggaag ttttaggaac ttcaatgcgg   3060
gcattgtaca tagtaagaga ccctcgagct tggatctatt cagtgctata tggtagtaaa   3120
ccaagtcttt attctttgaa gaatgtacca gagcacttag caaaattgtt taaaatagag   3180
gaaggtaaaa gcaaatgtaa ttcgaattct ggctatgctt ttgagtatga atcactgaag   3240
aaagaattag aaatatccca atcaaatgct atctccttat tatctcattt gtgggtagca   3300
aacactgcag cagccttgag aataaataca gatttgctgc ctaccaatta ccatctggtc   3360
aagtttgaag atattgttca ttttcctcag aagactactg aaaggatttt tgctttcctt   3420
ggcattcctt tgtctcctgc tagtttaaac caaatgctat ttgccacttc cacaaacctt   3480
ttttatcttc catatgaggg ggaaatatca ccatctaata ctaatatttg gaaaacaaac   3540
ttgcctagag atgaaattaa actaattgaa aacatttgct ggacactgat ggatcatcta   3600
ggatatccaa agtttatgga ctaaatgctg caggtcggca aaatttgcac taatgtgtcc   3660
caacctactt tgtggatatg aactagaaaa ctttgtttat tcttgtacat gtatgtatgt   3720
gtgtagagtg agtgcgtgtg tccagtatgt tatttgcaca gagatatttt caaaataggc   3780
accatatttg gcctagcagg atttattttt atgttaccac ttttcttgcc tttgtttctg   3840
aatttttttc tgctaaaatg tttctgctac agaggtatat attctggggt tctgaaatat   3900
ggggttttaa tggactttaa ctcaacttct ttggaaacta tttatctatc ttaggacctc   3960
aaacactaca aacggccttg caattgctgc tgtatctagt catctctcgc tcttaatatg   4020
gactacaaaa ctttatgttt tgaaaacgtc taacatttac cttgcacaca aaaacgagaa   4080
ataaaaaacc aaaaattaaa aaaaaaaaaa aaaaaaaaaa a                      4121
```

<210> SEQ ID NO 20
<211> LENGTH: 27150
<212> TYPE: DNA
<213> ORGANISM: human genomic clone
<220> FEATURE:
<221> NAME/KEY: misc_feature
<222> LOCATION: (1)...(27150)
<223> OTHER INFORMATION: n = A,T,C or G

<400> SEQUENCE: 20

```
gttggatact aatggtacaa tgtgttactg tgacagttag tattaggtgt caacctgact     60
agactgaggg attcctagat ggctgatgaa gcgttgttcc tgggtgtgtc tgtgagggtg    120
ttggcagagg agactggcat ttgaggcagt ggactgggag aggaaaaccc accttcaatg    180
tgggggtgga caacatctaa taggctgcca gcaaggctag aagaaagcag gcagcagaac    240
tgggatagac aggttgcttg ctgagttggc ttgctctctt tcttttcctg ctgtgccaca    300
tacttggctt cctctcctcc tgacctcgga catcagactc caggttcttt agcatttgga    360
cttgaaccag cagcatgtca ggggttctcg ggccttcagt ctcagactga atgctgcact    420
```

-continued

```
gttggcttcc ctggtttcga ggcttttgga attggactga gcagtgctac cagcttctct    480
ttccccagct ggcagatgac ctactctgga acttcccctt gtaatcctat aaaccaattc    540
tccctaacaa ccttatctta ttggttttgt ccctttggag aaccctgact aatacagtta    600
gtattaaaat aaaatttaca aacatgcaaa atcatacagt atgttgatga agatagagct    660
atatatagtg gagctataaa gaagaacaag gaaatgataa acacaaaatc caggacagaa    720
gttacctctg ggatggttgg tgggagcaga caatgtgaaa atggaaggtc agatggaggg    780
cttaactact aatattaact gcatatttct tacagtggtt ggtgtgtaca ctcatgtcca    840
ttttattact atctttcata ttacatatgt ttcataacat tttgtagaat gtgtgagtat    900
atgaattcta aatctaaatc ccagttgtgg ccacaacaac gtatcaatac catagggag    960
ggcttccaaa ttcccagcta gggtcaatgc atttttttca ttgtcaacat attagtgcaa   1020
tctattttgc atatccaaat acctacagtt caacagagag gggcaataaa gctcgtatat   1080
aaaagaatca acacaatagt ggtatataac tgcctagaga caactaatgc aaggatgtgg   1140
gaacaatatc caataataaa caatcacaca caagggctga ctcgctattg agggtatgtg   1200
ccccactagc atagtactat gacactcagt cctacttcag aggtgcacac tctcctactc   1260
tcctcactga aaggtggagt ttctgactgg agcctctgga atttgctcct tggtcccaac   1320
atacaagcca tgaaaaagaa agcatccaaa cctacaaagc accaaccaaa agatgagata   1380
ctgtagaatt ttattgctac ccaaaaaata tgtgtgaata gcctgtgaat taacagaaaa   1440
gttcattcta ggtacttaat agttttatat tgatataatc ctctgttatg tatggtgtta   1500
aggtaatata tacatataca tttatatgta atttgaatac acttcctcca actggtttcc   1560
atttattcta tcatagtcag tggagtaaat gtaatttcta aaacaagctg agtttatgta   1620
tacttaactg gaaaaaattg aaatggaaaa aatacaataa tgtagacaat cacaaatata   1680
tgcctatcaa atgaaggtac gaatgcagtt atgcttaatg ttatgcaaat ggcacctgtg   1740
gccgggcagg gtggctcgtg cctataatcc tagcacttta ggaggatgac ggggcagatt   1800
acctgaggtc aggagtttga gaccagtctg gccaatatgg caaaaccctg tctctactaa   1860
aaatacaaaa aaatcagctt gatgtggtgg tgggtgccta taatctcagc tactccagag   1920
gctgaggcac aagaatcgct tgaacccggg aggcggaggt tgcagtgagc caatattgtg   1980
ccacggcact ccagcctggg tgacaggact ctgtctccaa gaagaaaaga aaaaaaaaaa   2040
aagctcttgt gacatggaat aaaactgaat gacaacatca aacttgaatt cagaaatgtt   2100
tgtatctcaa taaatctcag aaataagtat actttggaaa aagacaaaat atggctctgg   2160
aaatgaagat attgaaggtg aagtgaaagg ctgaatcaaa tttgtttact gaaatatgaa   2220
gcttaaaaaa gcagtatttc taaatcatat taatcatttc taaataatat tgtgtaattt   2280
ttattttaca agtttgtgca actcaattaa tacagtaagt actaaaatag gtggctgatt   2340
agtatagata tctacatatc ttaactatat atgtcaaaat tatttgaaaa tatttttaat   2400
attttctcac ttaaaaacag atgcatcata ttttatattg gtttttctct ttgggcatat   2460
actgtaagag aataaaagta aatatacctc tgctgcctct ctctctctct cataattaag   2520
acaagaatat tggagatggt cacaaagagg aaataattac tataattaat ttacatactt   2580
tttgaaaatc cttgcgccaa ctctgaggga gtttactgat agaaaaatga agatttaaaa   2640
ttaagaaact tgcataagac ctcagaacta gtagataccg actaggggat ttgtacttat   2700
ttctaattcc aaagatcatt attaaatata aacttgttgt gtctattaca ttttcaacgg   2760
```

-continued

```
caatgtcccc cttcaaatta aggatgaaaa tgggggaaag gtaaaaacaa agcttgtgaa   2820
aaacccacca gtacaacctg ctgcttgcac agagaaaacc ttatgcctct taaggtaatg   2880
aaattttaag tttgtgtgtg tgtatacaag cacgcatctt tttattcatg tgttcaacaa   2940
taggatattt tagatagttt tataattacc gttaggaaac agtcaaagta acaactggat   3000
atgtgtacat ttcagtttac ttcagtaaat ctagagagat aatcagaagt tagttggtgt   3060
acataagcca actgtaagca tgttgtgctc cagttagcac tgaactagcc agggtgccca   3120
gattaatgtt taaaaataac agtaaaaacc ttctgttttg tttatgtggg gttaacttat   3180
agtagctata tcctttgtat gaacttatat tttaatgtgt atcccctcaa agcaatttca   3240
tcatttcttg gttgtattgt ttttatacat ataaatctcc cttcaatgtt aagtgaaata   3300
ttgcattaaa gcatcaaatt aaaatggtcc ataaagttaa actaaccata ttttaaagtt   3360
gcaagcaatg taaacaaatc tagagaaaaa gtaatctttt ggaacagagt gaaggaatga   3420
acatattaaa acaaaaaaaa tcaataaaac ttggcattaa tttttcagta tagtacaagg   3480
gtttggagca ttatttgcat agtgcaatga acaaggtaaa aataaactta ttgttcatca   3540
aggggtgtca gattttaatg caaggattga aaagtttatg tttctcattt agcaaatgag   3600
agaagtgcca gtaataggag ccaaattgac ttccaaaaag agaaacaagg agcattaaag   3660
atgttgcatg accatgaata tttccctctt taaaccataa agaataatgt atgtatcccg   3720
aggtcagaaa cagagcaaaa cacaatatat gagaggacac tggcttatct aggacagttg   3780
aaaacctgag acattaggtg aaattcaaca tcagtgttaa tacagttgaa agaaaaatta   3840
cattcaagag tcagcaatac agaaatcgtt taaagaaata gtataaaata ggaagaacaa   3900
ttgccatgta ctgtgaaaca gtatcggctt agattataat ttatctttct gtcctaccaa   3960
gtatcatctt ccctaatatt tcagtctttt aaatagttga tacaataatt aacacaccat   4020
tgttattgga atgattctcc ttgagtactt tatttgctgt gttcagattt agggtttctc   4080
ctttcttccc atttcactcc tttcctccct cctttgtttc ctttcttctg tcattattta   4140
gaagacaggg aaaagaacaa cagagtgttg tttttcccct aaaacaaact ctatttgaat   4200
gtatttgatc aactgttagt cacagaattc acagcattcg cttctacttg gtatagcctc   4260
ctttatgctg ggaaatttgt gaaaagtgga aaaagaatgt ttctttttag ttccctctaa   4320
gctgtcagct tcatggaggt agagcccatg tatactttgt tcaccgttgc attcccagga   4380
ttgagagctg tgcctggcac tttggatctg gaggtctcag gagggggag agaaagaaaa   4440
gaaaagcctg acggagcctg aatcaaatac actgagttgt ccatcttact gccattacta   4500
gcaatggtct acacacaggc cagtcagacc acactcaggc ctttttttc tctctctctc   4560
tccagggcat tccttgatat tcaaatacag agcaaacttg ggtagttgga gtgaatggga   4620
atggcaagag tgagttccag tggttttatt ctatttgcac ttatggataa cccagaatct   4680
ctcttagaag attgatggga tgtgctgtga gaagtatata gtcaaaacct agtggtgatc   4740
gctactcaaa tttacctatc ataattcccc ctagttaatt gatatgttag aatgttaggg   4800
aaacttacct ctggaagtag cgttatactc ccttctatta aaagaaaaaa agaaaaagaa   4860
aaaaaaagca tcttcaatgt gctaaccttg tgcatcactt tagtgatgta tacctcaagt   4920
aacttgcaag aagtttcttc tttttcctca taaccgtgct gtttcagaaa taaataagcc   4980
atgtctacta tagaacagct accacttctt ggggcttttc cttgggtggt aatcactacc   5040
ttgcatgccc ctcctctcac tctttctctt cctgatgaat tcctaagagt ttcaaagtct   5100
ctagagagat tgccaattcc tcactgagga tattcatagt caattgattt ttatgttctt   5160
```

-continued

```
cctttatgct aatcagtacc ttgacagtag atacattgat tgttcctttt attcaaaagt   5220
acccgttgat tcaaaagtaa caaaagtgtg gtgaataggc aaataaataa tgaattataa   5280
atccattcaa aattccttca aaaaacttta gaactgaaaa aacatgtgcc taaatcttgg   5340
tcaaaccact tatcagctga tttgctttgg acaaatcact tgacatgagt ttcaaacata   5400
tatgtaaaat aactacttga tagagttgtt gtgaggattg taatgataca caaaaacctt   5460
atgattcaat gtgcagcaca tattaagtga ttaattcatg acagatcctt atccaaagta   5520
aaccaattat tgacaattca gtcaacattt aaacaggcag taaacagccc acatattaat   5580
tgtcttgata tcttagaatg ttagggaacc ttacctctgg aagtagtgtt aaatcccttc   5640
tattaaaaaa aaaaaaagcg gcgtgaaccc gggaggcgga gcttgcagtg agccgagatc   5700
ccgccactgc actccagcct gggcgacaga gcgagactcc gtttcaaaaa aaaaaaaaaa   5760
aagcatcttc aatgtgctaa ccttgtacat cactttagtg atgtatacct caagtaactt   5820
gcaagaagtt tcttctttta gtgatatcat gcctgaatga agatcttact agcagcagga   5880
agggcagatg tagaatacag attcttaata caggtacatc cttgccattt agaaagttgc   5940
agtcaggacc tggaattaag ttaggggaac agagactcga gagtcagggg ttgggggagg   6000
tggagaagga ccaagttcag ttgctaaaat tctgggtttg gggatcggta ttcaacttgt   6060
cctgcatttt ccaactgctg gttcctcagc tccatacaaa atcttaatag cattactcaa   6120
agacctaggg aaaaggggta agataaaatt atcccaatca tagacaagtt gcttttagct   6180
ttttattttt gtattaacag gagtcttatt acacataggt ctgataaaac tggtttatga   6240
tcttcagtct gtttccagtg ctgcataact agataacgta tgaaggaaaa acgacgacga   6300
acaaaaaatt aattgcttgg aagacttagt tgaatctatc catgaaaaca gaatcaatta   6360
aacatgtatg tgttacttag actaaatata aataacccat ataaatggta gctcaaacat   6420
ctcaagtgtt tcagagaatg ttagaatcta ttgtttgaag tgtctattgt actctatgca   6480
aaaatccaaa gtcatttgcg tctttaaaaa tgatatggat aatttttctt ccgaaatgaa   6540
gtgaaatcat gattaatcag atatatcaga caatttggtc aacatttaaa taagcagcta   6600
atagcccaca tattaagtgt cttgatatct tagaatgtca ggtacccttg ccaggtgtgg   6660
tggctcatgc ctgtaatccc agcattttgg gaggcccagg tgggcagatc accaggtcaa   6720
gagattgaga ccagcctgac caatgtggtg aaacgctgtc actactaaaa atacaaaaat   6780
gagccaagca tggtggcgtg cacctgtaat cccagctatt caggaggctg acgtaggaga   6840
atcacttgaa cccggtaggc ggaggttgca gtgagccgag atcagaccac tgcactccag   6900
cctgggcaac aaagtgagac tccatcccca aaaaaaaaaa aaaaaaaaaa aagaatgtta   6960
ggtatcctta cctttggaag tggtgttata ctgcattcta tttatgcttt ttcctaaatc   7020
aacaaatgaa aacgtttcta tttctgatca aagttaatca agccaaacaa agcaattcaa   7080
aaattatcat taatatttac tcacttaaaa ttgtgatata ctttgtatac caagaatgcc   7140
aaagatactt ggtgatgtac agaaatcgtt gctgaacaat tatgccaacc aaaagtaagt   7200
ggtggaggag gttcttcttt gaatacattt gcagagggca atgtagcaag acctgggaat   7260
tttgatacaa ggaaggattg tcccattctt gtcaggcatt tattagttat tctctatgta   7320
aaaggacaat caaatgtcta atattttggt gtccacacct aaacgtacat attgttgtgt   7380
catcactttg ttaaaattta aattttaaat taaattctac aaactaaatc tatgcagatt   7440
tagcttcttt ctcctgagca gattttccta tttcctctga gttttcatta aattcaactc   7500
```

-continued

```
tgaatatggc ctttttattt catcttgagt aaatctatgt tgtttgaaaa tttaaaaagc   7560

caattatcat tatatttgtt acttcacttt tgtcagcaaa attaataagt cctttcaaaa   7620

ttttaaaatt tcaatcctat tattataata aaagcaatta tctcaattag gcctatgttt   7680

ggggaagtta atgtagaaaa agacggattt tacagataag aaattttgta agtgtttctt   7740

tcagaagtat cagatagtga taatccctct tttaattatt tcaaagaaca aaaataagag   7800

tagaagctat ttaaaatttt cctagatcac cctaagggtg caggacctgg gaacatgctg   7860

ggagagtcaa tccccttagg aattctgttt ctaaggcagg ggtctcaggc accatcacat   7920

gcatacatac ccaatggatg tgtcacccgc tcacccatac ataacattcc ttacagaaca   7980

atctgtgagt agacgctttc tccagcaaac tttctatttt agaataacta aatagtaggg   8040

ttcatgtcta aaatcttccc ttggggtggg agtaggtgag tacagaaaca agtaaataca   8100

actctgcatt gccatgtggg ggtgaaagct gggatacatt gtaaagatca ttttcgtaag   8160

cctgtacctt tcttttgcta tcaatgacgt gttcccatat tcattctcag tgtaactcat   8220

tttctttttc attttctgta actcttcttt ccctattact ccacatactc catctggcct   8280

tctcctgcca acaggtacat ttcttttttt cttttttttt tttttttttg aggcggagtc   8340

tcgctctgtc gcccaggctg gagtgcagtg gcgcatctcc actcactgca agctctgcct   8400

cccaggttca tgccattctc ctgcctcagc ctcccgtgta gctgggacta caggtgcccg   8460

ccaccacgcc cggctaattt tttgtacttt ttttttagta gagacggggt ttcaccgtgt   8520

tagccaggat ggtcttgatc tcctgacctc gtgatccacc cgcctcggcc tcccgaagtg   8580

ctgggattac aggcgtgagc cactgcaccc ggccgccaac aggtacattt ctgtattgtc   8640

tgtacaatgt taaaataaag ggaacagtag tttctgcttt cttgcttgct acctgcatgc   8700

aattgtaatt cctaccttga tcagatctaa tactactgac aatccagact ttttatatgt   8760

gatctgattc acgatcacat atcctaggaa ttgaaagtaa acactgagat tctgcccaat   8820

aatggaaata gtgttatcaa ccatgtagca tgcaatattc atgtagatat tatccaagta   8880

gcattttata tgcttgccgg taactctgag atagaatgaa taatctttct tgagattact   8940

agtgtagatt caggtcttca gtgccctctc aacctacatt cacatgaatt tcattcattt   9000

tgaaattaca gagggacaat catgagagat atgggaagga atatgttggg gagggggggc   9060

agtctccact cacactataa tggaagaaaa atgacagcca agttaggttt agctggaatc   9120

taacatatac agagctttat cactctggag gcacattttg acataataat aactactgag   9180

aaagaaccac ttttatctag gtcagaatga cagacttcca agtgttagag agcttggggg   9240

aaccacagtt tgaaacatca ggaagaagac tgcaatctgt acagagattt tcatcaagtc   9300

tccacactgc cttatgtttt catccaatac attgtaatta ctccactggc ttataatggc   9360

gtagcatttt gatttcagag cctaccaaaa taaaataaac cacactttat gacgactaca   9420

tttataataa gatgcagatg gtaaaggaaa cagatgcctc tgacatcatc tcccatttgc   9480

tttcaacttt tgcagacact ggcagtctgt aaactcattc aaagggatgc aagataagtc   9540

aggcagtttt ccaattctgt ttccagttta aaaagacact gcagtggcac tactttgagt   9600

cacagagtgt taattccaga aaaataaatt tgattctaag tctgtgtcag tctttaacgc   9660

aaaattaatc aactgggggg aaaatgcccc acaatattga gagttcagcg attagtaact   9720

actgattgtt ttgcttgaca gtgacagaaa ggataggatg ggagtgatgt gatggcgaac   9780

agctgtagct ccagggagga taaaaagtga aaggagagtt ttaaacagac aatcatgtct   9840

aaaataatct accagccctt gccacccaga ttgttcaaag acttattcct tatatttcta   9900
```

-continued

```
agtaaaaaac ttcaaggagg cttttaaagt cagtttccga cctcaaaaaa acatattcat   9960
tctgtatttc catctgtatt tcccagaaga aatcctatag ttctgatagg agctttcacc  10020
atttcctcag tgatatcact gaacattaaa cacagtaaaa gaaattttct ttttctttgt  10080
gcaagataag tgtgtcagaa gaccttttca aaaggataag gaacttttgt agtccatctt  10140
gaaagcaaga gatgcgtggg taaagcagca attgcaaggc ctttagcagt gtttgaggtc  10200
tctagataga ttagcacagt tacagatgaa ggggagttag acaaaaactt aaaattttcc  10260
catctcccct gaccccatga tataacttca tctaccactc tgtagcagaa actttttagc  10320
agacaaaatt ttcagaaaca aaggcaaggg aggtgatgac ataaaaataa atcctgctag  10380
gccaaatatg gtgccatttt ttaaaacaat ctctctgtgc aaacaacact gaacacatac  10440
acgcgtgcac acacacacac acactaaaga ataaacaaac tcttctgatt catatccaca  10500
aagtgggttg gtaagtatta ttagtgcaaa tttctgctga cctgcagcat ttagtccata  10560
aactttggat atcctaggcg atccatcaga gtccagcaga tgttttcaat tagtttaatt  10620
tcatctctag gcaagttctg tttccaaaca ttagtattag ttggtgatat ttccccttca  10680
tagggaaggt aaaaaaggtt tgtagaggtg gcaaacaata tttggtttaa actagcagga  10740
gacaaaggaa ttccaagaaa ggcaaaaatc ctttcagtag ttttctgagg aaaatgcaca  10800
atatcttcaa acttgaccag ctggtagcta gtaggcagca aatctgtatt tattctcaag  10860
gctgctgctg tatttgctag ccacaagtga gacaagaggg acactgcatt tgatttggat  10920
tttgataatt ctttcctcaa tggttcatac tcgaaagcat aacccgaatt taagttacat  10980
ttgcctttac ctccctctat tttaaacaat tttgctaaat gctctggtac attcttcaaa  11040
gaataaagac ttggtttact attgtacaac attgaataaa tccatgcccg agggtctctt  11100
actatgtaca atgccctcat cgaagctcct aaaacttcct gaaaaaaatg aagctttaac  11160
gtccagcttc cactgcttaa actgagcaca ggacgtgcac ttggatagta aaccaggtgt  11220
ctcctcaaag ccctaatata ttcagcatct ctatcaaagg cgcctttcat ttgacttctt  11280
tgttctggca aagactctct ccttttaaat tttctttttt tgtccttatt cattgcaaaa  11340
tattgggcca gtttacccct attgggttca tgcagatgga tgttttgcaa atgtaatttt  11400
gtgtcctgga ctaaagactg caaccagcct cggagtaaac gaaaatgccc actgcggata  11460
tctgacacct tccattcaca agcatctaca aatgagtcga tttccaactc agtttcagga  11520
atatcaatgt aggctgtagg aaccctgatg tagagaaaat cactactgtt gaaaaaaagt  11580
tgtttgagaa tttcagctcc tgaaccagga agtgaggtaa tgacaacatc aggaagatcc  11640
atgtggtgcc cttcagaaga caaagacttc ttgcttccct cagcctctgt ccttgtccat  11700
tttgcacaaa tgggctgact acaagtgctc cacacatcca aaagctcaat aaaccacaag  11760
gcaataacaa gtattaatat ccatcgcatt agttttctaa aagaaaggta aaaacgccat  11820
tggaaagtta aaatcaccaa gctaatgcac aaaattaatc caactgctat attaaattta  11880
aatccaaagg ggaaaataat cctatcatgt cttacaggct ttactattgc ttgagtgccc  11940
aaaccaaatc gggttatttg gccttgatca gccacactgg caaagccacc gaatcccaga  12000
taattgaatc ttgtcttcag gttatggtaa tcagttacaa tagaaacaac atgttcagta  12060
ttattgacat tgagagaaat ctgaagtcca ggattggaac tatcaataaa tctgcagctg  12120
gagacattga tatatggccc ataaaagaca tatgcaattc ttgtgattgt gggttccatc  12180
tgaaaagtaa cattaacaaa ttgagtccat cgttttttaa attcagcagc ttgctctgct  12240
```

-continued

```
tcctgtatac tggccatggg actattgcca tgatgatcaa accaaaacat tttgtaatgt  12300
gcatcccaca catccatcat ggcaccatta tacctattca taaacttata tgggatatat  12360
ttaaaatcaa tatccaaatt atgaaagaag gcactgacag aatttattgg ggaatcttct  12420
tgcctctcaa tatgatcaac aactagcaga gtttgggaat ttaagagaag caaagcacga  12480
tatacacttt tcagtctcat tgctgaagaa taagcagaca cggcttcccc actcacaaat  12540
accatttccc catgttgaga ggcagtgatt atttccccag ctgcatcacc aacctcctcg  12600
ccagtccact taagccactg cgcacattct cccagttgac cttcccaggg cttattacac  12660
tggcttgagg gtgatggagc aaacaccaat acattgttaa ggtggctcaa cttgggtcca  12720
tagagagctt cagaaacaaa tacttgtcca ttgggggcaa aagtaaatga gttctgatct  12780
ggatgctcat gtcctgggtt aaaacttctc cacccatcaa tccaggaata tggctgaaaa  12840
tgaactatgt catacacagc tcgtcccccc agcttcccag atttaaaaga cacaaaggtg  12900
ttggtctgtg tgtttggcaa cccagcccca taagtaacca caccccagtt agggaatgtg  12960
tgtatttttg cagtaccata atcagcaggt ggctgtggtg tgagctgggg atcataccag  13020
atgtattcag tgtgaagagt actccacctt tgggcagttg aaggaaccat cggtccatct  13080
ttaggtcggt gctttctaat ttgctgagct aaccaatttc cagctccatt ctttaagatg  13140
aacttatcca agaaaactag ctggctttct ggaccataaa accaattata attggaatct  13200
gctataccca cagttctttg gaagccaggt aaaagggtgg cataatagaa ccaaaagtgc  13260
atctttaacc agttattatc caagttgttg atattaaaat ggcgctgggc cagaaaaaca  13320
tactgtgtga cggatttagc tgtgtagctt ccataggcca caccttcatc caaagaacca  13380
tcaacaatat gattcaatag aaacattgtc ttttccatga catccactac agcctgtttc  13440
catatatttg ctttagatcc tttatctact ccagtcacca aggcccctgt gagtaatgct  13500
atcatattag tggcttggtg gttatggaga agctgtttgc cccatgagcg gaccttggaa  13560
tactcgtaca tttcctcagt aataacccat attttttcca ggtatttttg tcttcgatga  13620
ttatctaata agttatataa aaagtcaaag gcagtggcaa aacctgttaa ggaatggcca  13680
attggaacct catctcctgg tgcattctct actagccagt ctttgtagcc aaccatcctg  13740
tccatatatt ccaagacaaa ttcaaaggca actttgtctt ctgggcataa caaacagtac  13800
aatgctaaag gaggcagatt gttaccataa atttcattcc acttggcagc aaaatcagca  13860
tgctttggtg gaggtaggta gtatgttggg ttggacagca taactgtcac tgcacttctg  13920
atagctctaa aaagatgcaa atggcttgca cgagactttt gtctcattgc ttggatttct  13980
ccagcatcaa aatataaact tggatgaagc atacttttct tcagcttttg gttgggtctg  14040
aaatcttgca ctttctgtgt tttaaactga tctatatcat ctgtgaaaac tgcccattcg  14100
gaataattgc tcacagattc ctcaaaagta gagaaagcaa acatcaataa tgctaagaat  14160
agtaaatgtc ctgtaaacat taacgccatg atccatgggg gagctcctcc cttaggcata  14220
catgtcagat atgatgctca atgtgtttcc catctggtta gtataaaaca tacagtaaag  14280
gccttgataa gacaaagact gtaaatctga tatgctgtga aatccagctg acattcagta  14340
cattntaagc aagtgcagtt gccaaaaaga gaaacttaaa ttgtatatct ctgtccctgg  14400
cacagttttg cttccagtaa aactttgaat aacgttaaaa tctctaattt ttccataata  14460
cacagggaag tgatacaggt aaaaaacact atgaatttag catttacctc ctttacttaa  14520
atctatttaa cacaaagagt tggaacacac attgtaaaaa aagagaaaaa gcactccaaa  14580
attcaaatta agagtcattt ctagcacaga aaaccatcac tggtgataag ctcaccacac  14640
```

-continued

```
atgtatgatg catttgtgta tgtttgccca aagaagatga tgaagtactg acattcttcg  14700
agtgagtgga ctcagttgtc attcctctca actttttata cttcttgtct tgtgaatacg  14760
tttttctttc atttatgaga gagaaacatc ctcaacaagt gatcaaagtc ttagttggtt  14820
tttaaaaatt caaaattctt gccttcattt caaatatttt tcaggcttac ttactcatca  14880
gcctattatg acaaagagaa atcatgttca catcttcttt tatcagcttc atgtgtacaa  14940
acataaaaat ggaatatctt cagtcaccta gatacttctc gtccgatcat gaagtaaccg  15000
ccaacgggcg aaagaaaatt cccctttcag caacagtgag gtctctcttc tgctcttttt  15060
tcatgacact tttctgggga tgggggacaa aataaaaatt ctctgaggct tcaggtatgc  15120
tgagaatgaa tataaactga tgacttaaac attctgcaat cacttaatag aaattttaga  15180
atcacagtaa aatctcatat tatctgcaac ctaagctagg gcaagtgatt tttttcttat  15240
ccatttacac gcacttattt ggaaaccagt gaccgtcagc agaagacaag caactaacaa  15300
tacaaaatat acaagataga actctcccga caatatctat agtttaacgc cactaacgtg  15360
gcttcagtca cttaaaaaat gtttgtattc aaatgcagtt tacacaaaga tgagtcctgc  15420
tatccttgtt atttcttgtt cccaaggacc gagggacaaa aaactgaaag ttgaaaagat  15480
cttttttttt ttttttttta attccggggg aaggtttaga gttcatggga tcagaaggta  15540
tcttcctaac gagaactact cggaccagtc acttttctcg gcggggtaac cgcgaatcgt  15600
gaccaggcgc caagccgagg ggcgggagct ccgcgctcgg cgctcacctg tggccgagtc  15660
cctgtcctca ggtggagccg ccagagggag ctcggacccc ggtgtcgaaa gacgcctctc  15720
cgtgcccgtc cgcggctgga agaacctaag caagtttcag tcttggacaa gtctcccctc  15780
tgtaggaaac attcaggcta ggagtttcct gatccgcccc gcctgttgca ttttttcact  15840
ggcgtcctcc gaccctgccg cccccattct ccgctccccg ctctggggct gagtgaggca  15900
ggatggcgag agacccctga gccaccaagt ccgcttacct caggcagatc ccgacggggg  15960
ctcggcgccg cactgggccc caagggagac ggaggtggag agttccagaa aactgctctg  16020
cacggcgggc caggctcccg cggggctccg caagacccccc gcgtcgtctc ccgcgctacg  16080
gcaggcgctg ccccagctcg gtctcctcag ccgcgctcgg tccccgcgac ccgcacggcc  16140
cggacacgcc cgccctcagg aaacgccgga cgcttgtggg ggcaaccacg gaccgcagga  16200
cagagacccg cgggcggcgg gttctctcgg tggcgccgta tccagagcag cgcccgcgtc  16260
cccaggcggt gatgtcgccg cggccgagga tcctctgtgc cagctccggc cgcgcagccc  16320
ggggagggtg agagacggcg acgcgggccg gcaagcgggg gcggggcgga ggcaggacgg  16380
ggcggggttg aaggcggggc tgaaggcggg gcctcaggga aggcgagaga cagcgacgct  16440
ggctggcggg cgtggggcgg gacggagaca ggacagggcg gggtcagagg cggggcttcg  16500
gggaggacgg gaggagccgt gagcaggccg gcggcgggcg gggcggggcc gaaagcaggt  16560
gaggcggggc caagcgcccc gggtttctaa gcggaggaag ctctaggcgt ttgtgttctg  16620
ggcttgcagc ggtggccgcg cgctcccgga ggagtcgagc tggaggaggg gacagtttgg  16680
gagtgcgaga gtctaaagac gctgccaggc tggcgttaaa accttttggt tatgggaaga  16740
cgacaactat ataatagagc catagtgggg gctgtgggat tgactcaaat gatgggagga  16800
gctggagtgg gaggggataa gccctgggac gacagaaatc atccttttgg aaagagcaag  16860
ggctggggaa ggagggaatg agcactccct tggaactgag aggcagcctg gctgagcttg  16920
ctgtcctttg gaaaagcaaa accgaaatac ccagattaat ataggaggac aacttctgta  16980
```

-continued

```
gcccagatgc taacaaagat caagggaaaa cagaaaagac taatcagctt tactgatgga  17040
aaacaatttc tcaggcagta taaatagggg aagcatggga caaacaagta gaaggagcct  17100
cttatttaaa aatgggacct ggtattcggt aaagacctac atgcagacag gagaaggcag  17160
tgtgccccgg ctactacgac atgtgagtgc agtgccaggt cgtggaaatc ctagagcagg  17220
ctgggactcc tgttgcactc cacacatgga gcttctcaca gatagctgag atgacacttt  17280
ggcataaacc aacccaagct ctgacctcaa atgtaaaaaa taatagctta gtagtaataa  17340
aaatacaggg aaatatcaag cttcacaaat gaacaattcc attctcagtt ggggattagt  17400
aacacattca gtctcttcat ttcccatact attttggtaa tatttaataa gatatatttt  17460
aacattttaa aaataaatgt cttgcttaga tcatttgctg ctgaaaatca aacagtagac  17520
gactgctagc agaataaatt tcaaatcatt taactttgag gtgaaatgtg gcctctaact  17580
cctcatcact cttctgtttt ggccccgtag taacccctag cccagtccaa atagccacac  17640
ttgcttttgc ttgggtgctt cagtaactat gcttattcca ttctttccct cacagtgtcc  17700
tttacccaac caccccactt actagttaaa attcttctga ctgttgaaat tatctgatca  17760
tccaggtctc aactcagatg cttacattct tctgtaaata actcctaagt ttccctagcc  17820
agaatgtatt actccagaac tatatcattt gtacctatat tcggccgttt aggttgttta  17880
ttttctgctt tctatttcaa ctggttgact cctgtaccct attcaaaact ccttcaagtc  17940
atgagtagca ctcaagtccc ctttgtaagt actatatctg cttttgaaat gagttgaacc  18000
tcgaacaatt gggctgatac agagcctcgt ctcctccact gaggtttatt cccaaacaag  18060
gatcctcttc tgacacaact tcctgtaaaa tctggattgt gcctctacat ggcccctgat  18120
agaggaagag gacccatggc ctccaaccac atttatgaga gagtagagtt gggggaaacg  18180
gggagctgac tccagagatt cctatctgtt tgcagagggg agcctagaat ttagggttag  18240
taaacacagc tactagatgt acagaacatt tctcagaaca aagtgtgggg cagggttatt  18300
tctatggatt caaagtgtct catgatgcga gggcaaggtg agtcagagag aattaatgcg  18360
cgaacatctg ccaggcaaat attcttccaa tgttgttttc agattttgaa atatcagtat  18420
gatcattttc actttagaga agaatgaatt caggtaccga cattgtggcc tttcagctct  18480
gccccatgca tctgtgctga agcagtgggg atgcagctag cctcccagca ttctcagatg  18540
ggctttcaga ctaattcatt ttgaacagac atctttgcat agtggtaaaa tgtgaatgca  18600
ttaaaataaa acaagagcca caactgaaca attcaaatca ttggcagaaa gggtggtagg  18660
taaatggcac tgtcaaaaat gaagagagtc ttgttttctg tgaactaaaa atggatagct  18720
ccaattattg ctccttccac acatgaagat ggtacaaagt tagttaatta taaataatgc  18780
atccgaccat agaagggatg agctatatgc tatgttattg tacattaaaa acctttatga  18840
gtgtggcaag agacacatgt accaacagct gctaaattca gaatcctgga gcagtatctt  18900
atttaatgt aagtgaagaa cagtgcagtc tattgctctg ggatttctc tctatataaa  18960
aggatcttaa atctacatga gattttactc cgtgatttca aagtacttat gaaaatctgt  19020
tttctttatt tgcctatctt tcaacctacc cacaaccacc tatcttacaa cagaaacaat  19080
gctttctaga gtagattctc cagaacagaa gcctttctcg cgctcctttc cttcctttct  19140
tccttcctct ctctctcttt tatttttctt ttaaaatttt atttctcaac atctatccca  19200
gagcctggca ctttttgaaa aatgtttggt gaatgtttaa catgaattat cgccccccatt  19260
ttatgacaga agagaaaaag tcataaaggt ctaaagtggg ttactacatt ctaagcagag  19320
tcacacactc tttctcctga ctgtgctgag aagcctctta ccacacaacc cataattgga  19380
```

-continued

```
gctatgcctt gaggtgactt aattcaagtg aaacatgaga ctggaaagtc atacaacatt  19440
ttcaagagga tttctgcatt aattgtatat gttaagatag gcaaattcaa gctctgagcc  19500
tgagaacgat aaagtacaag ccataaaaca agcctagaca ctacataaag tccctgatct  19560
aaaatcacat ttgtccatga tctgttattc tggtggtttt taaataaatg gggccaagac  19620
attcaagaac tagttgctgt gcattcagca actcctatgc acaggtctcc aatacctggg  19680
ctttcaagca gcatagccat ttgaatatgg agacggcttt gttattcttc tcatagcata  19740
atccaccttt gctacagctt tggccgtgaa agctcagatg cagatttctc gaaccactta  19800
ccagggccag atgtatatta tattgatcca ctagcagtat tagaactagt gtctgcccca  19860
gaggttaggg atatagcatc tgtaactgtt tagaaacaga caccaaactt aagctgcaaa  19920
ttttattgcc cagttggcca gcagtaatag gccacaccaa taataaagac aaaaccacaa  19980
gtttaaagca ggcagtagag tctggaaata cttttttttt ttccgcaatt gctttgaata  20040
caaaacatct caaaatgaca gggattttgc ctgcagagtt gctaatgaag atgtggctaa  20100
gagtgtttct tgagtttgtt tatccagctg cacaagagtc agtatgacag taagtagatt  20160
tattaaaact taaaaatacc aaagccaaat tctgggggaa aaagtttccc cataagtcta  20220
ctaaagcctt gaattcataa atgagaagct ttattgctac catatttgct tacatacagt  20280
ttagcttttg atatgaaaga aaaatttaaa caaagtaaaa cttgcaaagg gatcataaga  20340
tgttttctcc agggctcttc caccctccct ttcccctggc ctggtatcct tacaccagtg  20400
tttctcaaca ggacatttgg caatgtctgg agaaatttca atgttggtct cggttagtgg  20460
gagggactgc tggaatctag tgaatagagg tcaggatgct actaaatagc ctgcaatgaa  20520
caggacaact tctcctctcc tcctgcctca caagtcaaag aattatgcag actagaaagt  20580
cagtactgct gagaatgaga aactctgacc catcccactg actctaaaaa ttgattatgt  20640
gctaattgtt ggtagttcaa atcaattcct aaattgtccc cctgacttgc caattaccta  20700
tttgcagttt gttctagagc cagccgttat ggctaaaatg tatgtgtccc tccaaaattt  20760
acatgttgga accaaattgg tagtattaag aggtggagcc gtttgggaag tcctcttctc  20820
atgaatgaca ttagtgccgt ataaaagagg tgccttaaaa aaaaggtgcc ctagtttcct  20880
tttggccttt tggtctcagt ctatgttgtg cttatataac agaatacctg accctgggta  20940
atttataatg aatggaaatt tatttcctca cagttttgga ggctaggaag tccaaggtca  21000
aggtgctggc agattagggc ccagtttctc tactgcaaag atggcacctg aaagctgcag  21060
cctccagaga tgaaggacat tatatcttca catggcagaa aaggaggaga aagagagaat  21120
ccactcccac cagccctttt tatagagcat taatccattc ttcatgaact aaacaggttt  21180
ctcatttggc cacacctcct aacactgttg cattggggaa tacgtttcca acacttggat  21240
ttgggggaac acgttgagac catagcacct tccatctctt cctccacatg aggacacagt  21300
gttcatttct ttattgcctc ttccattatg tgaggattca gcaagagata tcatcttgga  21360
agcagagagt aagccctccc cagacacaga atcttctggc accttgatcc tggaatttcc  21420
tgccttgaga actctgagaa ataaatttct gctatgtata aattacttta tctgtggtat  21480
ttcattatag cagcaaggac agactaagac actagctttc tctaatttat tcacagatga  21540
ctttttgttg tttaccagct actggctcca tttttcttca tttgacctaa aatacttcta  21600
aacctagctg tctcagccct tataaaaact tgagctatgc ctacaggcat aattggcagt  21660
aaactaatta ctaccaaata atatttggaa tgatgtgtct ttttgggtta tcagaaatgc  21720
```

-continued

```
ccttctgatg ttaataagag aatgtcattt tacccacaac ccctgtacat atcatgcacc  21780
ccaattacct ttactatcag atttatttcc actggaacag tgtttttcaa attacagttc  21840
ttagactacc agtatcagaa agttcatggt gctattaaaa atgtcaatta tcaaatctgt  21900
ctcagcctta tggattaaga atctcagtgt gtaacctggt attctgtacc ttaaaatgtt  21960
caagtgccta acaaattttg agagtcactg ttcgaacata attctcattc ttttctcctt  22020
gccacacaca cctgtgcctg agggtttgtt tggctacata acagaaacat tctcaggctg  22080
gcagaagcat aaggactgat taggattagg aactggtgtt gcagaataac tcagaaacat  22140
gtatgtagct attttgcaga acgtttaata gtcttgcctt taaattattt attcacatgt  22200
gaggaagtga gatattagag tcaagcaata aaggcaaata agatttataa aacagaaaag  22260
agaaaaaaat gaatacaacc tagaaacaat gaaagttgta ttttgggggg caagttgatt  22320
aaatggcagt tagcagagga gtttgttgcc cagaagtgag agtttagctg tagagcagaa  22380
gtgacaggtt cctctgtaga gtgttggcca ctaacccgcc atcagcacct gtatcttact  22440
cagatctagc cagtatcata tttcctcagt aggcttcctt gctggaaagc cactaaaagt  22500
ttccttttttc catccatgtg aggcagggag acttctccct ctgctcctga gcatttactt  22560
ccttctcttt ttctgagaat caatttcacc ttctccttca tggtgataca actcaacatg  22620
gctatccttc agcacaagtt tatatcactt tgactccacc atcgggcaga aatcaattgt  22680
ctttttttgaa cctcaaatcc aaattctcgg aaaagatgat ttcctagcag agtcagcgtt  22740
tcatcatgac tccagcagca atggaaagca gttcagggtc atatagttca aatactgcta  22800
caggggctga cattcgtggg ttcgagatat caatcatctt aggaagagag agctggctta  22860
taccttaaaa gtatctatta taaaatgaca caaaccagag agccatgcac ccccagggaa  22920
gcacataaaa gcagtgtatt tggtggtgag tagttgaggt gttggaggtt gaggtatggt  22980
gggatagtga aaggttgggg gggaggaaag gttcaaaaat gcccacgctt tatgtgaaca  23040
ggctgactcc tctttcttat cccctgaaaa ttattccttt tgtagaatgt attaaattta  23100
cctaattaga agaatcacct agaattactt gttaaaagta cgagatatga gatccaaaac  23160
cctacttgaa ggtagagtga ggaaggaaat ataagaagcc tgtattttta aattccatta  23220
tgatcctgca aaattaacaa atcaccatta gataaccttt taaaatactg ccagctacca  23280
acatcgccct aaacctgctg cccccaccaa taactgagcc cctgataacc accacagtct  23340
agttttatga gatcaatttg taaaaaatcc acatgtgagt gagttcatgc agtagttgtc  23400
tttctgtgcc tggcttattt cacttaacat aatgtcctcc aagttcatag atattgttgc  23460
aaatggctaa ataatattcc actgtgtata tgtaccacat tttctttatc cactcatcta  23520
ttgatggaca cttaggttga ttccatagct tggctattat gaatagagct gtaattaaca  23580
tagcagtgca gagatatata tcagtgtctc tttgacatac tgatatcatc acaaaaataa  23640
taactataag tgatgcatag gttaattaga tttagtcaaa ctgtaatcta catatacttc  23700
aaaacatgat attttacatg atacttacaa ttttacctgt caatttattt tattttattt  23760
ttctaatttt tttttttttg agacaaagtc tcacactgtt gcccaggctg gagagcaatg  23820
gcacgatctc agctcactgc aacctctgcc tcccaggttc aagtgattct ctgcctcagc  23880
ctccccagtg gccaccacac ttggctaatt tttgtatttt taatagagac agggttttgc  23940
catgttggcc aggctggtat caaactcccg atctcaggta atctgcctgc ctcagcctcc  24000
caaagttctg agattacagg cgtgaaccac tgtgcctggc cttacctgtc aattaaaata  24060
ataataataa taatgaaaat aataataata ataattggct agctacttaa aatagaacat  24120
```

-continued

```
aattttgttt cagattcaaa gacgtaaagt ttgatagaga tgggaggtag gtaatttatg  24180
tgggtgaagc cagccaggtg cttgttgtca tgtggaacgt aaggacccat gtcacgagat  24240
aatctgattt tgcaaagaaa gccagaaatc tgaacttgta tgggaaatta tctgattttt  24300
ctaatggctt aacttgtttt gaaaactctg tgaatgccaa ataaaatgga ttcaaatcat  24360
aaacggcaag gttttgactt ctgattgtga gctggctgca tgaaaataaa tttcctgatt  24420
ttgcatatgc tagttcagca ccccaggaat tcaactttcc attttaatgc tgggaaaaaa  24480
aatactatct tttcttttaa gttatctact actataactc ctctcagtct ggaacggtca  24540
aggactggtc atgtattcaa gcaatcttat ttattcctgc agttatgtat taagttttat  24600
ttccttaatt caataaatat tcactgagtg ctcaataacg cactgtggaa gacgctgaaa  24660
aaccccaagg ggaaaaaata ttcttcgcca aatggagctt ataatctgtg gatagaaaag  24720
gcacaaaagg catgaattat tacttcattt tttctgtatt ttaatcatta cttcatcata  24780
tttaaatggc tttgaaggtt catctatata ctgattccag tattttcaag agcacatcta  24840
atttgatgag gatggaagat tgttaatgac tcagaagctg ggaaaatagg tagaaactca  24900
aatgttgtaa gaaatcacta gaatgtttgc attttttcag aggttcactc cttctgttct  24960
aatacctgga gtccagccag gcacaaagca agctggctga ctactgcaga aaggaatgct  25020
ggaacctctc ttgctgacct gcttccagag tttccagcac agctagccag agacttccta  25080
tagacaatga ggaaattcaa aaacaaagaa tgtagtagtt tggctatttc tctaggagcc  25140
cttggggatg agactgagcc attttcctgc agctggctgc aaagcaggcc actgaaaaag  25200
atcagtatga aagaacaagg catactgttg gtatatgcgt cactgtgggc cagagctttt  25260
tgtcatagga ttcagtcaaa ctcaaaatgc aagatgaaag tcatcctctt tgtaaccgtt  25320
ttaaaaataa tacatagaaa agaagtgaac agaaccatgt tttccaaagt cctgatgcta  25380
aaaatcacaa aatcttaata gttcctgagc tggaaatgtg gactgcttgg cctgggatca  25440
agtctagaat ttgatgttct tggcaggtac atcaagtggt tagtatcagc agagaagcta  25500
aggaaatact gaagtcgaag gataaaggat gattccctcc ctgtaatggc tttactctga  25560
gttacctact gtgtgttgtc ctgggcttac ttccaggcaa ttctcatagg tttgtggtta  25620
catgctggat tttgggatga gatgatcctg agtttgaatc caagctttga gattatattg  25680
taagtttctg ggaggtattg ggccagttac ttaccttttc tgaatatagg tgtcctcctc  25740
tgtaaaatgg atttacaata ttactaactg tatagagtag ttgagaagct taaatgagaa  25800
gaggcaggta cgtttctcat tacagagctt taagggttgt tgcactttaa aagcaatttt  25860
acatacttta tttcatttag ccttttttaac aatcatgtga atgatacgtg attaactcaa  25920
ttttgtgtac catagaactg agaaagagga atttggaatc gaaaatatca taacttaaga  25980
tagtgtgaca aaaatagtat tccagtgtct accaacttgc tttctgaact tgtctaattt  26040
taaagaccga gaatatttga aggaaacatg cagcgcagtt ccttcattgt actggtgaag  26100
aatctgagct cgatgtgtga gagagaaaga aggcctgctg gaccagaaca caggtttctt  26160
tactacctat ctgcagctgt gccgctacat tgtagatgat gctatttgtt tttaagcata  26220
ttcagtgata tattaagttg cttctttaga tcttaaaaaa aaaaaaaaca actcataaag  26280
tgccgggcac ggtggctcac acctgtaatc ccagcacttt gggaggccga gatgggtgga  26340
tcacgaggtc aggagattga gaccattctg gctaacacag tgaaaccccg tctctactaa  26400
aaatacaaaa aaattagccg ggcgtagtgg cgggcgcctg tagtcccagc tactcaggag  26460
```

-continued

```
gctgaggcag gagaattgcg tgaacctggg aggcagaggt tgcagtgagc cgagatcgca  26520

cctctgcact ccagcctggg cgactaagca agactctgtc tccaaaaaaa aaaaaaaaaa  26580

aacctcataa agtaacaatt ctatatgcag cttatattag agcagttttt caaagaactt  26640

tctaggaccc aaaatttttc tgggagcatt tttaaaagcc gaatatctat atatccatta  26700

cagatccttt ctgaaataga gttttgatcg gggcataaaa atttgcattt ttatcaggtt  26760

taccaataca atattaagaa tgagctaatt aaaccattct gtccttggag acagaaattg  26820

ggcactgtcc ttcttttgtc ttcccatcag ttccagccag aattttaggc acatactttc  26880

cactcagtta actcactgaa ttgaatagtg gtggaatcaa attaaggcca aatgttttaa  26940

ttatataaaa atctatgaag cacatgtata gaggaatcat tttcaaagat ataattttta  27000

caatttactg tgaattacag gcataattat cctgccagat atacttgtct gcctagcaaa  27060

tatatgtata tatgatactt gtgaaatttg atacatactt cgcatatgta ttatatataa  27120

gagacaaaga gggatagaga gaggagaaaa                                  27150
```

<210> SEQ ID NO 21
<211> LENGTH: 1188
<212> TYPE: DNA
<213> ORGANISM: homo sapiens

<400> SEQUENCE: 21

```
atgtggctgc cgcgcgtctc cagcacagca gtgaccgcgc tcctcctggc gcagaccttc     60

ctcctcctct ttctggtttc ccggccaggg ccctcgtccc cagcaggcgg cgaggcgcgc    120

gtgcatgtgc tggtgctgtc ctcgtggcgc tcgggctcgt ccttcgtggg ccaactcttc    180

aaccagcacc ccgacgtctt ctacctaatg gagcccgcgt ggcacgtgtg gaccaccctg    240

tcgcagggca gcgccgcaac gctgcacatg gctgtgcgcg acctggtgcg ctccgtcttc    300

ctgtgcgaca tggacgtgtt tgatgcctat ctgccttggc gccgcaacct gtccgacctc    360

ttccagtggg ccgtgagccg tgcactgtgc tcgccacccg cctgcagtgc ctttccccga    420

ggcgccatca gcagcgaggc cgtgtgcaag ccactgtgcg cgcggcagtc cttcaccctg    480

gcccgggagg cctgccgctc ctacagccac gtggtgctca aggaggtgcg cttcttcaac    540

ctgcaggtgc tctacccgct gctcagcgac cccgcgctca acctacgcat cgtgcacctg    600

gtgcgcgacc cgcgggccgt gctgcgctcc cgggagcaga cagccaaggc tctggcgcgt    660

gacaacggca tcgtgctggg caccaacggc acgtgggtgg aggccgaccc cggcctgcgc    720

gtggtgcgcg aggtgtgccg tagccacgta cgcatcgccg aggccgccac actcaagccg    780

ccacccttc tgcgcggccg ctaccgcctg gtgcgcttcg aggacctggc gcgggagccg    840

ctggcagaaa tccgtgcgct ctacgccttc actgggctca gtctcacgcc acagctcgag    900

gcctggatcc ataacatcac ccacggatct ggacctggtg cgcgccgcga agccttcaag    960

acttcgtcca ggaatgcgct caacgtctcc caggcctggc gccatgcgct gccctttgcc   1020

aagatccgcc gcgtgcagga actgtgcgct ggtgcgctgc agctgctggg ctaccggcct   1080

gtgtactctg aggacgagca gcgcaacctc gcccttgatc tggtgctgcc acgaggcctg   1140

aacggcttca cttgggcatc atccaccgcc tcgcaccccc gaaattag               1188
```

<210> SEQ ID NO 22
<211> LENGTH: 3669
<212> TYPE: DNA
<213> ORGANISM: homo sapiens

<400> SEQUENCE: 22

-continued

```
atgcctaagg gaggagctcc cccatggatc atggcgttaa tgtttacagg acatttacta     60
ttcttagcat tattgatgtt tgctttctct acttttgagg aatctgtgag caattattcc    120
gaatgggcag ttttcacaga tgatatagat cagtttaaaa cacagaaagt gcaagatttc    180
agacccaacc aaaagctgaa gaaaagtatg cttcatccaa gtttatattt tgatgctgga    240
gaaatccaag caatgagaca aaagtctcgt gcaagccatt tgcatctttt tagagctatc    300
agaagtgcag tgacagttat gctgtccaac ccaacatact acctacctcc accaaagcat    360
gctgattttg ctgccaagtg gaatgaaatt tatggtaaca atctgcctcc tttagcattg    420
tactgtttgt tatgcccaga agacaaagtt gcctttgaat ttgtcttgga atatatggac    480
aggatggttg gctacaaaga ctggctagta gagaatgcac caggagatga ggttccaatt    540
ggccattcct taacaggttt tgccactgcc tttgactttt tatataactt attagataat    600
catcgaagac aaaaatacct ggaaaaaata tgggttatta ctgaggaaat gtacgagtat    660
tccaaggtcc gctcatgggg caaacagctt ctccataacc accaagccac taatatgata    720
gcattactca caggggcctt ggtgactgga gtagataaag gatctaaagc aaatatatgg    780
aaacaggctg tagtggatgt catggaaaag acaatgtttc tattgaatca tattgttgat    840
ggttctttgg atgaaggtgt ggcctatgga agctacacag ctaaatccgt cacacagtat    900
gtttttctgg cccagcgcca ttttaatatc aacaacttgg ataataactg gttaaagatg    960
cacttttggt tctattatgc caccctttta cctggcttcc aaagaactgt gggtatagca   1020
gattccaatt ataattggtt ttatggtcca gaaagccagc tagttttctt ggataagttc   1080
atcttaaaga atggagctgg aaattggtta gctcagcaaa ttagaaagca ccgacctaaa   1140
gatggaccga tggttccttc aactgcccaa aggtggagta ctcttcacac tgaatacatc   1200
tggtatgatc cccagctcac accacagcca cctgctgatt atggtactgc aaaaatacac   1260
acattcccta actggggtgt ggttacttat ggggctgggt tgccaaacac acagaccaac   1320
acctttgtgt cttttaaatc tgggaagctg gggggacgag ctgtgtatga catagttcat   1380
tttcagccat attcctggat tgatgggtgg agaagtttta acccaggaca tgagcatcca   1440
gatcagaact catttacttt tgccccccaat ggacaagtat ttgtttctga agctctctat   1500
ggacccaagt tgagccacct taacaatgta ttggtgtttg ctccatcacc ctcaagccag   1560
tgtaataagc cctgggaagg tcaactggga gaatgtgcgc agtggcttaa gtggactggc   1620
gaggaggttg gtgatgcagc tggggaaata atcactgcct ctcaacatgg ggaaatggta   1680
tttgtgagtg gggaagccgt gtctgcttat tcttcagcaa tgagactgaa aagtgtatat   1740
cgtgctttgc ttctcttaaa ttcccaaact ctgctagttg ttgatcatat tgagaggcaa   1800
gaagattccc caataaattc tgtcagtgcc ttctttcata atttggatat tgattttaaa   1860
tatatcccat ataagtttat gaataggtat aatggtgcca tgatggatgt gtgggatgca   1920
cattacaaaa tgttttggtt tgatcatcat ggcaatagtc ccatggccag tatacaggaa   1980
gcagagcaag ctgctgaatt taaaaaacga tggactcaat ttgttaatgt tacttttcag   2040
atggaatcca caatcacaag aattgcatat gtcttttatg ggccatatat caatgtctcc   2100
agctgcagat ttattgatag ttccaatcct ggacttcaga tttctctcaa tgtcaataat   2160
actgaacatg ttgtttctat tgtaactgat taccataacc tgaagacaag attcaattat   2220
ctgggattcg gtggctttgc cagtgtggct gatcaaggcc aaataacccg atttggtttg   2280
ggcactcaag caatagtaaa gcctgtaaga catgatagga ttattttccc ctttggattt   2340
```

-continued

```
aaatttaata tagcagttgg attaattttg tgcattagct tggtgatttt aactttccaa   2400

tggcgttttt acctttcttt tagaaaacta atgcgatgga tattaatact tgttattgcc   2460

ttgtggttta ttgagctttt ggatgtgtgg agcacttgta gtcagcccat ttgtgcaaaa   2520

tggacaagga cagaggctga gggaagcaag aagtctttgt cttctgaagg gcaccacatg   2580

gatcttcctg atgttgtcat tacctcactt cctggttcag gagctgaaat tctcaaacaa   2640

ctttttttca acagtagtga ttttctctac atcagggttc ctacagccta cattgatatt   2700

cctgaaactg agttggaaat cgactcattt gtagatgctt gtgaatggaa ggtgtcagat   2760

atccgcagtg ggcattttcg tttactccga ggctggttgc agtctttagt ccaggacaca   2820

aaattacatt tgcaaaacat ccatctgcat gaacccaata ggggtaaact ggcccaatat   2880

tttgcaatga ataaggacaa aaaaagaaaa tttaaaagga gagagtcttt gccagaacaa   2940

agaagtcaaa tgaaaggcgc ctttgataga gatgctgaat atattagggc tttgaggaga   3000

cacctggttt actatccaag tgcacgtcct gtgctcagtt taagcagtgg aagctggacg   3060

ttaaagcttc atttttttca ggaagtttta ggagcttcga tgagggcatt gtacatagta   3120

agagaccctc gggcatggat ttattcaatg ttgtacaata gtaaaccaag tctttattct   3180

ttgaagaatg taccagagca tttagcaaaa ttgtttaaaa tagagggagg taaaggcaaa   3240

tgtaacttaa attcgggtta tgctttcgag tatgaaccat tgaggaaaga attatcaaaa   3300

tccaaatcaa atgcagtgtc cctcttgtct cacttgtggc tagcaaatac agcagcagcc   3360

ttgagaataa atacagattt gctgcctact agctaccagc tggtcaagtt tgaagatatt   3420

gtgcattttc ctcagaaaac tactgaaagg atttttgcct ttcttggaat tcctttgtct   3480

cctgctagtt taaaccaaat attgtttgcc acctctacaa accttttta ccttccctat   3540

gaaggggaaa tatcaccaac taatactaat gtttggaaac agaacttgcc tagagatgaa   3600

attaaactaa ttgaaaacat ctgctggact ctgatggatc gcctaggata tccaaagttt   3660

atggactaa                                                           3669
```

<210> SEQ ID NO 23
<211> LENGTH: 3624
<212> TYPE: DNA
<213> ORGANISM: mouse

<400> SEQUENCE: 23

```
atggcgttta tgtttacaga acatttacta tttttaacat tgatgatgtg tagtttttct     60

acttgtgaag aatctgtgag caattattct gaatgggcag ttttcacaga cgatatacaa    120

tggcttaagt cacagaaaat acaagatttc aaactcaacc gaagacttca tccaaattta    180

tattttgatg ctggagatat acaaacattg aaacaaaagt ctcgtacaag ccatttgcat    240

atttttagag ctatcaaaag tgcagtgaca attatgctgt ccaatccatc atactaccta    300

cctccaccca agcatgctga gtttgctgcc aagtggaatg aaatttatgg taataatctt    360

cctcctttag cattgtattg tttattatgc ccagaagaca aggttgcctt tgaatttgtt    420

atggaataca tggatcggat ggttagctac aaagactggc tagttgagaa tgcaccaggg    480

gatgaggttc cagttggcca ttctttaaca ggttttgcca ctgcctttga ctttttatat    540

aatctattag gtaatcagcg taaacaaaaa tacctagaaa aaatttggat tgttactgag    600

gaaatgtatg aatattccaa gattcgatca tggggcaaac aacttcttca taaccatcaa    660

gctacaaata tgatagcttt actcataggg gccttggtta ctggagtaga taaaggatct    720

aaagcaaaca tatggaaaca agttgttgtt gatgtgatgg aaaagactat gtttctcttg    780
```

-continued

```
aagcatattg tagatggctc attggatgaa ggtgtggcct atggaagcta tacctcaaaa    840
tcagttacac agtatgtttt tttggcacaa cgccatttta acatcaacaa ctttgataat    900
aactggctaa aaatgcattt ttggttttat tatgctacac ttttgccagg ctatcaaaga    960
actgtaggca tagcagattc caattataat tggttttatg gtccagagag ccagctagtt   1020
ttcttggata agttcatttt acagaatgga gctggaaatt ggttagctca gcaaattaga   1080
aagcatcgac ctaaggatgg accaatggtt ccttccactg ctcagcggtg gagtactctt   1140
catactgaat acatctggta tgatccaaca ctcaccccac agcctcctgt tgattttggc   1200
actgcaaaaa tgcacacatt tcctaactgg ggtgtcgtga cttatggggg tgggctgcca   1260
aacacccaga ccaatacctt tgtgtctttt aaatctggga aactgggagg acgagctgtg   1320
tatgacatag ttcactttca gccatattcc tggattgatg gatggagaag ctttaaccca   1380
ggacatgaac atccagatca aaattcattt actttcgctc ctaatgggca ggtattcgtt   1440
tctgaggctc tttatggacc aaaattgagc caccttaaca acgtattggt gtttgcccca   1500
tcaccatcaa gtcaatgtaa tcagccctgg gaaggtcaac tgggagaatg tgcacagtgg   1560
ctcaagtgga ctggggaaga ggttggtgat gcagctgggg aagttattac tgctgctcaa   1620
catggtgata ggatgtttgt gagtggggaa gcagtgtctg cttattcttc tgccatgaga   1680
ctgaaaagtg tctatcgtgc tttacttctt ttaaattcac aaactctgct tgttgtcgat   1740
catattgaaa ggcaagaaac ttccccaata aattctgtca gtgccttctt tcataatttg   1800
gatattgatt ttaaatacat cccatacaag tttatgaata gatataatgg tgccatgatg   1860
gatgtgtggg atgcacacta taaaatgttt tggtttgatc accatggcaa cagtcctgtg   1920
gctaatatac aggaagcaga acaggctgct gaatttaaga aacggtggac acagtttgtt   1980
aatgttacat ttcatatgga atccacaatc acaagaattg cttatgtatt tttatgggcca  2040
tatgtcaatg tttccagctg cagatttatt gatagttcca gttctggact tcagatttct   2100
ttacatgtca acagtactga acatagtgtg tctgttgtaa ctgactatca aaaccttaaa   2160
agcagattca gttacctggg atttggtggt tttgccagtg tggctaatca aggacagata   2220
accagatttg gtttgggtac tcaagaaata gtaaaccctg taagacatga taaagttaat   2280
ttcccctttg ggtttaaatt taatatagca gttggattca ttttgtgtat tagtttggtt   2340
attttaactt ttcaatggcg gttttacctt tcctttagaa agctaatgcg ctgtgtatta   2400
atacttgtta ttgccttgtg gtttattgag cttctggatg tatggagtac atgcactcag   2460
cccatctgtg caaaatggac aaggactgaa gctaaggcaa atgagaaggt catgatttct   2520
gaagggcatc atgtggatct tcctaatgtt attattacct cactccctgg ttcaggagct   2580
gaaattctca aacagctttt tttcaacagc agtgattttc tctacatcag aattcctaca   2640
gcctacatgg atatccctga aactgaattt gaaattgact catttgtaga tgcttgtgag   2700
tggaaagtat cagatatccg cagtgggcac tttcatcttc ttcgagggtg gctgcagtct   2760
ttggtccagg atacaaaact tcacttgcaa aacatccatc tacatgaaac cagtaggagt   2820
aaactggccc aatattttac aactaataag gacaaaaagc gaaaattaaa aagaagggag   2880
tctttgcaag atcaaagaag tagaataaaa ggaccatttg atagagatgc tgaatatatt   2940
agggctttaa gaagacacct tgtttattac ccaagtgcac gtcctgtgct cagcttaagt   3000
agtggtagct ggacattgaa gcttcatttt tttcaggaag ttttaggaac ttcaatgcgg   3060
gcattgtaca tagtaagaga ccctcgagct tggatctatt cagtgctata tggtagtaaa   3120
```

-continued

| | |
|---|---|
| ccaagtcttt attctttgaa gaatgtacca gagcacttag caaaattgtt taaaatagag | 3180 |
| gaaggtaaaa gcaaatgtaa ttcgaattct ggctatgctt ttgagtatga atcactgaag | 3240 |
| aaagaattag aaatatccca atcaaatgct atctccttat tatctcattt gtgggtagca | 3300 |
| aacactgcag cagccttgag aataaataca gatttgctgc ctaccaatta ccatctggtc | 3360 |
| aagtttgaag atattgttca ttttcctcag aagactactg aaaggatttt tgctttcctt | 3420 |
| ggcattcctt tgtctcctgc tagtttaaac caaatgctat ttgccacttc cacaaacctt | 3480 |
| ttttatcttc catatgaggg ggaaatatca ccatctaata ctaatatttg gaaaacaaac | 3540 |
| ttgcctagag atgaaattaa actaattgaa aacatttgct ggacactgat ggatcatcta | 3600 |
| ggatatccaa agtttatgga ctaa | 3624 |